(12) United States Patent
Furstner et al.

(10) Patent No.: US 9,187,466 B2
(45) Date of Patent: Nov. 17, 2015

(54) BISARYL-BONDED ARYLTRIAZOLONES AND USE THEREOF

(75) Inventors: Chantal Furstner, Mülheim/Ruhr (DE); Joerg Keldenich, Wuppertal (DE); Martina Delbeck, Heiligenhaus (DE); Peter Kolkhof, Wuppertal (DE); Axel Kretschmer, Wuppertal (DE); Ingo Pluschkell, Bochum (DE); Elisabeth Pook, Wuppertal (DE); Carsten Schmeck, Mülheim (DE); Hubert Trubel, Wuppertal (DE)

(73) Assignee: Bayer Intellectual Property GmbH, Monheim (DE)

(*) Notice: Subject to any disclaimer, the term of this patent is extended or adjusted under 35 U.S.C. 154(b) by 0 days.

(21) Appl. No.: 13/580,817

(22) PCT Filed: Feb. 25, 2011

(86) PCT No.: PCT/EP2011/052781
§ 371 (c)(1),
(2), (4) Date: Nov. 30, 2012

(87) PCT Pub. No.: WO2011/104322
PCT Pub. Date: Sep. 1, 2011

(65) Prior Publication Data
US 2013/0190330 A1 Jul. 25, 2013

(30) Foreign Application Priority Data

Feb. 27, 2010 (DE) .......................... 10 2010 009 631

(51) Int. Cl.
| | |
|---|---|
| C07D 249/12 | (2006.01) |
| C07D 417/06 | (2006.01) |
| C07D 401/06 | (2006.01) |
| C07D 403/06 | (2006.01) |
| C07D 409/06 | (2006.01) |
| C07D 409/14 | (2006.01) |
| C07D 413/06 | (2006.01) |
| C07D 413/14 | (2006.01) |
| A61K 31/4196 | (2006.01) |
| A61K 31/422 | (2006.01) |
| A61K 31/4245 | (2006.01) |
| A61K 31/427 | (2006.01) |
| A61K 31/433 | (2006.01) |
| A61K 31/4439 | (2006.01) |

(Continued)

(52) U.S. Cl.
CPC .......... *C07D 417/06* (2013.01); *A61K 31/4196* (2013.01); *A61K 31/422* (2013.01); *A61K 31/427* (2013.01); *A61K 31/4245* (2013.01); *A61K 31/433* (2013.01); *A61K 31/4439* (2013.01); *A61K 31/506* (2013.01); *A61K 45/06* (2013.01); *C07D 249/12* (2013.01); *C07D 401/06* (2013.01); *C07D 403/06* (2013.01); *C07D 409/06* (2013.01); *C07D 409/14* (2013.01); *C07D 413/06* (2013.01); *C07D 413/14* (2013.01)

(58) Field of Classification Search
CPC .. C07D 249/12; C07D 403/06; C07D 409/06; C07D 409/14; C07D 413/06; C07D 413/14; C07D 417/06; C07D 401/06; A61K 45/06; A61K 31/506; A61K 31/4439; A61K 31/433; A61K 31/427; A61K 31/4245; A61K 31/422; A61K 31/4196
USPC ......... 514/256, 340, 363, 383, 384, 365, 374, 514/364; 548/136, 266.6, 263.2, 204, 236, 548/255, 131, 266.2; 546/272.4; 544/333
See application file for complete search history.

(56) References Cited

U.S. PATENT DOCUMENTS

| | | | |
|---|---|---|---|
| 5,276,049 A | 1/1994 | Himmelsbach et al. | |
| 5,281,614 A | 1/1994 | Ashton et al. | |
| 5,326,776 A | 7/1994 | Winn et al. | |

(Continued)

FOREIGN PATENT DOCUMENTS

| | | |
|---|---|---|
| CN | 1544418 A | 11/2004 |
| EP | 0051829 | 5/1982 |

(Continued)

OTHER PUBLICATIONS

Bronson, et al.,:"Discovery of the First Antibactrial Small Molecule Inhibitors of MurB," Bioorganic & Medicinal Chemistry Letters, 2003, 13: 873-875.
DeLuca, et al.,:"Hyponatremia in Paitents with Heart Failure," Am. J. Cardiol., 2005, vol. 96 (suppl.), 19L-23L.
Francis, et al.:"Comparison of Neuroendocrine Activation in Patients with Left Ventricular Dysfunction with and without Congestive Heart Failure," Circulation, Nov. 1990, 82(5): 1724-1729.
Lemmens-Gruber, et al.:"Vasopressin Antagonists," Cell. Mol. Life Sci., 2006, 63:1766-1779.
Palm, et al.:"Vasopressin Antagonists as Aquaretic Agents for the Treatment of Hyponatremia," Am. J. Med., 2006, 119(7A): S87-S92.
Saghi, et al.:"Vasopressin Antagonism: A Future Treatment Option in Heart Failure," Europ. Heart J., 2005, 26: 538-543.
Schrier, et al.:"Hormones and Hemodynamics in Heart Failure," New Engl. J. Med., Aug. 19, 1999, 341(8): 577-585.
Tang, et al.:"Vasopressin Receptor Antagonists in the Management of Acute Heart Failure," Expert Opin. Investig. Drugs, 2005, 14(5): 593-600.

(Continued)

*Primary Examiner* — Savitha Rao
*Assistant Examiner* — Angela Brown-Pettigrew
(74) *Attorney, Agent, or Firm* — Karen B. King

(57) ABSTRACT

The present invention relates to bisaryl-linked 5-aryl-1,2,4-triazolone derivatives according to the following formula:

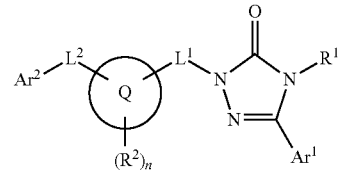

wherein $Ar^1$, $Ar^2$, $R^1$, $R^2$, $L^1$, $L^2$, Q and n are defined herein. The invention further related to the process of making the bisaryl-linked 5-aryl-1,2,4-triazolone derivatives.

9 Claims, No Drawings

(51) Int. Cl.
  *A61K 31/506* (2006.01)
  *A61K 45/06* (2006.01)

(56) References Cited

U.S. PATENT DOCUMENTS

| | | | |
|---|---|---|---|
| 5,468,448 A | 11/1995 | Nicolson et al. |
| 5,585,394 A | 12/1996 | Di Malta et al. |
| 5,681,841 A | 10/1997 | Himmelsbach et al. |
| 6,469,012 B1 | 10/2002 | Ellis et al. |
| 6,531,142 B1 | 3/2003 | Rabe et al. |
| 6,693,102 B2 | 2/2004 | Stasch et al. |
| 6,743,798 B1 | 6/2004 | Straub et al. |
| 6,746,989 B1 | 6/2004 | Müller et al. |
| 6,762,152 B1 | 7/2004 | Müller et al. |
| 6,833,364 B1 | 12/2004 | Straub et al. |
| 6,838,415 B1 | 1/2005 | Müller et al. |
| 6,864,287 B1 | 3/2005 | Alonso-Alija et al. |
| 6,924,251 B1 | 8/2005 | Schwarz et al. |
| 6,969,697 B2 | 11/2005 | Muller et al. |
| 7,080,644 B2 | 7/2006 | Gumaste et al. |
| 7,173,037 B2 | 2/2007 | Alonso-Alija et al. |
| 7,279,444 B2 | 10/2007 | Muller et al. |
| 7,642,275 B2 | 1/2010 | Bressi et al. |
| 7,674,825 B2 | 3/2010 | Alonso-Alija et al. |
| 8,084,481 B2 | 12/2011 | Meier et al. |
| 2001/0020100 A1 | 9/2001 | Manning et al. |
| 2002/0045651 A1 | 4/2002 | Brenner et al. |
| 2002/0172644 A1 | 11/2002 | Haslwanter et al. |
| 2003/0161790 A1 | 8/2003 | Wahi et al. |
| 2004/0071757 A1 | 4/2004 | Rolf et al. |
| 2004/0082798 A1 | 4/2004 | Alonso-Alija et al. |
| 2004/0176446 A1 | 9/2004 | Alonso-Alija et al. |
| 2006/0148779 A1 | 7/2006 | Bell et al. |
| 2007/0225333 A1 | 9/2007 | Bryans et al. |
| 2007/0281937 A1 | 12/2007 | Zelle et al. |
| 2008/0058314 A1 | 4/2008 | Kabra et al. |
| 2008/0139560 A1 | 6/2008 | Zelle et al. |
| 2010/0261771 A1 | 10/2010 | Bruggemeier |
| 2011/0245308 A1 | 10/2011 | Bruggemeier et al. |

FOREIGN PATENT DOCUMENTS

| | | |
|---|---|---|
| EP | 0412594 | 7/1990 |
| EP | 0533276 | 3/1993 |
| WO | 9317681 A1 | 9/1993 |
| WO | 9931099 | 6/1999 |
| WO | 0100595 | 1/2001 |
| WO | 0119355 | 3/2001 |
| WO | 02066447 | 8/2002 |
| WO | 2006117657 | 11/2006 |
| WO | 2007/134862 A1 | 11/2007 |

OTHER PUBLICATIONS

Hassan et al., "Aryl-Aryl Bond Formation One Century after the Discovery of the Ulmann Reaction," Chem Rev 2002, 102:1359-1469.
Arnswald, et al., "Unconventional Regiospecific Synthesis of Aromatic Carbonamides and Thiocarbonamides by Means of Tin-Mediated Friedel-Crafts Reactions." J. Org. Chem., 1993 58(25): 7022-7028.
Papadopoulos et al.,"Friedel-Crafts Thioacylation with Ethoxycarbonyl Isothiocyanate: A One-Step Synthesis of Aromatic Thioamides," J. Org. Chem 1976, 41(6): 962-965.
U.S. Appl. No. 12/301,616, filed in US on Jun. 15, 2009.
U.S. Appl. No. 13/132,897, filed in US on Jun. 15, 2009.
U.S. Appl. No. 13/255,515, filed in US on Aug. 9, 2011.
U.S. Appl. No. 13/818,337, filed in US on Feb. 22, 2013.
U.S. Appl. No. 13/819,885, filed in US on Feb. 28, 2013.
U.S. Appl. No. 13/426,444, filed in US Mar. 21, 2012.
Chang et al., Triazolinones as Nonpeptide Angiotensin II Antagonists. 1. Synthesis and Evaluation of Potent 2, 4, 5-Trisubstituted Triazoloinones, J. Med. Chem. 1993, vol. 36, Nr. 17, 2558-2568.
Dobosz et al., "Synthesis and Some Pharmacological Properties of 3-(4-phenyl-5-oxo-1,2,4-triazolin-1-ylmethyl)-1,2,-triazolin-5-thione Derivatives," Acta Polomiae Pharmaceutica 2002, vol. 59, No. 4, 281-290.
Finley, et al., "Arginine Vasopressin Antagonists for the Treatment of Heart Failure and Hyponatremia," Circulation 2008, 118:410-421, p. 412, col. 2.
Gines, P. et al., "Effects of stavaptan, a selective vasopressin V2 receptor antagonist, on ascites and serum sodium cirrhosis with hyponatremia," Hepatology, 2008, 48(1):204-212.
Goldsmith, et al., "Current treatments and novel pharmacologic treatments for hyponatremia in congestive heart failure," Am. J. Cardiol, 2005, 95(suppl): 14B-23B.
Patani, et al.: "Bioisosterism: A Rational Approach in Drug Design," Chem. Rev., 1996, 96:3147-3176.
Schrier, Robert W., The sea within us: Disorders of body water homeostasis, Current Opinion in Investigational Drugs, 2007, 8(4):304-311.
Verbalis, J.G., "AVP receptor antagonists as aquaretics: Review and assessment of clinical data," Cleveland Clinic Journal of Medicine, Sep. 2009, 73, S24-S33.
Declaration by Peter Kolkhof, Oct. 13, 2014.
Declaration by Kr. Elisabeth Pook, Oct. 23, 2014.
Mexican Application No. MX/2013/009862 (counterpart of U.S. Appl. No. 13/580,817), opposition proceedings, Office Action from Mexican Institute of Industrial Property, issued Mar. 28, 2014.
Mexican Application No. MX/2013/009862 (counterpart of U.S. Appl. No. 13/580,817), opposition proceedings, English translation of Office Action issued Mar. 28, 2014.
Mexican Application No. MX/a/2012/009862 (counterpart of U.S. Appl. No. 13/580,817), opposition proceedings, Applicant's response with amended claims, filed Sep. 25, 2014.
Mexican Application No. MX/a/2012/009862 (counterpart of U.S. Appl. No. 13/580,817), opposition proceedings, English translation of Applicant's response with amended claims, filed Sep. 25, 2014.
Eurasian Application No. 201290836 (counterpart of U.S. Appl. No. 13/580,817), Office Action, mailed Jan. 31, 2014.
Eurasian Application No. 201290836 (counterpart of U.S. Appl. No. 13/580,817), English translation of an Office Action, mailed Jan. 31, 2014.
Eurasian Application No. 201290836 (counterpart of U.S. Appl. No. 13/580,817), Applicant's response with amended clamis, filed May 30, 2014.
Eurasian Application No. 201290836 (counterpart of U.S. Appl. No. 13/580,817), English translation of Applicant's response with amended clamis, filed May 30, 2014.
European Application No. 11 704 637.5 (counterpart of U.S. Appl. No. 13/580,817), Office Action response with amended claims, filed Apr. 18, 2013.
European Application No. 11 704 637.5 (counterpart of U.S. Appl. No. 13/580,817), English translation of Office Action response, filed Apr. 18, 2013.
European Application No. 11 704 637.5 (counterpart of U.S. Appl. No. 13/580,817), Office Action, mailed Sep. 5, 2013.
European Application No. 11 704 637.5 (counterpart of U.S. Appl. No. 13/580,817), English translation of Office action, mailed Sep. 5, 2013.
European Application No. 11 704 637.5 (counterpart of U.S. Appl. No. 13/580,817), response to Office Action with amended claims, mailed Mar. 5, 2014.
European Application No. 11 704 637.5 (counterpart of U.S. Appl. No. 13/580,817), English translation of response to Office Action, mailed Mar. 5, 2014.
English translation of Official Action, dated Nov. 18, 2014, for JP Application No. 2010-554345.

BISARYL-BONDED ARYLTRIAZOLONES AND USE THEREOF

The present application relates to novel bisaryl-linked 5-aryl-1,2,4-triazolone derivatives, to processes for preparing them, to their use alone or in combinations for the treatment and/or prevention of diseases and also to their use for the production of medicaments for the treatment and/or prevention of diseases, more particularly for the treatment and/or prevention of cardiovascular disorders.

The liquid content of the human body is subject to various physiological control mechanisms, the purpose whereof is to keep it constant (volume homeostasis). In the process, both the volume filling of the vascular system and also the osmolarity of the plasma are continuously recorded by appropriate sensors (baroreceptors and osmoreceptors). The information which these sensors supply to the relevant centers in the brain regulates drinking behavior and controls fluid excretion via the kidneys by means of humoral and neural signals. The peptide hormone vasopressin is of central importance in this [Schrier R. W., Abraham, W. T., *New Engl. J. Med.* 341, 577-585 (1999)].

Vasopressin is produced in specialized endocrine neurons in the Nucleus supraopticus and N. paraventricularis in the wall of the third ventricle (hypothalamus) and transported from there along its neural processes into the posterior lobes of the hypophysis (neurohypophysis). There the hormone is released into the bloodstream according to stimulus. A loss of volume, e.g. as a result of acute bleeding, heavy sweating, prolonged thirst or diarrhoea, is a stimulus for intensified outpouring of the hormone. Conversely, the secretion of vasopressin is inhibited by an increase in the intravascular volume, e.g. as result of increased fluid intake.

Vasopressin exerts its action mainly via binding to three receptors, which are classified as V1a, V1b and V2 receptors and belong to the family of G protein-coupled receptors. V1a receptors are mainly located on the cells of the vascular smooth musculature. Their activation gives rise to vasoconstriction, as a result of which the peripheral resistance and blood pressure rise. Apart from this, V1a receptors are also detectable in the liver. V1b receptors (also named V3 receptors) are detectable in the central nervous system. Together with corticotropin-releasing hormone (CRH), vasopressin regulates the basal and stress-induced secretion of adrenocorticotropic hormone (ACTH) via the V1b receptor. V2 receptors are located in the distal tubular epithelium and the epithelium of the collecting tubules in the kidney. Their activation renders these epithelia permeable to water. This phenomenon is due to the incorporation of aquaporins (special water channels) in the luminal membrane of the epithelial cells.

The importance of vasopressin for the reabsorption of water from the urine in the kidney becomes clear from the clinical picture of diabetes insipidus, which is caused by a deficiency of the hormone, e.g. owing to hypophysis damage. Patients who suffer from this clinical picture excrete up to 20 liters of urine per 24 hours if they are not given replacement hormone. This volume corresponds to about 10% of the primary urine. Because of its great importance for the reabsorption of water from the urine, vasopressin is also synonymously referred to as antidiuretic hormone (ADH). Logically, pharmacological inhibition of the action of vasopressin/ADH on the V2 receptor results in increased urine excretion. In contrast to the action of other diuretics (thiazides and loop diuretics), however, V2 receptor antagonists cause increased water excretion, without substantially increasing the excretion of electrolytes. This means that by means of V2 antagonist drugs, volume homeostasis can be restored, without in the process affecting electrolyte homeostasis. Hence drugs with V2 antagonist activity appear particularly suitable for the treatment of all disease conditions which are associated with an overloading of the body with water, without the electrolytes being effectively increased in parallel. A significant electrolyte abnormality is measurable in clinical chemistry as hyponatremia (sodium concentration<135 mmol/L); it is the most important electrolyte abnormality in hospital patients, with an incidence of about 5% or 250000 cases per year in the USA alone. If the plasma sodium concentration falls below 115 mmol/L, comatose states and death are imminent.

Depending on the underlying cause, a distinction is made between hypovolemic, euvolemic and hypervolemic hyponatremia. The forms of hypervolemia with edema formation are clinically significant. Typical examples of this are the syndrome of inappropriate ADH/vasopressin secretion (SIAD) (e.g. after craniocerebral trauma or as paraneoplasia in carcinomas) and hypervolemic hyponatremia in liver cirrhosis, various renal diseases and heart failure [De Luca L. et al., *Am. J. Cardiol.* 96 (suppl.), 19L-23L (2005)]. In particular, patients with heart failure, in spite of their relative hyponatremia and hypervolemia, often display elevated vasopressin levels, which is seen as the consequence of generally disturbed neurohumoral regulation in heart failure [Francis G. S. et al., *Circulation* 82, 1724-1729 (1990)].

The disturbed neurohormonal regulation essentially manifests itself in an elevation of the sympathetic tone and inappropriate activation of the renin-angiotensin-aldosterone system. While the inhibition of these components by beta-receptor blockers on the one hand and by ACE inhibitors or angiotensin-receptor blockers on the other is now an inherent part of the pharmacological treatment of heart failure, the inappropriate elevation of vasopressin secretion in advanced heart failure is at present still not adequately treatable. Apart from the retention of water mediated by V2 receptors and the unfavorable hemodynamic consequences associated therewith in terms of increased backload, the emptying of the left ventricle, the pressure in the pulmonary blood vessels and cardiac output are also adversely affected by V1a-mediated vasoconstriction. Furthermore, on the basis of experimental data in animals, a direct hypertrophy-promoting action on the heart muscle is also attributed to vasopressin. In contrast to the renal effect of volume expansion, which is mediated by activation of V2 receptors, the direct action on the heart muscle is triggered by activation of V1a receptors.

For these reasons, substances which inhibit the action of vasopressin on the V2 and/or on the V1a receptor appear suitable for the treatment of heart failure. In particular, compounds with combined activity on both vasopressin receptors (V1a and V2) should both have desirable renal and also hemodynamic effects and thus offer an especially ideal profile for the treatment of patients with heart failure. The provision of such combined vasopressin antagonists also appears to make sense inasmuch as a volume diminution mediated solely via V2 receptor blockade can entail the stimulation of osmoreceptors and as a result a further compensatory increase in vasopressin release. As a result, in the absence of a component simultaneously blocking the V1a receptor, the harmful effects of the vasopressin, such as for example vasoconstriction and heart muscle hypertrophy, could be further intensified [Saghi P. et al., *Europ. Heart J.* 26, 538-543 (2005)].

It was an object of the present invention to provide novel compounds which act as potent selective or dual V1a/V2 receptor antagonists and as such are suitable for the treatment and/or prevention of diseases, more particularly for the treatment and/or prevention of cardiovascular disorders.

EP 0 412 594-A2, WO 92/20662-A1 and US 2001/0020100-A1 describe 4-(biphenylalkyl)-1,2,4-triazolones having angiotensin II-antagonistic action for the treatment of cardiovascular disorders. WO 99/31099-A1 claims variously substituted 1,2,4-triazolones as therapeutically useful integrin receptor antagonists. The use of 5-aryl-1,2,4-triazolones as medicaments with neuroprotective action is disclosed in WO 99/54315-A2, and WO 2006/117657-A1 describes 4,5-diaryltriazolone derivatives as antiinflammatory agents. WO 2006/078698-A1 claims various heterocyclic compounds as tyrosine phosphatase inhibitors for the treatment of diabetes. WO 2005/105779-A1 discloses 3-heterocyclyl-4-phenyltriazoles as inhibitors of the vasopressin V1A receptor, and WO 2007/134862-A1 describes amidically attached 5-aryl-1,2,4-triazolones as dual vasopressin antagonists. WO 00/58306-A1 and WO 00/68227-A1 disclose heterocyclically substituted benzoylpyrazoles and -isoxazoles as herbicides.

The present invention provides compounds of the general formula (I)

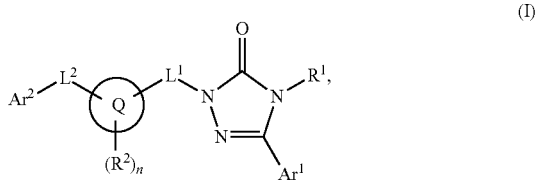

in which

R$^1$ represents (C$_1$-C$_6$)-alkyl, (C$_2$-C$_6$)-alkenyl or (C$_2$-C$_6$)-alkynyl, each of which may be mono- to trisubstituted by identical or different radicals selected from the group consisting of fluorine, chlorine, cyano, trifluoromethyl, oxo, hydroxyl, difluoromethoxy, trifluoromethoxy, (C$_1$-C$_4$)-alkoxy, (C$_3$-C$_7$)-cycloalkyl and phenyl,
  where (C$_3$-C$_7$)-cycloalkyl may be substituted up to two times by identical or different radicals selected from the group consisting of fluorine, trifluoromethyl, (C$_1$-C$_4$)-alkyl, oxo, hydroxyl, trifluoromethoxy and (C$_1$-C$_4$)-alkoxy
  and
  where phenyl may be substituted up to three times by identical or different radicals selected from the group consisting of halogen, cyano, nitro, difluoromethyl, trifluoromethyl, (C$_1$-C$_4$)-alkyl, hydroxyl, hydroxymethyl, difluoromethoxy, trifluoromethoxy, (C$_1$-C$_4$)-alkoxy, (C$_1$-C$_4$)-alkoxymethyl, hydroxycarbonyl, (C$_1$-C$_4$)-alkoxycarbonyl, aminocarbonyl, mono-(C$_1$-C$_4$)-alkylaminocarbonyl and di-(C$_1$-C$_4$)-alkylaminocarbonyl,
  or
  represents (C$_3$-C$_7$)-cycloalkyl which may be mono- or disubstituted by identical or different radicals selected from the group consisting of fluorine, trifluoromethyl, (C$_1$-C$_4$)-alkyl, oxo, hydroxyl, trifluoromethoxy and (C$_1$-C$_4$)-alkoxy, Ar$^1$ represents phenyl, thienyl or furyl, each of which may be mono- to trisubstituted by identical or different radicals selected from the group consisting of halogen, cyano, nitro, difluoromethyl, trifluoromethyl, (C$_1$-C$_4$)-alkyl, hydroxyl, trifluoromethoxy and (C$_1$-C$_4$)-alkoxy, L$^1$ represents the group —CH$_2$—, —C(=O)— or —SO$_2$—, Q represents a phenyl ring, a 5-membered heteroaryl ring having up to three ring heteroatoms from the group consisting of N, O and S or a 6-membered heteroaryl ring having up to three nitrogen ring atoms, R$^2$ represents a substituent selected from the group consisting of fluorine, chlorine, bromine, cyano, nitro, (C$_1$-C$_4$)-alkyl, (C$_3$-C$_6$)-cycloalkyl, phenyl, hydroxyl, (C$_1$-C$_4$)-alkoxy, amino, aminocarbonylamino, (C$_1$-C$_4$)-alkylcarbonylamino, hydroxycarbonyl, (C$_1$-C$_4$)-alkoxycarbonyl, aminocarbonyl, mono-(C$_1$-C$_4$)-alkylaminocarbonyl and di-(C$_1$-C$_4$)-alkyl-aminocarbonyl,
  where the (C$_1$-C$_4$)-alkyl substituent for its part may be substituted by hydroxyl, (C$_1$-C$_4$)-alkoxy, carbamoyloxy, hydroxycarbonyl, (C$_1$-C$_4$)-alkoxycarbonyl, aminocarbonyl, mono-(C$_1$-C$_4$)-alkylaminocarbonyl or di-(C$_1$-C$_4$)-alkylaminocarbonyl or up to three times by fluorine
  and
  where the phenyl substituent for its part may be substituted by fluorine, chlorine, cyano, methyl, trifluoromethyl or methoxy, n represents the number 0, 1 or 2,
  where in the case that the substituent R$^2$ occurs twice its meanings may be identical or different, L$^2$ represents a bond, represents —O— or represents a group of the formula —(CR$^{3A}$R$^{3B}$)$_p$— in which
  R$^{3A}$ represents hydrogen, fluorine or methyl,
  R$^{3B}$ represents hydrogen, fluorine, (C$_1$-C$_4$)-alkyl, hydroxycarbonyl, (C$_1$-C$_4$)-alkoxy-carbonyl or aminocarbonyl,
    where (C$_1$-C$_4$)-alkyl may be substituted by hydroxyl or carbamoyloxy or up to three times by fluorine,
  or
  R$^{3A}$ and R$^{3B}$ are attached to one another and together form a —(CH$_2$)$_r$ bridge in which
    r represents the number 2, 3, 4 or 5
    and a CH$_2$ group of this bridge may be replaced by —O—,
  and
  p represents the number 1 or 2,
    where in the case that the group —CR$^{3A}$R$^{3B}$— occurs twice the individual meanings of R$^{3A}$ and R$^{3B}$ may in each case be identical or different, and Ar$^2$ represents phenyl, naphthyl or 5- to 10-membered heteroaryl having up to three ring heteroatoms from the group consisting of N, O and S, each of which may be mono- to tri-substituted by identical or different radicals selected from the group consisting of halogen, cyano, nitro, difluoromethyl, trifluoromethyl, (C$_1$-C$_4$)-alkyl, hydroxyl, difluoromethoxy, trifluoromethoxy and (C$_1$-C$_4$)-alkoxy, and salts, solvates and solvates of the salts thereof.

Compounds according to the invention are the compounds of the formula (I) and their salts, solvates, and solvates of the salts; the compounds of the below-specified formulae embraced by formula (I), and their salts, solvates, and solvates of the salts; and also the compounds specified below as working examples and embraced by formula (I), and their salts, solvates, and solvates of the salts; insofar as the below-specified compounds embraced by formula (I) are not already salts, solvates, and solvates of the salts.

Depending on their structure, the compounds according to the invention may exist in different stereoisomeric forms, i.e. in the form of configurational isomers or if appropriate also as conformational isomers (enantiomers and/or diastereomers, including those in the case of atropisomers). The present invention therefore encompasses the enantiomers or diastereomers and the respective mixtures thereof. The stereoisomerically uniform constituents can be isolated from such mixtures of enantiomers and/or diastereomers in a known manner; chromatography processes are preferably used for this, in particular HPLC chromatography on an achiral or chiral phase.

Where the compounds according to the invention are able to occur in tautomeric forms, the present invention embraces all of the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass than the atomic mass which usually or predominantly occurs in nature. Examples of isotopes which can be incorporated into a compound according to the invention are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound according to the invention, especially those in which one or more radioactive isotopes have been incorporated, may be beneficial, for example, for the examination of the mechanism of action or of the active compound distribution in the body; due to comparatively easy preparability and detectability, especially compounds labelled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds according to the invention may therefore in some cases also constitute a preferred embodiment of the present invention. Isotopic variants of the compounds according to the invention can be prepared by generally used processes known to those skilled in the art, for example by the methods described below and the methods described in the working examples, by using corresponding isotopic modifications of the particular reagents and/or starting compounds therein.

Salts preferred in the context of the present invention are physiologically acceptable salts of the compounds of the invention. Also embraced are salts which, while not themselves suitable for pharmaceutical applications, may nevertheless be used, for example, for the isolation, purification or storage of the compounds of the invention.

Physiologically acceptable salts of the compounds of the invention embrace acid addition salts of mineral acids, carboxylic acids and sulfonic acids, examples being salts of hydrochloric acid, hydrobromic acid, sulfuric acid, phosphoric acid, methanesulfonic acid, ethanesulfonic acid, toluenesulfonic acid, benzenesulfonic acid, naphthalenedisulfonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also embrace salts with customary bases, such as—by way of example and preferably—alkali metal salts (e.g. sodium and potassium salts), alkaline earth metal salts (e.g. calcium and magnesium salts) and ammonium salts, derived from ammonia or from organic amines having 1 to 16 C atoms, such as—by way of example and preferably—ethylamine, diethylamine, triethylamine, N,N-diisopropylethylamine, monoethanolamine, diethanolamine, Triethanolamine, dimethylaminoethanol, diethylaminoethanol, procaine, dicyclohexylamine, dibenzylamine, N-methylpiperidine, N-methyl-morpholine, arginine, lysine and 1,2-ethylendiamine.

Solvates in the context of the invention are those forms of the compounds of the invention that form a complex in solid or liquid state by coordination with solvent molecules. Hydrates are one specific form of solvates, where the coordination is with water. Preferred solvates in the context of the present invention are hydrates.

Furthermore, the present invention also embraces prodrugs of the compounds of the invention. The term "prodrugs" denotes compounds which may themselves be biologically active or inactive but which during their residence time in the body are converted (metabolically or by hydrolysis, for example) into compounds of the invention.

In the context of the present invention, the substituents, unless otherwise specified, have the following definitions:

In the context of the invention, $(C_1-C_6)$-alkyl and $(C_1-C_4)$-alkyl represent a straight-chain or branched alkyl radical having 1 to 6 and 1 to 4 carbon atoms, respectively. Preference is given to a straight-chain or branched alkyl radical having 1 to 4 carbon atoms. The following may be mentioned by way of example and by way of preference: methyl, ethyl, n-propyl, isopropyl, n-butyl, isobutyl, sec-butyl, tert-butyl, n-pentyl, 2-pentyl, 3-pentyl, neopentyl, n-hexyl, 2-hexyl and 3-hexyl.

In the context of the invention, $(C_1-C_4)$-alkylcarbonyl represents a straight-chain or branched alkyl radical having 1 to 4 carbon atoms which is attached to the remainder of the molecule via a carbonyl group [—C(=O)—]. The following may be mentioned by way of example and by way of preference: acetyl, propionyl, n-butyryl, isobutyryl, n-pentanoyl and pivaloyl.

In the context of the invention, $(C_2-C_6)$-alkenyl represents a straight-chain or branched alkenyl radical having 2 to 6 carbon atoms and a double bond. Preference is given to a straight-chain or branched alkenyl radical having 3 to 6 carbon atoms. The following may be mentioned by way of example and by way of preference: vinyl, n-prop-1-en-1-yl, allyl, isopropenyl, 2-methyl-2-propen-1-yl, n-but-1-en-1-yl, n-but-2-en-1-yl, n-but-3-en-1-yl, n-pent-2-en-1-yl, n-pent-3-en-1-yl, n-pent-4-en-1-yl, 3-methylbut-2-en-1-yl and 4-methylpent-3-en-1-yl.

In the context of the invention, $(C_2-C_6)$-alkynyl represents a straight-chain or branched alkynyl radical having 2 to 6 carbon atoms and a triple bond. Preference is given to a straight-chain or branched alkynyl radical having 3 to 6 carbon atoms. The following may be mentioned by way of example and by way of preference: ethynyl, n-prop-1-yn-1-yl, n-prop-2-yn-1-yl, n-but-2-yn-1-yl, n-but-3-yn-1-yl, n-pent-2-yn-1-yl, n-pent-3-yn-1-yl and n-pent-4-yn-1-yl.

In the context of the invention, $(C_1-C_4)$-alkoxy represents a straight-chain or branched alkoxy radical having 1 to 4 carbon atoms. The following may be mentioned by way of example and by way of preference: methoxy, ethoxy, n-propoxy, iso-propoxy, n-butoxy, isobutoxy, sec-butoxy and tert-butoxy.

In the context of the invention, $(C_1-C_4)$-alkoxymethyl represents a straight-chain or branched alkoxy radical having 1 to 4 carbon atoms which is attached to the remainder of the molecule via a methylene group [—CH$_2$—] attached to the oxygen atom. The following may be mentioned by way of example and by way of preference: methoxymethyl, ethoxymethyl, n-propoxymethyl, iso-propoxymethyl, n-butoxymethyl and tert-butoxymethyl.

In the context of the invention, $(C_1-C_4)$-alkoxycarbonyl represents a straight-chain or branched alkoxy radical having 1 to 4 carbon atoms which is attached to the remainder of the molecule via a carbonyl group [—C(=O)—] attached to the oxygen atom. The following may be mentioned by way of example and by way of preference: methoxycarbonyl, ethoxycarbonyl, n-propoxycarbonyl, isopropoxycarbonyl, n-butoxycarbonyl and tert-butoxycarbonyl.

In the context of the invention, mono-$(C_1-C_4)$-alkylamino represents an amino group having a straight-chain or branched alkyl substituent having 1 to 4 carbon atoms. The following may be mentioned by way of example and by way of preference: methylamino, ethylamino, n-propylamino, isopropylamino, n-butylamino and tert-butylamino.

In the context of the invention, di-$(C_1-C_4)$-alkylamino represents an amino group having two identical or different straight-chain or branched alkyl substituents each having 1 to 4 carbon atoms. The following may be mentioned by way of example and by way of preference: N,N-dimethylamino, N,N-diethylamino, N-ethyl-N-methylamino, N-methyl-N-n-propylamino, N-isopropyl-N-methylamino, N-isopropyl-N-n-propylamino, N,N-diisopropylamino, N-n-butyl-N-methylamino, N,N-di-n-butylamino and N-tert-butyl-N-methylamino.

In the context of the invention, mono- and di-$(C_1-C_4)$-alkylaminocarbonyl represent amino groups which are attached to the remainder of the molecule via a carbonyl group [—C(=O)—] and which have, respectively, one straight-chain or branched and two identical or different straight-chain or branched N-alkyl substituents each having 1 to 4 carbon atoms. The following may be mentioned by way of example and by way of preference: methylaminocarbonyl, ethylaminocarbonyl, n-propylaminocarbonyl, isopropylaminocarbonyl, n-butylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N,N-diisopropylaminocarbonyl, N-n-butyl-N-methylamino-carbonyl and N-tert-butyl-N-methylaminocarbonyl.

In the context of the invention, $(C_1-C_4)$-alkylcarbonylamino represents an amino group having a straight-chain or branched alkylcarbonyl substituent which has 1 to 4 carbon atoms in the alkyl radical and is attached to the nitrogen atom via the carbonyl group. The following may be mentioned by way of example and by way of preference: acetylamino, propionylamino, n-butyrylamino, isobutyrylamino, n-pentanoylamino and pivaloylamino.

In the context of the invention, $(C_3-C_7)$-cycloalkyl and $(C_3-C_6)$-cycloalkyl represent monocyclic, saturated cycloalkyl groups having 3 to 7 and 3 to 6 carbon atoms, respectively. Preference is given to a cycloalkyl radical having 3 to 6 carbon atoms. The following may be mentioned by way of example and by way of preference: cyclopropyl, cyclobutyl, cyclopentyl, cyclohexyl and cycloheptyl.

5-membered heteroaryl in the definition of ring Q represents an aromatic heterocycle (hetero-aromatic) which has a total of 5 ring atoms and which contains up to three identical or different ring heteroatoms from the group consisting of N, O and S and is attached via carbon ring atoms or optionally a nitrogen ring atom. The following may be mentioned by way of example: furyl, pyrrolyl, thienyl, pyrazolyl, imidazolyl, 1,2-oxazolyl (isoxazolyl), 1,3-oxazolyl, 1,2-thiazolyl (isothiazolyl), 1,3-thiazolyl, 1,2,3-triazolyl, 1,2,4-triazolyl, 1,2,4-oxadiazolyl, 1,3,4-oxadiazolyl, 1,2,4-thiadiazolyl and 1,3,4-thiadiazolyl.

6-membered heteroaryl in the definition of ring Q represents an aromatic heterocycle (hetero-aromatic) having a total of 6 ring atoms and which contains one, two or three nitrogen ring atoms and is attached via carbon ring atoms. The following may be mentioned by way of example: pyridyl, pyrimidinyl, pyridazinyl, pyrazinyl, 1,2,4-triazinyl and 1,3,5-triazinyl. Preference is given to 6-membered heteroaryl having one or two nitrogen ring atoms such as pyridyl, pyrimidinyl, pyridazinyl and pyrazinyl.

In the context of the invention, 5- to 10-membered heteroaryl represents a mono- or optionally bicyclic aromatic heterocycle (heteroaromatic) which has a total of 5 to 10 ring atoms, which contains up to three ring heteroatoms from the group consisting of N, O and S and which is attached via a carbon ring atom or optionally a nitrogen ring atom. The following may be mentioned by way of example: furyl, pyrrolyl, thienyl, pyrazolyl, imidazolyl, thiazolyl, oxazolyl, isoxazolyl, isothiazolyl, triazolyl, oxadiazolyl, thiadiazolyl, pyridyl, pyrimidinyl, pyridazinyl, pyrazinyl, triazinyl, benzofuranyl, benzothienyl, benzimidazolyl, benzoxazolyl, benzothiazolyl, benzo-triazolyl, indolyl, indazolyl, quinolinyl, isoquinolinyl, naphthyridinyl, quinazolinyl, quinoxalinyl, phthalazinyl, pyrazolo[3,4-b]pyridinyl. Preference is given to mono- or optionally bicyclic 5- to 10-membered heteroaryl radicals having up to two heteroatoms from the group consisting of N, O and S. Particular preference is given to monocyclic 5- or 6-membered heteroaryl radicals having up to two heteroatoms from the group consisting of N, O and S, such as, for example, furyl, thienyl, thiazolyl, oxazolyl, isothiazolyl, isoxazolyl, pyrazolyl, imidazolyl, pyridyl, pyrimidinyl, pyridazinyl, pyrazinyl.

In the context of the invention, halogen includes fluorine, chlorine, bromine and iodine. Preference is given to chlorine, fluorine or bromine, particularly preferably fluorine or chlorine.

In the context of the invention, an oxo substituent represents an oxygen atom which is attached to a carbon atom via a double bond.

In the context of the present invention, all radicals which occur more than once are defined independently of one another. If radicals in the compounds according to the invention are substituted, the radicals may be mono- or polysubstituted, unless specified otherwise. Substitution by one or by two or three identical or different substituents is preferred. Particular preference is given to substitution by one or two identical or different substituents. Very particular preference is given to substitution by one substituent.

In the context of the present invention, preference is given to compounds of the formula (I) in which $R^1$ represents $(C_1-C_6)$-alkyl which may be mono- to trisubstituted by identical or different radicals selected from the group consisting of fluorine, trifluoromethyl, oxo, hydroxyl, methoxy, ethoxy, $(C_3-C_6)$-cycloalkyl and phenyl, where $(C_3-C_6)$-cycloalkyl may be substituted up to two times by identical or different radicals selected from the group consisting of fluorine, methyl, trifluoromethyl, ethyl and hydroxyl and where phenyl may be substituted up to two times by identical or different radicals selected from the group consisting of fluorine, chlorine, cyano, methyl, difluoromethyl, trifluoromethyl, ethyl, hydroxyl, methoxy, trifluoromethoxy, ethoxy, hydroxycarbonyl, methoxycarbonyl, ethoxycarbonyl and aminocarbonyl, or represents $(C_2-C_6)$-alkenyl or represents $(C_3-C_6)$-cycloalkyl which may be mono- or disubstituted by identical or different radicals selected from the group consisting of fluorine, methyl, trifluoromethyl, ethyl and hydroxyl, Ar¹ represents phenyl or thienyl, each of which may be mono- or disubstituted by identical or different radicals selected from the group consisting of fluorine, chlorine, cyano, methyl, trifluoromethyl, ethyl, hydroxyl, methoxy, trifluoromethoxy and ethoxy, L¹ represents the group —CH₂— or —SO₂—, Q represents a phenyl ring, a 5-membered heteroaryl ring having up to three ring heteroatoms from the group consisting of N, O and S or a 6-membered heteroaryl ring having up to two nitrogen ring atoms, R² represents a substituent selected from the group consisting of fluorine, chlorine, bromine, $(C_1-C_4)$-alkyl, $(C_3-C_6)$-cycloalkyl, phenyl, $(C_1-C_4)$-alkoxy, hydroxycarbonyl, $(C_1-C_4)$-alkoxycarbonyl, aminocarbonyl and mono-$(C_1-C_4)$-alkylaminocarbonyl, where the $(C_1-C_4)$-alkyl substituent for its part may be substituted by hydroxyl, $(C_1-C_4)$-alkoxy, carbamoyloxy, hydroxycarbonyl, $(C_1-C_4)$-alkoxycarbonyl or aminocarbonyl or up to three times by fluorine and where the phenyl substituent for its part may be substituted by fluorine, chlorine, methyl or trifluoromethyl, n represents the number 0 or 1, L² represents a bond or represents a group of the formula —(CR$^{3A}$R$^{3B}$)$_p$— in which R$^{3A}$ represents hydrogen or methyl, R$^{3B}$ represents hydrogen, $(C_1-C_4)$-alkyl, hydroxycarbonyl, $(C_1-C_4)$-alkoxycarbonyl or aminocarbonyl, where $(C_1-C_4)$-alkyl may be substituted by hydroxyl or carbamoyloxy, and p represents the number 1 or 2, where in the case that the group —CR$^{3A}$R$^{3B}$— occurs twice the individual meanings of R$^{3A}$ and R$^{3B}$ may in each case be identical or different, and Ar² represents phenyl which may be mono- or disubstituted by identical or different radicals selected from the group consisting of fluorine, chlorine, cyano, difluoromethyl, trifluoromethyl, $(C_1-C_4)$-alkyl, methoxy, difluoromethoxy, trifluoromethoxy and ethoxy, and salts, solvates and solvates of the salts thereof.

A particular embodiment of the present invention comprises compounds of the formula (I) in which R¹ represents $(C_1-C_4)$-alkyl which may be mono- or disubstituted by identical or different radicals selected from the group consisting of fluorine, trifluoromethyl, oxo and hydroxyl, or represents allyl or cyclopropyl, and salts, solvates and solvates of the salts thereof.

A further particular embodiment of the present invention comprises compounds of the formula (I) in which Ar¹ represents phenyl or thienyl, each of which is substituted by a radical selected from the group consisting of fluorine, chlorine, cyano, methyl, trifluoromethyl, ethyl, hydroxyl, methoxy, trifluoromethoxy and ethoxy, and salts, solvates and solvates of the salts thereof.

A further particular embodiment of the present invention comprises compounds of the formula (I) in which Ar² represents phenyl which is mono- or disubstituted by identical or different radicals selected from the group consisting of fluorine, chlorine, cyano, difluoromethyl, trifluoromethyl, $(C_1-C_4)$-alkyl, methoxy, difluoromethoxy, trifluoromethoxy and ethoxy, and salts, solvates and solvates of the salts thereof.

A further particular embodiment of the present invention comprises compounds of the formula (I) in which Q represents an optionally substituted phenyl ring of the formula

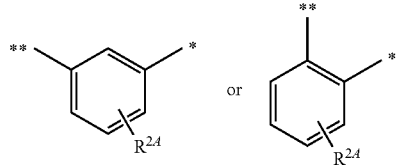

in which

\* denotes the point of attachment to the group L¹ and

\*\* denotes the point of attachment to the group L², and

R$^{2A}$ represents hydrogen, fluorine, chlorine, bromine, methyl, trifluoromethyl, hydroxymethyl, carbamoyloxymethyl, hydroxycarbonyl, methoxycarbonyl, ethoxycarbonyl, aminocarbonyl, methylaminocarbonyl or tert-butylaminocarbonyl, and salts, solvates and solvates of the salts thereof.

A further particular embodiment of the present invention comprises compounds of the formula (I) in which Q represents a pyridyl ring or pyrimidinyl ring of the formula

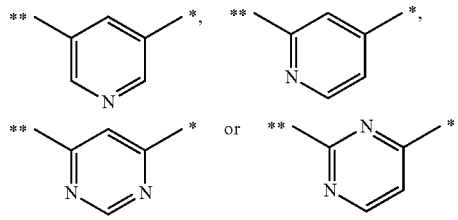

in which

\* denotes the point of attachment to the group L¹ and

\*\* denotes the point of attachment to the group L², and salts, solvates and solvates of the salts thereof.

A further particular embodiment of the present invention comprises compounds of the formula (I) in which Q represents an optionally substituted 5-membered heteroaryl ring of the formula

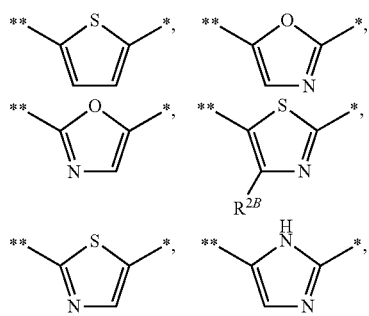

-continued

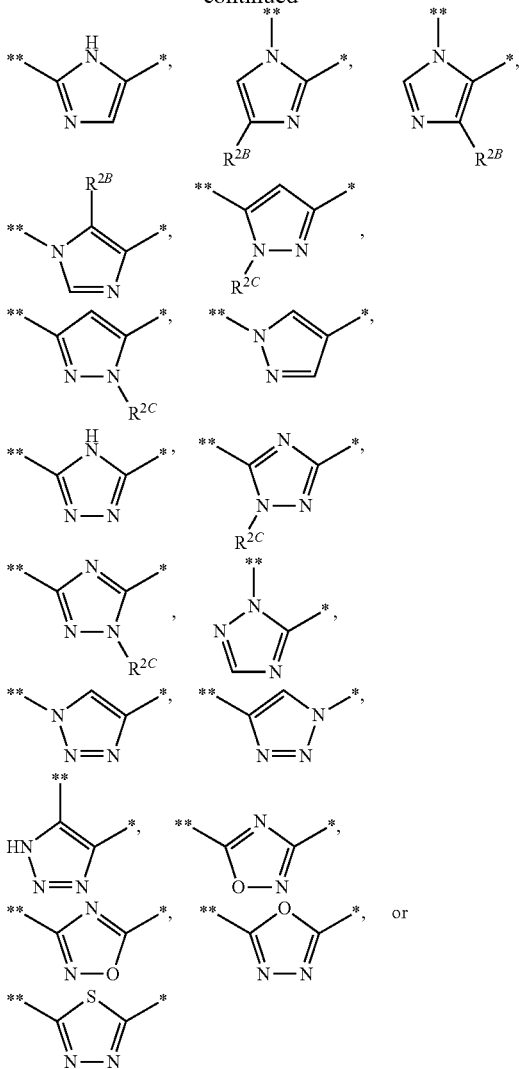

in which

* denotes the point of attachment to the group $L^1$
and
** denotes the point of attachment to the group $L^2$,
$R^{2B}$ represents hydrogen, methyl or trifluoromethyl
and
$R^{2C}$ represents hydrogen or methyl which may be substituted by hydroxycarbonyl, methoxycarbonyl or aminocarbonyl, and salts, solvates and solvates of the salts thereof.

Particular preference in the context of the present invention is given to compounds of the formula (I) in which $R^1$ represents ($C_1$-$C_4$)-alkyl which may be mono- or disubstituted by identical or different radicals selected from the group consisting of fluorine, trifluoromethyl, oxo, hydroxyl and phenyl,
where phenyl for its part may be substituted by a radical selected from the group consisting of fluorine, chlorine, methyl, trifluoromethyl, methoxy, hydroxycarbonyl and methoxycarbonyl, or
represents allyl or cyclopropyl,
$Ar^1$ represents phenyl or thienyl, each of which is substituted by a radical selected from the group consisting of fluorine and chlorine,
$L^1$ represents the group —$CH_2$—,
Q represents a pyridyl ring, a pyrimidinyl ring or an optionally substituted phenyl ring of the formula or
represents an optionally substituted 5-membered heteroaryl ring of the formula -continued

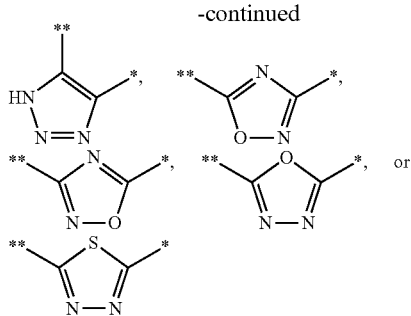

in which
* denotes the point of attachment to the group $L^1$
and
** denotes the point of attachment to the group $L^2$,
$R^{2A}$ represents hydrogen, fluorine, chlorine, bromine, methyl, trifluoromethyl, hydroxymethyl, carbamoyloxymethyl, hydroxycarbonyl, methoxycarbonyl, ethoxy-carbonyl, aminocarbonyl, methylaminocarbonyl or tert-butylaminocarbonyl,
$R^{2B}$ represents hydrogen, methyl or trifluoromethyl
and
$R^{2C}$ represents hydrogen or methyl which may be substituted by hydroxycarbonyl, methoxycarbonyl or aminocarbonyl,
$L^2$ represents a bond or the group —$CH_2$—
and
$Ar^2$ represents phenyl which is mono- or disubstituted by identical or different radicals selected from the group consisting of fluorine, chlorine, methyl, trifluoromethyl, methoxy and trifluoromethoxy,
and salts, solvates and solvates of the salts thereof.

Very particular preference in the context of the present invention is given to compounds of the formula (I) in which
$R^1$ represents $(C_1-C_4)$-alkyl which may be mono- or disubstituted by identical or different radicals selected from the group consisting of fluorine, trifluoromethyl and hydroxyl, or represents cyclopropyl,
$Ar^1$ represents p-chlorophenyl,
$L^1$ represents the group —$CH_2$—,
Q represents a pyrimidinyl ring of the formula

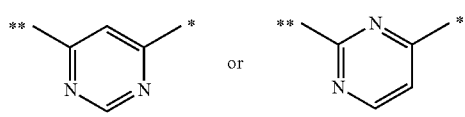

or
represents an optionally substituted 5-membered heteroaryl ring of the formula

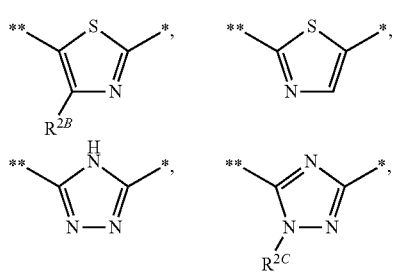

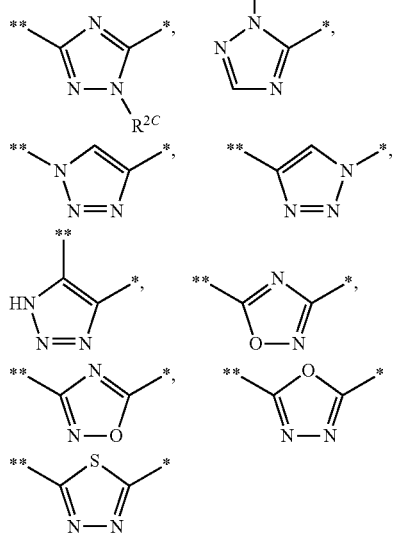

in which
* denotes the point of attachment to the group $L^1$
and
** denotes the point of attachment to the group $L^2$,
$R^{2B}$ represents hydrogen, methyl or trifluoromethyl
and
$R^{2C}$ represents hydrogen or methyl which may be substituted by hydroxycarbonyl, methoxycarbonyl or aminocarbonyl,
$L^2$ represents a bond or the group —$CH_2$—
and
$Ar^2$ represents phenyl which is mono- or disubstituted by identical or different radicals selected from the group consisting of fluorine, chlorine, methyl, trifluoromethyl, methoxy and trifluoromethoxy,
and salts, solvates and solvates of the salts thereof.

The definitions of radicals indicated specifically in the respective combinations or preferred combinations of radicals are replaced as desired irrespective of the particular combinations indicated for the radicals also by definitions of radicals of other combinations. Combinations of two or more of the abovementioned preferred ranges are very particularly preferred.

The invention furthermore provides a process for preparing the compounds of the formula (I) according to the invention, characterized in that a 5-aryl-1,2,4-triazolone derivative of the formula (II)

(II)

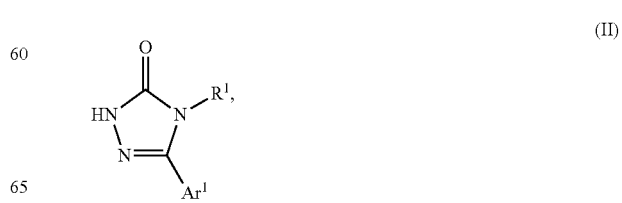

in which Ar¹ and R¹ have the meanings given above,
is reacted in the presence of a base either
[A] with a compound of the formula (III)

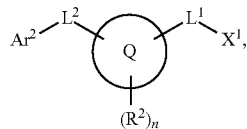

(III)

in which Ar², L¹, L², Q, R² and n have the meanings given above
and
X¹ represents a leaving group such as chlorine, bromine, iodine, mesylate or tosylate, to give a compound of the formula (I)
or
[B] in an alternative in the case that L² in formula (I) represents a bond and the group Ar² is attached to a carbon atom of ring Q
with a compound of the formula (IV)

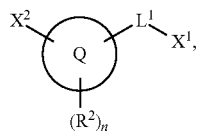

(IV)

in which L¹, Q, R² and n have the meanings given above,
X¹ represents a leaving group such as chlorine, bromine, iodine, mesylate or tosylate
and
X² represents a leaving group, such as chlorine, bromine, iodine, mesylate or triflate, which is attached to a carbon atom of ring Q,
to give an intermediate of the formula (V)

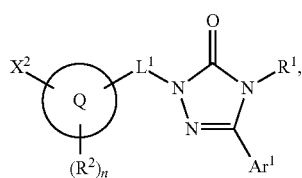

(V)

in which Ar¹, L¹, Q, R¹, R², X² and n have the meanings given above,
and this is then coupled in the presence of a suitable transition metal catalyst with a compound of the formula (VI)

Ar²-M  (VI), in which Ar² has the meaning given above
and
M represents a group of the formula —B(OR⁴)₂, —MgHal, —ZnHal or —Sn(R⁵)₃ in which
Hal represents halogen, in particular chlorine, bromine or iodine,
R⁴ represents hydrogen or (C₁-C₄)-alkyl or both radicals R⁴ are attached to one another and together form a —(CH₂)₂—, —(CH₂)₃—, —C(CH₃)₂—C(CH₃)₂— or —CH₂—C(CH₃)₂—CH₂— bridge
and
R⁵ represents (C₁-C₄)-alkyl,
to give a compound of the formula (I-A)

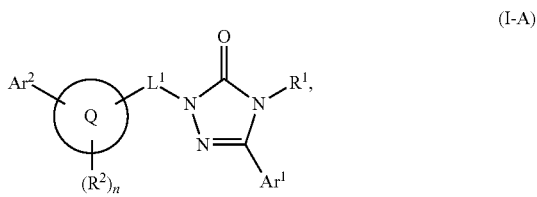

(I-A)

in which Ar¹, Ar², L¹, Q, R¹, R² and n have the meanings given above,
or
[C] in an alternative in the case that L² in formula (I) represents the group —(CR³ᴬR³ᴮ)ₚ—, as defined above, and is attached to a nitrogen atom of ring Q,
with a compound of the formula (VII)

(VII)

in which L¹, R² and n have the meanings given above,
Q' represents a 5-membered heteroaryl ring, as defined above under Q, which contains a trivalent nitrogen ring atom attached to the hydrogen atom indicated,
and
X¹ represents a leaving group such as chlorine, bromine, iodine, mesylate or tosylate, to give an intermediate of the formula (VIII)

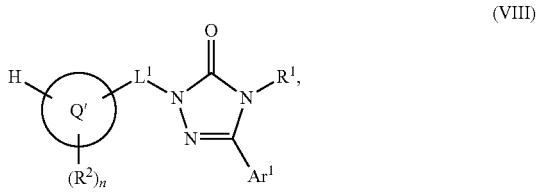

(VIII)

in which Ar¹, L¹, Q', R¹, R² and n have the meanings given above,
and this is then N-alkylated in the presence of a base with a compound of the formula (IX)

(IX)

in which Ar² has the meaning given above,
L²·⁴ represents the group —(CR³·⁴R³·ᴮ)$_p$—, as defined above,
and
X³ represents a leaving group such as chlorine, bromine, iodine, mesylate or tosylate,
to give a compound of the formula (I-B)

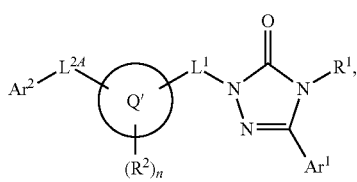

(I-B)

in which Ar¹, Ar², L¹, L²·⁴, Q', R¹, R² and n have the meanings given above,
and the resulting compounds of the formula (I), (I-A) or (I-B) are optionally separated into their enantiomers and/or diastereomers and/or converted with the appropriate (i) solvents and/or (ii) bases or acids into their solvates, salts and/or solvates of the salts.

Inert solvents for the process steps (II)+(III)→(I), (II)+(IV)→(V), (II)+(VII)→(VIII) and (VIII)+(IX)→(I-B) are, for example, halogenated hydrocarbons such as dichloromethane, trichloromethane, carbon tetrachloride, trichloroethylene or chlorobenzene, ethers such as diethyl ether, diisopropyl ether, methyl tert-butyl ether, tetrahydrofuran, 1,4-dioxane, 1,2-dimethoxyethane or bis-(2-methoxyethyl)ether, hydrocarbons such as benzene, toluene, xylene, pentane, hexane, cyclohexane or mineral oil fractions, or dipolar aprotic solvents such as acetone, methyl ethyl ketone, ethyl acetate, acetonitrile, N,N-dimethylformamide (DMF), N,N-dimethylacetamide (DMA), dimethyl sulfoxide (DMSO), N,N'-dimethylpropyleneurea (DMPU), N-methylpyrrolidinone (NMP) or pyridine. It is also possible to use mixtures of the solvents mentioned. Preference is given to using tetrahydrofuran, acetonitrile, acetone or dimethylformamide.

Suitable bases for process steps (II)+(III)→(I), (II)+(IV)→(V), (II)+(VII)→(VIII) and (VIII)+(IX)→(I-B) are the customary inorganic or organic bases. These preferably include alkali metal hydroxides such as, for example, lithium hydroxide, sodium hydroxide or potassium hydroxide, alkali metal or alkaline earth metal carbonates such as lithium carbonate, sodium carbonate, potassium carbonate, calcium carbonate or cesium carbonate, alkali metal alkoxides such as sodium methoxide or potassium methoxide, sodium ethoxide or potassium ethoxide or sodium tert-butoxide or potassium tert-butoxide, alkali metal hydrides such as sodium hydride or potassium hydride, amides such as sodium amide, lithium bis(trimethylsilyl)amide or potassium bis(trimethylsilyl)amide or lithium diisopropylamide, or organic amines such as triethylamine, N-methylmorpholine, N-methylpiperidine, N,N-diisopropylethylamine, pyridine, 1,5-diazabicyclo[4.3.0]non-5-ene (DBN), 1,8-diazabicyclo[5.4.0]undec-7-ene (DBU) or 1,4-diazabicyclo[2.2.2]octane (DABCO®). Preference is given to using potassium carbonate or cesium carbonate or sodium hydride.

Here, the base is employed in an amount of from 1 to 5 mol, preferably in an amount of from 1 to 2.5 mol, based on 1 mole of the compound of the formula (II) or (VIII). These process steps may optionally be carried out in an advantageous manner with addition of alkylation catalysts such as, for example, lithium bromide, sodium iodide, tetra-n-butylammonium bromide or benzyltriethyl-ammonium chloride. The reactions are generally carried out in a temperature range of from −20° C. to +150° C., preferably at from 0° C. to +80° C. The reactions can be carried out at atmospheric, at elevated or at reduced pressure (for example at from 0.5 to 5 bar); in general, the reactions are carried out at atmospheric pressure.

Suitable inert solvents for the process step (V)+(VI)→(I-A) are, for example, aromatic hydrocarbons such as benzene, toluene or xylene, ethers such as diethyl ether, diisopropyl ether, methyl tert-butyl ether, 1,2-dimethoxyethane, bis-(2-methoxyethyl)ether, tetrahydrofuran or 1,4-dioxane, or dipolar aprotic solvents such as acetonitrile, N,N-dimethylformamide (DMF), N,N-dimethylacetamide (DMA), dimethyl sulfoxide (DMSO), N,N'-dimethylpropyleneurea (DMPU), N-methylpyrrolidinone (NMP) or pyridine. It is also possible to use mixtures of the solvents mentioned. Preference is given to using toluene, tetrahydrofuran, 1,4-dioxane or dimethylformamide.

The coupling reaction (V)+(VI)→(I-A) is generally carried out with the aid of a transition metal catalyst. Suitable for this purpose are copper catalysts such as, for example, copper (I) iodide, and in particular palladium catalysts such as, for example, palladium on activated carbon, palladium(II) acetate, bis(triphenylphosphino)palladium(II) chloride, bis (acetonitrile)palladium(II) chloride, [1,1'-bis(diphenylphosphino)ferrocene]palladium(II) chloride, bis(dibenzylideneacetone)palladium(0), tris(dibenzylideneacetone)dipalladium(0) or tetrakis(triphenylphosphino)palladium(0), optionally in combination with additional phosphane ligands such as tri-tert-butylphosphine, 2-di-cyclohexylphosphino-2'-(N,N-dimethylamino)biphenyl, dicyclohexyl[2',4',6'-tris (1-methylethyl)-biphenyl-2-yl]phosphane (XPHOS) or 4,5-bis(diphenylphosphino)-9,9-dimethylxanthene (xantphos) [cf., for example, J. Hassan et al., *Chem. Rev.* 102, 1359-1469 (2002); V. Farina, V. Krishna-murthy and W. J. Scott, in: *The Stille Reaction*, Wiley, New York, 1998].

Coupling with an aryl boronate [M=B(OR⁴)₂; "Suzuki coupling"] is generally carried out with addition of an inorganic base. Suitable for this purpose are in particular alkali metal carbonates, bicarbonates, phosphates, hydrogenphosphates, acetates or fluorides such as sodium carbonate, potassium carbonate, sodium bicarbonate, potassium bicarbonate, tripotassium phosphate, disodium hydrogenphosphate, dipotassium hydrogenphosphate, sodium acetate, potassium acetate, potassium fluoride and cesium fluoride. Such bases can also be employed in the form of their aqueous solutions. Preference is given to using sodium carbonate or potassium carbonate or tripotassium phosphate.

The process step (V)+(VI)→(I-A) is generally carried out in a temperature range of from +20° C. to +200° C., preferably at from +60° C. to +150° C., at atmospheric pressure. However, it is also possible to carry out the reaction at reduced or at elevated pressure (for example at from 0.5 to 5 bar). It may optionally be advantageous to carry out the reaction with microwave irradiation.

In a particular variant of the process [A] described above, compounds of the formula (I) according to the invention may optionally also be prepared by initially reacting, instead of the compound (II), a temporarily protected 1,2,4-triazolone derivative of the formula (X)

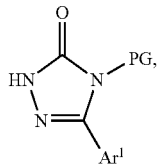

(X)

in which Ar¹ has the meaning given above
and
PG represents a suitable protective group such as, for example, allyl or p-methoxybenzyl, with a compound of the formula (III); the resulting product of the formula (XI)

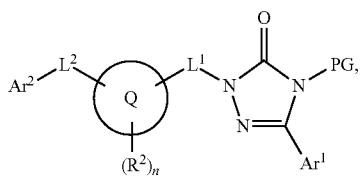

(XI)

in which Ar¹, Ar², L¹, L², PG, Q, R² and n have the meanings given above,
can then, after removal of the protective group, which gives the compound of the formula (XII)

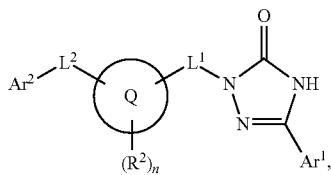

(XII)

in which Ar¹, Ar², L¹, L², Q, R² and n have the meanings given above, be converted by base-induced reaction with a compound of the formula (XIII)

$$R^1—X^4 \quad \text{(XIII),}$$

in which R¹ has the meaning given above
and
X⁴ represents a leaving group such as chlorine, bromine, iodine, mesylate or tosylate,
into corresponding compounds of the formula (I).

An analogous transformation PG→R¹ can optionally also take place during the process variants [B] and [C] described above, in each case starting with the protected aryltriazolone (X).

Some of the compounds of the formula (XI) which are PG-protected in this manner also have significant vasopressin-antagonistic activity and are therefore also included in the scope of the present invention, i.e. the compounds of the formula (I).

Introduction and removal of the protective group PG is carried out by customary methods known from the literature [see, for example, T. W. Greene and P. G. M. Wuts, *Protective Groups in Organic Synthesis*, Wiley, New York, 1999]. Thus, the allyl group is preferably removed with the aid of formic acid in the presence of the tetrakis(triphenylphosphine)palladium(0) catalyst and an amine base such as triethylamine. The removal of the p-methoxybenzyl protective group is preferably carried out with the aid of strong acids such as, for example, trifluoroacetic acid, or oxidatively, for example by treatment with 2,3-dichloro-5,6-dicyano-1,4-benzoquinone (DDQ) or ammonium cerium(IV) nitrate.

The subsequent reaction (XII)+(XIII)→(I) is carried out analogously to the process step (II)+(III)→(I) described above. Here, preferred inert solvents are acetone, acetonitrile, dimethylformamide, dimethyl sulfoxide, toluene, tetrahydrofuran, glycol dimethyl ether and mixtures thereof. Preferred for use as base is sodium hydride or potassium carbonate or cesium carbonate. The reaction is generally carried out at atmospheric pressure in a temperature range of from 0° C. to +150° C., preferably at from +20° C. to +80° C.

The 1,2,4-triazolone derivatives of the formula (II) can be prepared starting with carbohydrazides of the formula (XIV) by reaction with isocyanates of the formula (XV) or nitrophenyl carbamates of the formula (XVI) and subsequent base-induced cyclization of the hydrazinecarboxamide intermediates (XVII) (see Scheme 1):

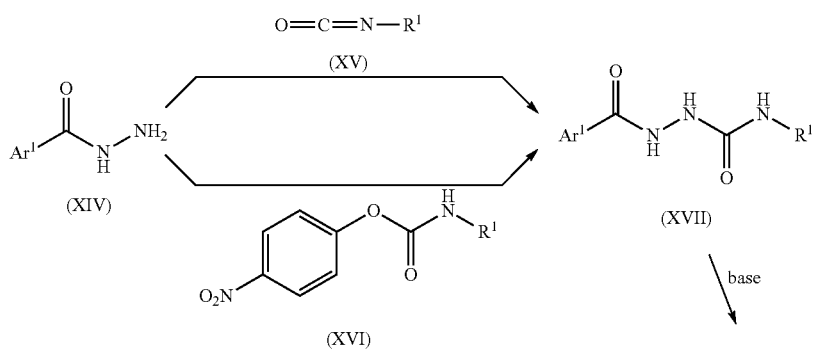

Scheme 1

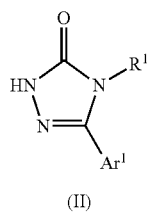

(II)

In an analogous manner, it is also possible to obtain temporarily protected 1,2,4-triazolone derivatives of the formula (X), in particular those in which PG represents allyl or p-methoxybenzyl.

Compounds of the formula (III) in which $L^1$ represents —$CH_2$— and $L^2$ represents a bond can be prepared, for example, analogously to the process [B] described above by transition metal-catalyzed coupling of the compound of the formula (VI) with a compound of the formula (XVIII) and subsequent free-radical halogenation of the intermediate (XIX) (Scheme 2):

Scheme 2

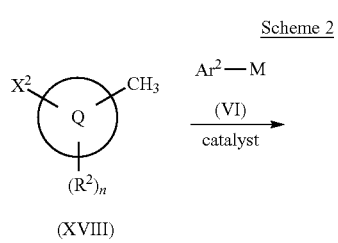

(XVIII)

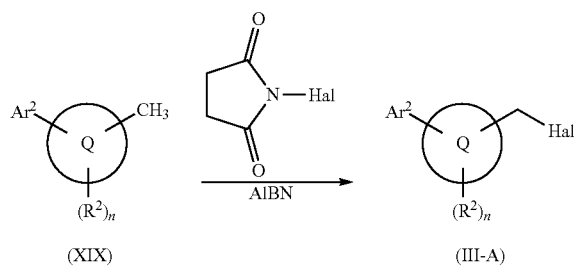

(XIX) (III-A)

In a variant of this process, coupling is carried out with an ester derivative of the formula (XX); the subsequent reduction to the primary alcohol of the formula (XXII) and customary conversion, in accordance with the literature, of the hydroxyl function into a leaving group gives the corresponding compound of the formula (III-B) (Scheme 3):

Scheme 3

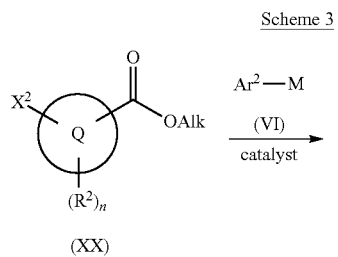

(XX)

-continued

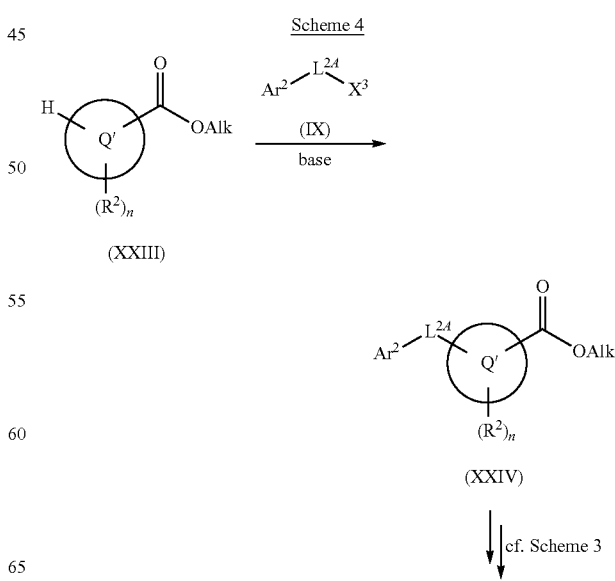

In a similar manner, it is possible to prepare compounds of the formula (III) in which $L^1$ represents —$CH_2$— and $L^2$ represents the group —$(CR^{3A}R^{3B})_p$—, which is attached to a nitrogen atom of ring Q from corresponding carboxylic esters of the formula (XXIV) which for their part can be obtained analogously to the process [C] described above (see Scheme 4):

Scheme 4

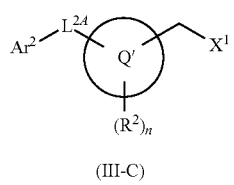

(III-C)

Compounds of the formula (I) according to the invention in which ring Q represents a 5-membered heteroaryl ring can optionally also be prepared similarly to methods known from the literature via a de novo synthesis of the heteroaryl system in question. Such process routes can be illustrated in an exemplary manner by Reaction Schemes 5-10 below:

Scheme 5

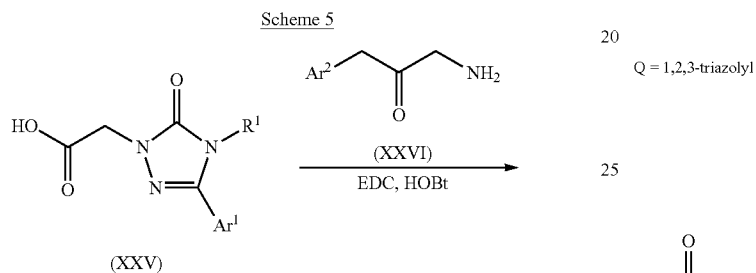

(XXVII)

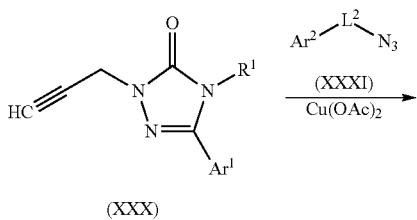

(XXX)

(XXXII)

Q = 1,2,3-triazolyl

Scheme 7

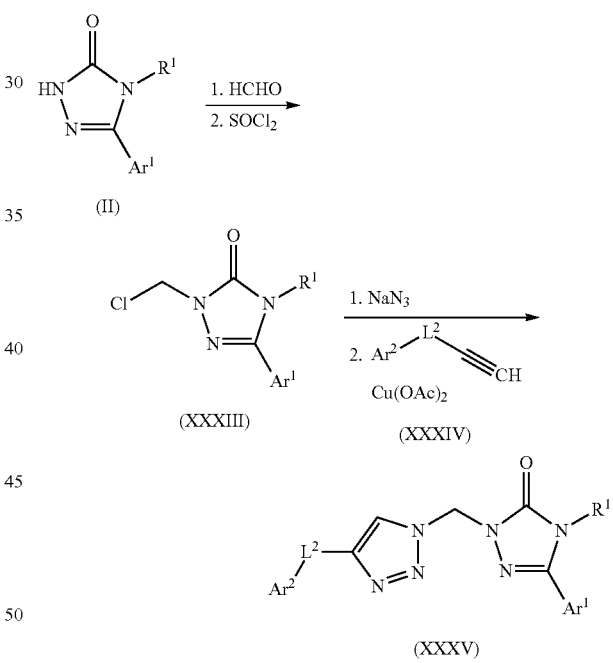

(XXXV)

Q = 1,2,3-triazolyl (regioisomer)

Scheme 6

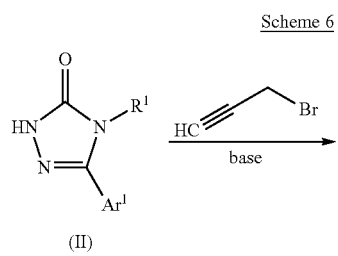

(II)

Scheme 8

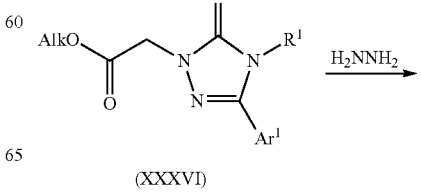

(XXXVI)

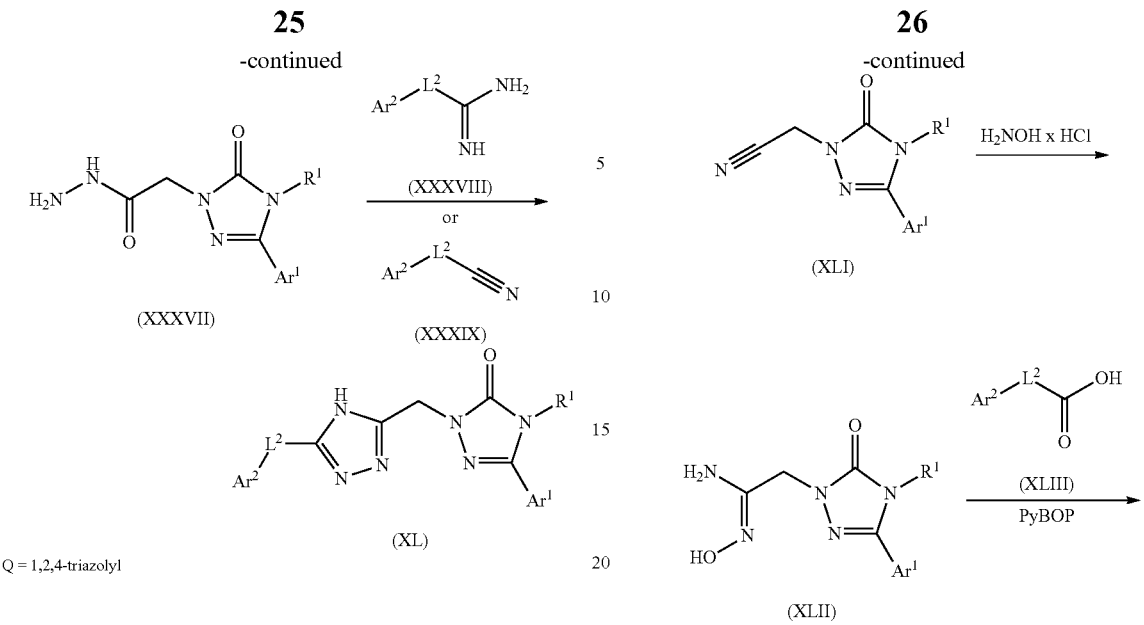
Q = 1,2,4-triazolyl
Scheme 9
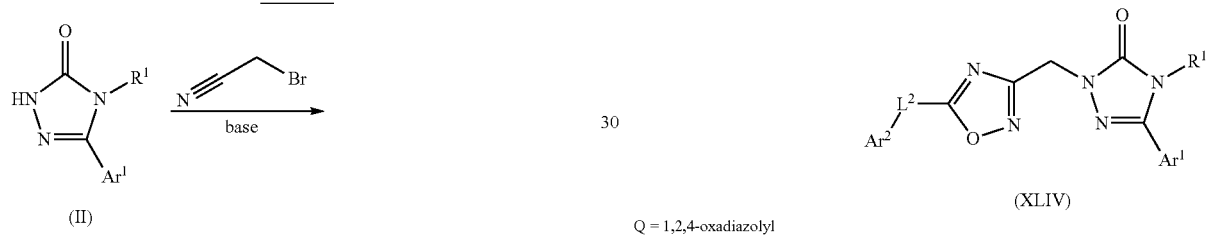
Q = 1,2,4-oxadiazolyl
Scheme 10
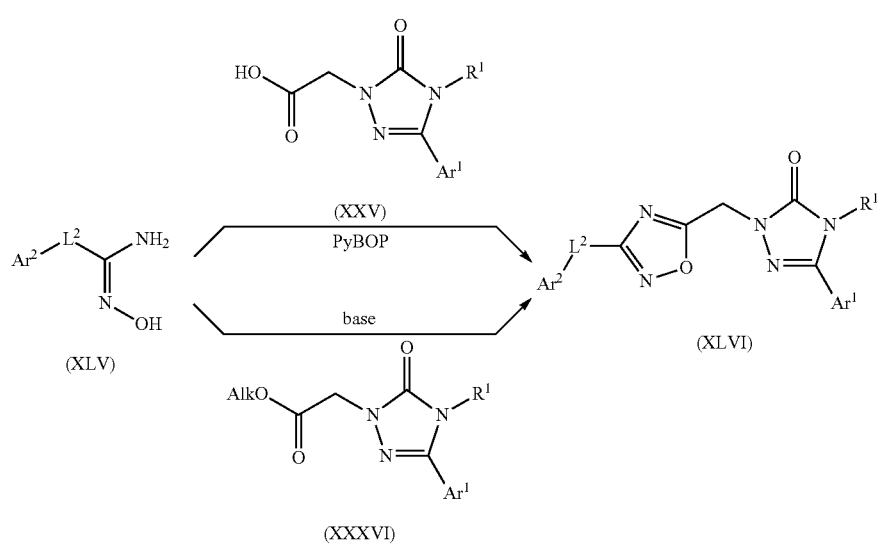
Q = 1,2,4-oxadiazolyl (regioisomer)

Further compounds of the formula (I) according to the invention can, if expedient, also be prepared by conversion of functional groups of individual radicals and substituents, in particular those listed under $R^1$, $R^2$, $Ar^1$ and $Ar^2$, starting with other compounds of the formula (I) obtained by the above processes. These conversions are carried out by customary processes familiar to the person skilled in the art and include, for example, reactions such as nucleophilic or electrophilic substitution reactions, transition metal-mediated coupling reactions (for example the Suzuki or Heck reaction), oxidation, reduction, hydrogenation, alkylation, acylation, amination, hydroxylation, etherification, esterification, ether cleavage and hydrolysis, formation of nitriles, carboxamides, sulfonamides, carbamates and ureas, and the introduction and removal of temporary protective groups [cf. also the preparation of the Working Examples described in detail in the Experimental Part below].

The intermediates of the formula (XXXVI) can be prepared in a simple manner by base-induced alkylation of the 5-aryl-1,2,4-triazol-3-ones of the formula (II) with haloacetic esters of the formula (XLVII); the corresponding carboxylic acids of the formula (XXV) can be obtained by subsequent ester hydrolysis (see Scheme 11):

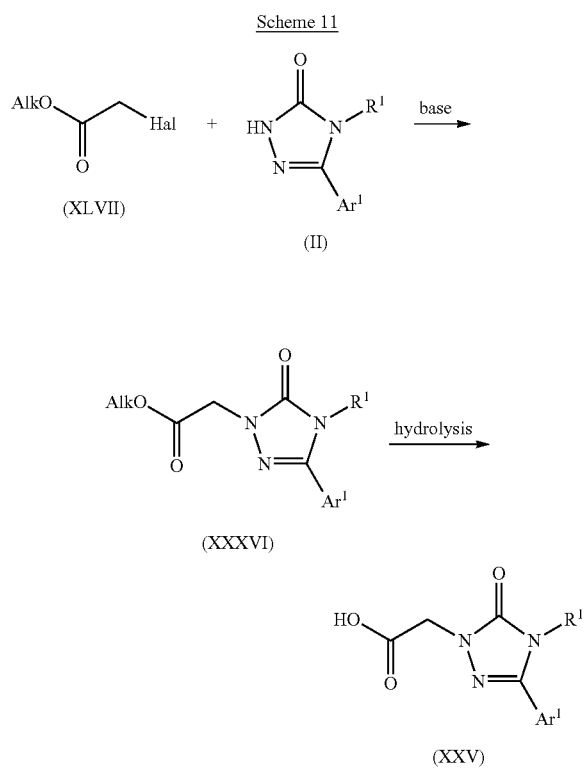

Alternatively, the compounds of the formula (XXXVI) can also be prepared from N-(alkoxy-carbonyl)arylthioamides of the formula (XLIX), which are known from the literature [see, for example, M. Arnswald, W. P. Neumann, *J. Org. Chem.* 58 (25), 7022-7028 (1993); E. P. Papadopoulos, *J. Org. Chem.* 41 (6), 962-965 (1976)], by reaction with hydrazinoacetic esters of the formula (XLVIII) and subsequent alkylation at N-4 of the triazolone (L) (Scheme 12):

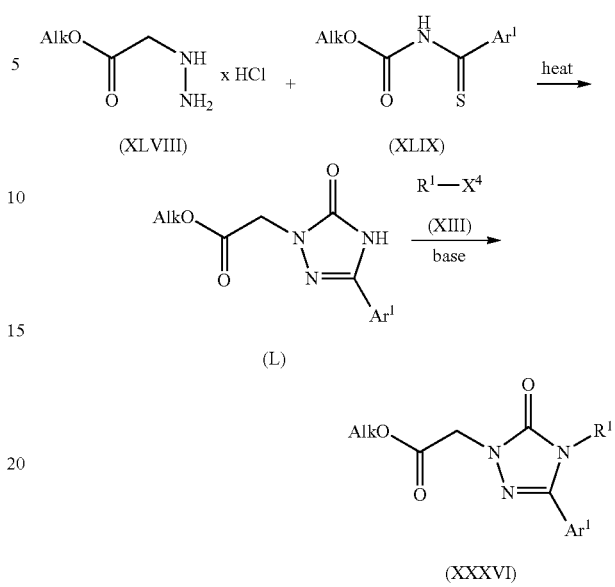

Separation of the compounds according to the invention into the corresponding enantiomers and/or diastereomers can take place where appropriate, depending on expediency, even at the stage of individual intermediates, as listed above, which are then reacted further in separated form in accordance with the above-described process steps. Such a separation of the stereoisomers can be carried out by conventional methods known to the person skilled in the art. Preference is given to using chromatographic methods, in particular HPLC chromatography on an achiral or chiral phase.

The compounds of the formulae (IV), (VI), (VII), (IX), (XIII), (XIV), (XV), (XVI), (XVIII), (XX), (XXIII), (XXVI), (XXXI), (XXXIV), (XXXVIII), (XXXIX), (XLIII), (XLV), (XLVII), (XLVIII) and (XLIX) are either commercially available or described as such in the literature, or they can be prepared in a manner obvious to the person skilled in the art analogously to the methods published in the literature. Numerous detailed procedures and literature references for preparing the starting materials can also be found in the Experimental Part in the section on the preparation of the starting materials and intermediates.

The compounds according to the invention possess valuable pharmacological properties and can be used for the prevention and/or treatment of various diseases and disease-induced states in humans and animals.

The compounds according to the invention are potent selective V1a, V2 or dual V1a/V2 receptor antagonists, which inhibit vasopressin activity in vitro and in vivo. In addition, the compounds according to the invention are also suitable as antagonists at the related oxytocin receptor.

The compounds according to the invention are particularly suitable for the prophylaxis and/or treatment of cardiovascular diseases. In this connection, the following may for example and preferably be mentioned as target indications: acute and chronic heart failure, arterial hypertension, coronary heart disease, stable and unstable angina pectoris, myocardial ischemia, myocardial infarction, shock, arteriosclerosis, atrial and ventricular arrhythmias, transitory and ischemic attacks, stroke, inflammatory cardiovascular diseases, peripheral and cardiac vascular diseases, peripheral circulation disorders, arterial pulmonary hypertension, spasms of the coronary arteries and peripheral arteries, thromboses, thromboembolic diseases, edema formation such as for example pulmonary edema, cerebral edema, renal edema or heart failure-related edema, and restenoses for example after thrombolysis treatments, percutaneous-transluminal angioplasties (PTA), transluminal coronary angioplasties (PTCA), heart transplants and bypass operations.

In the sense of the present invention, the term heart failure also includes more specific or related disease forms such as right heart failure, left heart failure, global insufficiency, ischemic cardiomyopathy, dilatative cardiomyopathy, congenital heart defects, heart valve defects, heart failure with heart valve defects, mitral valve stenosis, mitral valve insufficiency, aortic valve stenosis, aortic valve insufficiency, tricuspidal stenosis, tricuspidal insufficiency, pulmonary valve stenosis, pulmonary valve insufficiency, combined heart valve defects, heart muscle inflammation (myocarditis), chronic myocarditis, acute myocarditis, viral myocarditis, diabetic heart failure, alcohol-toxic cardiomyopathy, cardiac storage diseases, diastolic heart failure and systolic heart failure.

Furthermore, the compounds according to the invention are suitable for use as a diuretic for the treatment of edemas and in electrolyte disorders, in particular in hypervolemic and euvolemic hyponatremia.

The compounds according to the invention are also suitable for the prophylaxis and/or treatment of polycystic kidney disease (PCKD) and the syndrome of inadequate ADH secretion (SIADH).

In addition, the compounds according to the invention can be used for the prophylaxis and/or treatment of liver cirrhosis, ascites, diabetes mellitus and diabetic complications such as for example neuropathy and nephropathy, acute and chronic kidney failure and chronic renal insufficiency.

Further, the compounds according to the invention are suitable for the prophylaxis and/or treatment of central nervous disorders such as anxiety states and depression, of glaucoma and of cancer, in particular of pulmonary tumors.

Furthermore, the compounds according to the invention can be used for the prophylaxis and/or treatment of inflammatory diseases, asthmatic diseases, chronic-obstructive respiratory tract diseases (COPD), pain conditions, prostatic hypertrophy, incontinence, bladder inflammation, hyperactive bladder, diseases of the adrenals such as for example pheochromocytoma and adrenal apoplexy, diseases of the intestine such as for example Crohn's disease and diarrhea, or of menstrual disorders such as for example dysmenorrhea or of endometriosis.

By virtue of their activity profile, the compounds according to the invention are particularly suitable for the treatment and/or prophylaxis of acute and chronic heart failure, hypervolemic and euvolemic hyponatremia, liver cirrhosis, ascites, edemas, and the syndrome of inadequate ADH secretion (SIADH).

A further object of the present invention is the use of the compounds according to the invention for the treatment and/or prophylaxis of diseases, in particular of the diseases mentioned above.

A further object of the present invention is the use of the compounds according to the invention for the production of a medicament for the treatment and/or prophylaxis of diseases, in particular of the diseases mentioned above.

A further object of the present invention is the use of the compounds according to the invention in a method for the treatment and/or prophylaxis of diseases, in particular of the diseases mentioned above.

A further object of the present invention is a method for the treatment and/or prophylaxis of diseases, in particular of the diseases mentioned above, with the use of an effective quantity of at least one of the compounds according to the invention.

The compounds according to the invention can be used alone or if necessary in combination with other active substances. A further object of the present invention are medicaments which contain at least one of the compounds according to the invention and one or more other active substances, in particular for the treatment and/or prophylaxis of the diseases mentioned above. As combination active substances suitable for this, the following may for example and preferably be mentioned:

organic nitrates and NO donors, such as for example sodium nitroprusside, nitroglycerine, isosorbide mononitrate, isosorbide dinitrate, molsidomine or SIN-1, and inhalational NO;

diuretics, in particular loop diuretics and thiazides and thiazide-like diuretics;

positive-inotropically active compounds, such as for example cardiac glycosides (digoxin), and beta-adrenergic and dopaminergic agonists such as isoproterenol, adrenalin, noradrenalin, dopamine and dobutamine;

compounds which inhibit the degradation of cyclic guanosine monophosphate (cGMP) and/or cyclic adenosine monophosphate (cAMP), such as for example inhibitors of phosphodiesterases (PDE) 1, 2, 3, 4 and/or 5, in particular PDE 5 inhibitors such as sildenafil, vardenafil and tadalafil, and PDE 3 inhibitors such as amrinone and milrinone;

natriuretic peptides such as for example "atrial natriuretic peptide" (ANP, anaritide), "B-type natriuretic peptide" or "brain natriuretic peptide" (BNP, nesiritide), "C-type natriuretic peptide" (CNP) and urodilatin;

calcium sensitizers, such as for example and preferably levosimendan;

NO- and heme-independent activators of guanylate cyclase, such as in particular cinaciguat and also the compounds described in WO 01/19355, WO 01/19776, WO 01/19778, WO 01/19780, WO 02/070462 and WO 02/070510;

NO-independent, but heme-dependent stimulators of guanylate cyclase, such as in particular riociguat and also the compounds described in WO 00/06568, WO 00/06569, WO 02/42301 and WO 03/095451;

inhibitors of human neutrophil elastase (HNE), such as for example sivelestat or DX-890 (reltran);

compounds inhibiting the signal transduction cascade, such as for example tyrosine kinase inhibitors, in particular sorafenib, imatinib, gefitinib and erlotinib;

compounds influencing the energy metabolism of the heart, such as for example and preferably etomoxir, dichloroacetate, ranolazine or trimetazidine;

agents with antithrombotic action, for example and preferably from the group of the thrombocyte aggregation inhibitors, anticoagulants or profibrinolytic substances;

blood pressure-lowering active substances, for example and preferably from the group of the calcium antagonists, angiotensin AII antagonists, ACE inhibitors, vasopeptidase inhibitors, inhibitors of neutral endopeptidase, endothelin antagonists, renin inhibitors, alpha-receptor blockers, beta-receptor blockers, mineralocorticoid receptor antagonists and rho-kinase inhibitors; and/or active substances modifying the fat metabolism, for example and preferably from the group of the thyroid receptor agonists, cholesterol synthesis inhibitors such as for example and preferably HMG-CoA reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric gallic acid adsorbers, gallic acid reabsorption inhibitors and lipoprotein(a) antagonists.

In a preferred embodiment of the invention, the compounds according to the invention are administered in combination with a diuretic, such as for example and preferably furosemide, bumetanide, torsemide, bendroflumethiazide, chlorothiazide, hydrochlorothiazide, hydroflumethiazide, methyclothiazide, polythiazide, trichloromethiazide, chlorothalidone, indapamide, metolazone, quinethazone, acetazolamide, dichlorophenamide, methazolamide, glycerine, isosorbide, mannitol, amiloride or triamterene.

Agents with antithrombotic action are understood preferably to mean compounds from the group of the thrombocyte aggregation inhibitors, anticoagulants or profibrinolytic substances.

In a preferred embodiment of the invention, the compounds according to the invention are administered in combination with a thrombocyte aggregation inhibitor, such as for example and preferably aspirin, clopidogrel, ticlopidine or dipyridamole.

In a preferred embodiment of the invention, the compounds according to the invention are administered in combination with a thrombin inhibitor, such as for example and preferably ximelagatran, melagatran, dabigatran, bivalirudin or clexane.

In a preferred embodiment of the invention, the compounds according to the invention are administered in combination with a GPIIb/IIIa antagonist, such as for example and preferably tirofiban or abciximab.

In a preferred embodiment of the invention, the compounds according to the invention are administered in combination with a factor Xa inhibitor, such as for example and preferably riva-roxaban, DU-176b, apixaban, otamixaban, fidexaban, razaxaban, fondaparinux, idraparinux, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative.

In a preferred embodiment of the invention, the compounds according to the invention are administered in combination with a vitamin K antagonist, such as for example and preferably coumarin.

Blood pressure-lowering agents are understood preferably to mean compounds from the group of the calcium antagonists, angiotensin AII antagonists, ACE inhibitors, vasopeptidase inhibitors, inhibitors of neutral endopeptidase, endothelin antagonists, renin inhibitors, alpha-receptor blockers, beta-receptor blockers, mineralocorticoid receptor antagonists, rho-kinase inhibitors and diuretics.

In a preferred embodiment of the invention, the compounds according to the invention are administered in combination with a calcium antagonist, such as for example and preferably nifedipine, amlodipine, verapamil or diltiazem.

In a preferred embodiment of the invention, the compounds according to the invention are administered in combination with an angiotensin AII antagonist, such as for example and preferably losartan, candesartan, valsartan, telmisartan or embusartan.

In a preferred embodiment of the invention, the compounds according to the invention are administered in combination with an ACE inhibitor, such as for example and preferably enalapril, captopril, lisinopril, ramipril, delapril, fosinopril, quinopril, perindopril or trandopril.

In a preferred embodiment of the invention, the compounds according to the invention are administered in combination with a vasopeptidase inhibitor or inhibitor of neutral endopeptidase (NEP), such as for example and preferably omapatrilat or AVE-7688.

In a preferred embodiment of the invention, the compounds according to the invention are administered in combination with an endothelin antagonist, such as for example and preferably bosentan, darusentan, ambrisentan or sitaxsentan.

In a preferred embodiment of the invention, the compounds according to the invention are administered in combination with a renin inhibitor, such as for example and preferably aliskiren, SPP-600 or SPP-800.

In a preferred embodiment of the invention, the compounds according to the invention are administered in combination with an alpha-1 receptor blocker, such as for example and preferably prazosin.

In a preferred embodiment of the invention, the compounds according to the invention are administered in combination with a beta-receptor blocker, such as for example and preferably propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with a mineralocorticoid receptor antagonist, such as for example and preferably spironolactone, eplerenone, canrenone or potassium canrenoate.

In a preferred embodiment of the invention, the compounds according to the invention are administered in combination with a rho-kinase inhibitor, such as for example and preferably fasudil, Y-27632, SLx-2119, BF-66851, BF-66852, BF-66853, KI-23095 or BA-1049.

Fat metabolism-modifying agents are understood preferably to mean compounds from the group of the CETP inhibitors, thyroid receptor agonists, cholesterol synthesis inhibitors such as HMG-CoA reductase or squalene synthesis inhibitors, ACAT inhibitors, MTP inhibitors, PPAR-alpha, PPAR-gamma and/or PPAR-delta agonists, cholesterol absorption inhibitors, polymeric gallic acid adsorbers, gallic acid reabsorption inhibitors, lipase inhibitors and lipoprotein (a) antagonists.

In a preferred embodiment of the invention, the compounds according to the invention are administered in combination with a CETP inhibitor, such as for example and preferably torcetrapib, dalcetrapib, anacetrapib, BAY 60-5521 or CETP-vaccine (CETi-1).

In a preferred embodiment of the invention, the compounds according to the invention are administered in combination with a thyroid receptor agonist, such as for example and preferably D-thyroxine, 3,5,3'-triiodothyronine (T3), CGS 23425 or axitirome (CGS 26214).

In a preferred embodiment of the invention, the compounds according to the invention are administered in combination with an HMG-CoA reductase inhibitor from the class of the statins, such as for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, such as for example and preferably BMS-188494 or TAK-475.

In a preferred embodiment of the invention, the compounds according to the invention are administered in combination with an ACAT inhibitor, such as for example and preferably avasimibe, melinamide, pactimibe, eflucimibe or SMP-797.

In a preferred embodiment of the invention, the compounds according to the invention are administered in combination with an MTP inhibitor, such as for example and preferably implitapide, BMS-201038, R-103757 or JTT-130.

In a preferred embodiment of the invention, the compounds according to the invention are administered in combination with a PPAR-gamma agonist, such as for example and preferably pioglitazone or rosiglitazone.

In a preferred embodiment of the invention, the compounds according to the invention are administered in combination with a PPAR-delta agonist, such as for example and preferably GW-501516 or BAY 68-5042.

In a preferred embodiment of the invention, the compounds according to the invention are administered in combination with a cholesterol absorption inhibitor, such as for example and preferably ezetimibe, tiqueside or pamaqueside.

In a preferred embodiment of the invention, the compounds according to the invention are administered in combination with a lipase inhibitor, such as for example and preferably orlistat.

In a preferred embodiment of the invention, the compounds according to the invention are administered in combination with a polymeric gallic acid adsorber, such as for example and preferably cholestyramine, colestipol, colesolvam, cholestagel or colestimide.

In a preferred embodiment of the invention, the compounds according to the invention are administered in combination with a gallic acid reabsorption inhibitor, such as for example and preferably ASBT (=IBAT) inhibitors such as for example AZD-7806, S-8921, AK-105, BARI-1741, SC-435 or SC-635.

In a preferred embodiment of the invention, the compounds according to the invention are administered in combination with a lipoprotein(a) antagonist, such as for example and preferably gemcabene calcium (CI-1027) or nicotinic acid.

A further object of the present invention are medicaments which contain at least one compound according to the invention, usually together with one or more inert, non-toxic, pharmaceutically suitable auxiliaries, and the use thereof for the aforesaid purposes.

The compounds according to the invention can act systemically and/or locally. For this purpose, they can be administered in a suitable manner, such as for example by the oral, parenteral, pulmonary, nasal, sublingual, lingual, buccal, rectal, dermal, transdermal, conjunctival or otic routes or as an implant or stent.

For these administration routes, the compounds according to the invention can be administered in suitable administration forms.

For oral administration, administration forms which function according to the state of the art, releasing the compounds according to the invention rapidly and/or in a modified manner, which contain the compounds according to the invention in crystalline and/or amorphized and/or dissolved form, such as for example tablets (uncoated or coated tablets, for example with gastric juice-resistant or delayed dissolution or insoluble coatings, which control the release of the compound according to the invention), tablets rapidly disintegrating in the oral cavity or films/wafers, films/lyophilisates, capsules (for example hard or soft gelatine capsules), sugar-coated tablets, granules, pellets, powders, emulsions, suspensions, aerosols or solutions are suitable.

Parenteral administration can be effected by omitting an absorption step (e.g. intravenous, intra-arterial, intracardial, intraspinal or intralumbar administration) or by involving absorption (e.g. intra-muscular, subcutaneous, intracutaneous, percutaneous or intraperitoneal administration). Suitable administration forms for parenteral administration include injection and infusion preparations in the form of solutions, suspensions, emulsions, lyophilisates or sterile powders.

For the other administration routes, for example inhalation formulations (including powder inhalers and nebulizers), nasal drops, solutions or sprays, tablets for lingual, sublingual or buccal administration, tablets, films/wafers or capsules, suppositories, oral or ophthalmic preparations, vaginal capsules, aqueous suspensions (lotions, shakable mixtures), lipophilic suspensions, ointments, creams, transdermal therapeutic systems (e.g. plasters), milk, pastes, foams, dusting powders, implants or stents are suitable.

Oral or parenteral administration, in particular oral and intravenous administration, are preferred.

The compounds according to the invention can be converted into the stated administration forms. This can be effected in a manner known per se by mixing with inert, non-toxic, pharmaceutically suitable auxiliaries. These additives include carriers (for example microcrystalline cellulose, lactose, mannitol), solvents (e.g. liquid polyethylene glycols), emulsifiers and dispersants or wetting agents (for example sodium dodecylsulfate, polyoxysorbitan oleate), binders (for example polyvinylpyrrolidone), synthetic and natural polymers (for example albumin), stabilizers (e.g. antioxidants such as for example ascorbic acid), colorants (e.g. inorganic pigments such as for example iron oxides) and flavor and/or odor correctors.

In general, to achieve effective results in parenteral administration it has been found advantageous to administer quantities of about 0.001 to 10 mg/kg, preferably about 0.01 to 1 mg/kg body weight. In oral administration, the dosage is about 0.01 bis 100 mg/kg, preferably about 0.01 to 20 mg/kg and quite especially preferably 0.1 to 10 mg/kg body weight.

Nonetheless it can sometimes be necessary to deviate from said quantities, namely depending on body weight, administration route, individual response to the active substance, nature of the preparation and time or interval at which the administration takes place. Thus in some cases it can be sufficient to manage with less than the aforesaid minimum quantity, while in other cases the stated upper limit must be exceeded. In the event of administration of larger quantities, it may be advisable to divide these into several individual administrations throughout the day.

The following practical examples illustrate the invention. The invention is not limited to the examples.

Unless otherwise stated, the percentages stated in the following tests and examples are percent by weight, parts are parts by weight, and solvent ratios, dilution ratios and concentration information about liquid/liquid solutions are each based on volume.

EXAMPLES

Abbreviations and Acronyms

Ac acetyl
AIBN 2,2'-azobis-2-methylpropanenitrile
Alk alkyl
Boc tert-butoxycarbonyl
Ex. Example
CI chemical ionization (in MS)
DCI direct chemical ionization (in MS)
DME 1,2-dimethoxyethane DMF N,N-dimethylformamide
DMSO dimethyl sulfoxide
EDC N'-(3-dimethylaminopropyl)-N-ethylcarbodiimide hydrochloride
ee enantiomeric excess
EA ethyl acetate
eq. equivalent(s)
ESI electrospray ionization (in MS)
GC/MS gas chromatography-coupled mass spectrometry
h hour(s)
Hal halogen
HOBt 1-hydroxy-1H-benzotriazole hydrate
HPLC high pressure, high performance liquid chromatography
conc. concentrated
LC/MS liquid chromatography-coupled mass spectrometry
LDA lithium diisopropylamide
LiHMDS lithium hexamethyldisilazane
min minute(s)
MS mass spectrometry
MTBE methyl tert-butyl ether
NMR nuclear magnetic resonance spectrometry
OAc acetate
p para
Ph phenyl
PyBOP benzotriazol-1-yloxytris(pyrrolidino)phosphonium hexafluorophosphate
quant. quantitative (yield)
rac racemic/racemate
RT room temperature
$R_t$ retention time (in HPLC)
THF tetrahydrofuran
TMOF trimethyl orthoformate
UV ultraviolet spectrometry
v/v ratio by volume (of a solution)

LC/MS, GC/MS and HPLC Methods:

Method 1 (LC/MS):
MS instrument type: Micromass ZQ; HPLC instrument type: Waters Alliance 2795; column: Phenomenex Synergi 2.5μ MAX-RP 100A Mercury 20 mm×4 mm; mobile phase A: 1 1 of water+0.5 ml of 50% strength formic acid, mobile phase B: 1 1 of acetonitrile+0.5 ml of 50% strength formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 2 (LC/MS):
Instrument: Micromass Quattro Micro MS with HPLC Agilent Series 1100; column: Thermo Hypersil GOLD 3μ 20 mm×4 mm; mobile phase A: 1 1 of water+0.5 ml of 50% strength formic acid, mobile phase B: 1 1 of acetonitrile+0.5 ml of 50% strength formic acid; gradient: 0.0 min 100% A→3.0 min 10% A→4.0 min 10% A→4.01 min 100% A (flow rate 2.5 ml/min)→5.00 min 100% A; oven: 50° C.; flow rate: 2 ml/min; UV detection: 210 nm.

Method 3 (LC/MS):
Instrument: Micromass QuattroPremier with Waters UPLC Acquity; column: Thermo Hypersil GOLD 1.9μ 50 mm×1 mm; mobile phase A: 1 1 of water+0.5 ml of 50% strength formic acid, mobile phase B: 1 1 of acetonitrile+0.5 ml of 50% strength formic acid; gradient: 0.0 min 90% A→0.1 min 90% A→1.5 min 10% A→2.2 min 10% A; flow rate: 0.33 ml/min; oven: 50° C.; UV detection: 210 nm.

Method 4 (LC/MS):
Instrument: Waters Acquity SQD UPLC System; column: Waters Acquity UPLC HSS T3 1.8μ 50 mm×1 mm; mobile phase A: 1 1 of water+0.25 ml of 99% strength formic acid, mobile phase B: 1 1 of acetonitrile+0.25 ml of 99% strength formic acid; gradient: 0.0 min 90% A→1.2 min 5% A→2.0 min 5% A; flow rate: 0.40 ml/min; oven: 50° C.; UV detection: 210-400 nm.

Method 5 (LC/MS):
MS instrument type: Micromass ZQ; HPLC instrument type: HP 1100 Series; UV DAD; column: Phenomenex Gemini 3μ 30 mm×3.00 mm; mobile phase A: 1 1 of water+0.5 ml of 50% strength formic acid, mobile phase B: 1 1 of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 6 (LC/MS):
MS instrument type: Waters ZQ; HPLC instrument type: Agilent 1100 Series; UV DAD; column: Thermo Hypersil GOLD 3μ 20 mm×4 mm; mobile phase A: 1 1 of water+0.5 ml of 50% strength formic acid, mobile phase B: 1 1 of acetonitrile+0.5 ml of 50% strength formic acid; gradient: 0.0 min 100% A→3.0 min 10% A→4.0 min 10% A→4.1 min 100% A (flow rate 2.5 ml/min); oven: 55° C.; flow rate: 2 ml/min; UV detection: 210 nm.

Method 7 (LC/MS):
MS instrument type: Micromass ZQ; HPLC instrument type: Waters Alliance 2795; column: Phenomenex Synergi 2μ Hydro-RP Mercury 20 mm×4 mm; mobile phase A: 1 1 of water+0.5 ml of 50% strength formic acid, mobile phase B: 1 1 of acetonitrile+0.5 ml of 50% strength formic acid; gradient: 0.0 min 90% A→2.5 min 30% A→3.0 min 5% A→4.5 min 5% A; flow rate: 0.0 min 1 ml/min→2.5 min/3.0 min/4.5 min 2 ml/min; oven: 50° C.; UV detection: 210 nm.

Method 8 (LC/MS):
Instrument: Micromass Platform LCZ with HPLC Agilent Series 1100; column: Thermo Hypersil GOLD 3μ 20 mm×4 mm; mobile phase A: 1 1 of water+0.5 ml of 50% strength formic acid, mobile phase B: 1 1 of acetonitrile+0.5 ml of 50% strength formic acid; gradient: 0.0 min 100% A→0.2 min 100% A→2.9 min 30% A→3.1 min 10% A→5.5 min 10% A; flow rate: 0.8 ml/min; oven: 50° C.; UV detection: 210 nm.

Method 9 (LC/MS):
Instrument: Micromass Quattro LCZ with HPLC Agilent Serie 1100; column: Phenomenex Onyx Monolithic C18, 100 mm×3 mm; mobile phase A: 1 1 of water+0.5 ml of 50% strength formic acid, mobile phase B: 1 1 of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 208-400 nm.

Method 10 (LC/MS):
MS instrument type: Waters ZQ; HPLC instrument type: Waters Alliance 2795; column: Phenomenex Onyx Monolithic C18, 100 mm×3 mm; mobile phase A: 1 1 of water+0.5 ml of 50% strength formic acid, mobile phase B: 1 1 of acetonitrile+0.5 ml of 50% strength formic acid; gradient: 0.0 min 90% A→2 min 65% A→4.5 min 5% A→6 min 5% A; flow rate: 2 ml/min; oven: 40° C.; UV detection: 210 nm.

Method 11 (Chiral Analytical HPLC):
Stationary phase: Daicel Chiralcel OD-H; column: 250 mm×4 mm; flow rate: 1 ml/min; temperature: RT; UV detection: 230 nm; mobile phase:

Method 11a: isohexane/isopropanol 50:50 (v/v);

Method 11b: isohexane/methanol/ethanol 70:15:15 (v/v/v);

Method 11c: isohexane/isopropanol 75:25 (v/v).

Method 12 (Chiral Preparative HPLC):

Stationary phase: Daicel Chiralpak AD-H, 5 µm; column: 250 mm×20 mm; temperature: 40° C.; UV detection: 220 nm; mobile phase: isohexane/isopropanol 80:20 (v/v); flow rate: 15 ml/min Method 13 (Chiral Analytical HPLC):

Stationary phase: Daicel Chiralpak AD-H, 5 µm; column: 250 mm×4.6 mm; temperature: 40° C.; UV detection: 220 nm; mobile phase: isohexane/isopropanol 80:20 (v/v); flow rate: 1.0 ml/min Method 14 (Chiral Analytical HPLC):

Stationary phase: Daicel Chiralpak AD-H, 5 µm; column: 250 mm×4.6 mm; temperature: 30° C.; UV detection: 220 nm; mobile phase: isohexane/isopropanol/20% strength trifluoroacetic acid 75:24:1 (v/v/v); flow rate: 1.0 ml/min Method 15 (Preparative HPLC):

Instrument: Abimed Gilson Pump 305/306, Manometric Module 806; column: Grom-Sil 1200DS-4HE, 10 µm, 250 mm×30 mm; mobile phase A: water, mobile phase B: acetonitrile; gradient: 0.0 min 30% B→3 min 30% B→30 min 95% B→42 min 95% B→42.01 min 10% B→45 min 10% B; flow rate: 50 ml/min; column temperature: RT; UV detection: 210 nm.

Method 16 (Preparative HPLC):

column: Kromasil 100 C18, 5 µm, 250 mm×20 mm; mobile phase A: 0.2% strength trifluoroacetic acid, mobile phase B: acetonitrile; isocratic 55% A, 45% B; flow rate: 25 ml/min; column temperature: 30° C.; UV detection: 210 nm.

Method 17 (Chiral Preparative HPLC):

Stationary phase: Daicel Chiralpak AD-H, 5 µm; column: 250 mm×20 mm; temperature: 40° C.; UV detection: 220 nm; mobile phase: isohexane/ethanol 80:20 (v/v); flow rate: 15 ml/min Method 18 (Chiral Analytical HPLC):

Stationary phase: Daicel Chiralpak AS-H, 5 µm; column: 250 mm×4.6 mm; temperature: 40° C.; UV detection: 220 nm; mobile phase: isohexane/ethanol 80:20 (v/v); flow rate: 1 ml/min Method 19 (Preparative HPLC):

Column: Grom-Sil 1200DS-4HE, 10 µm, 250 mm×30 mm; mobile phase A: water, mobile phase B: acetonitrile; gradient: 0.0 min 10% B→3 min 10% B→30 min 95% B→42 min 95% B→42.01 min 10% B→45 min 10% B; flow rate: 50 ml/min; column temperature: RT; UV detection: 210 nm.

Method 20 (GC/MS):

Instrument: Micromass GCT, GC 6890; column: Restek RTX-35, 15 m×200 µm×0.33 µm; constant helium flow: 0.88 ml/min; oven: 70° C.; inlet: 250° C.; gradient: 70° C., 30° C./min→310° C. (maintained for 3 min).

Starting Materials and Intermediates:

Example 1A

Ethyl N-({2-[(4-chlorophenyl)carbonyl]hydrazinyl}carbonyl)glycinate

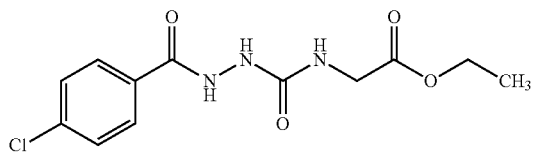 [SMILES: CCOC(=O)CNC(=O)NNC(=O)c1ccc(Cl)cc1]

A suspension of 12.95 g (75.9 mmol) of 4-chlorobenzohydrazide in 50 ml of dry THF was initially charged at 50° C., and a solution of 10.0 g (77.5 mmol) of ethyl 2-isocyanatoacetate in 100 ml of dry THF was added dropwise. Initially, a solution was obtained, and then a precipitate formed. After the addition had ended, the mixture was stirred at 50° C. for a further 2 h and then allowed to stand at RT overnight. The crystals were isolated by filtration, washed with a little diethyl ether and dried under high vacuum. This gave 21.43 g (89% of theory) of the title compound.

LC/MS [Method 1]: $R_t$=1.13 min; m/z=300 $(M+H)^+$ $^1$H-NMR (DMSO-$d_6$, 400 MHz): δ=1.19 (t, 3H), 3.77 (d, 2H), 4.09 (q, 2H), 6.88 (br. s, 1H), 7.57 (d, 2H), 7.91 (d, 2H), 8.21 (s, 1H), 10.29 (s, 1H).

Example 2A

[3-(4-Chlorophenyl)-5-oxo-1,5-dihydro-4H-1,2,4-triazol-4-yl]acetic acid

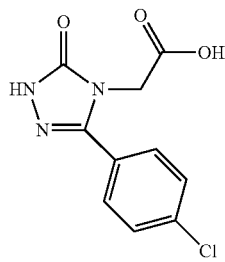 [SMILES: O=C(O)Cn1c(-c2ccc(Cl)cc2)n[nH]c1=O]

91 ml of 3 N aqueous sodium hydroxide solution were added to 21.43 g (67.9 mmol) of the compound from Example 1A, and the mixture was heated under reflux overnight. After cooling to RT, the mixture was adjusted to pH 1 by slow addition of about 20% strength hydrochloric acid. The precipitated solid was isolated by filtration, washed with water and dried at 60° C. under reduced pressure. This gave 17.55 g of the title compound in a purity of about 88% (90% of theory).

LC/MS [Method 1]: $R_t$=0.94 min; m/z=254 $(M+H)^+$ $^1$H-NMR (DMSO-$d_6$, 400 MHz): δ=4.45 (s, 2H), 7.65-7.56 (m, 4H), 12.09 (s, 1H), 13.25 (br. s, 1H).

Example 3A 5-(4-Chlorophenyl)-4-(3,3,3-trifluoro-2-oxopropyl)-2,4-dihydro-3H-1,2,4-triazol-3-one (ketone form) or 5-(4-chlorophenyl)-4-(3,3,3-trifluoro-2,2-dihydroxypropyl)-2,4-dihydro-3H-1,2,4-triazol-3-one (hydrate form)

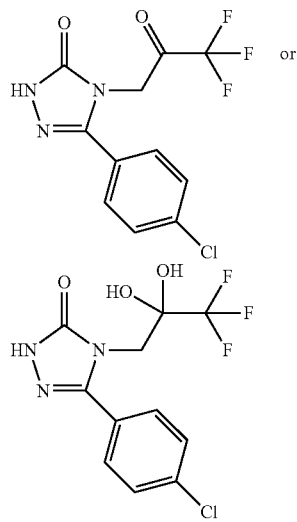

Under argon, 5.0 g (16.36 mmol) of the compound from Example 2A were dissolved in 200 ml of pyridine, and 17.18 g (81.8 mmol) of trifluoroacetic anhydride were added. During the addition, the temperature increased to about 35° C. After 30 min, the pyridine was removed on a rotary evaporator, and 1.5 liters of 0.5 N hydrochloric acid were added to the residue. This mixture was warmed to 70° C. and then filtered whilst still warm. The solid was washed with a little water. The entire filtrate was extracted three times with ethyl acetate. The combined organic phases were washed successively with water, saturated sodium bicarbonate solution and saturated sodium chloride solution, dried over sodium sulfate and freed from the solvent on a rotary evaporator. The residue was dried under high vacuum. This gave 3.56 g (68% of theory) of the title compound in the hydrate form.

LC/MS [Method 1]: $R_t$=1.51 min; m/z=306 (M+H)$^+$ and 324 (M+H)$^+$ (ketone or hydrate form)

$^1$H-NMR (DMSO-d$_6$, 400 MHz): δ=3.98 (s, 2H), 7.61 (d, 2H), 7.68 (br. s, 2H), 7.72 (d, 2H), 12.44 (s, 1H).

Example 4A 5-(4-Chlorophenyl)-4-(3,3,3-trifluoro-2-hydroxypropyl)-2,4-dihydro-3H-1,2,4-triazol-3-one

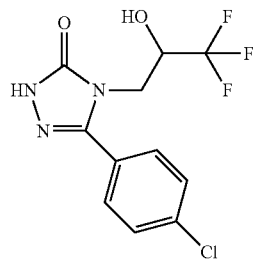 [SMILES: O=c1[nH]nc(-c2ccc(Cl)cc2)n1CC(O)C(F)(F)F]

3.56 g (11.0 mmol) of the compound from Example 3A were dissolved in 100 ml of methanol, and 3.75 g (99.5 mmol) of sodium borohydride were added with ice cooling. After 1.5 h, 200 ml of 1 M hydrochloric acid were added slowly. The methanol was removed on a rotary evaporator and the residue was diluted with 500 ml of water and extracted three times with ethyl acetate. The combined organic phases were washed with saturated sodium bicarbonate solution and then with saturated sodium chloride solution, dried over sodium sulfate and freed from the solvent on a rotary evaporator. The residue was dried under high vacuum. This gave 3.04 g (90% of theory) of the title compound.

LC/MS [Method 2]: $R_t$=1.80 min; m/z=308 (M+H)$^+$ $^1$H-NMR (DMSO-d$_6$, 400 MHz): δ=3.77 (dd, 1H), 3.92 (dd, 1H), 4.34-4.23 (m, 1H), 6.85 (d, 1H), 7.62 (d, 2H), 7.75 (d, 2H), 12.11 (s, 1H).

Example 5A 5-(4-Chlorophenyl)-4-[(2S)-3,3,3-trifluoro-2-hydroxypropyl]-2,4-dihydro-3H-1,2,4-triazol-3-one

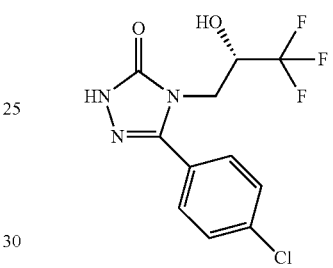

1.08 g (3.3 mmol) of the compound from Example 3A were dissolved in 11 ml of N,N-dimethylacetamide. Atmospheric oxygen was removed by application of reduced pressure, and the solution was saturated with argon. Under argon, 21 mg (0.033 mmol) of (N-[(1S,2S)-(+)-2-amino-1,2-diphenylethyl](4-toluenesulfonyl)amido)(p-cymene)ruthenium(II) chloride [CAS Reg.-Nr. 192139-90-5] were added to this solution. A mixture of 0.63 ml (16.6 mmol) of formic acid and 0.27 ml (1.91 mmol) of triethylamine was then added, and the reaction was stirred with exclusion of air at RT for 48 h. For work-up, the mixture was added to 10 ml of 0.1 N hydrochloric acid and extracted twice with in each case 20 ml of ethyl acetate. The combined organic phases were washed with saturated sodium bicarbonate solution, dried over sodium sulfate, filtered and concentrated under reduced pressure. The crude product was purified by chromatography on silica gel (mobile phase: cyclohexane/ethyl acetate 3:1, then 1:1). This gave 830 mg (81% of theory) of the target compound.

The enantiomeric excess (ee) was determined chromatographically according to Method 14 as 96%: S enantiomer $R_t$=5.73 min, R enantiomer $R_t$=6.82 min.

Example 6A

Methyl {3-(4-chlorophenyl)-5-oxo-4-(3,3,3-trifluoro-2-hydroxypropyl)-4,5-dihydro-1H-1,2,4-triazol-1-yl}acetate (Racemate)

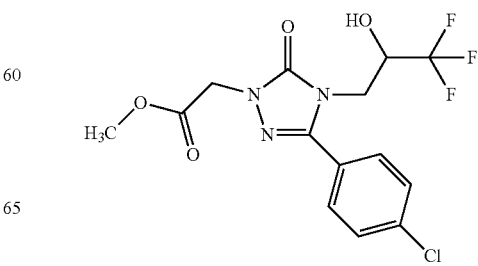

3.04 g (9.9 mmol) of the compound from Example 4A were dissolved in 100 ml of acetonitrile, and 1.07 g (9.9 mmol) of methyl chloroacetate, 2.73 g (19.8 mmol) of potassium carbonate and a small spatula tip of potassium iodide were added. The reaction mixture was heated under reflux for 1 h and then allowed to cool to RT and filtered. The filtrate was freed from the volatile components on a rotary evaporator and the residue was dried under high vacuum. This gave 3.70 g of the title compound in a purity of about 90%, (89% of theory).

LC/MS [Method 3]: $R_t$=1.10 min; m/z=380 (M+H)$^+$ $^1$H-NMR (DMSO-d$_6$, 400 MHz): δ=3.70 (s, 3H), 3.84 (dd, 1H), 3.99 (dd, 1H), 4.16-4.35 (m, 1H), 4.72 (s, 2H), 6.91 (d, 1H), 7.64 (d, 2H), 7.78 (d, 2H).

The racemic compound from Example 6A was separated into the enantiomers by preparative HPLC on a chiral phase [sample preparation: 3.6 g of racemate dissolved in 54 ml of ethyl acetate/isohexane (1:1 v/v), separated on the column in three portions; column: chiral silica gel phase based on the selector poly(N-methacryloyl-L-isoleucine-3-pentylamide), 430 mm×40 mm; mobile phase: stepped gradient isohexane/ethyl acetate 1:1 ethyl acetate isohexane/ethyl acetate 1:1; flow rate: 50 ml/min; temperature: 24° C.; UV detection: 260 nm]. This gave 1.6 g of enantiomer 1 (Example 7A), which eluted first, and 1.6 g of enantiomer 2 (Example 8A), which eluted later:

Example 7A

Methyl {3-(4-chlorophenyl)-5-oxo-4-[(2S)-3,3,3-trifluoro-2-hydroxypropyl]-4,5-dihydro-1H-1,2,4-triazol-1-yl}acetate (Enantiomer 1)

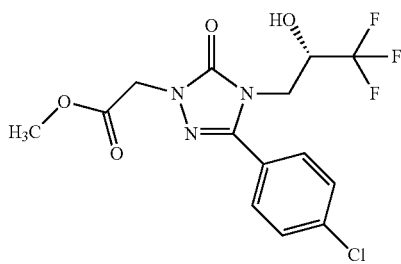 [SMILES: COC(=O)Cn1nc(-c2ccc(Cl)cc2)n(C[C@H](O)C(F)(F)F)c1=O]

Enantiomer which elutes first in the racemate separation of Example 6A.

$R_t$=3.21 min [column: chiral silica gel phase based on the selector poly(N-methacryloyl-L-isoleucine-3-pentylamide), 250 mm×4.6 mm; mobile phase: isohexane/ethyl acetate 1:1; flow rate: 1 ml/min; UV detection: 260 nm].

Example 8A

Methyl {3-(4-chlorophenyl)-5-oxo-4-[(2R)-3,3,3-trifluoro-2-hydroxypropyl]-4,5-dihydro-1H-1,2,4-triazol-1-yl}acetate (Enantiomer 2)

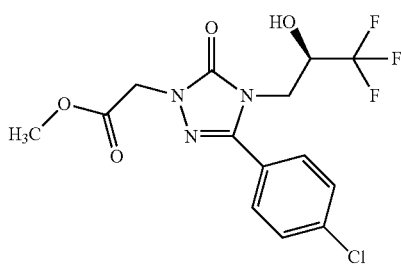 [SMILES: COC(=O)Cn1nc(-c2ccc(Cl)cc2)n(C[C@@H](O)C(F)(F)F)c1=O]

Enantiomer which elutes last in the racemate separation of Example 6A.

$R_t$=4.48 min [column: chiral silica gel phase based on the selector poly(N-methacryloyl-L-isoleucine-3-pentylamide), 250 mm×4.6 mm; mobile phase: isohexane/ethyl acetate 1:1; flow rate: 1 ml/min; UV detection: 260 nm].

Example 9A

Methyl {3-(4-chlorophenyl)-5-oxo-4-[(1E)-3,3,3-trifluoroprop-1-en-1-yl]-4,5-dihydro-1H-1,2,4-triazol-1-yl}acetate

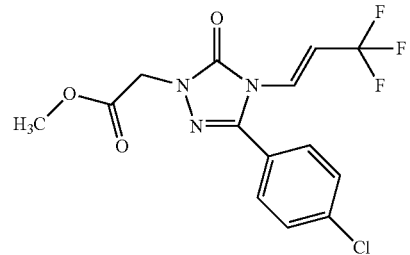 [SMILES: COC(=O)Cn1nc(-c2ccc(Cl)cc2)n(/C=C/C(F)(F)F)c1=O]

At RT, 5.0 g (13.12 mmol) of the compound from Example 8A together with 1.93 g (15.8 mmol) of 4-N,N-dimethylaminopyridine were initially charged in 70 ml of pyridine, 5.54 ml (32.92 mmol) of trifluoromethanesulfonic anhydride were added a little at a time and the mixture was stirred for 18 h. For work-up, 5 ml of 1 N hydrochloric acid were added and the pyridine was removed on a rotary evaporator. The residue was taken up in 50 ml of ethyl acetate and washed with 25 ml of water. The aqueous phase was re-extracted twice with in each case 25 ml of ethyl acetate. The combined organic phases were dried over sodium sulfate, filtered and concentrated under reduced pressure. The crude product was purified by chromatography on silica gel (mobile phase: cyclohexane/ethyl acetate 10:1, then 4:1). This gave 3.50 g (73% of theory) of the title compound.

LC/MS [Method 4]: $R_t$=1.14 min; m/z=362 (M+H)$^+$ $^1$H-NMR (400 MHz, DMSO-d$_6$): δ=7.68 (s, 4H), 7.18 (d, 1H), 6.85 (dd, 1H), 4.78 (s, 2H), 3.72 (s, 3H).

Example 10A

Methyl [3-(4-chlorophenyl)-5-oxo-4-(3,3,3-trifluoropropyl)-4,5-dihydro-1H-1,2,4-triazol-1-yl]-acetate

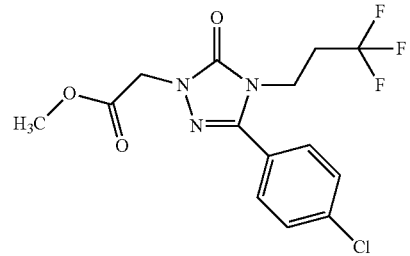 [SMILES: COC(=O)Cn1nc(-c2ccc(Cl)cc2)n(CCC(F)(F)F)c1=O]

1.3 g (3.59 mmol) of the compound from Example 9A and 150 mg of platinum on carbon (5%) were dissolved in 150 ml of methanol and hydrogenated at atmospheric pressure for 18 h. For work-up, the catalyst was filtered off through kieselguhr and the filtrate was concentrated on a rotary evaporator. Drying of the residue under high vacuum gave 1.26 g (89% of theory) of the title compound of a purity of 92%.

LC/MS [Method 4]: $R_t$=1.00 min; m/z=364 (M+H)$^+$ $^1$H-NMR (400 MHz, DMSO-d$_6$): δ=2.55-2.68 (m, 2H), 3.69 (s, 3H), 4.01 (t, 2H), 4.70 (s, 2H), 7.61-7.72 (m, 4H).

Example 11A

2-[(4-Chlorophenyl)carbonyl]-N-(prop-2-en-1-yl)hydrazinecarboxamide

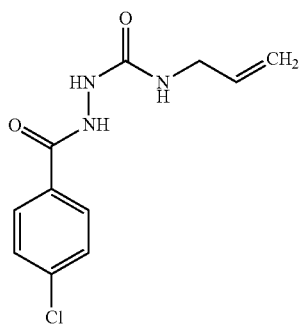 [SMILES: C=CCNC(=O)NNC(=O)c1ccc(Cl)cc1]

At 50° C., 5.00 g (29.3 mmol) of 4-chlorobenzohydrazide were suspended in 150 ml of dry THF. 2.63 ml (29.9 mmol) of allyl isocyanate, dissolved in 110 ml of dry THF, were then added dropwise. Initially, all of the starting material dissolved, and then a fine precipitate formed. The mixture was stirred at 50° C. for 2 h. After cooling to room temperature, diethyl ether was added. The colorless solid was filtered off with suction, washed with diethyl ether and dried under high vacuum. This gave 7.42 g (100% of theory) of the target compound.

LC/MS [Method 5]: $R_t$=1.51 min; MS [ESIpos]: m/z=254 (M+H)$^+$ $^1$H-NMR (400 MHz, DMSO-d$_6$): δ=3.60-3.70 (m, 2H), 5.01 (dd, 1H), 5.14 (dd, 1H), 5.72-5.86 (m, 1H), 6.70 (s, 1H), 7.56 (d, 2H), 7.85-7.95 (m, 3H), 10.21 (s, 1H).

Example 12A 5-(4-Chlorophenyl)-4-(prop-2-en-1-yl)-2,4-dihydro-3H-1,2,4-triazol-3-one

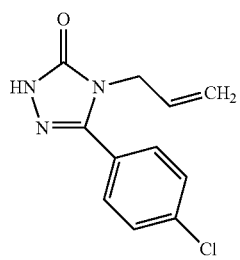 [SMILES: C=CCn1c(-c2ccc(Cl)cc2)n[nH]c1=O]

26.8 g (106 mmol) of 2-[(4-chlorophenyl)carbonyl]-N-(prop-2-en-1-yl)hydrazinecarboxamide from Example 11A were suspended in 210 ml of 3 M aqueous sodium hydroxide solution, and the mixture was heated under reflux for 20 h. After cooling, the pH was adjusted to 10 using semiconcentrated hydrochloric acid. The precipitated colorless solid was filtered off with suction, washed with water until neutral and then stirred with methanol. By filtration, the mixture was freed from insoluble components, the filtrate was concentrated under reduced pressure on a rotary evaporator and the residue was dried under high vacuum. This gave 21.5 g (86.4% of theory) of the title compound as a colorless solid.

LC/MS [Method 5]: $R_t$=1.79 min; MS [ESIpos]: m/z=236 (M+H)$^+$ $^1$H-NMR (400 MHz, DMSO-d$_6$): δ=4.30-4.35 (m, 2H), 4.91 (dd, 1H), 5.11 (dd, 1H), 5.76-5.90 (m, 1H), 7.58 (d, 2H), 7.65 (d, 2H), 12.05 (s, 1H).

Example 13A 5-(4-Chlorophenyl)-2-(prop-2-yn-1-yl)-4-(3,3,3-trifluoro-2-hydroxypropyl)-2,4-dihydro-3H-1,2,4-triazol-3-one

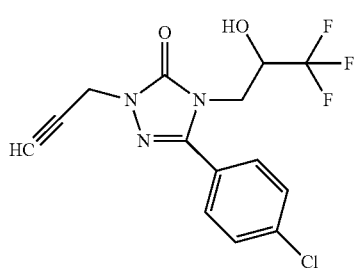 [SMILES: C#CCn1nc(-c2ccc(Cl)cc2)n(CC(O)C(F)(F)F)c1=O]

300 mg (0.98 mmol) of the compound from Example 4A were dissolved in 10 ml of acetonitrile, and 122 mg (1.02 mmol) of 3-bromo-1-propyne and 270 mg (1.95 mmol) of potassium carbonate were added. The mixture was heated at reflux for 1 h. For work-up, the reaction mixture was allowed to cool to RT and about 10 ml of water were added. The mixture was extracted twice with in each case 15 ml of ethyl acetate. The combined organic phases were dried over sodium sulfate, filtered and concentrated under reduced pressure. The crude product was purified chromatographically [Method 19]. This gave 166 mg (49% of theory) of the target compound.

LC/MS [Method 4]: $R_t$=0.97 min; m/z=346 (M+H)$^+$ $^1$H-NMR (CDCl$_3$, 400 MHz): δ=2.38 (t, 1H), 3.94-4.09 (m, 1H), 4.43-4.54 (m, 1H), 4.68 (d, 2H), 4.73-4.78 (m, 1H), 7.50 (d, 2H), 7.57 (d, 2H).

Example 14A 5-(4-Chlorophenyl)-2-(prop-2-yn-1-yl)-4-[(2S)-3,3,3-trifluoro-2-hydroxypropyl]-2,4-dihydro-3H-1,2,4-triazol-3-one

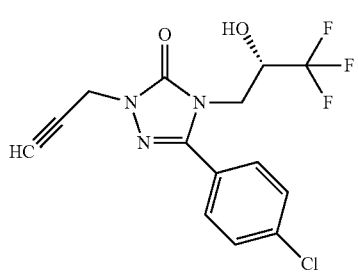 [SMILES: C#CCn1nc(-c2ccc(Cl)cc2)n(C[C@H](O)C(F)(F)F)c1=O]

1110 mg (3.61 mmol) of the compound from Example 5A were dissolved in 30 ml of acetonitrile, and 451 mg (3.79 mmol) of 3-bromo-1-propyne and 2.35 g (7.22 mmol) of cesium carbonate were added. The mixture was heated under reflux for 1 h. For work-up, the reaction mixture was allowed to cool to RT, and about 30 ml of water were added. The mixture was extracted twice with in each case 30 ml of ethyl acetate. The combined organic phases were dried over sodium sulfate, filtered and concentrated under reduced pressure. The crude product was purified by chromatography on silica gel (mobile phase: cyclohexane/ethyl acetate 10:1, then 3:1). This gave 203 mg (16% of theory) of the title compound.

LC/MS [Method 3]: $R_t$=1.11 min; m/z=346 (M+H)$^+$ $^1$H-NMR (CDCl$_3$, 400 MHz): δ=2.38 (t, 1H), 3.94-4.09 (m, 1H), 4.43-4.54 (m, 1H), 4.68 (d, 2H), 4.73-4.78 (m, 1H), 7.50 (d, 2H), 7.57 (d, 2H).

Example 15A

Methyl 3-{[3-(4-chlorophenyl)-1-(2-methoxy-2-oxoethyl)-5-oxo-1,5-dihydro-4H-1,2,4-triazol-4-yl]methyl}benzenecarboxylate

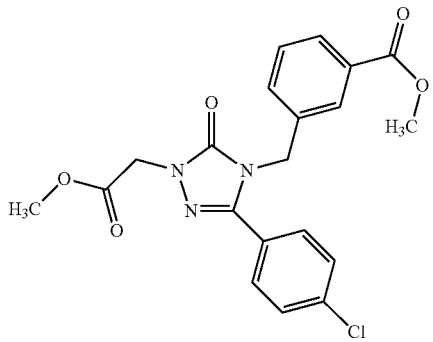 [SMILES: COC(=O)Cn1nc(-c2ccc(Cl)cc2)n(Cc2cccc(C(=O)OC)c2)c1=O]

200 mg (0.75 mmol) of methyl [3-(4-chlorophenyl)-5-oxo-4,5-dihydro-1H-1,2,4-triazol-1-yl]acetate [preparation according to WO 2007/134862 Example 222A] were suspended in 7.5 ml of acetone, 365 mg (1.12 mmol) of cesium carbonate and 223 mg (0.97 mmol) of methyl 3-bromomethylbenzoate were added and the mixture was heated at the boil for 1 h. After cooling, the mixture was filtered through Extrelut and the filter cake was rinsed with acetone. The filtrate was concentrated under reduced pressure and the residue was purified by chromatography on silica gel (mobile phase: cyclohexane/ethyl acetate 4:1→1:1). The target compound was obtained as a colorless foam (165 mg, 53% of theory).

MS [DCI]: m/z=433 (M+NH$_4$)$^+$, 416 (M+H)$^+$ $^1$H-NMR (400 MHz, DMSO-d$_6$): δ=3.71 (s, 3H), 3.82 (s, 3H), 4.75 (s, 2H), 5.08 (s, 2H), 7.32 (d, 1H), 7.46 (t, 1H), 7.55 (s, 4H), 7.66 (s, 1H), 7.82 (d, 1H).

Example 16A

Methyl 3-{[3-(4-chlorophenyl)-1-(2-hydrazino-2-oxoethyl)-5-oxo-1,5-dihydro-4H-1,2,4-triazol-4-yl]methyl}benzenecarboxylate

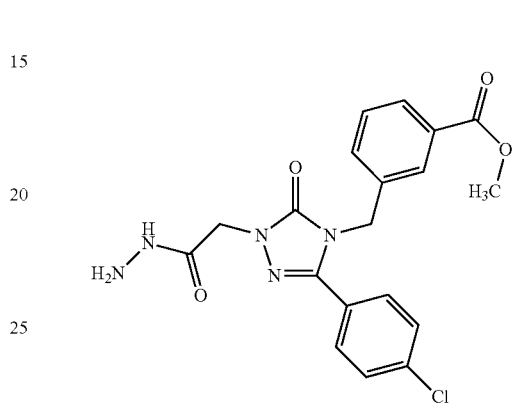

172 mg (0.41 mmol) of the compound from Example 15A were suspended in 1 ml of ethanol, and 40 μl (0.83 mmol) of hydrazine hydrate were added. The mixture was heated under reflux for 4 h and then allowed to stand at room temperature for 18 h. The reaction was concentrated under reduced pressure on a rotary evaporator and the residue was dried under high vacuum. This gave 161 mg (94% of theory) of the target compound as a colorless solid.

MS [DCI]: m/z=433 (M+NH$_4$)$^+$, 416 (M+H)$^+$ $^1$H-NMR (400 MHz, DMSO-d$_6$): δ=3.82 (s, 3H), 4.31 (d, 2H), 4.43 (s, 2H), 5.05 (s, 2H), 7.37 (d, 1H), 7.42-7.57 (m, 5H), 7.71 (s, 1H), 7.83 (d, 1H), 9.30 (t, 1H).

The following compounds were obtained in an analogous manner:

| Example | Name | Structure | Starting material | Analytical data |
|---|---|---|---|---|
| 17A | 2-[3-(4-chlorophenyl)-4-(4-methoxybenzyl)-5-oxo-4,5-dihydro-1H-1,2,4-triazol-1-yl]-acetohydrazide | 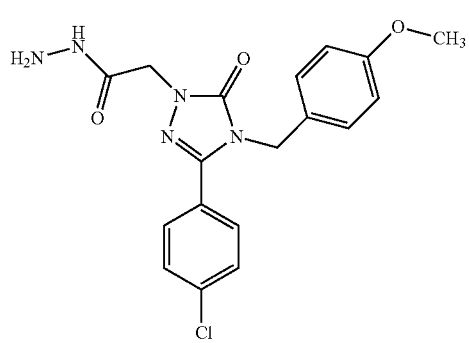 [SMILES: COc1ccc(Cn2c(-c3ccc(Cl)cc3)nn(CC(=O)NN)c2=O)cc1] | WO 2007/134862 Ex. 78A | LC/MS [Method 5]: $R_t$ = 1.88 min; MS [ESIpos]: m/z = 388 (M + H)$^+$ |

| Example | Name | Structure | Starting material | Analytical data |
|---|---|---|---|---|
| 18A | 2-[3-(4-chlorophenyl)-5-oxo-4-(3,3,3-trifluoro-2-hydroxypropyl)-4,5-dihydro-1H-1,2,4-triazol-1-yl]acetohydrazide | 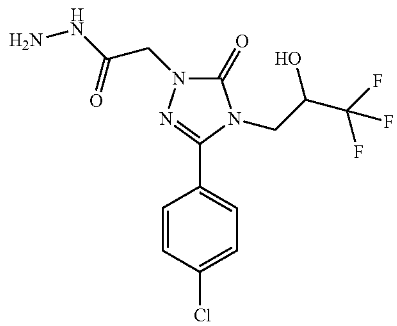 [SMILES: NNC(=O)Cn1nc(-c2ccc(Cl)cc2)n(CC(O)C(F)(F)F)c1=O] | Ex. 6A | LC/MS [Method 5]: $R_t$ = 1.83 min; MS [ESIpos]: m/z = 380 (M + Na)$^+$ |
| 19A | 2-{3-(4-chlorophenyl)-5-oxo-4-[(2S)-3,3,3-trifluoro-2-hydroxypropyl]-4,5-dihydro-1H-1,2,4-triazol-1-yl}acetohydrazide (enantiomer I) | 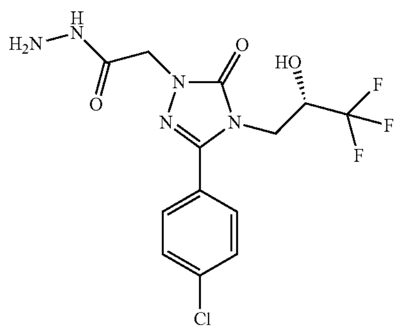 [SMILES: NNC(=O)Cn1nc(-c2ccc(Cl)cc2)n(C[C@H](O)C(F)(F)F)c1=O] | Ex. 7A | $^1$H-NMR (400 MHz, DMSO-$d_6$): δ = 3.33 (br. s, 2H), 3.77-3.86 (m, 1H), 3.91-3.99 (m, 1H), 4.33-4.43 (m, 2H), 6.93 (br. s, 1H), 7.61-7.66 (m, 2H), 7.72-7.79 (m, 2H), 9.21-9.30 (br. s, 1H). |
| 20A | 2-{3-(4-chlorophenyl)-5-oxo-4-[(2R)-3,3,3-trifluoro-2-hydroxypropyl]-4,5-dihydro-1H-1,2,4-triazol-1-yl)acetohydrazide (enantiomer II) | 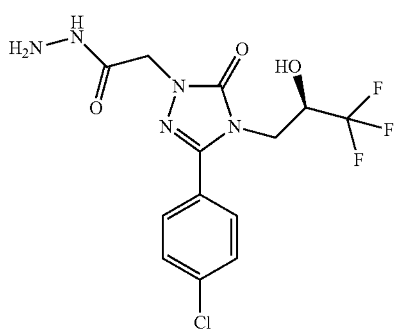 [SMILES: NNC(=O)Cn1nc(-c2ccc(Cl)cc2)n(C[C@@H](O)C(F)(F)F)c1=O] | Ex. 8A | LC/MS [Method 3]: $R_t$ = 0.90 min; MS [ESIpos]: m/z = 380 (M + H)$^+$ |

Example 21A

2-[3-(4-Chlorophenyl)-4-cyclopropyl-5-oxo-4,5-dihydro-1H-1,2,4-triazol-1-yl]acetohydrazide

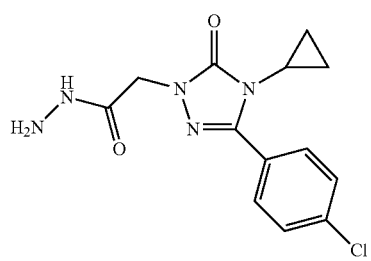 [SMILES: NNC(=O)Cn1nc(-c2ccc(Cl)cc2)n(C2CC2)c1=O]

50 mg (0.17 mmol) of [3-(4-chlorophenyl)-4-cyclopropyl-5-oxo-4,5-dihydro-1H-1,2,4-triazol-1-yl]-acetic acid [preparation according to WO 2007/134862 Example 88A] were dissolved in 0.4 ml of methanol and diluted with 0.6 ml of toluene, and 128 μl (0.26 mmol) of trimethylsilyldiazomethane solution (2 M in hexanes) were then added dropwise until a slight yellow color remained. The reaction was stirred for 1 h and then evaporated to dryness. The residue was taken up in 1 ml of ethanol, 43 mg (0.85 mmol) of hydrazine hydrate were added and the mixture was stirred under reflux for 2.5 h. After cooling, the solution was concentrated under reduced pressure and the residue was dried under high vacuum. This gave 54 mg (96% of theory) of the title compound in a purity of 93% as a colorless solid.

LC/MS [Method 5]: $R_t$=1.65 min; MS [ESIpos]: m/z=308 (M+H)$^+$.

The two compounds below were obtained in an analogous manner:

| Example | Name | Structure | Starting material | Analytical data |
|---|---|---|---|---|
| 22A | 2-[3-(5-chloro-thiophen-2-yl)-4-(2-fluoro-benzyl)-5-oxo-4,5-dihydro-1H-1,2,4-triazol-1-yl]-acetohydrazide | 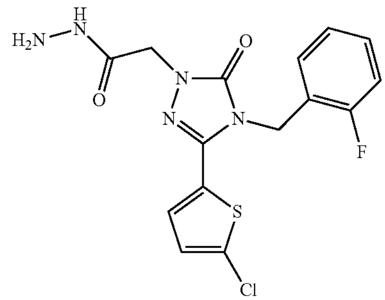 [SMILES: NNC(=O)Cn1nc(-c2ccc(Cl)s2)n(Cc2ccccc2F)c1=O] | WO 2007/ 134862 Ex. 154A | LC/MS [Method 7]: $R_t$ = 1.73 min; MS [ESIpos]: m/z = 382 $(M + H)^+$ |
| 23A | 2-[3-(4-chloro-phenyl)-5-oxo-4-(3,3,3-tri-fluoropropyl)-4,5-dihydro-1H-1,2,4-triazol-1-yl]-acetohydrazide | 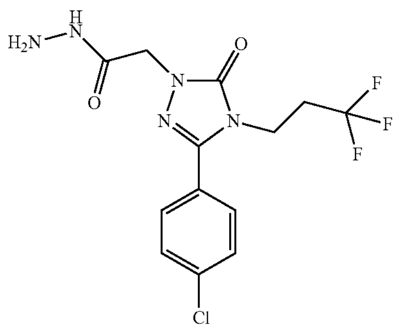 [SMILES: NNC(=O)Cn1nc(-c2ccc(Cl)cc2)n(CCC(F)(F)F)c1=O] | 10A | LC/MS [Method 6]: $R_t$ = 1.75 min; MS [ESIpos]: m/z = 384 $(M + H)^+$ |

Example 24A

[3-(5-Chlorothiophen-2-yl)-4-(2-fluorobenzyl)-5-oxo-4,5-dihydro-1H-1,2,4-triazol-1-yl]acetonitrile

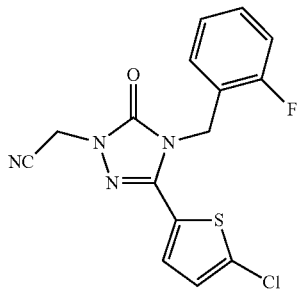 [SMILES: N#CCn1nc(-c2ccc(Cl)s2)n(Cc2ccccc2F)c1=O]

A mixture of 250 mg (0.81 mmol) of 5-(5-chloro-2-thienyl)-4-(2-fluorobenzyl)-2,4-dihydro-3H-1,2,4-triazol-3-one [preparation according to WO 2007/134862 Example 154A], 67 μl (0.97 mmol) of bromoacetonitrile and 223 mg (1.61 mmol) of potassium carbonate was stirred in 8 ml of dry DMF at an oil bath temperature of 100° C. for 1 h. After cooling, the mixture was filtered through kieselguhr, the filtrate was concentrated under reduced pressure and the residue was partitioned between MTBE and water. The organic phase was washed successively with 10 ml of water and 10 ml of saturated sodium chloride solution, dried over sodium sulfate, filtered and concentrated under reduced pressure. The residue was purified chromatographically on silica gel (mobile phase: cyclohexane/ethyl acetate 4:1). This gave 258 mg (92% of theory) of the target compound as a slightly yellowish solid.

MS [DCI]: m/z=366 $(M+NH_4)^+$, 349 $(M+H)^+$
$^1$H-NMR (400 MHz, CDCl$_3$): δ=4.81 (s, 2H), 5.11 (s, 2H), 6.87 (d, 1H), 6.97 (s, 1H), 7.05-7.16 (m, 3H), 7.28-7.36 (m, 1H).

Example 25A (1Z)-2-[3-(5-Chlorothiophen-2-yl)-4-(2-fluorobenzyl)-5-oxo-4,5-dihydro-1H-1,2,4-triazol-1-yl]-N'-hydroxyethaneimidamide

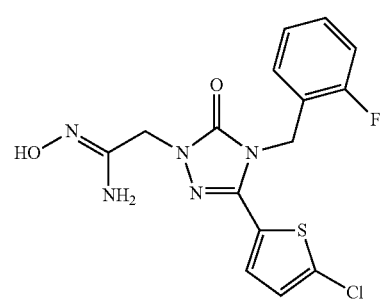 [SMILES: N/C(Cn1nc(-c2ccc(Cl)s2)n(Cc2ccccc2F)c1=O)=N\O]

250 mg (0.66 mmol) of the compound from Example 24A and 92 mg (1.32 mmol) of hydroxylamine hydrochloride were suspended in 3.3 ml of ethanol, and the mixture was heated to the boil. 193 μl (1.39 mmol) of triethylamine were added to the hot solution and heating under reflux was continued for a further 1 h. On cooling of the reaction, a colorless solid crystallized out; this solid was filtered off and washed with a little ethanol. This gave 174 mg (69% of theory) of the target compound as a colorless solid. The mother liquor was concentrated under reduced pressure on a rotary evaporator, and the residue was partitioned between water and ethyl acetate. The organic phase was washed successively with 10 ml of water and 10 ml of saturated sodium chloride solution, dried over sodium sulfate, filtered and concentrated under reduced pressure. This gave a further 69 mg (24% of theory) of the target compound in a purity of 87% as a slightly yellowish solid.

MS [ESIpos]: m/z=382 (M+H)$^+$ $^1$H-NMR (400 MHz, DMSO-d$_6$): δ=4.36 (s, 2H), 5.11 (s, 2H), 5.46 (s, 2H), 7.04-7.12 (m, 1H), 7.12-7.28 (m, 4H), 7.30-7.41 (m, 1H), 9.27 (s, 1H).

Example 26A

1-Amino-3-[3-(trifluoromethyl)phenyl]acetone hydrochloride

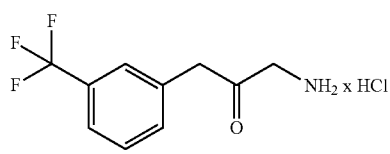

Under argon and with ice cooling, 1.13 g (11.8 mmol) of diformylamide sodium salt were added a little at a time to a solution of 2.67 g (11.2 mmol) of 1-chloro-3-[3-(trifluoromethyl)phenyl]propan-2-one in 11 ml of DMF. The mixture was stirred in an ice bath for 1 h and then at RT overnight. The mixture was then diluted with 25 ml of ethyl acetate and washed successively with in each case 15 ml of 0.5 N hydrochloric acid, water, saturated sodium bicarbonate solution and once more with water. The organic phase was dried over sodium sulfate, filtered and concentrated under reduced pressure. The dark oily residue was pre-purified on a short silica gel column (mobile phase: dichloromethane/ethanol 95:5). This gave 2.0 g of a dark-brown solid. This was taken up in 25 ml of a 7 N solution of hydrogen chloride in isopropanol, and the mixture was stirred overnight. The solvent was removed under reduced pressure on a rotary evaporator, and the residue was dissolved in about 15 ml of methanol. 100 ml of diethyl ether were stirred into this solution, and the precipitated solid was isolated by filtration. The filter cake was washed with about 10 ml of diisopropyl ether and dried under high vacuum. This gave 0.79 g (28% of theory) of the target compound as a brown solid.

LC/MS [Method 8]: R$_t$=2.30 min; MS [ESIpos]: m/z=218 (M−HCl)$^+$ $^1$H-NMR (400 MHz, DMSO-d$_6$): δ=4.00-4.11 (m, 4H), 7.49-7.70 (m, 4H), 8.17 (br. d, 1H).

Example 27A

2-[3-(4-Chlorophenyl)-4-cyclopropyl-5-oxo-4,5-dihydro-1H-1,2,4-triazol-1-yl]-N-{2-oxo-3-[3-(trifluoromethyl)phenyl]propyl}acetamide

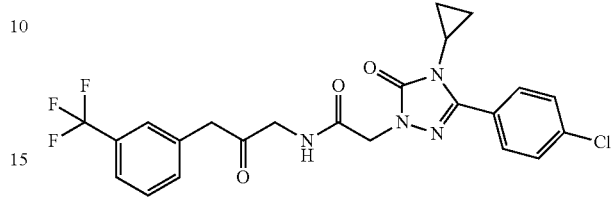

391 mg (2.90 mmol) of HOBt and 513 mg (2.67 mmol) of EDC were added to a solution of 654 mg (2.23 mmol) of [3-(4-chlorophenyl)-4-cyclopropyl-5-oxo-4,5-dihydro-1H-1,2,4-triazol-1-yl]acetic acid [preparation according to WO 2007/134862 Example 88A] and 650 mg (2.56 mmol) of the compound from Example 26A in 4.4 ml of dry DMF. 465 μl (2.67 mmol) of N,N-diisopropylethylamine were then added, and the reaction was stirred overnight. For work-up, the reaction was diluted with 20 ml of ethyl acetate and extracted twice with in each case 15 ml of water. The organic phase was dried over sodium sulfate, filtered and concentrated under reduced pressure. The residue that remained was recrystallized from acetonitrile. This gave 610 mg (56% of theory) of the target compound as very fine colorless crystals. A further 84 mg (8% of theory) of the target compound were obtained from a second crystallization of the concentrated mother liquor in the form of slightly yellowish crystals.

MS [ESIpos]: m/z=493 (M+H)$^+$ $^1$H-NMR (400 MHz, CDCl$_3$): δ=0.73-0.83 (m, 2H), 0.97-1.09 (m, 2H), 2.94-3.04 (m, 1H), 3.80 (s, 2H), 4.25 (d, 2H), 4.53 (s, 2H), 6.91-7.02 (m, 1H), 7.39 (d, 1H), 7.43-7.51 (m, 4H), 7.57 (d, 1H), 7.71 (d, 2H).

Example 28A

2-[(5-Bromopyridin-3-yl)methyl]-5-(4-chlorophenyl)-4-(3,3,3-trifluoro-2-hydroxypropyl)-2,4-dihydro-3H-1,2,4-triazol-3-one

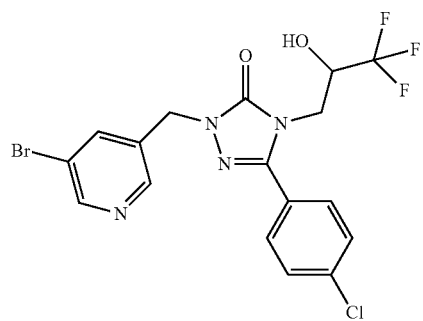 [SMILES: O=c1n(Cc2cncc(Br)c2)nc(-c2ccc(Cl)cc2)n1CC(O)C(F)(F)F]

300 mg (0.98 mmol) of the compound from Example 4A and 953 mg (2.93 mmol) of cesium carbonate were dissolved in 4 ml of DMF, and 261 mg (1.10 mmol) of 3-bromo-5-

(chloromethyl)-pyridine hydrochloride were added. The mixture was stirred initially at 40° C. for 20 h and then at 70° C. for 24 h. To bring the reaction to completion, a further 130 mg (0.55 mmol) of 3-bromo-5-(chloromethyl)pyridine hydrochloride and 450 mg (1.38 mmol) of cesium carbonate were then added, and the reaction was stirred at 70° C. for another 20 h. After cooling to RT, 10 ml of water were added and the mixture was extracted three times with in each case 10 ml of ethyl acetate. The combined organic phases were dried over magnesium sulfate, filtered and concentrated under reduced pressure. The crude product was purified by preparative HPLC [Method 19]. This gave 263 mg (56% of theory) of the target compound.

LC/MS [Method 4]: $R_t$=1.07 min; MS [ESIpos]: m/z=477 and 479 (M+H)$^+$.

Example 29A

2-[(5-Bromopyridin-3-yl)methyl]-5-(4-chlorophenyl)-4-[(2S)-3,3,3-trifluoro-2-hydroxypropyl]-2,4-dihydro-3H-1,2,4-triazol-3-one

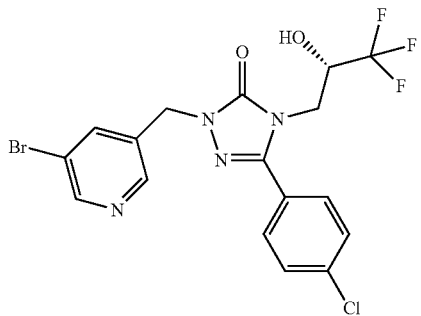 [SMILES: O=c1n(Cc2cncc(Br)c2)nc(-c2ccc(Cl)cc2)n1C[C@H](O)C(F)(F)F]

171 mg (0.56 mmol) of the compound from Example 5A and 543 mg (1.67 mmol) of cesium carbonate were dissolved in 11 ml of acetonitrile, and 135 mg (0.56 mmol) of 3-bromo-5-(chloromethyl)pyridine hydrochloride were added. The mixture was stirred at 65° C. for 5 h. After cooling to RT, 10 ml of water were added and the mixture was extracted three times with in each case 10 ml of ethyl acetate. The combined organic phases were dried over sodium sulfate, filtered and concentrated under reduced pressure. The crude product was purified by preparative HPLC [Method 19]. This gave 102 mg (38% of theory) of the target compound.

LC/MS [Method 4]: $R_t$=1.05 min; MS [ESIpos]: m/z=477 and 479 (M+H)$^+$.

Example 30A 5-(4-Chlorophenyl)-2-[(5-chloro-2-thienyl)methyl]-4-[(2S)-3,3,3-trifluoro-2-hydroxypropyl]-2,4-dihydro-3H-1,2,4-triazol-3-one

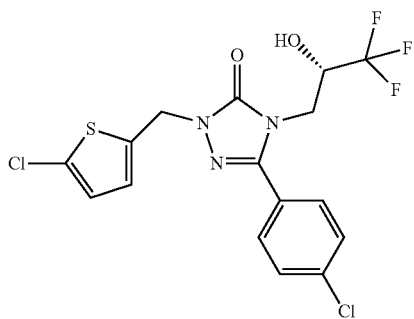 [SMILES: O=c1n(Cc2ccc(Cl)s2)nc(-c2ccc(Cl)cc2)n1C[C@H](O)C(F)(F)F]

119 mg (0.39 mmol) of the compound from Example 5A and 107 mg (0.77 mmol) of potassium carbonate were dissolved in 5 ml of acetonitrile, and 65 mg (0.39 mmol) of 2-chloro-5-(chloromethyl)thiophene were added. The mixture was stirred under reflux for 2 h. After cooling to RT, 10 ml of water were added and the mixture was extracted three times with in each case 10 ml of ethyl acetate. The combined organic phases were washed with 10 ml of saturated sodium chloride solution, dried over sodium sulfate, filtered and concentrated under reduced pressure. The crude product was purified by chromatography on silica gel (mobile phase: cyclohexane/ethyl acetate 10:1→8:1→5:1→1:1). This gave 114 mg (65% of theory) of the target compound.

LC/MS [Method 4]: $R_t$=1.20 min; MS [ESIpos]: m/z=438 and 440 (M+H)$^+$.

Example 31A 5-(4-Chlorophenyl)-2-[(2-chloro-1,3-thiazol-5-yl)methyl]-4-[(2S)-3,3,3-trifluoro-2-hydroxypropyl]-2,4-dihydro-3H-1,2,4-triazol-3-one

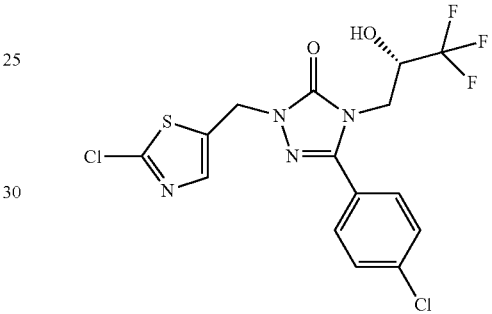

500 mg (1.63 mmol) of the compound from Example 5A and 449 mg (3.25 mmol) of potassium carbonate were dissolved in 4 ml of acetonitrile, and 287 mg (1.71 mmol) of 2-chloro-5-(chloromethyl)-1,3-thiazole were added. The mixture was stirred at 80° C. for 1.5 h. After cooling to RT, 10 ml of water were added and the mixture was extracted three times with in each case 10 ml of ethyl acetate. The combined organic phases were washed with 10 ml of saturated sodium chloride solution, dried over sodium sulfate, filtered and concentrated under reduced pressure. The crude product was purified by chromatography on silica gel (mobile phase: cyclohexane/ethyl acetate 7:1, then 1:1). This gave 619 mg (87% of theory) of the target compound.

LC/MS [Method 3]: $R_t$=1.24 min; MS [ESIpos]: m/z=439 and 441 (M+H)$^+$.

Example 32A

Ethyl 1-(2,6-dichlorobenzyl)-1H-imidazol-5-carboxylate

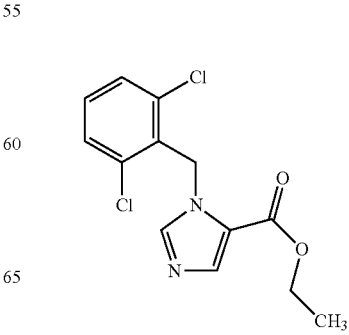

258 mg (1.84 mmol) of ethyl 1H-imidazole-4-carboxylate together with 486 mg (2.03 mmol) of 2,6-dichlorobenzyl bromide were dissolved in 7 ml of DMF, and 720 mg (2.21 mmol) of cesium carbonate were added. The mixture was stirred at 80° C. for 16 h. After cooling to RT, 10 ml of water were added and the mixture was extracted twice with in each case 10 ml of ethyl acetate. The combined organic phases were dried over sodium sulfate and freed from the solvent on a rotary evaporator. The crude product was purified chromatographically [Method 19]. This gave 220 mg (40% of theory) of the target compound.

LC/MS [Method 3]: $R_t$=1.03 min; MS [ESIpos]: m/z=299 and 301 (M+H)$^+$ $^1$H-NMR (400 MHz, CDCl$_3$): δ=1.37 (t, 3H), 4.34 (q, 2H), 5.44 (s, 2H), 7.27-7.33 (m, 1H), 7.37-7.43 (m, 2H), 7.68 (d, 2H).

A further fraction gave 110 mg (20% of theory) of the regioisomer ethyl 1-(2,6-dichlorobenzyl)-1H-imidazole-4-carboxylate:

LC/MS [Method 3]: $R_t$=1.12 min; MS [ESIpos]: m/z=299 and 301 (M+H)$^+$.

Example 33A

Ethyl 1-(2,6-dichlorobenzyl)-4-nitro-1H-imidazole-2-carboxylate

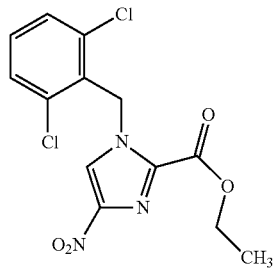 [SMILES: CCOC(=O)c1nc([N+](=O)[O-])cn1Cc1c(Cl)cccc1Cl]

1000 mg (5.4 mmol) of ethyl 4-nitro-1H-imidazole-2-carboxylate together with 1426 mg (5.94 mmol) of 2,6-dichlorobenzyl bromide were dissolved in 37 ml of DMF, and 2112 mg (6.48 mmol) of cesium carbonate were added. The mixture was stirred at 75° C. for 4 h. After cooling to RT, the mixture was added to 100 ml of ice-water. The precipitated product was filtered off and washed with water. The beige solid was dried under high vacuum. This gave 1500 mg (81% of theory) of the target compound.

LC/MS [Method 1]: $R_t$=2.05 min; MS [ESIpos]: m/z=344 and 346 (M+H)$^+$ $^1$H-NMR (400 MHz, DMSO-d$_6$): δ=1.35 (t, 3H), 4.41 (q, 2H), 5.96 (s, 2H), 7.53 (dd, 1H), 7.59-7.64 (m, 2H), 7.96 (s, 1H).

Example 34A

Methyl 1-(2-chlorophenyl)-1H-imidazole-4-carboxylate

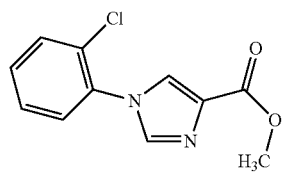 [SMILES: COC(=O)c1cn(-c2ccccc2Cl)cn1]

200 mg (1.59 mmol) of methyl 1H-imidazole-4-carboxylate, 496 mg (3.17 mmol) of 2-chloro-phenylboronic acid, 100 mg of 3 Å molecular sieve and 432 mg (2.28 mmol) of copper(II) acetate were initially charged in 2 ml of dichloromethane, and 256 µl (3.17 mmol) of pyridine were added. The mixture was stirred at RT for 20 h. For work-up, the mixture was filtered through a little kieselguhr, the filter residue was rinsed with about 15 ml of ethyl acetate and the combined filtrates were washed with 5 ml of water. The organic phase was dried over sodium sulfate, filtered and concentrated under reduced pressure. The crude product was purified by chromatography on silica gel (mobile phase: cyclohexane/ethyl acetate 3:1→1:1→1:3). This gave 55 mg (13% of theory) of the target compound.

LC/MS [Method 3]: $R_t$=0.90 min; MS [ESIpos]: m/z=237 (M+H)$^+$ $^1$H-NMR (400 MHz, DMSO-d$_6$): δ=3.79 (s, 3H), 7.53-7.58 (m, 2H), 7.64 (dd, 1H), 7.70-7.77 (m, 1H), 8.05 (d, 1H), 8.20 (d, 1H).

Example 35A

Ethyl 1-(2-chlorophenyl)-1H-pyrazole-4-carboxylate

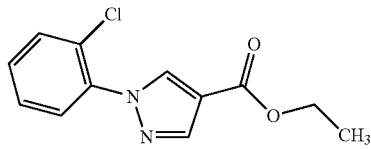 [SMILES: CCOC(=O)c1cnn(-c2ccccc2Cl)c1]

400 mg (2.85 mmol) of ethyl 1H-pyrazole-4-carboxylate, 893 mg (5.71 mmol) of 2-chlorophenyl-boronic acid, 100 mg of 3 Å molecular sieve and 778 mg (4.28 mmol) of copper(II) acetate were initially charged in 2 ml of dichloromethane, and 461 µl (5.71 mmol) of pyridine were added. The mixture was stirred at RT for 20 h. For work-up, the mixture was filtered through a little kieselguhr, the filter residue was rinsed with about 10 ml of dichloromethane and the combined filtrates were concentrated under reduced pressure. The crude product was purified by chromatography on silica gel (mobile phase: cyclohexane/ethyl acetate 10:1, then 5:1). This gave 71 mg (10% of theory) of the target compound.

LC/MS [Method 3]: $R_t$=1.15 min; MS [ESIpos]: m/z=251 (M+H)$^+$.

Example 36A

[1-(2,6-Dichlorobenzyl)-1H-imidazol-5-yl]methanol

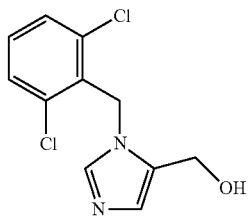 [SMILES: OCc1cncn1Cc1c(Cl)cccc1Cl]

220 mg (0.74 mmol) of the compound from Example 32A were dissolved in 3 ml of THF, and 0.74 ml (0.74 mmol) of a 1 M solution of lithium aluminum hydride in THF was added dropwise at 0° C. The mixture was stirred at RT for 1 h. For work-up, 5 ml of a saturated potassium sodium tartrate solution were added with ice cooling, the mixture was diluted with 10 ml of ethyl acetate and the precipitated solid was filtered off. The crude product was purified chromatographically [Method 19]. This gave 188 mg (99% of theory) of the target compound.

LC/MS [Method 3]: $R_t$=0.51 min; MS [ESIpos]: m/z=257 and 259 (M+H)$^+$.

Example 37A

[1-(2,6-Dichlorobenzyl)-4-nitro-1H-imidazol-2-yl]methanol

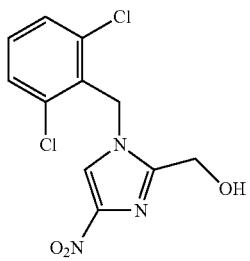 [SMILES: O=[N+]([O-])c1cn(Cc2c(Cl)cccc2Cl)c(CO)n1]

1200 mg (3.5 mmol) of the compound from Example 33A together with 15 mg (0.35 mmol) of lithium chloride were dissolved in 53 ml 1,2-dimethoxyethane, and 198 mg (5.23 mmol) of sodium borohydride were added at 0° C. The mixture was stirred at RT for 1 h. For work-up, 25 ml of a saturated potassium sodium tartrate solution were added with ice cooling and the mixture was extracted with 50 ml of ethyl acetate. The organic phase was dried over sodium sulfate, filtered and concentrated under reduced pressure. The crude product was purified by chromatography on silica gel (mobile phase: ethyl acetate/cyclohexane 1:1). This gave 800 mg (76% of theory) of the target compound.

LC/MS [Method 5]: $R_t$=1.82 min; MS [ESIpos]: m/z=302 and 304 (M+H)$^+$.

Example 38A

[1-(2-Chlorophenyl)-1H-imidazol-4-yl]methanol

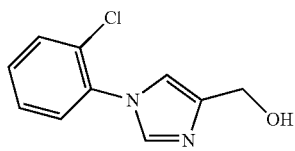 [SMILES: OCc1cn(-c2ccccc2Cl)cn1]

50 mg (0.21 mmol) of the compound from Example 34A were dissolved in 1 ml of THF, and 222 µl (0.22 mmol) of a 1 N solution of lithium aluminum hydride in THF were added at −10° C. Over a period of one hour, the mixture was then warmed to RT. For work-up, 2 ml of water and 5 ml of saturated potassium sodium tartrate solution were added and the mixture was extracted twice with in each case 10 ml of ethyl acetate. The combined organic phases were dried over sodium sulfate, filtered and concentrated under reduced pressure. This gave 34 mg (56% of theory) of the target compound in a purity of 73%.

LC/MS [Method 3]: $R_t$=0.34 min; MS [ESIpos]: m/z=209 (M+H)$^+$.

Example 39A

[1-(2-Chlorophenyl)-1H-pyrazol-4-yl]methanol

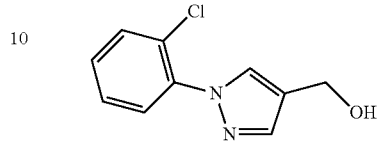

80 mg (0.32 mmol) of the compound from Example 35A were dissolved in 2 ml of THF, and 335 µl (0.34 mmol) of a 1 N solution of lithium aluminum hydride in THF were added at −10° C. Over a period of one hour, the mixture was then warmed to RT. For work-up, 2 ml of water and 5 ml of saturated potassium sodium tartrate solution were added and the mixture was extracted twice with in each case 10 ml of ethyl acetate. The combined organic phases were dried over sodium sulfate, filtered and concentrated under reduced pressure. This gave 61 mg (83% of theory) of the target compound in a purity of 91%.

LC/MS [Method 3]: $R_t$=0.76 min; MS [ESIpos]: m/z=209 (M+H)$^+$.

Example 40A 5-(Chloromethyl)-1-(2,6-dichlorobenzyl)-1H-imidazole

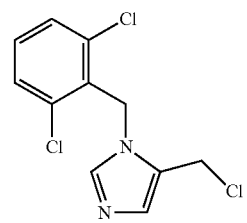 [SMILES: ClCc1cncn1Cc1c(Cl)cccc1Cl]

45 mg (0.18 mmol) of the compound from Example 36A together with 27 mg (0.26 mmol) of triethylamine were dissolved in 1 ml of toluene, and 25 mg (0.21 mmol) of thionyl chloride were added dropwise at RT. The mixture was stirred at RT for 1 h. Under reduced pressure, the reaction mixture was freed from all volatile components. This gave 48 mg (99% of theory) of the target compound, which was reacted further without any further purification.

Example 41A 2-(Chloromethyl)-1-(2,6-dichlorobenzyl)-4-nitro-1H-imidazole

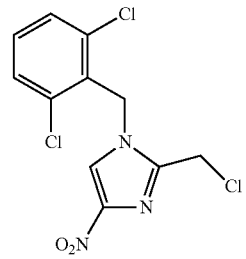 [SMILES: O=[N+]([O-])c1cn(Cc2c(Cl)cccc2Cl)c(CCl)n1]

210 mg (0.70 mmol) of the compound from Example 37A were dissolved in 10 ml of dichloromethane, and 145 μl (1.04 mmol) of triethylamine and 61 μl (0.83 mmol) of thionyl chloride were added at 0° C. The mixture was stirred at RT for 24 h. A further 200 μl (2.72 mmol) of thionyl chloride were then added, and the mixture was stirred under reflux for 15 min. Under reduced pressure, the reaction mixture was then freed from all volatile components. This gave, in a purity of 88%, 200 mg (80% of theory) of the target compound, which was reacted further without any further purification.

LC/MS [Method 3]: $R_t$=1.16 min; MS [ESIpos]: m/z=320 and 322 (M+H)$^+$ $^1$H-NMR (400 MHz, DMSO-d$_6$): δ=5.03 (s, 2H), 5.61 (s, 2H), 7.52-7.57 (m, 1H), 7.62-7.65 (m, 2H), 7.86-7.88 (m, 1H).

Example 42A 4-(Bromomethyl)-1-(2-chlorophenyl)-1H-imidazole

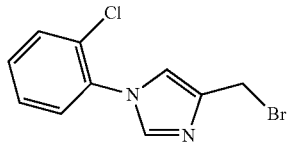

48 mg (0.16 mmol) of the compound from Example 38A and 63 mg (0.24 mmol) of triphenylphosphine were dissolved in 1.6 ml of THF, and 80 mg (0.24 mmol) of carbon tetrabromide were added at RT. The mixture was then stirred at RT for 16 h. For work-up, the mixture was filtered through 20 g of kieselguhr, the filter residue was rinsed with ethyl acetate and the filtrate was concentrated under reduced pressure. The residue was purified chromatographically on silica gel (mobile phase: cyclohexane/ethyl acetate 5:1, then 1:1). This gave 17 mg (39% of theory) of the target compound which was immediately reacted further.

LC/MS [Method 4]: $R_t$=0.34 min; MS [ESIpos]: m/z=209 (M-Br+OH+H)$^+$.

Example 43A 4-(Bromomethyl)-1-(2-chlorophenyl)-1H-pyrazole

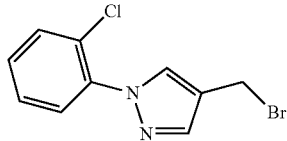 [SMILES: Clc1ccccc1-n1cc(CBr)cn1]

61 mg (0.27 mmol) of the compound from Example 39A and 105 mg (0.40 mmol) of triphenylphosphine were dissolved in 1.6 ml of THF, and 132 mg (0.40 mmol) of carbon tetrabromide were added at RT. The mixture was then stirred at RT for 16 h. For work-up, the mixture was filtered through 20 g of kieselguhr, the filter residue was rinsed with ethyl acetate and the filtrate was concentrated under reduced pressure. The residue was purified chromatographically on silica gel (mobile phase: cyclohexane/ethyl acetate 10:1, then 5:1). This gave 30 mg (42% of theory) of the target compound which was immediately reacted further.

LC/MS [Method 4]: $R_t$=0.67 min; MS [ESIpos]: m/z=209 (M-Br+OH+H)$^+$.

Example 44A

Ethyl 2-(2-chlorophenyl)-1,3-oxazole-5-carboxylate

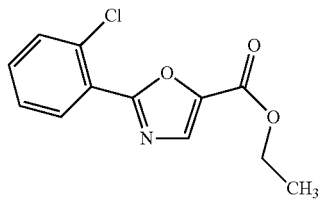 [SMILES: CCOC(=O)c1cnc(-c2ccccc2Cl)o1]

Under argon, 300 mg (1.71 mmol) of ethyl 2-bromo-1,3-oxazole-5-carboxylate together with 422 mg (2.56 mmol) of 2-chlorophenylboronic acid were dissolved in 7 ml of toluene, and 67 mg (0.17 mmol) of 2-dicyclohexylphosphino-2'-(N,N-dimethylamino)biphenyl, 78 mg (0.085 mmol) of tris(dibenzylideneacetone)dipalladium and 725 mg (3.42 mmol) of potassium phosphate were added successively. The mixture was heated to 110° C. and stirred at this temperature for 20 h. For work-up, the reaction mixture was allowed to cool to RT and diluted with 20 ml of ethyl acetate and 20 ml of water. After phase separation, the aqueous phase was extracted two more times with in each case 20 ml of ethyl acetate. The combined organic phases were dried over magnesium sulfate, filtered and concentrated under reduced pressure. The residue was purified by preparative HPLC [Method 19]. This gave 217 mg (50% of theory) of the target compound.

LC/MS [Method 3]: $R_t$=1.21 min; MS [ESIpos]: m/z=252 (M+H)$^+$.

Example 45A

Ethyl 2-(2,3-dichlorophenyl)-1,3-oxazole-5-carboxylate

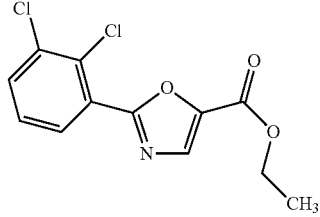 [SMILES: CCOC(=O)c1cnc(-c2cccc(Cl)c2Cl)o1]

300 mg (1.71 mmol) of ethyl 2-bromo-1,3-oxazole-5-carboxylate were reacted analogously to the process of Example 44A. This gave 174 mg (31% of theory) of the target compound in a purity of 87%.

LC/MS [Method 4]: $R_t$=1.19 min; MS [ESIpos]: m/z=286 and 288 (M+H)$^+$.

Example 46A

Methyl 5-(2-chlorophenyl)thiophene-2-carboxylate

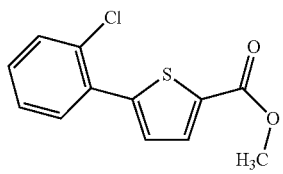 [SMILES: COC(=O)c1ccc(-c2ccccc2Cl)s1]

Under argon, 310 mg (1.40 mmol) of methyl 5-bromothiophene-2-carboxylate together with 328 mg (2.10 mmol) of 2-chlorophenylboronic acid were dissolved in 10 ml of dioxane, and 81 mg (0.07 mmol) of tetrakis(triphenylphosphine)palladium(0) were added. The mixture was heated to 110° C., 1.4 ml (2.80 mmol) of 2 M aqueous sodium carbonate solution were added and the mixture was stirred at this temperature for 20 h. For work-up, the reaction mixture was allowed to cool to RT and diluted with 20 ml of ethyl acetate and 20 ml of water. After phase separation, the aqueous phase was extracted two more times with in each case 20 ml of ethyl acetate. The combined organic phases were dried over sodium sulfate, filtered and concentrated under reduced pressure. The residue was purified chromatographically on silica gel (mobile phase: cyclohexane/ethyl acetate 15:1, then 10:1). This gave 289 mg (61% of theory) of the target compound in a purity of 75%.

LC/MS [Method 2]: $R_t$=2.58 min; MS [ESIpos]: m/z=253 (M+H)$^+$ $^1$H-NMR (400 MHz, DMSO-$d_6$): δ=3.85 (s, 3H), 7.45-7.48 (m, 2H), 7.53 (d, 1H), 7.64 (dd, 1H), 7.73 (dd, 1H), 7.85 (d, 1H).

Example 47A

Methyl 5-(2,3-dichlorophenyl)thiophene-2-carboxylate

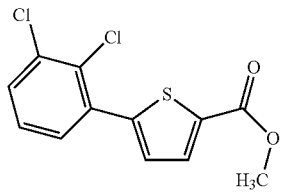 [SMILES: COC(=O)c1ccc(-c2cccc(Cl)c2Cl)s1]

300 mg (1.36 mmol) of methyl 5-bromothiophene-2-carboxylate were reacted analogously to the process of Example 46A. This gave 273 mg (58% of theory) of the target compound in a purity of 83%.

LC/MS [Method 4]: $R_t$=1.30 min; MS [ESIpos]: m/z=287 (M+H)$^+$.

Example 48A 5-(2-Chlorophenyl)thiophene-2-carboxylic acid

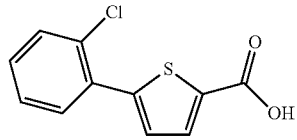 [SMILES: O=C(O)c1ccc(-c2ccccc2Cl)s1]

289 mg (1.14 mmol) of the compound from Example 46A were dissolved in 2 ml of THF/methanol (1:1), and 1.14 ml (2.29 mmol) of 2 M aqueous sodium hydroxide solution were added. The reaction mixture was stirred at 80° C. for 2 h. After cooling to RT, the solvent was removed on a rotary evaporator and the residue was taken up in 5 ml of water and washed with 5 ml of ethyl acetate. The aqueous phase was acidified with 1 N hydrochloric acid and extracted twice with in each case 5 ml of ethyl acetate. The combined organic phases were dried over sodium sulfate, filtered and concentrated under reduced pressure. This gave, in a purity of 91%, 218 mg (73% of theory) of the target compound.

LC/MS [Method 2]: $R_t$=2.16 min; MS [ESIpos]: m/z=239 (M+H)$^+$.

Example 49A 5-(2,3-Dichlorophenyl)thiophene-2-carboxylic acid

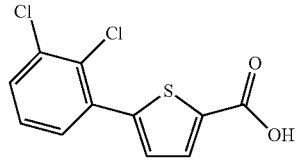 [SMILES: O=C(O)c1ccc(-c2cccc(Cl)c2Cl)s1]

273 mg (0.79 mmol) of the compound from Example 47A were reacted analogously to the process of Example 48A. This gave, in a purity of 92%, 228 mg (97% of theory) of the target compound.

LC/MS [Method 4]: $R_t$=1.07 min; MS [ESIpos]: m/z=271 and 273 (M–H)$^-$.

Example 50A

[2-(2-Chlorophenyl)-1,3-oxazol-5-yl]methanol

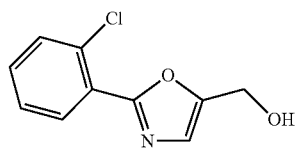 [SMILES: OCc1cnc(-c2ccccc2Cl)o1]

217 mg (0.86 mmol) of the compound from Example 44A were reacted analogously to the process of Example 39A. This gave, in a purity of 89%, 181 mg (89% of theory) of the target compound.

LC/MS [Method 4]: $R_t$=0.75 min; MS [ESIpos]: m/z=210 (M+H)$^+$.

Example 51A

[2-(2,3-Dichlorophenyl)-1,3-oxazol-5-yl]methanol

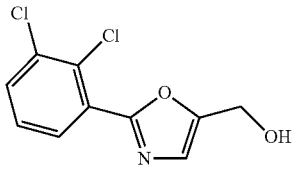 [SMILES: OCc1cnc(-c2cccc(Cl)c2Cl)o1]

186 mg (0.65 mmol) of the compound from Example 45A were reacted analogously to the process of Example 39A. This gave, in a purity of 86%, 89 mg (48% of theory) of the target compound.

LC/MS [Method 4]: $R_t$=0.87 min; MS [ESIpos]: m/z=244 and 246 (M+H)$^+$.

Example 52A

[5-(2-Chlorophenyl)-2-thienyl]methanol

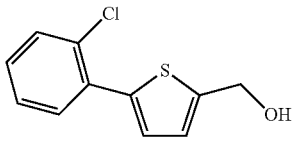 [SMILES: OCc1ccc(-c2ccccc2Cl)s1]

350 mg (1.47 mmol) of the compound from Example 48A were dissolved in 5 ml of THF, the mixture was cooled to 0° C. and 0.20 ml (1.47 mmol) of triethylamine and 0.21 ml (1.61 mmol) of isobutyl chloroformate were added. The mixture was stirred at 0° C. for 1 h. The suspension was then filtered through a Seitz frit into a flask cooled to 0° C., and the residue was rinsed with about 2 ml of THF. With vigorous stirring, the filtrate obtained was then added to a solution, cooled to 0° C., of 166 mg (4.40 mmol) of sodium borohydride in 2 ml of water. After 1 h, 5 ml of saturated sodium bicarbonate solution were added and the mixture was warmed to RT. The mixture was extracted with 15 ml of ethyl acetate. The organic phase was washed successively with in each case 5 ml of saturated sodium bicarbonate solution and saturated sodium chloride solution. After drying over sodium sulfate, the mixture was filtered and concentrated under reduced pressure. The crude product was purified by chromatography on silica gel (mobile phase: cyclohexane/ethyl acetate 10:1, then 5:1). This gave 252 mg (63% of theory) of the title compound in a purity of 83%.

LC/MS [Method 3]: $R_t$=1.12 min; MS [ESIpos]: m/z=206 (M−H$_2$O+H)$^+$ $^1$H-NMR (400 MHz, DMSO-d$_6$): δ=4.66 (d, 2H), 5.54 (t, 1H), 6.99 (d, 1H), 7.27 (d, 1H), 7.33-7.43 (m, 2H), 7.55-7.62 (m, 2H).

Example 53A

[5-(2,3-Dichlorophenyl)-2-thienyl]methanol

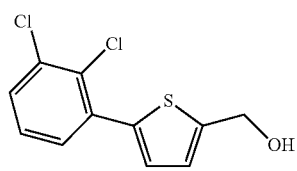 [SMILES: OCc1ccc(-c2cccc(Cl)c2Cl)s1]

268 mg (0.98 mmol) of the compound from Example 49A were reacted analogously to the process of Example 52A. This gave, in a purity of 87%, 184 mg (63% of theory) of the target compound.

LC/MS [Method 4]: $R_t$=1.10 min; MS [ESIpos]: m/z=241 and 243 (M−H$_2$O+H)$^+$ $^1$H-NMR (400 MHz, DMSO-d$_6$): δ=4.67 (d, 2H), 5.58 (t, 1H), 7.01 (d, 1H), 7.29 (d, 1H), 7.39-7.44 (m, 1H), 7.55-7.58 (m, 1H), 7.62-7.66 (m, 1H).

Example 54A 5-(Bromomethyl)-2-(2-chlorophenyl)-1,3-oxazole

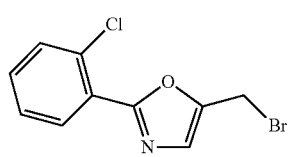 [SMILES: Clc1ccccc1-c1ncc(CBr)o1]

181 mg (0.77 mmol) of the compound from Example 50A and 242 mg (0.92 mmol) of triphenyl-phosphine were dissolved in 4 ml of THF, and 306 mg (0.92 mmol) of carbon tetrabromide were added at RT. The mixture was then stirred at RT for 16 h. For work-up, the mixture was filtered through 20 g of kieselguhr, the filter residue was rinsed with ethyl acetate and the filtrate was concentrated under reduced pressure. The residue was purified by preparative HPLC [Method 19]. This gave 112 mg (42% of theory) of the target compound in a purity of 80% which were immediately reacted further.

LC/MS [Method 4]: $R_t$=1.09 min; MS [ESIpos]: m/z=272 and 274 (M+H)$^+$.

Example 55A 5-(Bromomethyl)-2-(2,3-dichlorophenyl)-1,3-oxazole

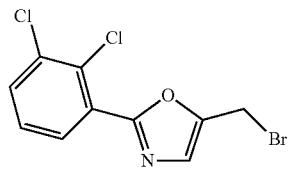 [SMILES: Clc1cccc(-c2ncc(CBr)o2)c1Cl]

89 mg (0.31 mmol) of the compound from Example 51A were reacted analogously to the process of Example 54A. This gave, in a purity of 87%, 50 mg (52% of theory) of the target compound.

LC/MS [Method 4]: $R_t$=1.15 min; MS [ESIpos]: m/z=308 (M+H)$^+$.

Example 56A 2-(Bromomethyl)-5-(2-chlorophenyl)thiophene

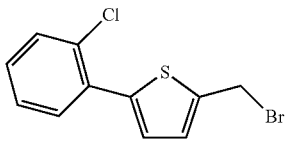 [SMILES: Clc1ccccc1-c1ccc(CBr)s1]

200 mg (0.74 mmol) of the compound from Example 52A and 291 mg (1.11 mmol) of triphenylphosphine were dissolved in 8 ml of THF, and 367 mg (1.11 mmol) of carbon tetrabromide were added at RT. The mixture was then stirred at RT for 16 h. For work-up, the mixture was filtered through 20 g of kieselguhr, the filter residue was rinsed with ethyl acetate and the filtrate was concentrated under reduced pressure. The residue was purified chromatographically on silica gel (mobile phase: cyclohexane/ethyl acetate 10:1, then 5:1). This gave 113 mg of contaminated target product (32% pure, 17% of theory) which were immediately reacted further.

LC/MS [Method 4]: $R_t$=1.37 min; MS [ESIpos]: m/z=207 (M−HBr)$^+$.

Example 57A 2-(Bromomethyl)-5-(2,3-dichlorophenyl)thiophene

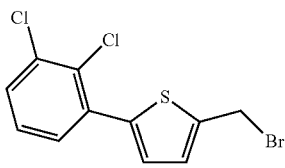 [SMILES: Clc1cccc(-c2ccc(CBr)s2)c1Cl]

89 mg (0.31 mmol) of the compound from Example 53A were reacted analogously to the process of Example 56A. This gave, in a purity of 86%, 70 mg (30% of theory) of the target compound.

LC/MS [Method 4]: $R_t$=1.08 min; MS [ESIpos]: m/z=241 and 243 (M−HBr)$^+$.

Example 58A

Methyl 2-[2-(trifluoromethyl)phenyl]isonicotinate

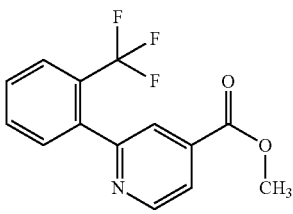 [SMILES: COC(=O)c1ccnc(-c2ccccc2C(F)(F)F)c1]

Under an atmosphere of argon, 500 mg (2.31 mmol) of methyl 2-bromoisonicotinate and 694 mg (3.47 mmol) of 2-(trifluoromethyl)phenylboronic acid were dissolved in 10 ml of toluene. 106 mg (0.12 mmol) of tris(dibenzylideneacetone)dipalladium, 91 mg (0.23 mmol) of tri-tert-butylphosphine and 982 mg (4.63 mmol) of potassium phosphate were then added, and under argon the mixture was heated to 110° C. for 20 h. For work-up, the mixture was diluted at RT with 15 ml of ethyl acetate and 15 ml of water, the organic phase was separated off and the aqueous phase was extracted two more times with in each case 15 ml of ethyl acetate. The combined organic phases were dried over magnesium sulfate, filtered and concentrated under reduced pressure. The crude product was purified by chromatography on silica gel (mobile phase: cyclohexane/ethyl acetate 20:1, then 10:1). This gave 498 mg (59% of theory) of the target compound in a purity of 77%. A second product fraction of lower purity was purified further according to Method 19. This gave a further 54 mg (8% of theory) of the target compound.

LC/MS [Method 2]: $R_t$=2.21 min; MS [ESIpos]: m/z=282 (M+H)$^+$.

Example 59A

Methyl 2-(2-chlorophenyl)isonicotinate

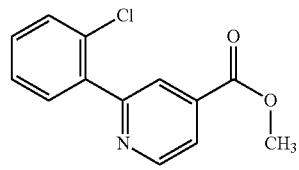 [SMILES: COC(=O)c1ccnc(-c2ccccc2Cl)c1]

500 mg (2.31 mmol) of methyl 2-bromoisonicotinate and 597 mg (3.47 mmol) of 2-chlorophenylboronic acid were reacted with one another analogously to the process of Example 58A. This gave 323 mg (56% of theory) of the target compound.

LC/MS [Method 3]: $R_t$=1.15 min; MS [ESIpos]: m/z=248 (M+H)$^+$.

Example 60A

Methyl 2-(2,3-dichlorophenyl)isonicotinate

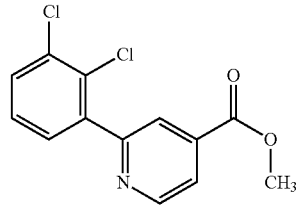 [SMILES: COC(=O)c1ccnc(-c2cccc(Cl)c2Cl)c1]

Under an atmosphere of argon, 250 mg (1.16 mmol) of methyl 2-bromoisonicotinate and 331 mg (1.74 mmol) of 2,3-dichlorophenylboronic acid were dissolved in 5 ml of toluene. 53 mg (0.06 mmol) of tris(dibenzylideneacetone) dipalladium, 46 mg (0.12 mmol) of 2-dicyclohexylphosphino-2'-(N,N-dimethylamino)biphenyl and 491 mg (2.31 mmol) of potassium phosphate were then added, and under argon the mixture was heated to 110° C. for 20 h. For work-up, the mixture was diluted at RT with 15 ml of ethyl acetate and 15 ml of water, the organic phase was separated off and the aqueous phase was extracted two more times with in each case 15 ml of ethyl acetate. The combined organic phases were dried over magnesium sulfate, filtered and concentrated under reduced pressure. The crude product was purified chromatographically [Method 19]. This gave 138 mg (42% of theory) of the target compound in a purity of 87%.

LC/MS [Method 4]: $R_t$=1.13 min; MS [ESIpos]: m/z=282 and 284 (M+H)$^+$.

Example 61A

{2-[2-(Trifluoromethyl)phenyl]pyridin-4-yl}methanol

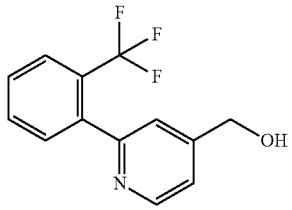 [SMILES: OCc1ccnc(-c2ccccc2C(F)(F)F)c1]

432 mg (1.54 mmol) of the compound from Example 58A were dissolved in 10 ml of THF, and 1.08 ml (1.08 mmol) of a 1 M solution of lithium aluminum hydride in THF were added at −10° C. After the addition had ended, the mixture was stirred at RT for 2 h. For work-up, 4 ml of a saturated sodium potassium tartrate solution were added at RT, and the mixture was extracted with 15 ml of ethyl acetate. The organic phase was washed once with 10 ml of saturated sodium potassium tartrate solution, dried over magnesium sulfate, filtered and concentrated under reduced pressure. This gave 497 mg (>100% of theory) of the target compound which were reacted further without any further purification.

LC/MS [Method 2]: $R_t$=1.40 min; MS [ESIpos]: m/z=254 (M+H)$^+$.

Example 62A

[2-(2-Chlorophenyl)pyridin-4-yl]methanol

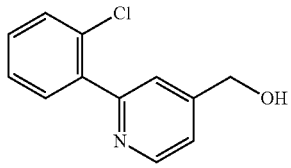 [SMILES: OCc1ccnc(-c2ccccc2Cl)c1]

323 mg (1.24 mmol) of the compound from Example 59A were reacted analogously to the process of Example 61A. This gave 303 mg (>100% of theory) of the target compound which were reacted further without any further purification.

$^1$H-NMR (400 MHz, DMSO-d$_6$): δ=4.61 (d, 2H), 5.47 (t, 1H), 7.33-7.37 (m, 1H), 7.42-7.48 (m, 2H), 7.53-7.60 (m, 3H), 8.61 (d, 1H).

Example 63A

[2-(2,3-Dichlorophenyl)pyridin-4-yl]methanol

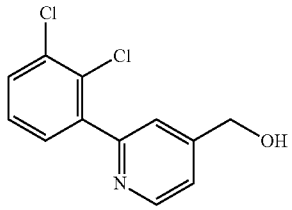 [SMILES: OCc1ccnc(-c2cccc(Cl)c2Cl)c1]

138 mg (0.49 mmol) of the compound from Example 60A were reacted analogously to the process of Example 61A. This gave 132 mg (90% of theory) of the target compound in a purity of 84% which were reacted further without any further purification.

LC/MS [Method 2]: $R_t$=0.78 min; MS [ESIpos]: m/z=254 and 256 (M+H)$^+$.

Example 64A 4-(Bromomethyl)-2-[2-(trifluoromethyl)phenyl]pyridine

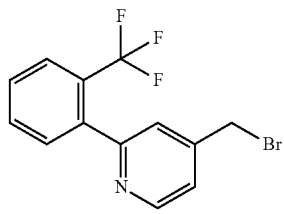 [SMILES: FC(F)(F)c1ccccc1-c1cc(CBr)ccn1]

495 mg (1.96 mmol) of the compound from Example 61A and 615 mg (2.35 mmol) of triphenylphosphine were dissolved in 15 ml of THF, and 778 mg (2.35 mmol) of carbon tetrabromide were added at RT. After the addition had ended, the mixture was stirred ar RT for 16 h. For work-up, the mixture was filtered through 20 g of kieselguhr and the filtrate was concentrated under reduced pressure. The residue was purified chromatographically on silica gel (mobile phase: first cyclohexane/ethyl acetate 70:30, then ethyl acetate). This gave, in a purity of 90%, 149 mg (22% of theory) of the target compound, which were immediately reacted further.

LC/MS [Method 3]: $R_t$=1.23 min; MS [ESIpos]: m/z=318 (M+H)$^+$.

Example 65A 4-(Bromomethyl)-2-(2-chlorophenyl)pyridine

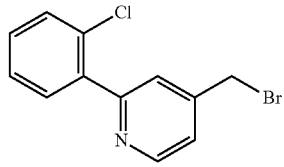 [SMILES: Clc1ccccc1-c1cc(CBr)ccn1]

294 mg (1.34 mmol) of the compound from Example 62A were reacted analogously to the process of Example 64A. This gave, in a purity of 89%, 242 mg (57% of theory) of the target compound, which were immediately reacted further.

LC/MS [Method 4]: $R_t$=1.08 min; MS [ESIpos]: m/z=282 and 284 (M+H)$^+$.

Example 66A 4-(Bromomethyl)-2-(2,3-dichlorophenyl)pyridine

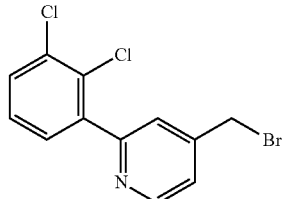

131 mg (0.52 mmol) of the compound from Example 63A were reacted analogously to the process of Example 54A. This gave 81 mg (50% of theory) of the target compound, which were immediately reacted further.

LC/MS [Method 4]: $R_t$=1.08 min; MS [ESIpos]: m/z=316, 318 and 320 (M+H)$^+$.

Example 67A

4-Methyl-2-[2-(trifluoromethyl)phenyl]pyrimidine

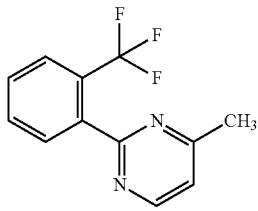 [SMILES: Cc1ccnc(-c2ccccc2C(F)(F)F)n1]

Under an atmosphere of argon, 250 mg (1.95 mmol) of 2-chloro-4-methylpyrimidine and 583 mg (2.92 mmol) of 2-(trifluoromethyl)phenylboronic acid were dissolved in 8 ml of toluene. 89 mg (0.10 mmol) of tris(dibenzylideneacetone) dipalladium, 77 mg (0.19 mmol) of 2-dicyclohexyl-phosphino-2'-(N,N-dimethylamino)biphenyl and 826 mg (3.89 mmol) of potassium phosphate were then added, and under argon the mixture was heated at 110° C. for 20 h. For work-up, the mixture was diluted at RT with 15 ml of ethyl acetate and 15 ml of water, the organic phase was separated off and the aqueous phase extracted two more times with in each case 15 ml of ethyl acetate. The combined organic phases were dried over magnesium sulfate, filtered and concentrated under reduced pressure. The crude product was purified chromatographically on silica gel (mobile phase: cyclohexane/ethyl acetate 9:1, then 4:1). This gave 249 mg (54% of theory) of the target compound in a purity of 87%.

LC/MS [Method 3]: $R_t$=1.02 min; MS [ESIpos]: m/z=239 (M+H)$^+$.

Example 68A 2-(2-Chlorophenyl)-4-methylpyrimidine

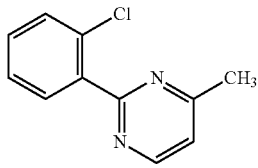

250 mg (1.95 mmol) of 2-chloro-4-methylpyrimidine were reacted analogously to the process of Example 67A. This gave 202 mg (34% of theory) of the target compound in a purity of 66%.

LC/MS [Method 3]: $R_t$=0.90 min; MS [ESIpos]: m/z=205 (M+H)$^+$.

Example 69A

4-Methyl-6-[2-(trifluoromethyl)phenyl]pyrimidine

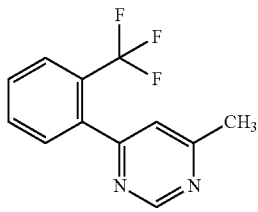 [SMILES: Cc1cc(-c2ccccc2C(F)(F)F)ncn1]

250 mg (1.95 mmol) of 4-chloro-6-methylpyrimidine were reacted analogously to the process of Example 67A. This gave 332 mg (70% of theory) of the target compound.

LC/MS [Method 3]: $R_t$=1.04 min; MS [ESIpos]: m/z=239 (M+H)$^+$.

Example 70A

4-Methyl-6-[2-chlorophenyl]pyrimidine

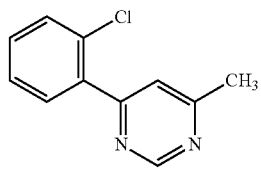

250 mg (1.95 mmol) of 4-chloro-6-methylpyrimidine were reacted analogously to the process of Example 67A. This gave 191 mg (43% of theory) of the target compound.

LC/MS [Method 3]: $R_t$=0.99 min; MS [ESIpos]: m/z=205 (M+H)$^+$.

Example 71A 4-(2,3-Dichlorophenyl)-6-methylpyrimidine

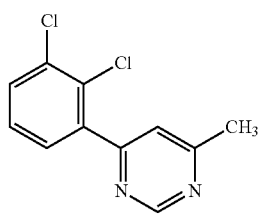

250 mg (1.95 mmol) of 4-chloro-6-methylpyrimidine were reacted analogously to the process of Example 67A. This gave 185 mg (40% of theory) of the target compound.

LC/MS [Method 6]: $R_t$=1.93 min; MS [ESIpos]: m/z=239 and 241 (M+H)$^+$.

Example 72A

2-Methyl-5-[2-(trifluoromethyl)phenyl]-1,3,4-thiadiazole

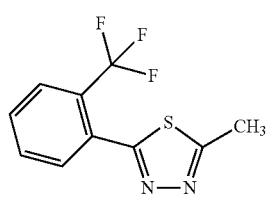

500 mg (1.95 mmol) of 2-bromo-5-methyl-1,3,4-thiadiazole were reacted analogously to the process of Example 67A. This gave 331 mg (36% of theory) of the target compound in a purity of 75%.

LC/MS [Method 4]: $R_t$=0.93 min; MS [ESIpos]: m/z=245 (M+H)$^+$.

Example 73A 2-(2-Chlorophenyl)-5-methyl-1,3,4-thiadiazole

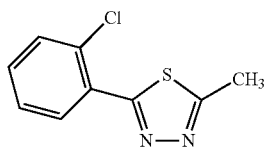

315 mg (1.76 mmol) of 2-bromo-5-methyl-1,3,4-thiadiazole were reacted analogously to the process of Example 44A. This gave 155 mg (36% of theory) of the target compound.

LC/MS [Method 4]: $R_t$=0.92 min; MS [ESIpos]: m/z=211 (M+H)$^+$ $^1$H-NMR (400 MHz, DMSO-d$_6$): δ=2.82 (s, 3H), 7.52-7.62 (m, 2H), 7.70 (dd, 1H), 8.10 (dd, 1H).

Example 74A 2-(2,3-Dichlorophenyl)-5-methyl-1,3,4-thiadiazole

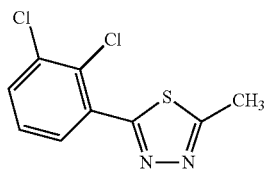

310 mg (1.73 mmol) of 2-bromo-5-methyl-1,3,4-thiadiazole were reacted analogously to the process of Example 44A. This gave 91 mg (21% of theory) of the target compound.

LC/MS [Method 6]: $R_t$=2.13 min; MS [ESIpos]: m/z=245 and 247 (M+H)$^+$.

Example 75A 5-(2-Chlorophenyl)-2-methyl-1,3-thiazole

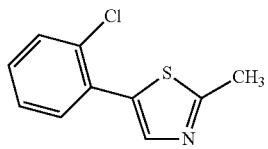

756 mg (2.92 mmol) of 5-bromo-2-methyl-1,3-thiazole hydrobromide were reacted analogously to the process of Example 67A. In this reaction, 2.49 g (11.68 mmol) of potassium phosphate were used as base. This gave 181 mg (30% of theory) of the target compound.

LC/MS [Method 2]: $R_t$=2.21 min; MS [ESIpos]: m/z=210 (M+H)$^+$.

Example 76A

2-Methyl-5-[2-(trifluoromethyl)phenyl]-1,3-thiazole

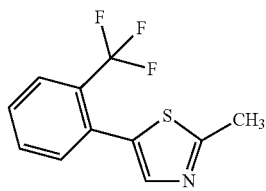 [SMILES: Cc1ncc(-c2ccccc2C(F)(F)F)s1]

430 mg (1.66 mmol) of 5-bromo-2-methyl-1,3-thiazole hydrobromide were reacted analogously to the process of Example 44A. In this reaction, 1.41 g (6.64 mmol) of potassium phosphate were used as base. This gave 52 mg (13% of theory) of the target compound.

LC/MS [Method 4]: $R_t$=1.08 min; MS [ESIpos]: m/z=244 (M+H)$^+$.

Example 77A 5-(3-Chloro-2-fluorophenyl)-2-methyl-1,3-thiazole

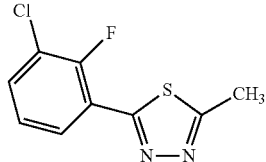

586 mg (2.26 mmol) of 5-bromo-2-methyl-1,3-thiazole hydrobromide were reacted analogously to the process of Example 44A. In this reaction, 1.92 g (9.05 mmol) of potassium phosphate were used as base. This gave 147 mg (29% of theory) of the target compound.

LC/MS [Method 3]: $R_t$=1.27 min; MS [ESIpos]: m/z=228 (M+H)$^+$.

Example 78A

5-[2-Fluoro-3-(trifluoromethyl)phenyl]-2-methyl-1,3-thiazole

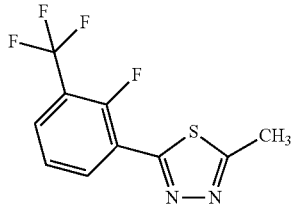 [SMILES: Cc1nnc(-c2cccc(C(F)(F)F)c2F)s1]

350 mg (1.35 mmol) of 5-bromo-2-methyl-1,3-thiazole hydrobromide were reacted analogously to the process of Example 44A. In this reaction, 1.15 g (5.41 mmol) of potassium phosphate were used as base. The reaction time was 2 h.

Example 79A 5-(2-Chlorophenyl)-2-methyl-4-(trifluoromethyl)-1,3-thiazole

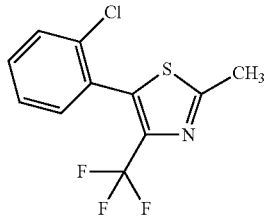 [SMILES: Cc1nc(C(F)(F)F)c(-c2ccccc2Cl)s1]

635 mg (1.94 mmol) of 5-bromo-2-methyl-4-(trifluoromethyl)-1,3-thiazole hydrobromide were reacted analogously to the process of Example 44A. In this reaction, 1.15 g (5.41 mmol) of potassium phosphate were used as base. This gave 142 mg (26% of theory) of the target compound.

LC/MS [Method 3]: $R_t$=1.34 min; MS [ESIpos]: m/z=278 (M+H)$^+$.

Example 80A 4-(Bromomethyl)-2-[2-(trifluoromethyl)phenyl]pyrimidine

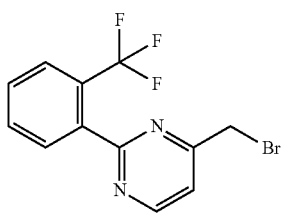

247 mg (1.04 mmol) of the compound from Example 67A together with 185 mg (1.04 mmol) of N-bromosuccinimide and 17 mg (0.10 mmol) of 2,2'-azobis-2-methylpropanenitrile in 3 ml of carbon tetrachloride were heated under reflux for 18 h. For work-up, the reaction mixture was cooled to RT, and 10 ml of dichloromethane were added. The mixture was washed with 5 ml of water, and the aqueous phase was re-extracted twice with in each case 5 ml of dichloromethane. The combined organic phases were dried over magnesium sulfate, filtered and concentrated under reduced pressure. The crude product was briefly dried under high vacuum and reacted further without further purification. This gave 303 mg of product which contained the target compound in a purity of 20% (corresponds to 20% of theory). The main component of the crude product was unreacted starting material (Example 67A).

LC/MS [Method 4]: $R_t$=1.02 min; MS [ESIpos]: m/z=317 and 319 (M+H)$^+$.

Example 81A 4-(Bromomethyl)-2-(2-chlorophenyl)pyrimidine

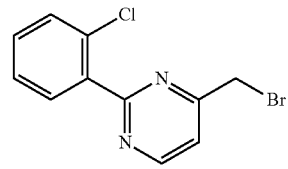 [SMILES: Clc1ccccc1-c1nccc(CBr)n1]

200 mg (0.98 mmol) of the compound from Example 68A were reacted analogously to the process of Example 80A. This gave 259 mg (19% of theory) of the target compound in a purity of about 20%. The main component of the crude product was unreacted starting material (Example 68A).

LC/MS [Method 4]: $R_t$=1.00 min; MS [ESIpos]: m/z=283 and 285 (M+H)$^+$.

Example 82A 4-(Bromomethyl)-6-[2-(trifluoromethyl)phenyl]pyrimidine

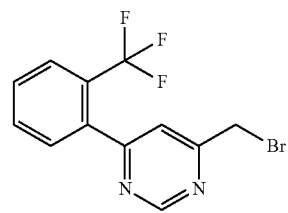 [SMILES: FC(F)(F)c1ccccc1-c1cc(CBr)ncn1]

332 mg (1.39 mmol) of the compound from Example 69A were reacted analogously to the process of Example 80A. The crude product was purified chromatographically [Method 19]. This gave 37 mg (8% of theory) of the target compound.

LC/MS [Method 3]: $R_t$=1.19 min; MS [ESIpos]: m/z=317 and 319 (M+H)$^+$.

Example 83A 4-(Bromomethyl)-6-[2-chlorophenyl]pyrimidine

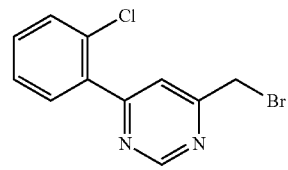 [SMILES: Clc1ccccc1-c1cc(CBr)ncn1]

191 mg (0.93 mmol) of the compound from Example 70A were reacted analogously to the process of Example 80A. The crude product was purified chromatographically [Method 19]. This gave 27 mg (10% of theory) of the target compound.

Example 84A 4-(Bromomethyl)-6-(2,3-dichlorophenyl)pyrimidine

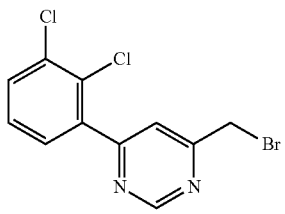 [SMILES: Clc1cccc(-c2cc(CBr)ncn2)c1Cl]

185 mg (0.93 mmol) of the compound from Example 71A were reacted analogously to the process of Example 80A. The crude product was purified chromatographically [Method 19]. This gave 23 mg (9% of theory) of the target compound.

LC/MS [Method 6]: $R_t$=2.32 min; MS [ESIpos]: m/z=317, 319 and 321 (M+H)$^+$.

Example 85A 2-(Bromomethyl)-5-[2-(trifluoromethyl)phenyl]-1,3,4-thiadiazole

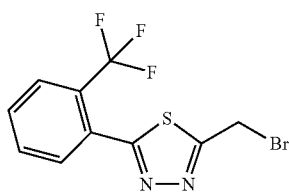 [SMILES: FC(F)(F)c1ccccc1-c1nnc(CBr)s1]

172 mg (0.70 mmol) of the compound from Example 72A together with 251 mg (1.41 mmol) of N-bromosuccinimide and 12 mg (0.07 mmol) of 2,2'-azobis-2-methylpropanenitrile in 5 ml of carbon tetrachloride were heated under reflux for 8 h. For work-up, the reaction mixture was cooled to RT, and 10 ml of dichloromethane were added. The mixture was washed with 5 ml of water, and the aqueous phase was re-extracted twice with in each case 5 ml of dichloromethane. The combined organic phases were dried over magnesium sulfate, filtered and concentrated under reduced pressure. The crude product was purified chromatographically [Method 19]. This gave 33 mg (15% of theory) of the target compound.

LC/MS [Method 4]: $R_t$=1.05 min; MS [ESIpos]: m/z=323 and 325 (M+H)$^+$.

Example 86A 2-(Bromomethyl)-5-(2-chlorophenyl)-1,3,4-thiadiazole

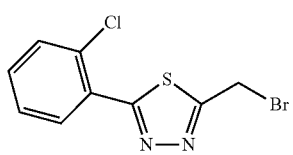 [SMILES: Clc1ccccc1-c1nnc(CBr)s1]

185 mg (0.88 mmol) of the compound from Example 73A were reacted analogously to the process of Example 85A. The crude product was purified chromatographically [Method 19]. This gave 31 mg (12% of theory) of the target compound.

LC/MS [Method 6]: $R_t$=2.21 min; MS [ESIpos]: m/z=289 and 291 (M+H)$^+$.

Example 87A 2-(Bromomethyl)-5-(2,3-dichlorophenyl)-1,3,4-thiadiazole

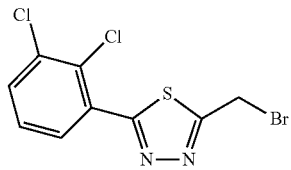 [SMILES: Clc1cccc(-c2nnc(CBr)s2)c1Cl]

91 mg (0.37 mmol) of the compound from Example 74A were reacted analogously to the process of Example 85A. The crude product was purified chromatographically [Method 19]. This gave 38 mg (32% of theory) of the target compound.

LC/MS [Method 3]: $R_t$=1.30 min; MS [ESIpos]: m/z=323, 325 and 327 (M+H)$^+$.

Example 88A 2-(Bromomethyl)-5-(2-chlorophenyl)-1,3-thiazole

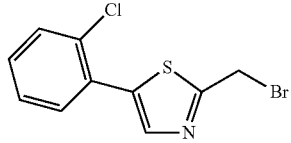 [SMILES: Clc1ccccc1-c1cnc(CBr)s1]

180 mg (0.86 mmol) of the compound from Example 75A together with 229 mg (1.29 mmol) of N-bromosuccinimide and 14 mg (0.09 mmol) of 2,2'-azobis-2-methylpropanenitrile in 5 ml of carbon tetrachloride were heated under reflux for 8 h. For work-up, the reaction mixture was cooled to RT, and 10 ml of dichloromethane were added. The mixture was washed with 5 ml of water, and the aqueous phase was re-extracted twice with in each case 5 ml of dichloromethane. The combined organic phases were dried over magnesium sulfate, filtered and concentrated under reduced pressure. The crude product was purified chromatographically [Method 19]. This gave 66 mg (27% of theory) of the target compound.

LC/MS [Method 2]: $R_t$=2.42 min; MS [ESIpos]: m/z=288 and 290 (M+H)$^+$.

Example 89A 2-(Bromomethyl)-5-[2-(trifluoromethyl)phenyl]-1,3-thiazole

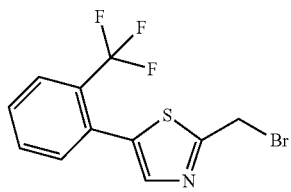 [SMILES: FC(F)(F)c1ccccc1-c1cnc(CBr)s1]

110 mg (0.45 mmol) of the compound from Example 76A were reacted analogously to the process of Example 88A. The crude product was purified chromatographically [Method 19]. This gave 40 mg (27% of theory) of the target compound.

LC/MS [Method 4]: $R_t$=1.17 min; MS [ESIpos]: m/z=322 and 324 (M+H)$^+$.

Example 90A 2-(Bromomethyl)-5-(3-chloro-2-fluorophenyl)-1,3-thiazole

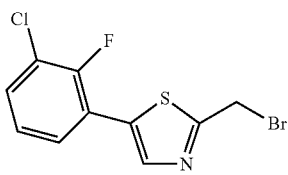 [SMILES: Fc1c(Cl)cccc1-c1cnc(CBr)s1]

142 mg (0.62 mmol) of the compound from Example 77A were reacted analogously to the process of Example 88A. The crude product was purified chromatographically [Method 19]. This gave 70 mg (37% of theory) of the target compound.

LC/MS [Method 4]: $R_t$=1.21 min; MS [ESIpos]: m/z=306 and 308 (M+H)$^+$.

Example 91A 2-(Bromomethyl)-5-[2-fluoro-3-(trifluoromethyl)phenyl]-1,3-thiazole

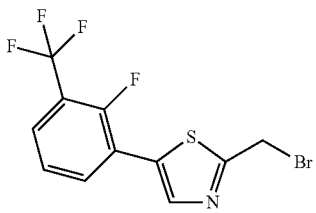 [SMILES: Fc1c(-c2cnc(CBr)s2)cccc1C(F)(F)F]

120 mg (0.46 mmol) of the compound from Example 78A were reacted analogously to the process of Example 88A. The crude product was purified chromatographically [Method 19]. This gave 60 mg (38% of theory) of the target compound.

LC/MS [Method 4]: $R_t$=1.20 min; MS [ESIpos]: m/z=340 and 342 (M+H)$^+$.

Example 92A 2-(Bromomethyl)-5-(2-chlorophenyl)-4-(trifluoromethyl)-1,3-thiazole

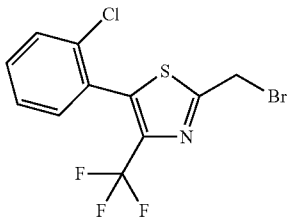 [SMILES: FC(F)(F)c1nc(CBr)sc1-c1ccccc1Cl]

140 mg (0.50 mmol) of the compound from Example 79A were reacted analogously to the process of Example 88A. The crude product was purified chromatographically [Method 19]. This gave 49 mg (27% of theory) of the target compound.

LC/MS [Method 4]: $R_t$=1.27 min; MS [ESIpos]: m/z=356 and 358 (M+H)$^+$.

Example 93A 5-(4-Chlorophenyl)-4-cyclopropyl-2-(1H-1,2,4-triazol-5-ylsulfonyl)-2,4-dihydro-3H-1,2,4-triazol-3-one

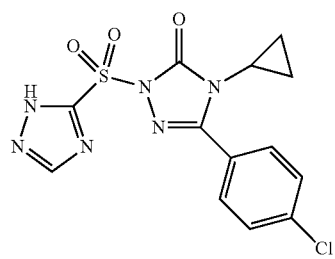 [SMILES: O=c1n(S(=O)(=O)c2ncn[nH]2)nc(-c2ccc(Cl)cc2)n1C1CC1]

300 mg (1.27 mmol) of 5-(4-chlorophenyl)-4-cyclopropyl-2,4-dihydro-3H-1,2,4-triazol-3-one [preparation according to WO 2007/134862 Example 36A] were dissolved in 10 ml of THF, and 143 mg (1.27 mmol) of potassium tert-butoxide were added at −78° C. Over a period of 30 min, the reaction mixture was warmed to RT, and the mixture was stirred at this temperature for a further 20 min. The mixture was then once more cooled to −78° C., and 213 mg (1.27 mmol) of 1H-1,2,4-triazole-5-sulfonyl chloride, dissolved in 5 ml of THF, were added. Over a period of 30 min, the reaction mixture was warmed to RT, and the mixture was stirred at this temperature for a further 20 h. For work-up, 10 ml of water were added. The mixture was extracted twice with in each case 15 ml of ethyl acetate. The combined organic phases were dried over sodium sulfate, filtered and concentrated under reduced pressure. The crude product was purified chromatographically [Method 19]. This gave 136 mg (29% of theory) of the target compound.

LC/MS [Method 5]: $R_t$=1.91 min; m/z=367 (M+H)$^+$.

Example 94A 5-(4-Chlorophenyl)-4-(4-methoxybenzyl)-2-(1H-1,2,4-triazol-5-ylsulfonyl)-2,4-dihydro-3H-1,2,4-triazol-3-one

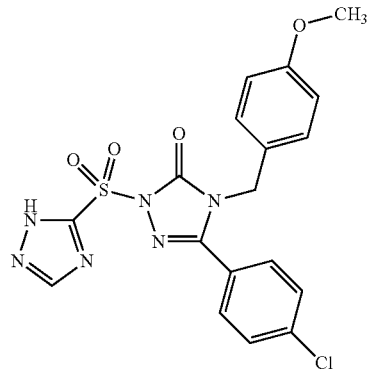 [SMILES: COc1ccc(Cn2c(-c3ccc(Cl)cc3)nn(S(=O)(=O)c3ncn[nH]3)c2=O)cc1]

529 mg (1.68 mmol) of 5-(4-chlorophenyl)-4-(4-methoxybenzyl)-2,4-dihydro-3H-1,2,4-triazol-3-one [preparation according to WO 2007/134862 Example 55A] were dissolved in 10 ml of acetonitrile, and 1.09 g (3.35 mmol) of cesium carbonate and 281 mg (1.68 mmol) of 1H-1,2,4-triazole-5-sulfonyl chloride, dissolved in 5 ml of acetonitrile, were added successively. The reaction mixture was stirred at RT for 90 min. For work-up, 10 g of silica gel were added and the solvent was removed under reduced pressure. The crude product, adsorbed on silica gel, was purified by chromatography on silica gel (mobile phase: first ethyl acetate, then dichloromethane/methanol 90:10→80:20). This gave 268 mg (32% of theory) of the target compound.

LC/MS [Method 5]: $R_t$=2.21 min; m/z=447 (M+H)$^+$.

Example 95A 5-(4-Chlorophenyl)-2-({1-[2-(trifluoromethyl)benzyl]-1H-1,2,4-triazol-5-yl}sulfonyl)-2,4-dihydro-3H-1,2,4-triazol-3-one

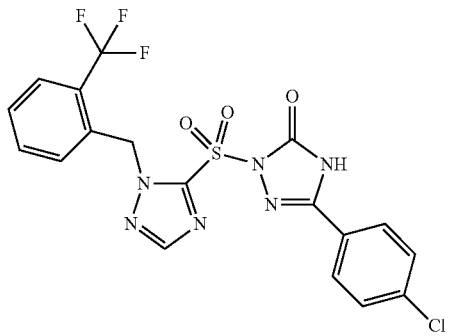 [SMILES: O=c1[nH]c(-c2ccc(Cl)cc2)nn1S(=O)(=O)c1ncnn1Cc1ccccc1C(F)(F)F]

230 mg (0.38 mmol) of the compound from Example 116 were dissolved in 5 ml of acetonitrile, and 417 mg (0.76 mmol) of ammonium cerium(IV) nitrate, dissolved in 5 ml of water, were added. The mixture was then stirred at 70° C. for 20 h. For work-up, the mixture was concentrated under reduced pressure, and the residue was taken up in 15 ml of water and extracted twice with in each case 15 ml of ethyl acetate. The combined organic phases were dried over magnesium sulfate, filtered and concentrated under reduced pressure. The crude product was purified by chromatography on silica gel (mobile phase: dichloromethane/methanol 99:1→90:10). This gave 130 mg (70% of theory) of the target compound.

LC/MS [Method 3]: $R_t$=1.22 min; m/z=485 (M+H)$^+$ $^1$H-NMR (400 MHz, CDCl$_3$): δ=5.59 (s, 2H), 7.38 (d, 1H), 7.44 (d, 2H), 7.45-7.55 (m, 2H), 7.70 (d, 1H), 7.81 (d, 2H), 8.12 (s, 1H).

Example 96A

4-Allyl-5-(4-chlorophenyl)-2-[(5-methyl-1H-imidazol-4-yl)methyl]-2,4-dihydro-3H-1,2,4-triazol-3-one

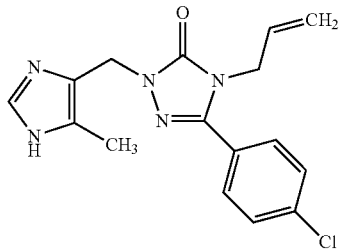 [SMILES: C=CCn1c(-c2ccc(Cl)cc2)nn(Cc2nc[nH]c2C)c1=O]

100 mg (0.89 mmol) of 4-hydroxymethyl-5-methyl-1H-imidazole, 252 mg (1.07 mmol) of the compound from Example 12A and 370 mg (2.68 mmol) of potassium carbonate were dissolved in 4.5 ml of DMF and 4.5 ml of water, and the mixture was stirred in a microwave oven at 200° C. for 75 min. After cooling to RT, for work-up, the mixture was diluted with 10 ml of water and extracted twice with in each case 15 ml of ethyl acetate. The combined organic phases were dried over sodium sulfate, filtered and concentrated under reduced pressure. The crude product was purified by chromatography on silica gel (mobile phase: first cyclohexane/ethyl acetate 1:1, then dichloromethane/methanol 10:1). This gave 153 mg (52% of theory) of the target compound in a purity of 73%.

LC/MS [Method 3]: $R_t$=0.82 min; MS [ESIpos]: m/z=330 (M+H)$^+$.

Example 97A 5-(4-Chlorophenyl)-4-cyclopropyl-2-[(5-methyl-1H-imidazol-4-yl)methyl]-2,4-dihydro-3H-1,2,4-triazol-3-one

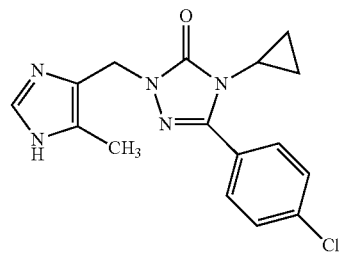 [SMILES: Cc1[nH]cnc1Cn1nc(-c2ccc(Cl)cc2)n(C2CC2)c1=O]

Analogously to the compound in Example 96A, 181 mg (1.62 mmol) of 4-hydroxymethyl-5-methyl-1H-imidazole, 381 mg (1.62 mmol) of 5-(4-chlorophenyl)-4-cyclopropyl-2,4-dihydro-3H-1,2,4-triazol-3-one [preparation according to WO 2007/134862 Example 36A] and 670 mg (4.85 mmol) of potassium carbonate were reacted with one another. This gave 180 mg (47% of theory) of the target compound in a purity of 76%.

LC/MS [Method 1]: $R_t$=0.82 min; MS [ESIpos]: m/z=330 (M+H)$^+$.

Example 98A

Ethyl bromo[2-(trifluoromethyl)phenyl]acetate

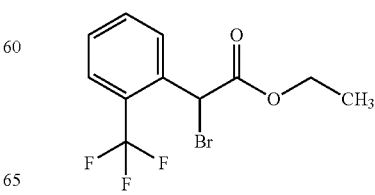

585 mg (3.89 mmol) of sodium bromate were initially charged in 2 ml of water, and 300 mg (1.29 mmol) of ethyl 2-(trifluoromethyl)phenylacetate, dissolved in 2.5 ml of ethyl acetate, were added at RT. A solution of 403 mg (3.89 mmol) of sodium bisulfite in 3.8 ml of water was then added slowly. The mixture was stirred at RT for 18 h. 5 ml of 10% strength aqueous sodium dithionite solution were then added. The mixture was extracted with 15 ml of ethyl acetate, and the organic phase was washed in each case once with 5 ml of 10% strength sodium dithionite solution and 5 ml of saturated sodium chloride solution. The organic phase was dried over sodium sulfate, filtered and concentrated under reduced pressure. The crude product was purified by chromatography on silica gel (mobile phase: cyclohexane/ethyl acetate 20:1, then 10:1). This gave 186 mg of a mixture consisting of the title compound and the starting material ethyl 2-(trifluoromethyl) phenylacetate (ratio 16:84 according to GC/MS [Method 20]). This mixture was once more reacted with 362 mg (2.40 mmol) of sodium bromate and 250 mg (2.40 mmol) of sodium bisulfite according to the procedure described above. Work-up gave a mixture of 31% title compound and 69% ethyl 2-(trifluoromethyl)phenylacetate, which was reacted further without any further purification.

GC/MS [Method 20]: $R_t$=4.28 min; MS [ESIpos]: m/z=237 $(M-CO_2C_2H_5)^+$.

Example 99A 2-(2-Bromobenzyl)-5-(4-chlorophenyl)-4-cyclopropyl-2,4-dihydro-3H-1,2,4-triazol-3-one

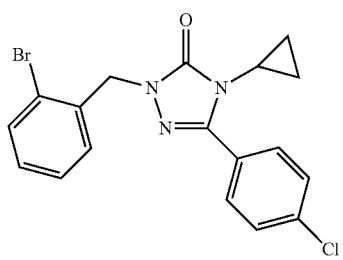 [SMILES: O=c1n(Cc2ccccc2Br)nc(-c2ccc(Cl)cc2)n1C1CC1]

1.04 g (4.41 mmol) of 5-(4-chlorophenyl)-4-cyclopropyl-2,4-dihydro-3H-1,2,4-triazol-3-one [preparation according to WO 2007/134862 Example 36A] and 2.16 g (6.62 mmol) of cesium carbonate were suspended in 35 ml of acetonitrile, and 1.32 g (5.30 mmol) of 2-bromobenzyl bromide were added. The mixture was stirred under reflux for 18 h. The precipitated solid was then filtered off and the filtrate was concentrated under reduced pressure. The solid that remained was stirred in about 50 ml of diethyl ether and then filtered off and washed with a little diethyl ether. Drying under reduced pressure gave 1.05 g (59% of theory) of the target compound as a white solid.

LC/MS [Method 4]: $R_t$=1.19 m; MS [ESIpos]: m/z=404 and 406 $(M+H)^+$ $^1$H-NMR (400 MHz, DMSO-$d_6$): δ=0.58-0.65 (m, 2H), 0.85-0.93 (m, 2H), 3.20 (tt, 1H), 4.99 (s, 2H), 7.18-7.30 (m, 2H), 7.34-7.41 (m, 1H), 7.56-7.61 (m, 2H), 7.65 (d, 1H), 7.80 (d, 2H).

Example 100A 2-(5-Bromo-2-fluorobenzyl)-5-(4-chlorophenyl)-4-cyclopropyl-2,4-dihydro-3H-1,2,4-triazol-3-one

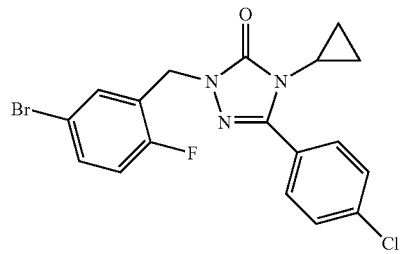 [SMILES: O=c1n(Cc2cc(Br)ccc2F)nc(-c2ccc(Cl)cc2)n1C1CC1]

300 mg (1.27 mmol) of 5-(4-chlorophenyl)-4-cyclopropyl-2,4-dihydro-3H-1,2,4-triazol-3-one [preparation according to WO 2007/134862 Example 36A] and 622 mg (1.91 mmol) of cesium carbonate were suspended in 5 ml of acetonitrile, and 536 mg (1.40 mmol) of 4-bromo-2-(bromomethyl)-1-fluorobenzene were added. The mixture was stirred under reflux for 18 h. The precipitated solid was then filtered off and the filtrate was concentrated under reduced pressure to a volume of about 1.5 ml. After addition of 0.5 ml of 1 N hydrochloric acid, the mixture was directly purified chromatographically [Method 19]. This gave 427 mg (56% of theory) of the target compound in a purity of 71%.

LC/MS [Method 4]: $R_t$=1.23 min; MS [ESIpos]: m/z=422 and 424 $(M+H)^+$.

Example 101A 2-(3-Bromobenzyl)-5-(4-chlorophenyl)-4-(3,3,3-trifluoro-2-hydroxypropyl)-2,4-dihydro-3H-1,2,4-triazol-3-one

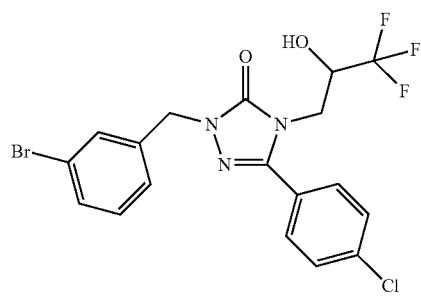 [SMILES: O=c1n(Cc2cccc(Br)c2)nc(-c2ccc(Cl)cc2)n1CC(O)C(F)(F)F]

400 mg (1.30 mmol) of the compound from Example 4A and 635 mg (1.95 mmol) of cesium carbonate were suspended in 3 ml of acetonitrile, and 357 mg (1.43 mmol) of 3-bromobenzyl bromide were added. The mixture was stirred under reflux for 20 h. The precipitated solid was then filtered off, and the filtrate was concentrated under reduced pressure to a volume of about 1.5 ml and directly purified chromatographically [Method 19]. This gave 507 mg (82% of theory) of the target compound.

LC/MS [Method 4]: $R_t$=1.21 min; MS [ESIpos]: m/z=476 and 478 (M+H)$^+$.

Example 102A 2-(3-Bromobenzyl)-5-(4-chlorophenyl)-4-[(2S)-3,3,3-trifluoro-2-hydroxypropyl]-2,4-dihydro-3H-1,2,4-triazol-3-one

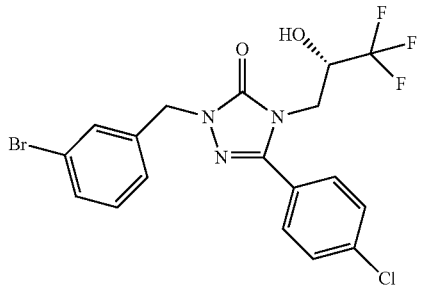 [SMILES: O=c1n(Cc2cccc(Br)c2)nc(-c2ccc(Cl)cc2)n1C[C@H](O)C(F)(F)F]

80 mg (0.26 mmol) of the compound from Example 5A were reacted analogously to the preparation of Example 101A. This gave 95 mg (76% of theory) of the target compound.

LC/MS [Method 4]: $R_t$=1.21 min; MS [ESIpos]: m/z=476 and 478 (M+H)$^+$.

Example 103A 2-(3-Bromo-5-fluorobenzyl)-5-(4-chlorophenyl)-4-[(2S)-3,3,3-trifluoro-2-hydroxypropyl]-2,4-dihydro-3H-1,2,4-triazol-3-one

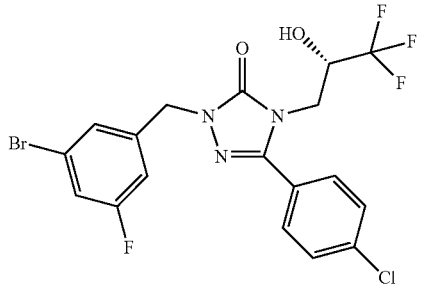 [SMILES: O=c1n(Cc2cc(F)cc(Br)c2)nc(-c2ccc(Cl)cc2)n1C[C@H](O)C(F)(F)F]

219 mg (0.71 mmol) of the compound from Example 5A and 191 mg (0.71 mmol) of 1-bromo-3-(bromomethyl)-5-fluorobenzene were reacted analogously to the preparation of Example 101A. This gave 181 mg (51% of theory) of the target compound.

LC/MS [Method 4]: $R_t$=1.24 min; MS [ESIpos]: m/z=494 and 496 (M+H)$^+$.

Example 104A

Methyl 4-bromo-2-{[3-(4-chlorophenyl)-5-oxo-4-(3,3,3-trifluoro-2-hydroxypropyl)-4,5-dihydro-1H-1,2,4-triazol-1-yl]methyl}benzoate

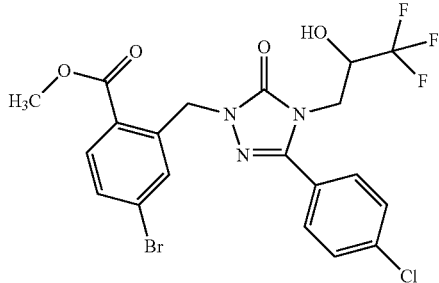 [SMILES: COC(=O)c1ccc(Br)cc1Cn1nc(-c2ccc(Cl)cc2)n(CC(O)C(F)(F)F)c1=O]

450 mg (1.30 mmol) of the compound from Example 4A and 715 mg (2.19 mmol) of cesium carbonate were suspended in 6 ml of acetonitrile, and 708 mg (1.61 mmol) of methyl 4-bromo-2-(bromomethyl)benzoate were added. The mixture was stirred under reflux for 20 h. The precipitated solid was filtered off and the filtrate was concentrated under reduced pressure to a volume of about 1.5 ml. After addition of 1 ml of 1 N hydrochloric acid, the mixture was directly purified chromatographically [Method 19]. This gave 545 mg (64% of theory) of the target compound in a purity of 92%.

LC/MS [Method 4]: $R_t$=1.24 min; MS [ESIpos]: m/z=534 and 536 (M+H)$^+$ $^1$H-NMR (400 MHz, DMSO-$d_6$): δ=3.81-3.90 (m, 4H), 4.01 (dd, 1H), 4.24-4.34 (m, 1H), 5.29-5.40 (m, 2H), 6.89 (d, 1H), 7.42 (d, 1H), 7.64 (d, 2H), 7.69 (dd, 1H), 7.74 (d, 2H), 7.84 (d, 1H).

Example 105A

Methyl 4-bromo-2-({3-(4-chlorophenyl)-5-oxo-4-[(2S)-3,3,3-trifluoro-2-hydroxypropyl]-4,5-dihydro-1H-1,2,4-triazol-1-yl}methyl)benzoate

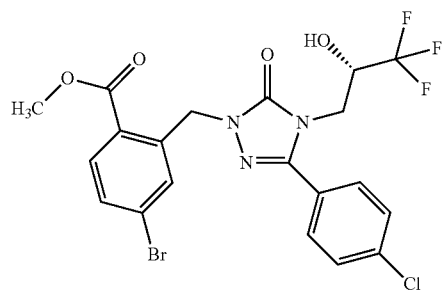 [SMILES: COC(=O)c1ccc(Br)cc1Cn1nc(-c2ccc(Cl)cc2)n(C[C@H](O)C(F)(F)F)c1=O]

515 mg (1.67 mmol) of the compound from Example 5A and 818 mg (2.51 mmol) of cesium carbonate were suspended in 10 ml of acetonitrile, and 810 mg (1.84 mmol) of methyl 4-bromo-2-(bromomethyl)benzoate were added. The mixture was stirred under reflux for 3 h. After cooling to RT, 15 ml of water were added and the mixture was extracted three times with in each case 10 ml of ethyl acetate. The combined organic phases were dried over sodium sulfate, filtered and concentrated under reduced pressure. The residue was purified chromatographically [Method 19]. This gave 455 mg (51% of theory) of the target compound.

LC/MS [Method 4]: $R_t$=1.21 min; MS [ESIpos]: m/z=534 and 536 (M+H)$^+$.

Example 106A

Methyl 5-methyl-2'-(trifluoromethyl)biphenyl-2-carboxylate

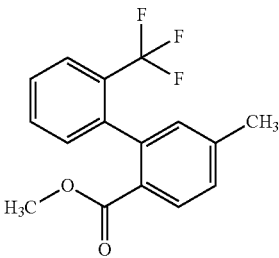 [SMILES: COC(=O)c1ccc(C)cc1-c1ccccc1C(F)(F)F]

Under argon, 500 mg (2.18 mmol) of methyl 2-bromo-4-methylbenzoate together with 655 mg (3.27 mmol) of 2-(trifluoromethyl)phenylboronic acid were dissolved in 10 ml of toluene, and 86 mg (0.22 mmol) of 2-dicyclohexylphosphino-2'-(N,N-dimethylamino)biphenyl, 100 mg (0.11 mmol) of tris(dibenzylideneacetone)dipalladium and 927 mg (4.37 mmol) of potassium phosphate were added successively. The mixture was heated to 110° C. and stirred at this temperature for 20 h. For work-up, the reaction mixture was allowed to cool to RT and diluted with 20 ml of ethyl acetate and 20 ml of water. After phase separation, the aqueous phase was extracted two more times with in each case 20 ml of ethyl acetate. The combined organic phases were dried over magnesium sulfate, filtered and concentrated under reduced pressure. The residue was purified by chromatography on silica gel (mobile phase: first cyclohexane/ethyl acetate 30:1, then 20:1). This gave 597 mg (86% of theory) of the target compound.

GC/MS [Method 20]: $R_t$=5.55 min; MS [EIpos]: m/z=294 (M)$^+$.

Example 107A

Methyl 2'-chloro-5-methylbiphenyl-2-carboxylate

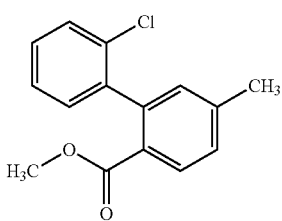 [SMILES: COC(=O)c1ccc(C)cc1-c1ccccc1Cl]

500 mg (2.18 mmol) of methyl 2-bromo-4-methylbenzoate and 512 mg (3.27 mmol) of 2-chlorophenylboronic acid were reacted analogously to the preparation of Example 107A. This gave 275 mg (48% of theory) of the target compound.

LC/MS [Method 4]: $R_t$=1.22 min; MS [ESIpos]: m/z=261 (M+H)$^+$.

Example 108A

Methyl 5-(bromomethyl)-2'-(trifluoromethyl)biphenyl-2-carboxylate

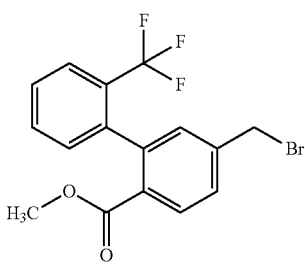 [SMILES: COC(=O)c1ccc(CBr)cc1-c1ccccc1C(F)(F)F]

590 mg (2.01 mmol) of the compound from Example 107A, 357 mg (2.01 mmol) of N-bromosuccinimide and 33 mg (0.20 mmol) of 2,2'-azobis-2-methylpropanenitrile in 8 ml of carbon tetrachloride were heated under reflux for 16 h. After cooling to RT, the mixture was diluted with 10 ml of dichloromethane and washed with 10 ml of water. The organic phase was dried over magnesium sulfate, filtered and concentrated under reduced pressure. The crude product was purified chromatographically [Method 19]. This gave 346 mg (30% of theory) of the target compound in a purity of 64% which were immediately reacted further.

LC/MS [Method 4]: $R_t$=1.27 min; MS [DCI]: m/z=390 and 392 (M+NH$_4$)$^+$.

Example 109A

Methyl 5-(bromomethyl)-2'-chlorobiphenyl-2-carboxylate

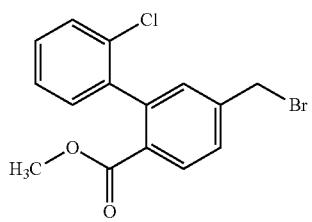 [SMILES: COC(=O)c1ccc(CBr)cc1-c1ccccc1Cl]

270 mg (1.04 mmol) of the compound from Example 108A and N-bromosuccinimide were reacted analogously to the preparation of Example 109A. This gave 232 mg (66% of theory) of the target compound which were immediately reacted further.

LC/MS [Method 4]: $R_t$=1.22 min; MS [DCI]: m/z=356 and 358 (M+NH$_4$)$^+$.

Example 110A

Dimethyl 2'-chlorobiphenyl-3,5-dicarboxylate

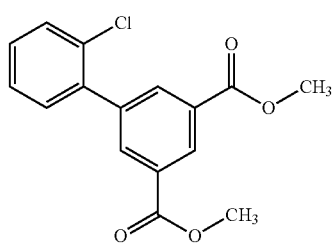 [SMILES: COC(=O)c1cc(C(=O)OC)cc(-c2ccccc2Cl)c1]

Under argon, 500 mg (1.83 mmol) of dimethyl 5-bromoisophthalate together with 429 mg (2.75 mmol) of 2-chlorophenylboronic acid were dissolved in 8 ml of toluene, and 72 mg (0.18 mmol) of 2-dicyclohexylphosphino-2'-(N,N-dimethylamino)biphenyl, 84 mg (0.09 mmol) of tris(dibenzylideneacetone)dipalladium and 777 mg (3.66 mmol) of potassium phosphate were added successively. The mixture was heated to 110° C. and stirred at this temperature for 20 h. For work-up, the reaction mixture was allowed to cool to RT and diluted with 20 ml of ethyl acetate. The solid was filtered off with suction and the residue was washed three times with in each case 10 ml of ethyl acetate. The combined filtrates were washed twice with in each case 10 ml of water. The organic phase was dried over magnesium sulfate, filtered and concentrated under reduced pressure. The residue was purified chromatographically [Method 19]. This gave 305 mg (55% of theory) of the target compound.

LC/MS [Method 4]: $R_t$=1.24 min; MS [EIpos]: m/z=305 (M+H)$^+$ $^1$H-NMR (400 MHz, DMSO-d$_6$): δ=3.92 (s, 6H), 7.46-7.55 (m, 3H), 7.60-7.68 (m, 1H), 8.23 (d, 2H), 8.52 (t, 1H).

Example 111A

Methyl 2'-chloro-5-(hydroxymethyl)biphenyl-3-carboxylate

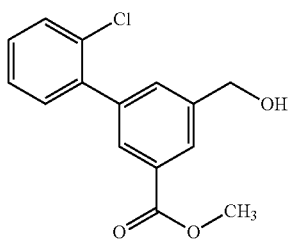 [SMILES: COC(=O)c1cc(CO)cc(-c2ccccc2Cl)c1]

305 mg (1.00 mmol) of the compound from Example 110A were dissolved in 6 ml of THF, and 0.5 ml (0.50 mmol) of a 1 M solution of lithium aluminum hydride in THF was added at −10° C. The reaction mixture was then stirred at RT for 1 h. For work-up, 3 ml of saturated aqueous sodium potassium tartrate solution were added at RT, and the mixture was extracted with 15 ml of ethyl acetate. The organic phase was washed once with 10 ml of saturated sodium potassium tartrate solution, dried over magnesium sulfate, filtered and concentrated under reduced pressure. The residue was purified chromatographically [Method 19]. This gave 189 mg (68% of theory) of the target compound.

LC/MS [Method 4]: $R_t$=1.03 min; MS [ESIpos]: m/z=277 (M+H)$^+$ $^1$H-NMR (400 MHz, DMSO-d$_6$): δ=3.88 (s, 3H), 4.63 (d, 2H), 5.43 (t, 1H), 7.43-7.47 (m, 3H), 7.58-7.62 (m, 1H), 7.62-7.64 (m, 1H), 7.84-7.87 (m, 1H), 7.97-8.00 (m, 1H).

Example 112A

Methyl 5-(bromomethyl)-2'-chlorobiphenyl-3-carboxylate

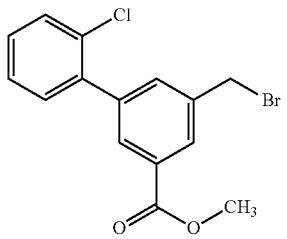 [SMILES: COC(=O)c1cc(CBr)cc(-c2ccccc2Cl)c1]

187 mg (0.68 mmol) of the compound from Example 111A and 266 mg (1.01 mmol) of triphenyl-phosphine were dissolved in 6 ml of THF, and 336 mg (1.01 mmol) of carbon tetrabromide were added at RT. The mixture was then stirred at RT for 16 h. For work-up, the mixture was filtered through 20 g of kieselguhr, the filter cake was washed with ethyl acetate and the filtrate was concentrated under reduced pressure. The residue was purified chromatographically on silica gel (mobile phase: cyclohexane/ethyl acetate 7:3). This gave 275 mg (>100% of theory) of the target compound, which were immediately reacted further.

$^1$H-NMR (400 MHz, DMSO-d$_6$): δ=3.89 (s, 3H), 4.86 (s, 2H), 7.44-7.50 (m, 3H), 7.58-7.64 (m, 1H), 7.80-7.82 (m, 1H), 7.90-7.92 (m, 1H), 8.08-8.11 (m, 1H).

Example 113A and Example 114A

Methyl 5-bromo-2'-chlorobiphenyl-3-carboxylate and methyl 2,2''-dichloro-1,1':3',1''-terphenyl-5'-carboxylate

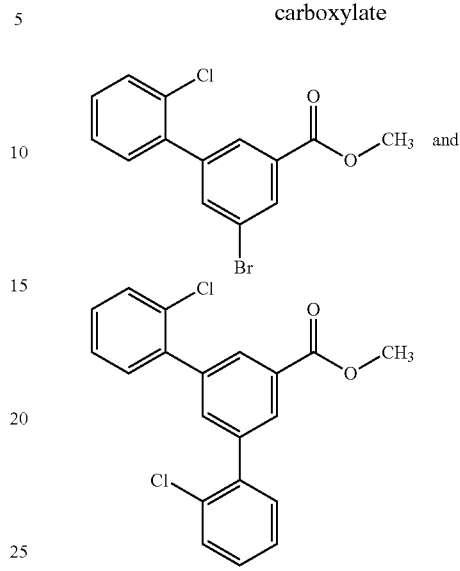

Under argon, 60 mg (0.05 mmol) of tetrakis(triphenylphosphine)palladium(0) were added to 300 mg (1.02 mmol) of methyl 3,5-dibromobenzoate in 6 ml of dioxane. The mixture was heated to 110° C., and 1.0 ml (2.00 mmol) of 2 M aqueous sodium carbonate solution and 239 mg (1.53 mmol) of 2-chlorophenylboronic acid, dissolved in 1 ml of dioxane, were added successively. The mixture was then stirred at 110° C. for 1 h. For work-up, the reaction mixture was allowed to cool to RT and diluted with 20 ml of ethyl acetate and 20 ml of water. After phase separation, the aqueous phase was extracted two more times with in each case 20 ml of ethyl acetate. The combined organic phases were dried over magnesium sulfate, filtered and concentrated under reduced pressure. The residue was separated into the components by preparative HPLC [Method 19]. This gave 142 mg (43% of theory) of methyl 5-bromo-2'-chlorobiphenyl-3-carboxylate (Example 113A) and 166 mg (46% of theory) of methyl 2,2''-dichloro-1,1':3',1''-terphenyl-5'-carboxylate (Example 114A) as reaction products.

Example 113A:

GC/MS [Method 20]: $R_t$=7.50 min; MS [ESIpos]: m/z=324 and 326 (M)$^+$.

Example 114A

GC/MS [Method 20]: $R_t$=10.26 min; MS [ESIpos]: m/z=356 and 358 (M)$^+$.

Example 115A (5-Bromo-2'-chlorobiphenyl-3-yl)methanol

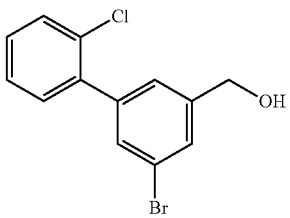 [SMILES: OCc1cc(Br)cc(-c2ccccc2Cl)c1]

170 mg (0.52 mmol) of the compound from Example 113A were dissolved in 6 ml of THF, and 0.37 ml (0.37 mmol) of a 1 M solution of lithium aluminum hydride in THF was added at −10° C. The mixture was then stirred at RT for 1 h. For work-up, 4 ml of saturated aqueous sodium potassium tartrate solution were added at RT, and the mixture was extracted with 15 ml of ethyl acetate. The organic phase was washed once with 10 ml of saturated sodium potassium tartrate solution, dried over magnesium sulfate, filtered and concentrated under reduced pressure. This gave 177 mg (>100% of theory) of the target compound.

LC/MS [Method 2]: $R_t$=2.39 min

GC/MS [Method 20]: $R_t$=7.67 min; MS [ESIpos]: m/z=296 and 298 (M)$^+$.

Example 116A (2,2''-Dichloro-1,1':3',1''-terphenyl-5'-yl)methanol

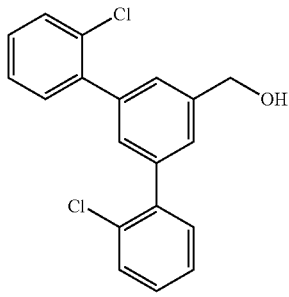 [SMILES: OCc1cc(-c2ccccc2Cl)cc(-c2ccccc2Cl)c1]

311 mg (0.87 mmol) of the compound from Example 114A were reacted analogously to the preparation of Example 115A. This gave 283 mg (91% of theory) of the target compound.

LC/MS [Method 2]: $R_t$=2.63 min

MS [DCI]: m/z=346 (M+NH$_4$)$^+$.

Example 117A

3'-Bromo-5'-(bromomethyl)-2-chlorobiphenyl

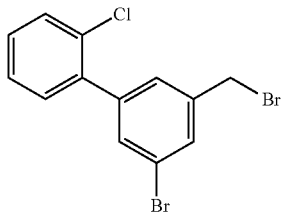 [SMILES: Clc1ccccc1-c1cc(Br)cc(CBr)c1]

177 mg (0.60 mmol) of the compound from Example 115A and 187 mg (0.71 mmol) of triphenyl-phosphine were dissolved in 4 ml of THF, and 237 mg (0.71 mmol) of carbon tetrabromide were added at RT. The mixture was then stirred at RT for 16 h. For work-up, the mixture was filtered through 20 g of kieselguhr and the filtrate was concentrated under reduced pressure. The residue was purified chromatographically [Method 19]. This gave, in a purity of 79%, 129 mg (60% of theory) of the target compound, which were immediately reacted further.

LC/MS [Method 4]: $R_t$=1.41 min.

Example 118A

5'-(Bromomethyl)-2,2''-dichloro-1,1':3',1''-terphenyl

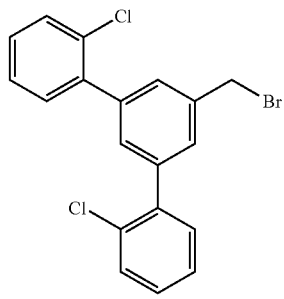 [SMILES: Clc1ccccc1-c1cc(CBr)cc(-c2ccccc2Cl)c1]

280 mg (0.85 mmol) of the compound from Example 116A were reacted analogously to the preparation of Example 117A. Purification of the crude product was carried out by chromatography on silica gel (mobile phase: cyclohexane/ ethyl acetate 10:1). This gave 300 mg (76% of theory) of the target compound.

GC/MS [Method 20]: $R_t$=10.64 min; MS [ESIpos]: m/z=390, 392 and 394 (M)$^+$

MS [DCI]: m/z=408, 410 and 412 (M+NH$_4$)$^+$.

Example 119A

2-[(3-Bromophenyl)sulfonyl]-5-(4-chlorophenyl)-4-[(2S)-3,3,3-trifluoro-2-hydroxypropyl]-2,4-dihydro-3H-1,2,4-triazol-3-one

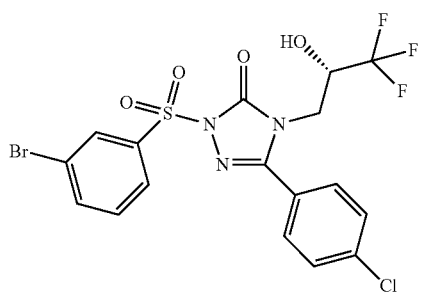 [SMILES: O=c1n(S(=O)(=O)c2cccc(Br)c2)nc(-c2ccc(Cl)cc2)n1C[C@H](O)C(F)(F)F]

360 mg (1.17 mmol) of the compound from Example 5A were dissolved in 10 ml of THF and, at 0° C., 94 mg (2.34 mmol) of sodium hydride (60% strength dispersion in mineral oil) were added. After 20 min, 299 mg (1.17 mmol) of 3-bromobenzenesulfonyl chloride were added, and the mixture was stirred at 0° C. for 1 h. For work-up, 10 ml of water were added and the mixture was extracted twice with in each case 15 ml of ethyl acetate. The combined organic phases were dried over sodium sulfate, filtered and concentrated under reduced pressure. The crude product was purified by chromatography on silica gel (mobile phase: cyclohexane/ ethyl acetate 8:1, then 1:1). This gave 181 mg (27% of theory) of the target compound.

Example 120A

2-[(3-Bromophenyl)sulfonyl]-5-(4-chlorophenyl)-4-[(1E)-3,3,3-trifluoroprop-1-en-1-yl]-2,4-dihydro-3H-1,2,4-triazol-3-one

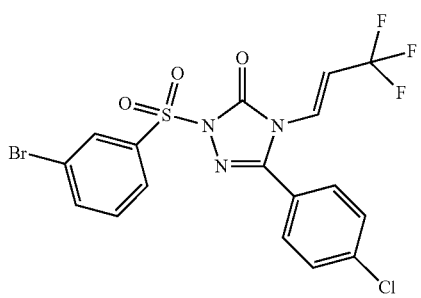 [SMILES: O=c1n(S(=O)(=O)c2cccc(Br)c2)nc(-c2ccc(Cl)cc2)n1/C=C/C(F)(F)F]

500 mg (1.63 mmol) of the compound from Example 5A were dissolved in 10 ml of acetonitrile, and 449 mg (3.25 mmol) of potassium carbonate and 415 mg (1.63 mmol) of 3-bromobenzenesulfonyl chloride were added. The mixture was heated under reflux for 2 h. For work-up, 10 ml of water were added and the mixture was extracted twice with in each case 15 ml of ethyl acetate. The combined organic phases were dried over sodium sulfate, filtered and concentrated under reduced pressure. The crude product was purified by chromatography on silica gel (mobile phase: cyclohexane/ethyl acetate 8:1→5:1→1:1). This gave 285 mg (34% of theory) of the target compound.

LC/MS [Method 4]: $R_t$=1.31 min; MS [ESIpos]: m/z=508 and 510 (M+H)+

$^1$H-NMR (400 MHz, CDCl$_3$): δ=6.72 (dq, 1H), 6.89-6.95 (m, 1H), 7.62-7.66 (m, 2H), 7.67-7.73 (m, 3H), 8.05-8.11 (m, 2H), 8.14 (t, 1H).

Example 121A 5-(4-Chlorophenyl)-4-cyclopropyl-2-(hydroxymethyl)-2,4-dihydro-3H-1,2,4-triazol-3-one

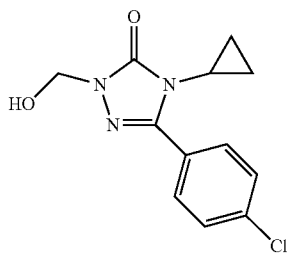 [SMILES: O=c1n(CO)nc(-c2ccc(Cl)cc2)n1C1CC1]

7 ml of a 37% strength solution of formaldehyde in water were added to 1000 mg (4.24 mmol) of 5-(4-chlorophenyl)-4-cyclopropyl-2,4-dihydro-3H-1,2,4-triazol-3-one [preparation according to WO 2007/134862 Example 36A], and the mixture was stirred at RT for 20 h. The precipitated solid was filtered off with suction and washed with water. Drying under high vacuum gave 878 mg (62% of theory) of the target compound.

$^1$H-NMR (400 MHz, CDCl$_3$): δ=0.71-0.78 (m, 2H), 0.98-1.06 (m, 2H), 2.98 (m, 1H), 5.34 (s, 2H), 7.46 (d, 2H), 7.69 (d, 2H).

Example 122A 2-(Chloromethyl)-5-(4-chlorophenyl)-4-cyclopropyl-2,4-dihydro-3H-1,2,4-triazol-3-one

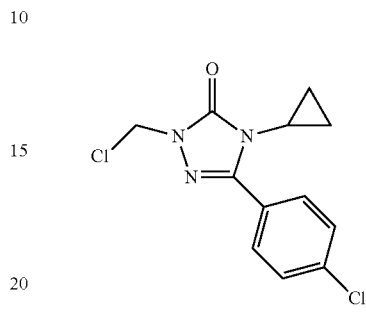

875 mg (3.29 mmol) of the compound from Example 121A were suspended in 3 ml of dichloromethane, and a drop of DMF and 288 µl (3.95 mmol) of thionyl chloride were added. The mixture was stirred at RT for 3 h. For work-up, 5 ml of saturated aqueous sodium bicarbonate solution were added. The mixture was extracted once with 10 ml of tert-butyl methyl ether. The organic phase was washed once with 5 ml of water, dried over sodium sulfate, filtered and concentrated under reduced pressure. Drying of the residue under high vacuum gave 803 mg (86% of theory) of the target compound.

$^1$H-NMR (400 MHz, CDCl$_3$): δ=0.74-0.80 (m, 2H), 1.00-1.06 (m, 2H), 2.98 (m, 1H), 5.66 (s, 2H), 7.48 (d, 2H), 7.72 (d, 2H).

WORKING EXAMPLES

Example 1

5-(5-Chlorothiophen-2-yl)-4-(2-fluorobenzyl)-2-({3-[2-(trifluoromethyl)phenyl]-1,2,4-oxadiazol-5-yl}methyl)-2,4-dihydro-3H-1,2,4-triazol-3-one

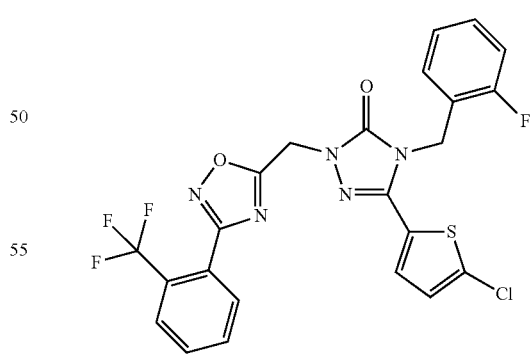

Under argon, 95 mg (0.18 mmol) of benzotriazol-1-yloxytris(pyrrolidino)phosphonium hexafluorophosphate were added to a solution of 56 mg (0.15 mmol) of [3-(5-chloro-2-thienyl)-4-(2-fluorobenzyl)-5-oxo-4,5-dihydro-1H-1,2,4-triazol-1-yl]acetic acid [preparation according to WO 2007/134862 Example 154A] and 32 µl (0.18 mmol) of N,N-diisopropylethylamine in 1.5 ml of dry DMF. After 20 min of stirring, 34 mg (0.17 mmol) of N'-hydroxy-2-(trifluoromethyl)benzene-carboximidamide were added. The mixture was then stirred at RT for 16 h. For work-up, 10 ml of water were added and the mixture was extracted three times with in each case 10 ml of ethyl acetate. The combined organic phases were washed with in each case 10 ml of water and saturated sodium chloride solution, filtered through Extrelut and concentrated under reduced pressure. The residue was dissolved in 2 ml of DMF and stirred in a microwave oven at 250° C. for 15 min. After cooling, the solvent was removed under reduced pressure on a rotary evaporator and the crude product was chromatographed on silica gel (mobile phase: cyclohexane/ethyl acetate 4:1). This gave 60 mg (72% of theory) of the target compound as a yellow resin.

LC/MS [Method 9]: $R_t$=4.25 min; MS [ESIpos]: m/z=536 (M+H)$^+$ $^1$H-NMR (400 MHz, CDCl$_3$): δ=5.15 (s, 2H), 5.42 (s, 2H), 6.35 (d, 2H), 6.93 (d, 2H), 7.01-7.29 (m, 3H), 7.23-7.34 (m, 1H), 7.60-7.70 (m, 2H), 7.76-7.89 (m, 2H).

Example 2

2-{[3-(2-Chlorobenzyl)-1,2,4-oxadiazol-5-yl]methyl}-5-(4-chlorophenyl)-4-[(2S)-3,3,3-trifluoro-2-hydroxypropyl]-2,4-dihydro-3H-1,2,4-triazol-3-one

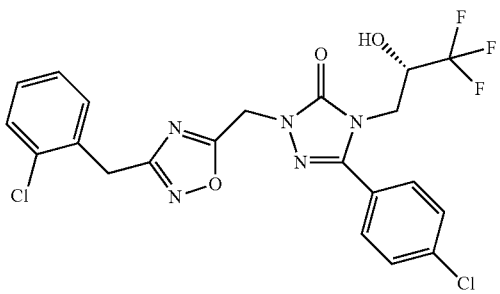 [SMILES: O=c1n(Cc2nc(Cc3ccccc3Cl)no2)nc(-c2ccc(Cl)cc2)n1C[C@H](O)C(F)(F)F]

50 mg (0.13 mmol) of the compound from Example 7A were dissolved in 2 ml of toluene, 51 mg (0.28 mmol) of (1Z)-2-(2-chlorophenyl)-N'-hydroxyethaneimidamide and 38 mg (0.28 mmol) of potassium carbonate were added and the mixture was heated under reflux for 6 h. For work-up, 10 ml of water were added and the mixture was extracted twice with in each case 10 ml of ethyl acetate. The combined organic phases were washed once with 10 ml of water and 10 ml of saturated sodium chloride solution, dried over sodium sulfate, filtered and concentrated under reduced pressure. The crude product was purified chromatographically [Method 19]. This gave 40 mg (59% of theory) of the target compound.

LC/MS [Method 4]: $R_t$=1.19 min; MS [ESIpos]: m/z=514 (M+H)$^+$ $^1$H-NMR (400 MHz, CDCl$_3$): δ=3.97 (dd, 1H), 4.04 (dd, 1H), 4.22 (s, 2H), 4.47-4.59 (m, 1H), 4.64 (br. s, 1H), 5.25 (d, 1H), 5.32 (d, 1H), 7.19-7.29 (m, 3H), 7.35-7.42 (m, 1H), 7.46-7.51 (m, 2H), 7.54-7.60 (m, 2H).

Example 3

5-(4-Chlorophenyl)-2-{[3-(2-methylbenzyl)-1,2,4-oxadiazol-5-yl]methyl}-4-[(2S)-3,3,3-trifluoro-2-hydroxypropyl]-2,4-dihydro-3H-1,2,4-triazol-3-one

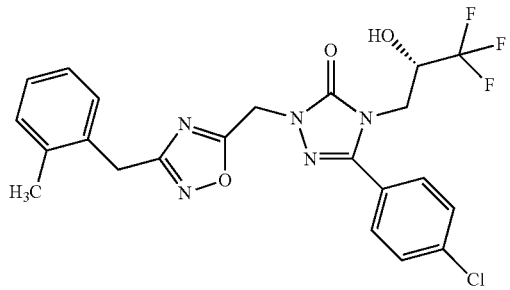 [SMILES: Cc1ccccc1Cc1noc(Cn2nc(-c3ccc(Cl)cc3)n(C[C@H](O)C(F)(F)F)c2=O)n1]

Analogously to the preparation of the compound in Example 2, 50 mg (0.13 mmol) of the compound from Example 7A gave 45 mg (69% of theory) of the title compound.

LC/MS [Method 3]: $R_t$=1.38 min; MS [ESIpos]: m/z=494 (M+H)$^+$ $^1$H-NMR (400 MHz, CDCl$_3$): δ=2.33 (s, 3H), 3.97 (dd, 1H), 4.01-4.08 (m, 3H), 4.44 (d, 1H), 4.47-4.54 (m, 1H), 5.23 (d, 1H), 5.30 (d, 1H), 7.13-7.22 (m, 4H), 7.49 (d, 2H), 7.55 (d, 2H).

Example 4

5-(4-Chlorophenyl)-4-[(2S)-3,3,3-trifluoro-2-hydroxypropyl]-2-({3-[3-(trifluoromethyl)benzyl]-1,2,4-oxadiazol-5-yl}methyl)-2,4-dihydro-3H-1,2,4-triazol-3-one

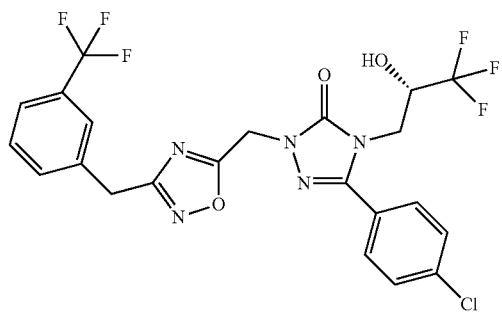 [SMILES: O=c1n(Cc2nc(Cc3cccc(C(F)(F)F)c3)no2)nc(-c2ccc(Cl)cc2)n1C[C@H](O)C(F)(F)F]

Analogously to the preparation of the compound in Example 2, 50 mg (0.13 mmol) of the compound from Example 7A gave 24 mg (34% of theory) of the title compound.

LC/MS [Method 3]: $R_t$=1.43 min; MS [ESIpos]: m/z=548 (M+H)$^+$

¹H-NMR (400 MHz, CDCl₃): δ=3.99 (dd, 1H), 4.06 (dd, 1H), 4.14 (s, 2H), 4.45-4.57 (m, 2H), 5.23-5.34 (m, 2H), 7.41-7.60 (m, 8H).

Example 5

5-(4-Chlorophenyl)-2-{[3-(2-methylphenyl)-1,2,4-oxadiazol-5-yl]methyl}-4-[(2S)-3,3,3-trifluoro-2-hydroxypropyl]-2,4-dihydro-3H-1,2,4-triazol-3-one

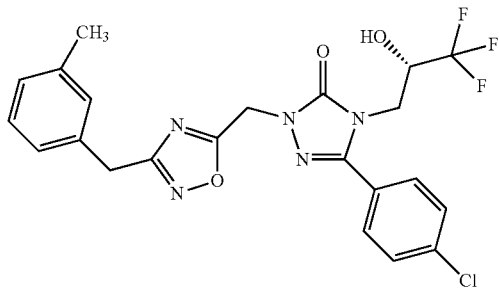 [SMILES: Cc1cccc(Cc2noc(Cn3nc(-c4ccc(Cl)cc4)n(C[C@H](O)C(F)(F)F)c3=O)n2)c1]

Analogously to the preparation of the compound in Example 2, 50 mg (0.13 mmol) of the compound from Example 7A gave, after a reaction time of 20 h, 47 mg (74% of theory) of the title compound.

LC/MS [Method 4]: $R_t$=1.22 min; MS [ESIpos]: m/z=480 (M+H)⁺

¹H-NMR (400 MHz, CDCl₃): δ=2.60 (s, 3H), 3.98-4.06 (m, 1H), 4.06-4.12 (m, 1H), 4.50 (d, 1H), 4.56 (d, 1H), 5.34-5.44 (m, 2H), 7.31 (d, 2H), 7.36-7.42 (m, 1H), 7.47-7.53 (m, 2H), 7.55-7.61 (m, 2H), 7.94 (d, 1H).

Example 6

5-(4-Chlorophenyl)-2-{[3-(2-chlorophenyl)-1,2,4-oxadiazol-5-yl]methyl}-4-[(2S)-3,3,3-trifluoro-2-hydroxypropyl]-2,4-dihydro-3H-1,2,4-triazol-3-one

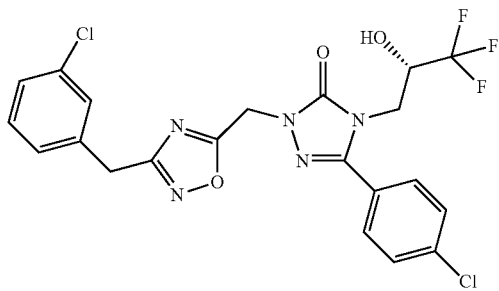 [SMILES: O=c1n(Cc2nc(Cc3cccc(Cl)c3)no2)nc(-c2ccc(Cl)cc2)n1C[C@H](O)C(F)(F)F]

Analogously to the preparation of the compound in Example 2, 50 mg (0.13 mmol) of the compound from Example 7A gave, after a reaction time of 20 h, 52 mg (79% of theory) of the title compound.

LC/MS [Method 4]: $R_t$=1.17 min; MS [ESIpos]: m/z=500 and 502 (M+H)⁺

¹H-NMR (400 MHz, CDCl₃): δ=3.95-4.15 (m, 2H), 4.51-4.62 (m, 1H), 5.33-5.48 (m, 2H), 7.34-7.56 (m, 5H), 7.56-7.64 (m, 2H), 7.89 (d, 1H).

Example 7

5-(4-Chlorophenyl)-2-{[3-(2,6-difluorophenyl)-1,2,4-oxadiazol-5-yl]methyl}-4-[(2S)-3,3,3-trifluoro-2-hydroxypropyl]-2,4-dihydro-3H-1,2,4-triazol-3-one

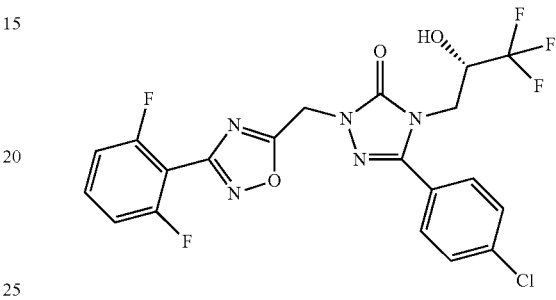

Analogously to the preparation of the compound in Example 2, 50 mg (0.13 mmol) of the compound from Example 7A gave, after a reaction time of 2 h, 46 mg (70% of theory) of the title compound.

LC/MS [Method 4]: $R_t$=1.13 min; MS [ESIpos]: m/z=502 (M+H)⁺

¹H-NMR (400 MHz, CDCl₃): δ=3.99 (dd, 1H), 4.08 (dd, 1H), 4.53-4.62 (m, 1H), 4.66 (d, 1H), 5.36-5.49 (m, 2H), 7.01-7.10 (m, 2H), 7.44-7.54 (m, 3H), 7.58-7.64 (m, 2H).

Example 8

5-(4-Chlorophenyl)-2-{[3-(2,3-difluorophenyl)-1,2,4-oxadiazol-5-yl]methyl}-4-[(2S)-3,3,3-trifluoro-2-hydroxypropyl]-2,4-dihydro-3H-1,2,4-triazol-3-one

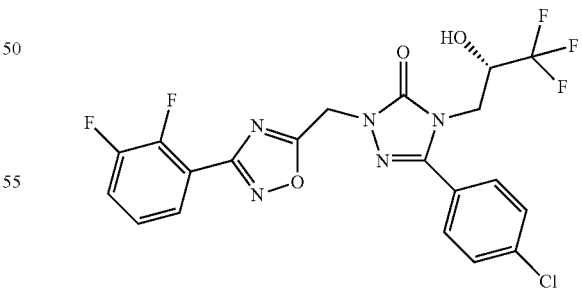

Analogously to the preparation of the compound in Example 2, 50 mg (0.13 mmol) of the compound from Example 7A gave, after a reaction time of 2 h, 47 mg (71% of theory) of the title compound.

LC/MS [Method 4]: $R_t$=1.18 min; MS [ESIpos]: m/z=502 (M+H)⁺

¹H-NMR (400 MHz, CDCl₃): δ=4.03 (dd, 1H), 4.07-4.13 (m, 1H), 4.38 (d, 1H), 4.52-4.59 (m, 1H), 5.35-5.47 (m, 2H), 7.17-7.25 (m, 1H), 7.34 (q, 1H), 7.51 (d, 2H), 7.58 (d, 2H), 7.79 (t, 1H).

Example 9

5-(4-Chlorophenyl)-4-[(2S)-3,3,3-trifluoro-2-hydroxypropyl]-2-({3-[2-(trifluoromethyl)phenyl]-1,2,4-oxadiazol-5-yl}methyl)-2,4-dihydro-3H-1,2,4-triazol-3-one

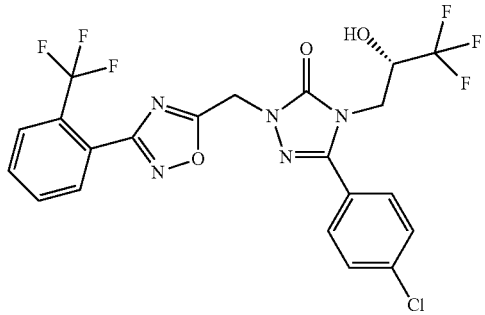 [SMILES: O=c1n(Cc2nc(-c3ccccc3C(F)(F)F)no2)nc(-c2ccc(Cl)cc2)n1C[C@H](O)C(F)(F)F]

Analogously to the preparation of the compound in Example 2, 50 mg (0.13 mmol) of the compound from Example 7A gave 50 mg (71% of theory) of the title compound.

LC/MS [Method 3]: R$_t$=1.39 min; MS [ESIpos]: m/z=534 (M+H)⁺

¹H-NMR (400 MHz, CDCl₃): δ=4.01 (dd, 1H), 4.08 (dd, 1H), 4.47-4.51 (m, 1H), 4.52-4.61 (m, 1H), 5.36-5.47 (m, 2H), 7.50 (d, 2H), 7.59 (d, 2H), 7.63-7.69 (m, 2H), 7.76-7.87 (m, 2H).

Example 10

5-(4-Chlorophenyl)-4-[(2S)-3,3,3-trifluoro-2-hydroxypropyl]-2-({3-[3-(trifluoromethyl)phenyl]-1,2,4-oxadiazol-5-yl}methyl)-2,4-dihydro-3H-1,2,4-triazol-3-one

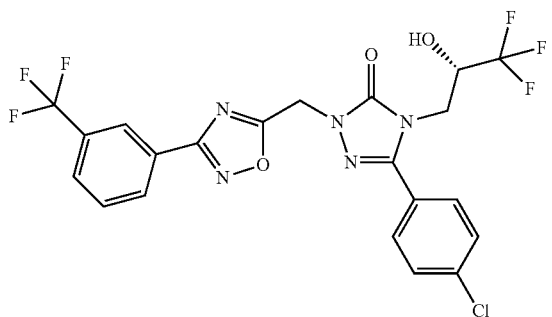 [SMILES: O=c1n(Cc2nc(-c3cccc(C(F)(F)F)c3)no2)nc(-c2ccc(Cl)cc2)n1C[C@H](O)C(F)(F)F]

Analogously to the preparation of the compound in Example 2, 50 mg (0.13 mmol) of the compound from Example 7A gave, after a reaction time of 2 h, 44 mg (62% of theory) of the title compound.

LC/MS [Method 4]: R$_t$=1.25 min; MS [ESIpos]: m/z=534 (M+H)⁺

¹H-NMR (400 MHz, CDCl₃): δ=4.05 (dd, 1H), 4.08-4.14 (m, 1H), 4.37 (d, 1H), 4.52-4.58 (m, 1H), 5.35-5.45 (m, 2H), 7.50 (d, 2H), 7.56-7.61 (m, 2H), 7.63 (d, 1H), 7.77 (d, 1H), 8.26 (d, 1H), 8.34 (s, 1H).

Example 11

5-(4-Chlorophenyl)-4-[(2S)-3,3,3-trifluoro-2-hydroxypropyl]-2-({3-[3-(trifluoromethoxy)phenyl]-1,2,4-oxadiazol-5-yl}methyl)-2,4-dihydro-3H-1,2,4-triazol-3-one

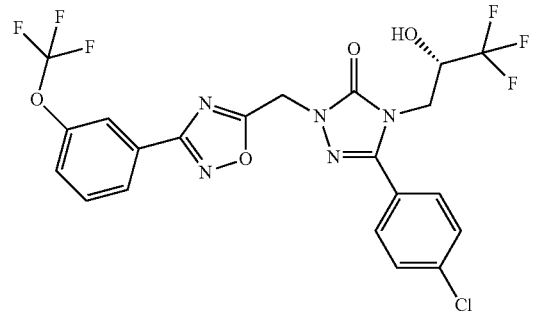 [SMILES: O=c1n(Cc2nc(-c3cccc(OC(F)(F)F)c3)no2)nc(-c2ccc(Cl)cc2)n1C[C@H](O)C(F)(F)F]

Analogously to the preparation of the compound in Example 2, 50 mg (0.13 mmol) of the compound from Example 7A gave, after a reaction time of 2 h, 53 mg (73% of theory) of the title compound.

LC/MS [Method 4]: R$_t$=1.27 min; MS [ESIpos]: m/z=550 (M+H)⁺

¹H-NMR (400 MHz, CDCl₃): δ=4.04 (dd, 1H), 4.08-4.12 (m, 1H), 4.47 (d, 1H), 4.52-4.59 (m, 1H), 5.34-5.44 (m, 2H), 7.37 (d, 1H), 7.46-7.55 (m, 3H), 7.56-7.61 (m, 2H), 7.93 (s, 1H), 8.01 (d, 1H).

Example 12

5-(4-Chlorophenyl)-2-{[3-(2,3-dichlorophenyl)-1,2,4-oxadiazol-5-yl]methyl}-4-[(2S)-3,3,3-trifluoro-2-hydroxypropyl]-2,4-dihydro-3H-1,2,4-triazol-3-one

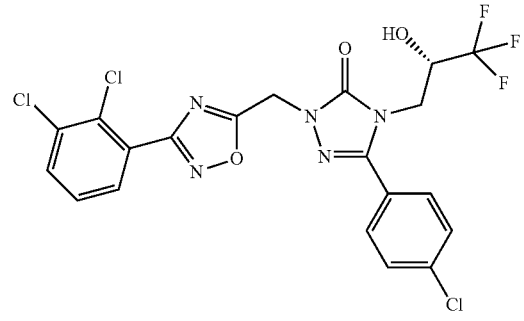 [SMILES: O=c1n(Cc2nc(-c3cccc(Cl)c3Cl)no2)nc(-c2ccc(Cl)cc2)n1C[C@H](O)C(F)(F)F]

Analogously to the preparation of the compound in Example 2, 50 mg (0.13 mmol) of the compound from Example 7A gave, after a reaction time of 20 h, 51 mg (72% of theory) of the title compound.

LC/MS [Method 4]: R$_t$=1.26 min; MS [ESIpos]: m/z=534 and 536 (M+H)⁺

¹H-NMR (400 MHz, CDCl₃): δ=3.86 (dd, 1H), 3.99-4.06 (m, 1H), 4.26-4.32 (m, 1H), 5.58 (s, 2H), 6.94 (d, 1H), 7.57 (t, 1H), 7.65 (d, 2H), 7.78 (d, 2H), 7.86 (d, 1H), 7.91 (d, 1H).

Example 13

5-(4-Chlorophenyl)-4-[(2S)-3,3,3-trifluoro-2-hydroxypropyl]-2-({3-[2-(trifluoromethoxy)phenyl]-1,2,4-oxadiazol-5-yl}methyl)-2,4-dihydro-3H-1,2,4-triazol-3-one

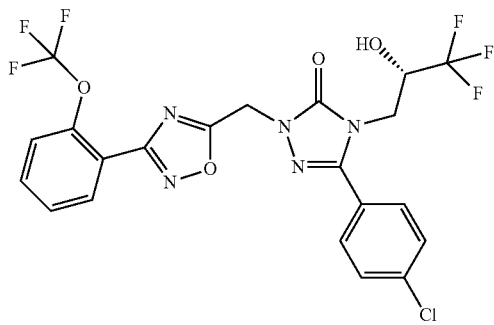 [SMILES: O=c1n(Cc2nc(-c3ccccc3OC(F)(F)F)no2)nc(-c2ccc(Cl)cc2)n1C[C@H](O)C(F)(F)F]

Analogously to the preparation of the compound in Example 2, 50 mg (0.13 mmol) of the compound from Example 7A gave, after a reaction time of 20 h, 37 mg (52% of theory) of the title compound.

LC/MS [Method 4]: R_t=1.25 min; MS [ESIpos]: m/z=550 (M+H)⁺

¹H-NMR (400 MHz, CDCl₃): δ=3.87 (dd, 1H), 4.02 (dd, 1H), 4.25-4.34 (m, 1H), 5.57 (s, 2H), 6.94 (d, 1H), 7.60-7.67 (m, 4H), 7.73-7.80 (m, 3H), 8.09 (dd, 1H).

Example 14

5-(5-Chlorothiophen-2-yl)-4-(2-fluorobenzyl)-2-({5-[3-(trifluoromethyl)benzyl]-1,2,4-oxadiazol-3-yl}methyl)-2,4-dihydro-3H-1,2,4-triazol-3-one

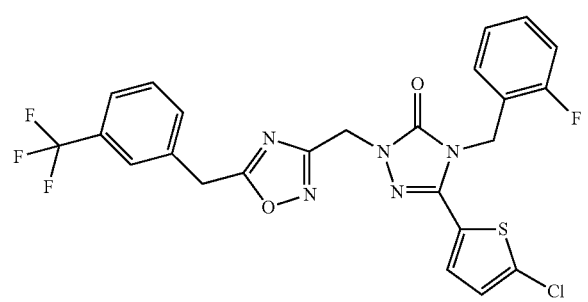 [SMILES: O=c1n(Cc2noc(Cc3cccc(C(F)(F)F)c3)n2)nc(-c2ccc(Cl)s2)n1Cc1ccccc1F]

Under argon, 81 mg (0.16 mmol) of benzotriazol-1-yloxytris(pyrrolidino)phosphonium hexafluorophosphate were added to a solution of 29 mg (0.14 mmol) of 3-(trifluoromethyl)phenylacetic acid and 27 µl (0.16 mmol) of N,N-diisopropylethylamine in 1.3 ml of dry DMF. After 30 min of stirring, 50 mg (0.13 mmol) of the compound from Example 25A were added and the mixture was stirred at RT for 18 h. 2 ml of water were then added, and the mixture was extracted three times with in each case 5 ml of ethyl acetate. The combined organic phases were washed with in each case 5 ml of water and sodium chloride solution, filtered though Extrelut and concentrated under reduced pressure. The residue was dissolved in 2 ml of DMF and stirred in a microwave oven at 250° C. for 15 min. After cooling, the solvent was removed under reduced pressure on a rotary evaporator and the crude product was purified by chromatography [Method 15]. This gave 25 mg (34% of theory) of the target compound as a dark-yellow resin.

LC/MS [Method 9]: R_t=4.28 min; MS [ESIpos]: m/z=550 (M+H)⁺

¹H-NMR (400 MHz, CDCl₃): δ=5.12 (s, 2H), 5.20 (s, 2H), 6.32 (d, 2H), 6.90 (d, 2H), 7.04-7.19 (m, 3H), 7.22-7.34 (m, 1H), 7.43-7.55 (m, 2H), 7.55-7.62 (m, 2H).

Example 15

5-(5-Chlorothiophen-2-yl)-4-(2-fluorobenzyl)-2-({5-[2-(trifluoromethyl)phenyl]-1,2,4-oxadiazol-3-yl}methyl)-2,4-dihydro-3H-1,2,4-triazol-3-one

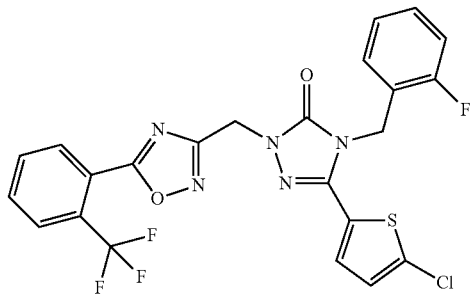 [SMILES: O=c1n(Cc2noc(-c3ccccc3C(F)(F)F)n2)nc(-c2ccc(Cl)s2)n1Cc1ccccc1F]

Analogously to the preparation of the compound in Example 14, 50 mg (0.13 mmol) of the compound from Example 25A gave 35 mg (49% of theory) of the title compound.

MS [ESIpos]: m/z=536 (M+H)⁺

¹H-NMR (400 MHz, CDCl₃): δ=5.16 (s, 2H), 5.35 (s, 2H), 6.33 (d, 2H), 6.92 (d, 2H), 7.04-7.13 (m, 2H), 7.13-7.20 (m, 1H), 7.23-7.33 (m, 1H), 7.68-7.78 (m, 2H), 7.83-7.92 (m, 1H), 7.96-8.05 (m, 1H).

Example 16

5-(5-Chlorothiophen-2-yl)-4-(2-fluorobenzyl)-2-({5-[2-(trifluoromethyl)benzyl]-1,2,4-oxadiazol-3-yl}methyl)-2,4-dihydro-3H-1,2,4-triazol-3-one

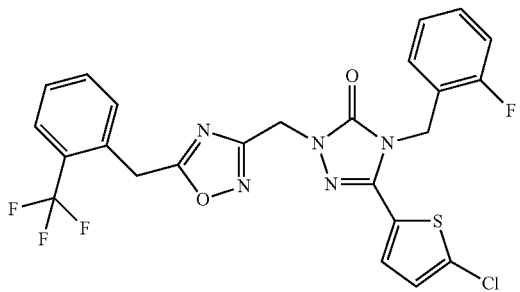 [SMILES: O=c1n(Cc2noc(Cc3ccccc3C(F)(F)F)n2)nc(-c2ccc(Cl)s2)n1Cc1ccccc1F]

Analogously to the preparation of the compound in Example 14, 50 mg (0.13 mmol) of the compound from Example 25A gave 15 mg (20% of theory) of the title compound.

MS [CIpos]: m/z=550 (M+H)+

$^1$H-NMR (400 MHz, CDCl$_3$): δ=4.93 (s, 2H), 5.14 (s, 2H), 5.20 (s, 2H), 6.82 (d, 2H), 6.90 (d, 2H), 7.04-7.18 (m, 3H), 7.25-7.35 (m, 1H), 7.35-7.50 (m, 2H), 7.50-7.59 (m, 1H), 7.66-7.75 (m, 1H).

Example 17

5-(4-Chlorophenyl)-2-{[5-(2-chlorophenyl)-1,3,4-oxadiazol-2-yl]methyl}-4-[(2S)-3,3,3-trifluoro-2-hydroxypropyl]-2,4-dihydro-3H-1,2,4-triazol-3-one

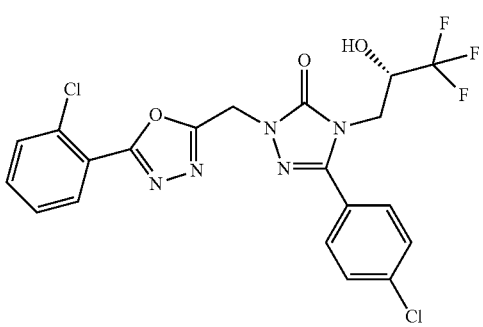

85 mg (0.28 mmol) of the compound from Example 5A were dissolved in 5 ml of acetonitrile, and 180 mg (0.55 mmol) of cesium carbonate and 66 mg (0.29 mmol) of 2-(chloromethyl)-5-(2-chloro-phenyl)-1,3,4-oxadiazole were added. The mixture was stirred at 80° C. for 1 h. For work-up, the mixture was cooled to RT, and 10 ml of water were added. The mixture was extracted twice with in each case 15 ml of ethyl acetate. The combined organic phases were dried over sodium sulfate, filtered and concentrated under reduced pressure. The crude product was purified chromatographically [Method 19]. This gave 66 mg (48% of theory) of the target compound.

LC/MS [Method 4]: R$_t$=1.12 min; MS [ESIpos]: m/z=500 (M+H)+

$^1$H-NMR (400 MHz, DMSO-d$_6$): δ=3.85 (dd, 1H), 4.01 (dd, 1H), 4.25-4.31 (m, 1H), 5.41-5.51 (m, 2H), 6.90 (d, 1H), 7.55-7.60 (m, 1H), 7.61-7.69 (m, 3H), 7.70-7.78 (m, 3H), 7.94 (dd, 1H).

Example 18

5-(4-Chlorophenyl)-2-{[5-(2-chlorophenyl)-1,3,4-thiadiazol-2-yl]methyl}-4-[(2S)-3,3,3-trifluoro-2-hydroxypropyl]-2,4-dihydro-3H-1,2,4-triazol-3-one

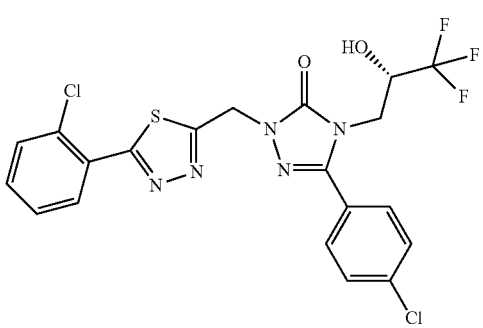 [SMILES: O=c1n(Cc2nnc(-c3ccccc3Cl)o2)nc(-c2ccc(Cl)cc2)n1C[C@H](O)C(F)(F)F]

30 mg (0.10 mmol) of the compound from Example 5A were dissolved in 3 ml of acetonitrile, and 48 mg (0.15 mmol) of cesium carbonate and 28 mg (0.10 mmol) of the compound from Example 86A were added. The mixture was stirred at 70° C. for 8 h. For work-up, the mixture was cooled to RT, diluted with 5 ml of methanol and filtered. The filtrate was concentrated under reduced pressure and the crude product was then purified chromatographically [Method 19]. This gave 11 mg (22% of theory) of the target compound.

LC/MS [Method 6]: R$_t$=2.48 min; MS [ESIpos]: m/z=516 (M+H)+

$^1$H-NMR (400 MHz, DMSO-d$_6$): δ=3.85 (dd, 1H), 4.01 (dd, 1H), 4.24-4.35 (m, 1H), 5.56-5.65 (m, 2H), 6.92 (s, 1H), 7.53-7.59 (m, 1H), 7.59-7.67 (m, 3H), 7.72 (dd, 1H), 7.77 (d, 2H), 8.14 (dd, 1H).

Example 19

5-(4-Chlorophenyl)-2-{[5-(2,3-dichlorophenyl)-1,3,4-thiadiazol-2-yl]methyl}-4-[(2S)-3,3,3-trifluoro-2-hydroxypropyl]-2,4-dihydro-3H-1,2,4-triazol-3-one

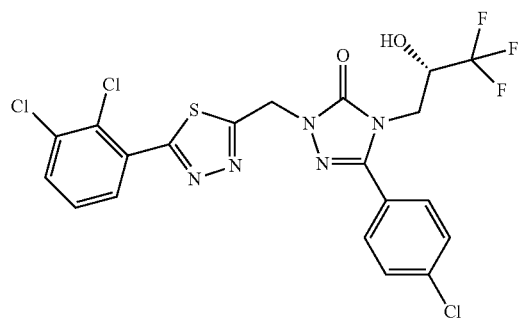 [SMILES: O=c1n(Cc2nnc(-c3cccc(Cl)c3Cl)s2)nc(-c2ccc(Cl)cc2)n1C[C@H](O)C(F)(F)F]

Analogously to the preparation of Example 18, 36 mg (0.12 mmol) of the compound from Example 5A were reacted with 38 mg (0.12 mmol) of the compound from Example 87A. This gave 33 mg (48% of theory) of the target compound.

LC/MS [Method 4]: R$_t$=1.25 min; MS [ESIpos]: m/z=550 and 552 (M+H)+

$^1$H-NMR (400 MHz, DMSO-d$_6$): δ=3.85 (dd, 1H), 4.01 (dd, 1H), 4.25-4.35 (m, 1H), 5.56-5.66 (m, 2H), 6.94 (br. s, 1H), 7.57 (t, 1H), 7.64 (d, 2H), 7.78 (d, 2H), 7.90 (dd, 1H), 8.05 (dd, 1H).

Example 20

5-(4-Chlorophenyl)-4-[(2S)-3,3,3-trifluoro-2-hydroxypropyl]-2-({5-[2-(trifluoromethyl)phenyl]-1,3,4-thiadiazol-2-yl}methyl)-2,4-dihydro-3H-1,2,4-triazol-3-one

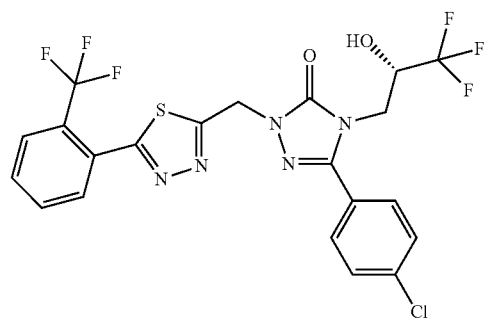 [SMILES: O=c1n(Cc2nnc(-c3ccccc3C(F)(F)F)s2)nc(-c2ccc(Cl)cc2)n1C[C@H](O)C(F)(F)F]

Analogously to the preparation of Example 18, 33 mg (0.11 mmol) of the compound from Example 5A were reacted with 35 mg (0.11 mmol) of the compound from Example 85A. This gave 16 mg (27% of theory) of the target compound.

LC/MS [Method 3]: $R_t$=1.33 min; MS [ESIpos]: m/z=550 (M+H)$^+$ $^1$H-NMR (400 MHz, DMSO-d$_6$): δ=3.86 (dd, 1H), 4.02 (dd, 1H), 4.25-4.35 (m, 1H), 5.56-5.65 (m, 2H), 6.92 (br. s, 1H), 7.62-7.67 (m, 2H), 7.75-7.88 (m, 5H), 7.97-8.01 (m, 1H).

Example 21

5-(4-Chlorophenyl)-4-cyclopropyl-2-({5-[3-(trifluoromethyl)phenyl]-4H-1,2,4-triazol-3-yl}methyl)-2,4-dihydro-3H-1,2,4-triazol-3-one

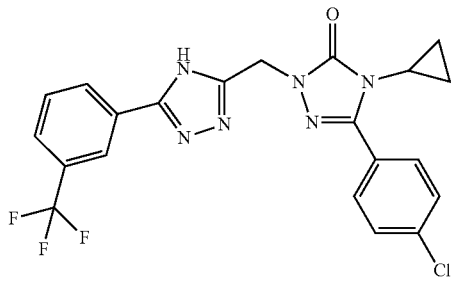 [SMILES: O=c1n(Cc2nnc(-c3cccc(C(F)(F)F)c3)[nH]2)nc(-c2ccc(Cl)cc2)n1C1CC1]

100 mg (0.33 mmol) of the compound from Example 21A were dissolved in 1.6 ml of DMF, 109 mg (0.49 mmol) of 3-trifluoromethylbenzamidine hydrochloride were added and the mixture was stirred in a microwave oven at 150° C. for 45 min. After cooling, the reaction was concentrated under reduced pressure on a rotary evaporator and the residue that remained was purified chromatographically [Method 19]. This gave 70 mg (47% of theory) of the target compound as a colorless solid.

LC/MS [Method 7]: $R_t$=2.33 min; MS [ESIpos]: m/z=461 (M+H)$^+$ $^1$H-NMR (400 MHz, CDCl$_3$): δ=0.74-0.84 (m, 2H), 0.99-1.10 (m, 2H), 2.96-3.06 (m, 1H), 5.28 (s, 2H), 7.45 (d, 2H), 7.53 (t, 1H), 7.64 (d, 1H), 7.68 (d, 2H), 8.25 (d, 1H), 8.36 (s, 1H).

Example 22

5-(4-Chlorophenyl)-4-cyclopropyl-2-({5-[2-(trifluoromethyl)benzyl]-4H-1,2,4-triazol-3-yl}methyl)-2,4-dihydro-3H-1,2,4-triazol-3-one

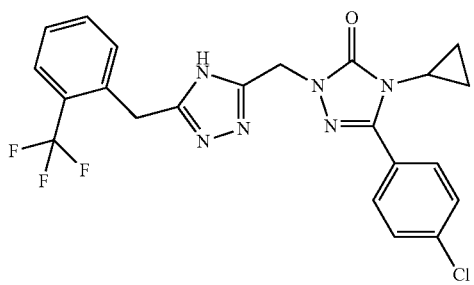 [SMILES: O=c1n(Cc2nnc(Cc3ccccc3C(F)(F)F)[nH]2)nc(-c2ccc(Cl)cc2)n1C1CC1]

Analogously to the preparation of the compound in Example 21, 100 mg (0.33 mmol) of the compound from Example 21A gave 54 mg (35% of theory) of the title compound.

MS [ESIpos]: m/z=475 (M+H)$^+$ $^1$H-NMR (400 MHz, CDCl$_3$): δ=0.70-0.80 (m, 2H), 0.96-1.06 (m, 2H), 2.92-3.03 (m, 1H), 4.30 (s, 2H), 5.15 (s, 2H), 7.30-7.40 (m, 2H), 7.40-7.51 (m, 3H), 7.61-7.71 (m, 3H), 10.80 (br. s, 1H).

Example 23

5-(4-Chlorophenyl)-4-cyclopropyl-2-({5-[3-(trifluoromethyl)benzyl]-4H-1,2,4-triazol-3-yl}methyl)-2,4-dihydro-3H-1,2,4-triazol-3-one

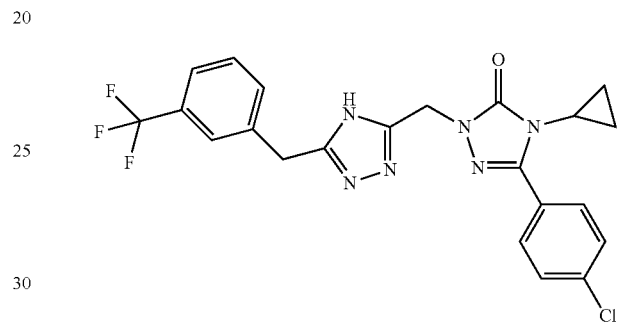

Analogously to the preparation of the compound in Example 21, 75 mg (0.24 mmol) of the compound from Example 21A gave 55 mg (48% of theory) of the title compound.

LC/MS [Method 5]: $R_t$=2.42 min; MS [ESIpos]: m/z=475 (M+H)$^+$ $^1$H-NMR (400 MHz, CDCl$_3$): δ=0.70-0.79 (m, 2H), 0.96-1.06 (m, 2H), 2.93-3.03 (m, 1H), 4.14 (s, 2H), 5.15 (s, 2H), 7.38-7.51 (m, 5H), 7.56 (s, 1H), 7.62-7.70 (m, 2H).

Example 24

5-(4-Chlorophenyl)-4-cyclopropyl-2-{[5-(2,6-dichlorobenzyl)-4H-1,2,4-triazol-3-yl]methyl}-2,4-dihydro-3H-1,2,4-triazol-3-one

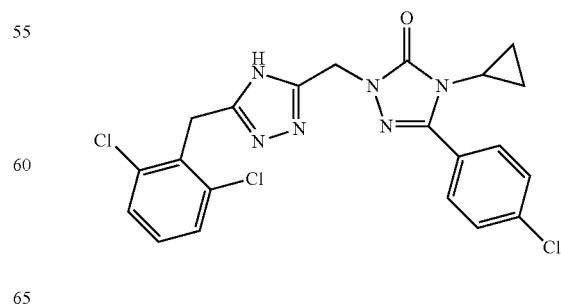

58 mg (0.24 mmol) of 2-(2,6-dichlorophenyl)ethaneimidamide hydrochloride were initially charged in 1 ml of dry methanol, 66 µl (0.24 mmol) of a 25% strength methanolic sodium methoxide solution were added and the mixture was stirred at RT for 1 h. 50 mg (0.16 mmol) of the compound from Example 21A, dissolved in 0.6 ml of methanol, were then added. The reaction was stirred at room temperature overnight. The precipitated colorless solid was filtered off with suction, washed with a little methanol and dried under high vacuum. The solid was then suspended in xylene and stirred under reflux for 4 h. After cooling, the mixture was concentrated under reduced pressure and the residue was purified by chromatography [Method 19]. This gave 30 mg (39% of theory) of the target compound as a colorless solid.

LC/MS [Method 5]: $R_t$=2.38 min; MS [ESIpos]: m/z=476 (M+H)$^+$ $^1$H-NMR (400 MHz, CDCl$_3$): δ=0.70-0.80 (m, 2H), 0.96-1.06 (m, 2H), 2.93-3.04 (m, 1H), 4.46 (s, 2H), 5.13 (s, 2H), 7.19 (t, 1H), 7.35 (d, 2H), 7.44 (d, 2H), 7.67 (d, 2H), 11.00 (br. s, 1H).

Example 25

5-(5-Chlorothiophen-2-yl)-4-(2-fluorobenzyl)-2-({5-[3-(trifluoromethyl)phenyl]-4H-1,2,4-triazol-3-yl}methyl)-2,4-dihydro-3H-1,2,4-triazol-3-one

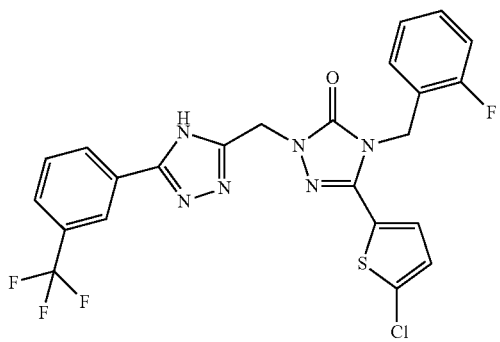 [SMILES: O=c1n(Cc2nnc(-c3cccc(C(F)(F)F)c3)[nH]2)nc(-c2ccc(Cl)s2)n1Cc1ccccc1F]

100 mg (0.26 mmol) of the compound from Example 22A were dissolved in 1.0 ml of DMF, 88 mg (0.39 mmol) of 3-(trifluoromethyl)benzenecarboximidamide hydrochloride were added and the mixture was stirred in a microwave oven at 220° C. for 30 min. After cooling, the reaction was concentrated under reduced pressure on a rotary evaporator, and the residue was purified chromatographically [Method 19]. This gave 71 mg (51% of theory) of the target compound as a colorless resin.

MS [ESIpos]: m/z=535 (M+H)$^+$ $^1$H-NMR (400 MHz, CDCl$_3$): δ=5.14 (s, 2H), 5.34 (s, 2H), 6.85 (s, 1H), 6.95 (s, 1H), 7.04-7.16 (m, 3H), 7.28-7.37 (m, 1H), 7.50-7.60 (m, 1H), 7.61-7.70 (m, 1H), 8.20-8.30 (m, 1H), 8.35 (s, 1H), 12.00 (br. s, 1H).

Example 26

5-(5-Chlorothiophen-2-yl)-4-(2-fluorobenzyl)-2-({5-[2-(trifluoromethyl)benzyl]-4H-1,2,4-triazol-3-yl}methyl)-2,4-dihydro-3H-1,2,4-triazol-3-one

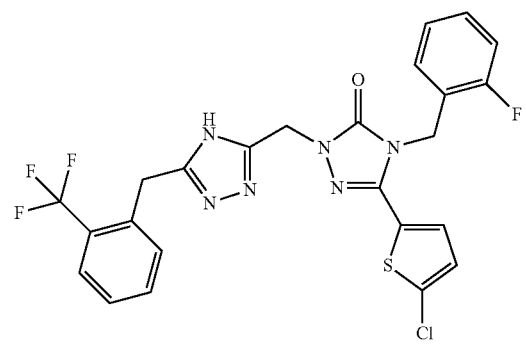 [SMILES: O=c1n(Cc2nnc(Cc3ccccc3C(F)(F)F)[nH]2)nc(-c2ccc(Cl)s2)n1Cc1ccccc1F]

Analogously to the preparation of the compound in Example 25, 75 mg (0.20 mmol) of the compound from Example 22A gave 19 mg (18% of theory) of the title compound.

LC/MS [Method 5]: $R_t$=2.62 min; MS [ESIpos]: m/z=549 (M+H)$^+$ $^1$H-NMR (400 MHz, CDCl$_3$): δ=4.32 (s, 2H), 5.11 (s, 2H), 5.21 (s, 2H), 6.82 (d, 1H), 6.90 (d, 1H), 7.03-7.16 (m, 3H), 7.25-7.32 (m, 1H), 7.32-7.44 (m, 2H), 7.45-7.52 (m, 1H), 7.68 (d, 1H), 10.70 (br. s, 1H).

Example 27

5-(5-Chlorothiophen-2-yl)-4-(2-fluorobenzyl)-2-({5-[3-(trifluoromethyl)benzyl]-4H-1,2,4-triazol-3-yl}methyl)-2,4-dihydro-3H-1,2,4-triazol-3-one

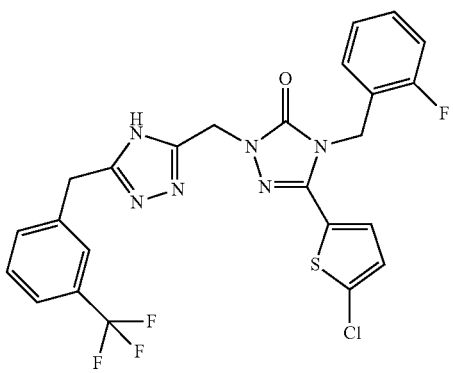 [SMILES: O=c1n(Cc2nnc(Cc3cccc(C(F)(F)F)c3)[nH]2)nc(-c2ccc(Cl)s2)n1Cc1ccccc1F]

Analogously to the preparation of the compound in Example 25, 75 mg (0.20 mmol) of the compound from Example 22A gave 29 mg (27% of theory) of the title compound.

MS [ESIpos]: m/z=549 (M+H)$^+$
$^1$H-NMR (400 MHz, CDCl$_3$): δ=4.15 (s, 2H), 5.11 (s, 2H), 5.22 (s, 2H), 6.84 (d, 1H), 6.91 (d, 1H), 7.03-7.15 (m, 3H), 7.25-7.34 (m, 1H), 7.44 (d, 1H), 7.48-7.53 (m, 2H), 7.58 (s, 1H), 11.10 (br. s, 1H).

Example 28

Methyl 3-{[3-(4-chlorophenyl)-5-oxo-1-({5-[2-(trifluoromethyl)benzyl]-4H-1,2,4-triazol-3-yl}-methyl)-1,5-dihydro-4H-1,2,4-triazol-4-yl]methyl}benzenecarboxylate

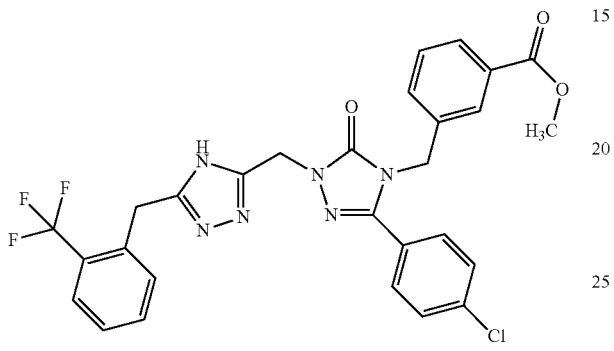

77 mg (0.27 mmol) of 2-[2-(trifluoromethyl)phenyl]ethaneimidamide hydrobromide were dissolved in 1 ml of dry methanol, 74 µl (0.27 mmol) of a 25% strength methanolic sodium methoxide solution were added and the mixture was stirred for 30 min 75 mg (0.18 mmol) of the compound from Example 16A were then added, and the mixture was stirred initially at RT for 16 h and then under reflux for 5 h. The mixture was then directly purified chromatographically [Method 19]. This gave 67 mg (64% of theory) of the target compound as a colorless foam.

LC/MS [Method 5]: R$_t$=2.59 min; MS [ESIpos]: m/z=583 (M+H)$^+$
$^1$H-NMR (400 MHz, CDCl$_3$): δ=3.88 (s, 3H), 4.31 (s, 2H), 5.00 (s, 2H), 5.25 (s, 2H), 7.29-7.44 (m, 8H), 7.49 (d, 1H), 7.58 (d, 1H), 7.90 (s, 1H), 7.95 (d, 1H).

Example 29

Methyl 3-{[3-(4-chlorophenyl)-1-{[5-(2,6-dichlorobenzyl)-4H-1,2,4-triazol-3-yl]methyl}-5-oxo-1,5-dihydro-4H-1,2,4-triazol-4-yl]methyl}benzenecarboxylate

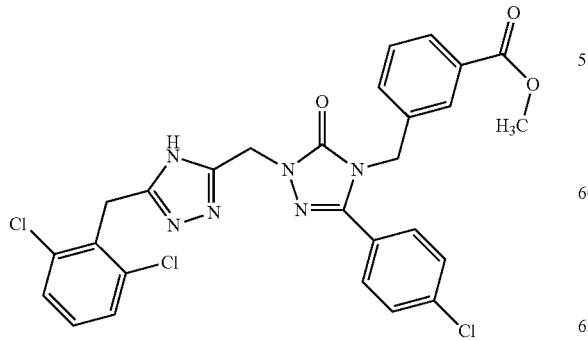

Analogously to the preparation of the compound in Example 28, 80 mg (0.19 mmol) of the compound from Example 16A gave 67 mg (60% of theory) of the title compound.

MS [ESIpos]: m/z=583 and 585 (M+H)$^+$
$^1$H-NMR (400 MHz, CDCl$_3$): δ=3.90 (s, 3H), 4.49 (s, 2H), 5.00 (s, 2H), 5.24 (s, 2H), 7.19 (t, 1H), 7.28-7.44 (m, 8H), 7.88-8.00 (m, 2H), 11.20 (br. s, 1H).

Example 30

5-(4-Chlorophenyl)-4-(3,3,3-trifluoro-2-hydroxypropyl)-2-({5-[2-(trifluoromethyl)benzyl]-4H-1,2,4-triazol-3-yl}methyl)-2,4-dihydro-3H-1,2,4-triazol-3-one

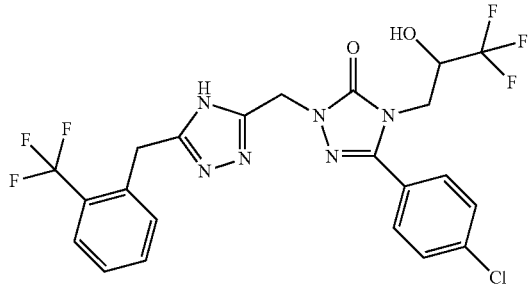 [SMILES: O=c1n(Cc2nnc(Cc3ccccc3C(F)(F)F)[nH]2)nc(-c2ccc(Cl)cc2)n1CC(O)C(F)(F)F]

370 mg (0.97 mmol) of the compound from Example 18A were dissolved in 5 ml of DMF, 349 mg (1.46 mmol) of 2-[2-(trifluoromethyl)phenyl]ethaneimidamide hydrochloride were added and the mixture was stirred in a microwave oven at 200° C. for 90 min. After cooling, the reaction was diluted with 5 ml of methanol and directly purified chromatographically [Method 19]. This gave 170 mg (32% of theory) of the target compound.

LC/MS [Method 3]: R$_t$=1.24 min; MS [ESIpos]: m/z=547 (M+H)$^+$
$^1$H-NMR (400 MHz, CDCl$_3$): δ=3.87-4.00 (m, 2H), 4.21 (s, 2H), 4.56-4.62 (m, 1H), 5.03-5.21 (m, 2H), 5.70 (br. s, 1H), 7.31 (d, 1H), 7.38 (t, 1H), 7.44 (d, 2H), 7.49 (t, 1H), 7.59 (s, 2H), 7.67 (d, 1H), 11.48 (br. s, 1H).

Example 31

3-{[3-(4-Chlorophenyl)-5-oxo-1-({5-[2-(trifluoromethyl)benzyl]-4H-1,2,4-triazol-3-yl}methyl)-1,5-dihydro-4H-1,2,4-triazol-4-yl]methyl}benzenecarboxylic acid

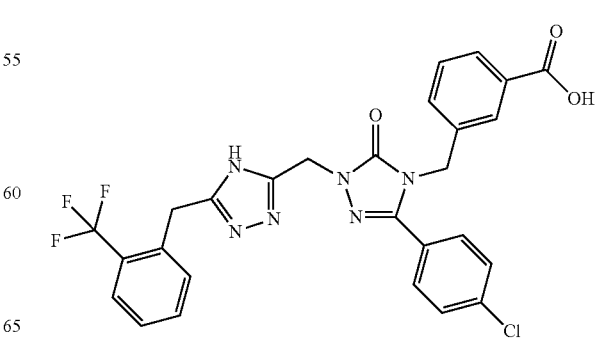

62 mg (0.11 mmol) of the compound from Example 28 were suspended in 1 ml of ethanol, and 213 µl (0.21 mmol) of 1 M aqueous sodium hydroxide solution were added. The mixture was stirred at 50° C. for 4 h. After cooling to RT, the reaction was neutralized with 215 µl of 1 M hydrochloric acid and concentrated under reduced pressure, and the residue was purified by chromatography [Method 19]. This gave 37 mg (61% of theory) of the target compound as a colorless foam.

MS [ESIpos]: m/z=569 (M+H)$^+$ $^1$H-NMR (400 MHz, DMSO-d$_6$): δ=4.04-4.35 (m, 2H), 4.90-5.25 (m, 4H), 7.25-7.38 (m, 1H), 7.38-7.54 (m, 7H), 7.54-7.65 (m, 1H), 7.65-7.78 (m, 2H), 7.80 (d, 1H), 13.02 (br. s, 1H), 13.65-13.93 (br. s, 1H).

Example 32

3-{[3-(4-Chlorophenyl)-1-{[5-(2,6-dichlorobenzyl)-4H-1,2,4-triazol-3-yl]methyl}-5-oxo-1,5-dihydro-4H-1,2,4-triazol-4-yl]methyl}benzenecarboxylic acid

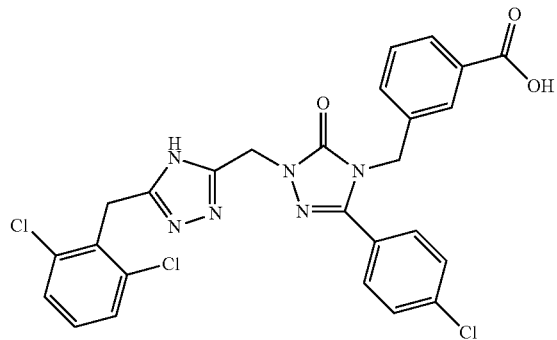 [SMILES: O=C(O)c1cccc(Cn2c(-c3ccc(Cl)cc3)nn(Cc3nnc(Cc4c(Cl)cccc4Cl)[nH]3)c2=O)c1]

Analogously to the preparation of the compound in Example 31, 60 mg (0.10 mmol) of the compound from Example 29 gave 40 mg (68% of theory) of the title compound.

MS [ESIpos]: m/z=569 (M+H)$^+$ $^1$H-NMR (400 MHz, DMSO-d$_6$): δ=4.16-4.44 (m, 2H), 4.85-5.25 (m, 4H), 7.24-7.40 (m, 2H), 7.43 (t, 1H), 7.45-7.58 (m, 6H), 7.70 (s, 1H), 7.82 (d, 1H), 13.03 (br. s, 1H), 13.70 (br. s, 1H).

Example 33

5-(4-Chlorophenyl)-4-cyclopropyl-2-[(5-{2-[3-(trifluoromethyl)phenyl]propan-2-yl}-4H-1,2,4-triazol-3-yl)methyl]-2,4-dihydro-3H-1,2,4-triazol-3-one

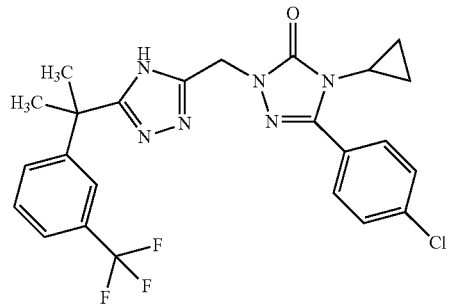 [SMILES: CC(C)(c1cccc(C(F)(F)F)c1)c1nnc(Cn2nc(-c3ccc(Cl)cc3)n(C3CC3)c2=O)[nH]1]

42 mg (0.14 mmol) of the compound from Example 21A were dissolved in 1.2 ml of DMF, 40 mg (0.15 mmol) of 2-methyl 2-[3-(trifluoromethyl)phenyl]propaneimidamide hydrochloride and 9 mg (0.16 mmol) of sodium methoxide were added and the mixture was stirred in a microwave reactor at 180° C. for 2 h. After cooling to RT, the mixture was purified directly by preparative HPLC [Method 19]. This gave 2 mg (3% of theory) of the target compound as a colorless foam.

LC/MS [Method 1]: R$_t$=2.06 min; MS [ESIpos]: m/z=503 (M+H)$^+$ $^1$H-NMR (400 MHz, CDCl$_3$): δ=0.75-0.79 (m, 2H), 1.00-1.05 (m, 2H), 1.79 (s, 6H), 2.96-3.02 (m, 1H), 5.16 (s, 2H), 7.38-7.43 (q, 1H), 7.45 (d, 2H), 7.46-7.49 (m, 2H), 7.59 (s, 1H), 7.67 (d, 2H).

Example 34

5-(4-Chlorophenyl)-4-cyclopropyl-2-({5-[1-(2-fluorophenyl)-1-methylethyl]-4H-1,2,4-triazol-3-yl}methyl)-2,4-dihydro-3H-1,2,4-triazol-3-one

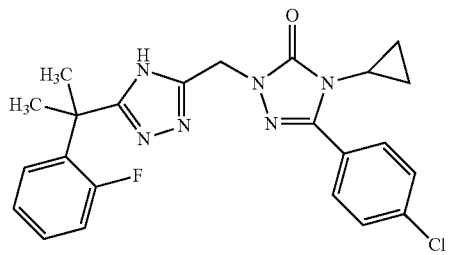 [SMILES: CC(C)(c1nnc(Cn2nc(-c3ccc(Cl)cc3)n(C3CC3)c2=O)[nH]1)c1ccccc1F]

60 mg (0.20 mmol) of the compound from Example 21A were dissolved in 1 ml of DMF, and 63 mg (0.29 mmol) of 2-(2-fluorophenyl)-2-methylpropaneimidamide hydrochloride and 17 mg (0.31 mmol) of sodium methoxide were added. The suspension was stirred at 150° C. for 8 h. The reaction was then brought to completion by 45 min of stirring in a microwave reactor at 200° C. The suspension was diluted with about 1 ml of methanol and filtered, and the filtrate was purified by preparative HPLC [Method 19]. This gave 13 mg (15% of theory) of the title compound.

LC/MS [Method 5]: R$_t$=2.30 min; MS [ESIpos]: m/z=453 (M+H)$^+$ $^1$H-NMR (400 MHz, CDCl$_3$): δ=0.75 (m, 2H), 0.95 (m, 2H), 1.88 (s, 6H), 2.99 (m, 1H), 5.32 (s, 2H), 6.93-7.00 (m, 1H), 7.14-7.21 (m, 1H), 7.38-7.49 (m, 4H), 7.62-7.72 (m, 2H).

Example 35

5-(4-Chlorophenyl)-4-cyclopropyl-2-[(5-{2-[3-(trifluoromethyl)phenyl]ethyl}-4H-1,2,4-triazol-3-yl)methyl]-2,4-dihydro-3H-1,2,4-triazol-3-one

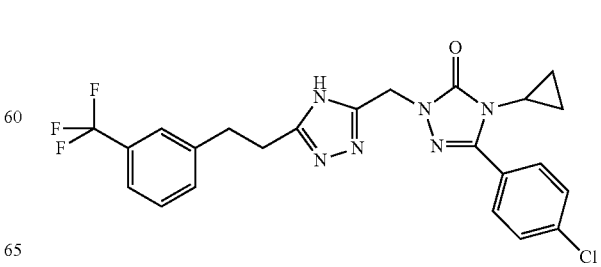

50 mg (0.16 mmol) of the compound from Example 21A were taken up in 1 ml of DMF, 62 mg (0.24 mmol) of 3-[3-(trifluoromethyl)phenyl]propaneimidamide hydrochloride were added and the mixture was stirred in a microwave oven at 180° C. for 1 h. After cooling, the reaction mixture was diluted with methanol and the solution was directly separated by preparative HPLC [Method 19]. This gave 11 mg (14% of theory) of the title compound.

LC/MS [Method 1]: $R_t$=1.96 min; MS [ESIpos]: m/z=489 (M+H)$^+$ $^1$H-NMR (400 MHz, CDCl$_3$): δ=0.71-0.81 (m, 2H), 0.98-1.06 (m, 2H), 2.99 (m, 1H), 3.03-3.09 (m, 2H), 3.10-3.16 (m, 2H), 5.16 (s, 2H), 7.37 (d, 2H), 7.41-7.48 (m, 4H), 7.68 (d, 2H).

Example 36

5-(4-Chlorophenyl)-4-cyclopropyl-2-{[5-(2-ethoxybenzyl)-4H-1,2,4-triazol-3-yl]methyl}-2,4-dihydro-3H-1,2,4-triazol-3-one

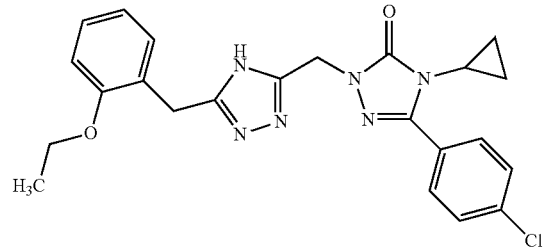 [SMILES: CCOc1ccccc1Cc1nnc(Cn2nc(-c3ccc(Cl)cc3)n(C3CC3)c2=O)[nH]1]

50 mg (0.16 mmol) of the compound from Example 21A were taken up in 1 ml of DMF, 52 mg (0.24 mmol) of 2-(2-ethoxyphenyl)ethaneimidamide hydrochloride were added and the mixture was stirred in a microwave oven at 200° C. for 1 h. After cooling, the reaction was diluted with about 1 ml of methanol and the solution was directly separated by preparative HPLC [Method 19]. This gave 21 mg (28% of theory) of the title compound.

LC/MS [Method 3]: $R_t$=1.14 min; MS [ESIpos]: m/z=451 (M+H)$^+$ $^1$H-NMR (400 MHz, CDCl$_3$): δ=0.75-0.79 (m, 2H), 0.97-1.02 (m, 2H), 1.44 (t, 3H), 2.97 (m, 1H), 4.09-4.14 (m, 4H), 5.10 (s, 2H), 6.91 (t, 2H), 7.25 (t, 2H), 7.41 (2d, 2H), 7.67 (d, 2H).

Example 37

5-(4-Chlorophenyl)-4-cyclopropyl-2-{[5-(3-fluorobenzyl)-4H-1,2,4-triazol-3-yl]methyl}-2,4-dihydro-3H-1,2,4-triazol-3-one

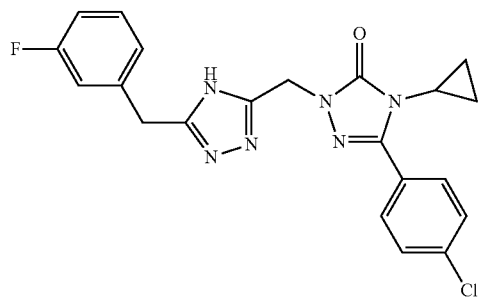 [SMILES: O=c1n(Cc2nnc(Cc3cccc(F)c3)[nH]2)nc(-c2ccc(Cl)cc2)n1C1CC1]

Analogously to the preparation of the compound in Example 36, 50 mg (0.16 mmol) of the compound from Example 21A gave 11 mg (16% of theory) of the title compound.

LC/MS [Method 5]: $R_t$=2.16 min; MS [ESIpos]: m/z=425 (M+H)$^+$ $^1$H-NMR (400 MHz, CDCl$_3$): δ=0.75-0.79 (m, 2H), 0.99-1.05 (m, 2H), 2.98 (m, 1H), 4.10 (s, 2H), 5.15 (s, 2H), 6.93 (m, 1H), 7.00 (d, 1H), 7.07 (d, 1H), 7.23-7.30 (m, 1H), 7.44 (d, 2H), 7.67 (d, 2H).

Example 38

5-(4-Chlorophenyl)-4-cyclopropyl-2-{[5-(2-methoxybenzyl)-4H-1,2,4-triazol-3-yl]methyl}-2,4-dihydro-3H-1,2,4-triazol-3-one

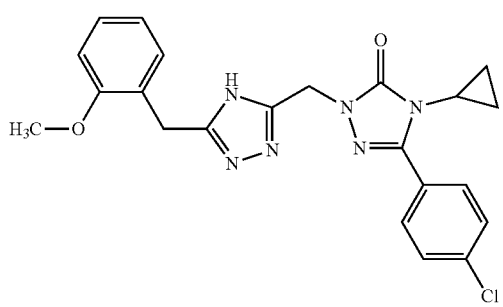 [SMILES: COc1ccccc1Cc1nnc(Cn2nc(-c3ccc(Cl)cc3)n(C3CC3)c2=O)[nH]1]

Analogously to the preparation of the compound in Example 36, 50 mg (0.16 mmol) of the compound from Example 21A gave 11 mg (16% of theory) of the title compound.

LC/MS [Method 3]: $R_t$=1.09 min; MS [ESIpos]: m/z=437 (M+H)$^+$.

Example 39

5-(4-Chlorophenyl)-4-cyclopropyl-2-{[5-(3-methylbenzyl)-4H-1,2,4-triazol-3-yl]methyl}-2,4-dihydro-3H-1,2,4-triazol-3-one

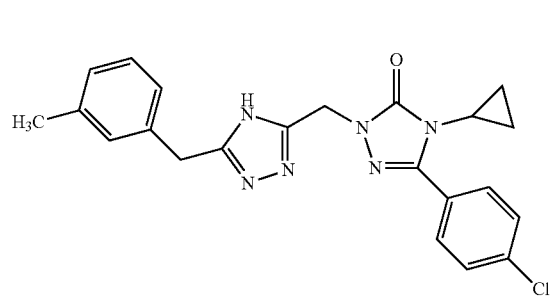 [SMILES: Cc1cccc(Cc2nnc(Cn3nc(-c4ccc(Cl)cc4)n(C4CC4)c3=O)[nH]2)c1]

Analogously to the preparation of the compound in Example 36, 50 mg (0.16 mmol) of the compound from Example 21A gave 11 mg (16% of theory) of the title compound.

LC/MS [Method 3]: $R_t$=1.13 min; MS [ESIpos]: m/z=421 (M+H)$^+$ $^1$H-NMR (400 MHz, CDCl$_3$): δ=0.73-0.79 (m, 2H), 0.97-1.04 (m, 2H), 2.31 (s, 3H), 2.93-3.01 (m, 1H), 4.07 (s, 2H), 5.13 (s, 2H), 7.04-7.11 (m, 3H), 7.18-7.23 (m, 1H), 7.43 (d, 2H), 7.67 (d, 2H).

Example 40

2-{[5-(2-Chlorobenzyl)-4H-1,2,4-triazol-3-yl]methyl}-5-(4-chlorophenyl)-4-cyclopropyl-2,4-dihydro-3H-1,2,4-triazol-3-one

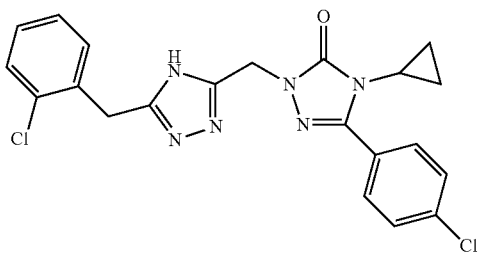 [SMILES: O=c1n(Cc2nnc(Cc3ccccc3Cl)[nH]2)nc(-c2ccc(Cl)cc2)n1C1CC1]

Analogously to the preparation of the compound in Example 36, 50 mg (0.16 mmol) of the compound from Example 21A gave 22 mg (31% of theory) of the title compound.

LC/MS [Method 3]: $R_t$=1.13 min; MS [ESIpos]: m/z=441 (M+H)$^+$ $^1$H-NMR (400 MHz, CDCl$_3$): δ=0.74-0.79 (m, 2H), 0.99-1.04 (m, 2H), 2.98 (m, 1H), 4.25 (s, 2H), 5.14 (s, 2H), 7.21-7.23 (m, 2H), 7.30-7.32 (m, 1H), 7.38-7.40 (m, 1H), 7.44 (d, 2H), 7.67 (d, 2H).

Example 41

5-(4-Chlorophenyl)-4-cyclopropyl-2-{[5-(2-fluorobenzyl)-4H-1,2,4-triazol-3-yl]methyl}-2,4-dihydro-3H-1,2,4-triazol-3-one

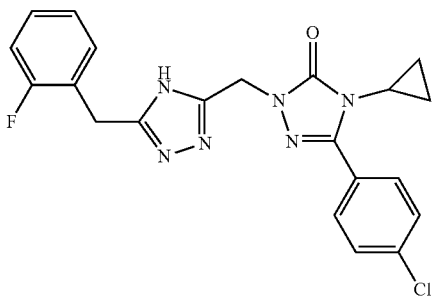 [SMILES: O=c1n(Cc2nnc(Cc3ccccc3F)[nH]2)nc(-c2ccc(Cl)cc2)n1C1CC1]

Analogously to the preparation of the compound in Example 36, 50 mg (0.16 mmol) of the compound from Example 21A gave 11 mg (16% of theory) of the title compound.

LC/MS [Method 5]: $R_t$=2.07 min; MS [ESIpos]: m/z=425 (M+H)$^+$ $^1$H-NMR (400 MHz, CDCl$_3$): δ=0.74-0.79 (m, 2H), 0.98-1.05 (m, 2H), 2.98 (m, 1H), 4.14 (s, 2H), 5.14 (s, 2H), 7.03-7.12 (m, 2H), 7.21-7.31 (m, 2H), 7.44 (d, 2H), 7.67 (d, 2H).

Example 42

5-(4-Chlorophenyl)-2-{[5-(2,6-dichlorobenzyl)-4H-1,2,4-triazol-3-yl]methyl}-4-(4-methoxybenzyl)-2,4-dihydro-3H-1,2,4-triazol-3-one

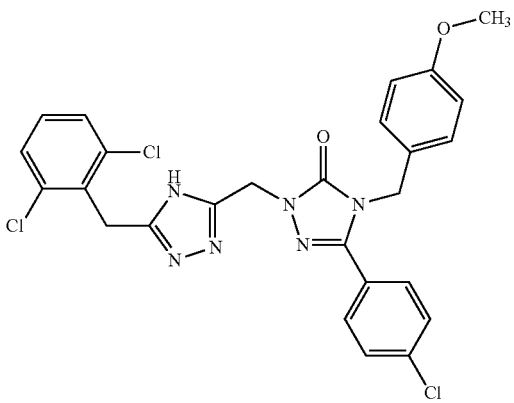 [SMILES: COc1ccc(Cn2c(-c3ccc(Cl)cc3)nn(Cc3nnc(Cc4c(Cl)cccc4Cl)[nH]3)c2=O)cc1]

Analogously to the preparation of the compound in Example 36, 70 mg (0.18 mmol) of the compound from Example 17A gave 36 mg (36% of theory) of the title compound.

LC/MS [Method 3]: $R_t$=1.30 min; MS [ESIpos]: m/z=557 (M+H)$^+$ $^1$H-NMR (400 MHz, CDCl$_3$): δ=3.78 (s, 3H), 4.47 (s, 2H), 4.86 (s, 2H), 5.22 (s, 2H), 6.82 (d, 2H), 7.06 (d, 2H), 7.18 (t, 1H), 7.33-7.39 (m, 6H).

Example 43

5-(4-Chlorophenyl)-2-{[5-(2,6-dichlorobenzyl)-4H-1,2,4-triazol-3-yl]methyl}-4-[(2R)-3,3,3-trifluoro-2-hydroxypropyl]-2,4-dihydro-3H-1,2,4-triazol-3-one

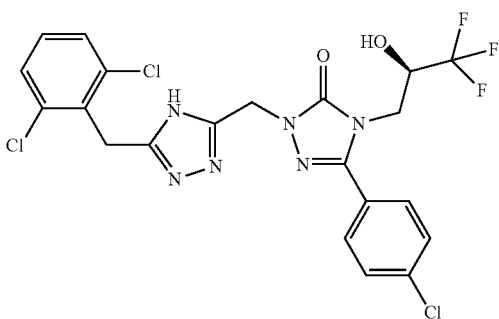 [SMILES: O=c1n(Cc2nnc(Cc3c(Cl)cccc3Cl)[nH]2)nc(-c2ccc(Cl)cc2)n1C[C@@H](O)C(F)(F)F]

Analogously to the preparation of the compound in Example 36, 70 mg (0.18 mmol) of the compound from Example 20A gave 21 mg (21% of theory) of the title compound.

LC/MS [Method 3]: $R_t$=1.23 min; MS [ESIpos]: m/z=548 (M+H)$^+$ $^1$H-NMR (400 MHz, CDCl$_3$): δ=3.86-3.99 (m, 2H), 4.36-4.45 (m, 2H), 4.56-4.66 (m, 1H), 5.07 (d, 1H), 5.18 (d, 1H), 7.20 (t, 1H), 7.35 (d, 2H), 7.44 (d, 2H), 7.58 (d, 2H).

Example 44

5-(4-Chlorophenyl)-4-[(2R)-3,3,3-trifluoro-2-hydroxypropyl]-2-({5-[3-(trifluoromethyl)benzyl]-4H-1,2,4-triazol-3-yl}methyl)-2,4-dihydro-3H-1,2,4-triazol-3-one

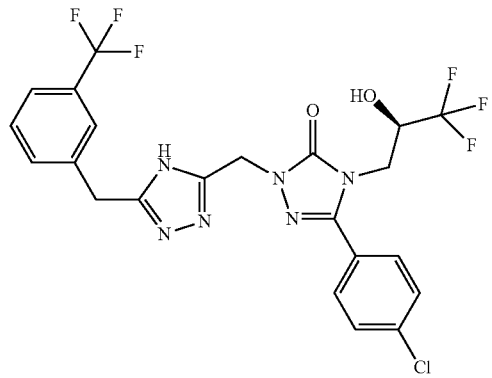 [SMILES: O=c1n(Cc2nnc(Cc3cccc(C(F)(F)F)c3)[nH]2)nc(-c2ccc(Cl)cc2)n1C[C@@H](O)C(F)(F)F]

Analogously to the preparation of the compound in Example 36, 70 mg (0.18 mmol) of the compound from Example 20A gave 21 mg (21% of theory) of the title compound.

LC/MS [Method 5]: $R_t$=2.43 min; MS [ESIpos]: m/z=547 (M+H)$^+$ $^1$H-NMR (400 MHz, CDCl$_3$): δ=3.86-4.00 (m, 2H), 4.05 (s, 2H), 4.56-4.66 (m, 1H), 5.08 (d, 1H), 5.21 (d, 1H), 7.38-7.47 (m, 4H), 7.50-7.55 (m, 2H), 7.61 (d, 2H).

Example 45

5-(4-Chlorophenyl)-4-[(2R)-3,3,3-trifluoro-2-hydroxypropyl]-2-[(5-{2-[3-(trifluoromethyl)phenyl]-ethyl}-4H-1,2,4-triazol-3-yl)methyl]-2,4-dihydro-3H-1,2,4-triazol-3-one

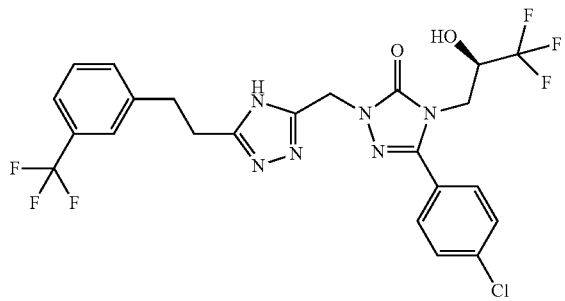 [SMILES: O=c1n(Cc2nnc(CCc3cccc(C(F)(F)F)c3)[nH]2)nc(-c2ccc(Cl)cc2)n1C[C@@H](O)C(F)(F)F]

Analogously to the preparation of the compound in Example 36, 70 mg (0.18 mmol) of the compound from Example 20A gave 18 mg (17% of theory) of the title compound.

LC/MS [Method 5]: $R_t$=2.49 min; MS [ESIpos]: m/z=561 (M+H)$^+$ $^1$H-NMR (400 MHz, CDCl$_3$): δ=2.91-2.99 (m, 2H), 3.02-3.10 (m, 2H), 3.87-4.01 (m, 2H), 4.59-4.69 (m, 1H), 5.09 (d, 1H), 5.25 (d, 1H), 7.32 (d, 1H), 7.38 (m, 1H), 7.41-7.49 (m, 2H), 7.44 (d, 2H), 7.63 (d, 2H).

Example 46

2-{[5-(2-Chlorobenzyl)-4H-1,2,4-triazol-3-yl]methyl}-5-(4-chlorophenyl)-4-[(2R)-3,3,3-trifluoro-2-hydroxypropyl]-2,4-dihydro-3H-1,2,4-triazol-3-one

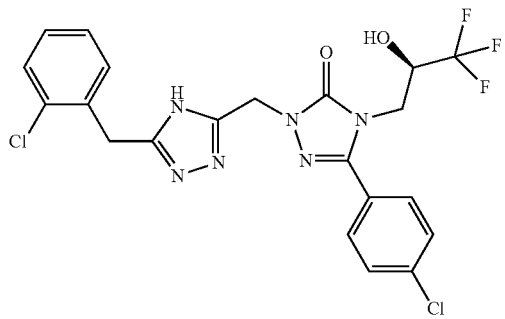 [SMILES: O=c1n(Cc2nnc(Cc3ccccc3Cl)[nH]2)nc(-c2ccc(Cl)cc2)n1C[C@@H](O)C(F)(F)F]

Analogously to the preparation of the compound in Example 36, 70 mg (0.18 mmol) of the compound from Example 20A gave 17 mg (18% of theory) of the title compound.

LC/MS [Method 5]: $R_t$=2.30 min; MS [ESIpos]: m/z=513 (M+H)$^+$ $^1$H-NMR (400 MHz, CDCl$_3$): δ=3.83-3.97 (m, 2H), 4.04-4.16 (m, 2H), 4.59-4.70 (m, 1H), 5.03 (d, 1H), 5.14 (d, 1H), 7.19-7.25 (m, 3H), 7.36-7.40 (m, 1H), 7.42 (d, 2H), 7.59 (d, 2H).

Example 47

5-(4-Chlorophenyl)-2-{[5-(2-methoxybenzyl)-4H-1,2,4-triazol-3-yl]methyl}-4-[(2R)-3,3,3-trifluoro-2-hydroxypropyl]-2,4-dihydro-3H-1,2,4-triazol-3-one

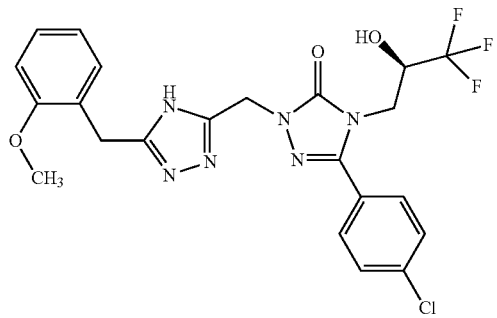 [SMILES: COc1ccccc1Cc1nnc(Cn2nc(-c3ccc(Cl)cc3)n(C[C@@H](O)C(F)(F)F)c2=O)[nH]1]

Analogously to the preparation of the compound in Example 36, 70 mg (0.18 mmol) of the compound from Example 20A gave 16 mg (17% of theory) of the title compound.

LC/MS [Method 5]: $R_t$=2.25 min; MS [ESIpos]: m/z=509 (M+H)$^+$ $^1$H-NMR (400 MHz, CDCl$_3$): δ=3.86 (s, 3H), 3.83-3.99 (m, 2H), 4.01 (s, 2H), 4.63-4.71 (m, 1H), 5.01 (d, 1H), 5.19 (d, 1H), 6.02 (d, 1H), 6.88-6.95 (m, 2H), 7.13-7.19 (m, 1H), 7.25-7.29 (m, 1H), 7.43 (d, 2H), 7.61 (d, 2H), 11.03-11.15 (br. s, 1H).

Example 48

5-(4-Chlorophenyl)-2-{[5-(2-fluorobenzyl)-4H-1,2,4-triazol-3-yl]methyl}-4-[(2R)-3,3,3-trifluoro-2-hydroxypropyl]-2,4-dihydro-3H-1,2,4-triazol-3-one

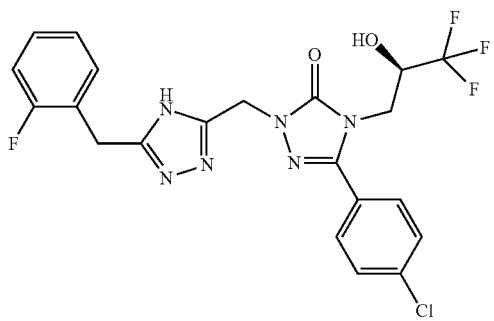 [SMILES: O=c1n(Cc2nnc(Cc3ccccc3F)[nH]2)nc(-c2ccc(Cl)cc2)n1C[C@@H](O)C(F)(F)F]

Analogously to the preparation of the compound in Example 36, 100 mg (0.26 mmol) of the compound from Example 20A gave 34 mg (26% of theory) of the title compound.

LC/MS [Method 5]: $R_t$=2.24 min; MS [ESIpos]: m/z=497 (M+H)$^+$ $^1$H-NMR (400 MHz, CDCl$_3$): δ=3.83-3.98 (m, 2H), 3.97-4.03 (m, 2H), 4.59-4.71 (m, 1H), 5.02 (d, 1H), 5.15 (d, 1H), 6.00 (br. s, 1H), 7.02-7.12 (m, 2H), 7.15-7.21 (m, 1H), 7.22-7.30 (m, 1H), 7.42 (d, 2H), 7.60 (d, 2H), 11.87 (br. s, 1H).

Example 49

2-{[5-(2-Chlorobenzyl)-4H-1,2,4-triazol-3-yl]methyl}-5-(4-chlorophenyl)-4-[(2S)-3,3,3-trifluoro-2-hydroxypropyl]-2,4-dihydro-3H-1,2,4-triazol-3-one

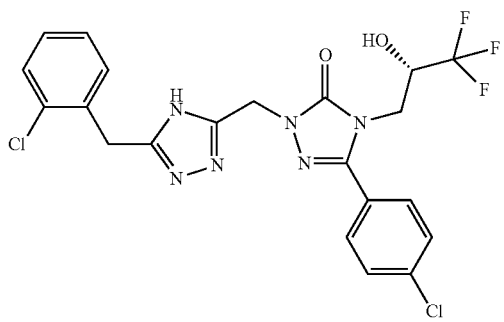 [SMILES: O=c1n(Cc2nnc(Cc3ccccc3Cl)[nH]2)nc(-c2ccc(Cl)cc2)n1C[C@H](O)C(F)(F)F]

Analogously to the preparation of the compound in Example 36, 138 mg (0.36 mmol) of the compound from Example 19A gave 35 mg (19% of theory) of the title compound.

LC/MS [Method 3]: $R_t$=1.20 min; MS [ESIpos]: m/z=513 and 515 (M+H)$^+$ $^1$H-NMR (400 MHz, CDCl$_3$): δ=3.89 (dd, 1H), 3.96 (dd, 1H), 4.07-4.18 (m, 2H), 4.58-4.69 (m, 1H), 5.05+5.16 (2d, 2H), 5.90 (br. s, 1H), 7.20-7.25 (m, 3H), 7.36-7.41 (m, 1H), 7.43 (d, 2H), 7.57-7.61 (m, 2H), 11.65 (br. s, 1H).

Example 50

5-(4-Chlorophenyl)-2-{[5-(2-fluorobenzyl)-4H-1,2,4-triazol-3-yl]methyl}-4-[(2S)-3,3,3-trifluoro-2-hydroxypropyl]-2,4-dihydro-3H-1,2,4-triazol-3-one

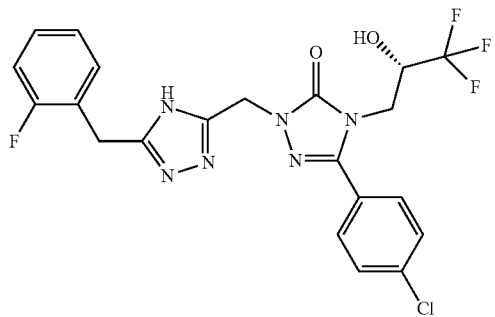 [SMILES: O=c1n(Cc2nnc(Cc3ccccc3F)[nH]2)nc(-c2ccc(Cl)cc2)n1C[C@H](O)C(F)(F)F]

Analogously to the preparation of the compound in Example 36, 124 mg (0.33 mmol) of the compound from Example 19A gave 37 mg (23% of theory) of the title compound.

LC/MS [Method 3]: $R_t$=1.16 min; MS [ESIpos]: m/z=497 (M+H)$^+$ $^1$H-NMR (400 MHz, CDCl$_3$): δ=3.89 (dd, 1H), 3.97 (dd, 1H), 3.98-4.08 (m, 2H), 4.61-4.70 (m, 1H), 5.04+5.16 (2d, 2H), 5.86 (br. s, 1H), 7.03-7.31 (m, 4H), 7.43 (d, 2H), 7.59 (d, 2H), 11.65 (br. s, 1H).

Example 51

5-(4-Chlorophenyl)-2-{[5-(2,6-dichlorobenzyl)-4H-1,2,4-triazol-3-yl]methyl}-4-[(2S)-3,3,3-trifluoro-2-hydroxypropyl]-2,4-dihydro-3H-1,2,4-triazol-3-one

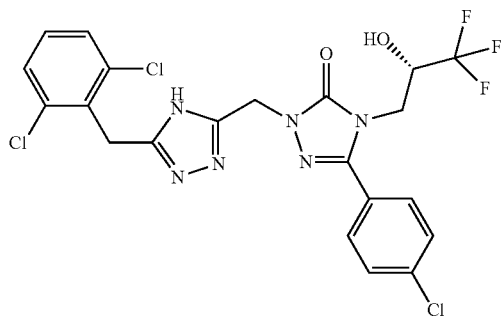 [SMILES: O=c1n(Cc2nnc(Cc3c(Cl)cccc3Cl)[nH]2)nc(-c2ccc(Cl)cc2)n1C[C@H](O)C(F)(F)F]

Analogously to the preparation of the compound in Example 36, 106 mg (0.28 mmol) of the compound from Example 19A gave 49 mg (32% of theory) of the title compound.

LC/MS [Method 4]: $R_t$=1.08 min; MS [ESIpos]: m/z=547 and 549 (M+H)$^+$ $^1$H-NMR (400 MHz, CDCl$_3$): δ=3.88 (dd, 1H), 3.96 (dd, 1H), 4.34-4.46 (m, 2H), 4.57-4.67 (m, 1H), 5.03-5.22 (m, 2H), 7.16-7.23 (m, 1H), 7.35 (d, 2H), 7.44 (d, 2H), 7.60 (d, 2H).

Example 52

5-(4-Chlorophenyl)-4-[(2S)-3,3,3-trifluoro-2-hydroxypropyl]-2-({5-[3-(trifluoromethoxy)benzyl]-4H-1,2,4-triazol-3-yl}methyl)-2,4-dihydro-3H-1,2,4-triazol-3-one

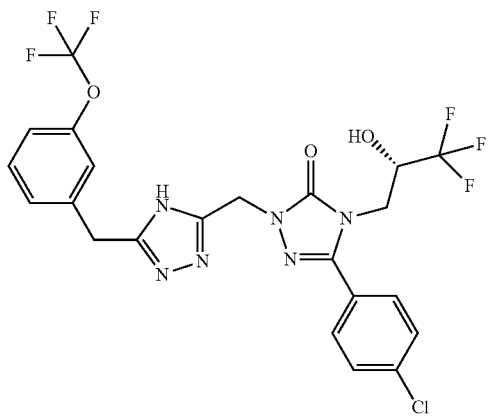 [SMILES: O=c1n(Cc2nnc(Cc3cccc(OC(F)(F)F)c3)[nH]2)nc(-c2ccc(Cl)cc2)n1C[C@H](O)C(F)(F)F]

Analogously to the preparation of the compound in Example 36, 120 mg (0.32 mmol) of the compound from Example 19A gave 83 mg (47% of theory) of the title compound.

LC/MS [Method 2]: $R_t$=2.39 min; MS [ESIpos]: m/z=563 (M+H)$^+$ $^1$H-NMR (400 MHz, CDCl$_3$): δ=3.86-3.96 (m, 2H), 3.95-4.05 (m, 2H), 4.57-4.67 (m, 1H), 5.04-5.24 (m, 2H), 7.09-7.17 (m, 3H), 7.30-7.36 (m, 1H), 7.45 (d, 2H), 7.60 (d, 2H).

Example 53

5-(4-Chlorophenyl)-4-[(2S)-3,3,3-trifluoro-2-hydroxypropyl]-2-({5-[2-(trifluoromethyl)benzyl]-4H-1,2,4-triazol-3-yl}methyl)-2,4-dihydro-3H-1,2,4-triazol-3-one

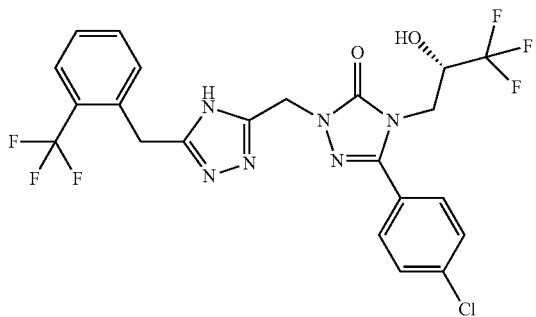 [SMILES: O=c1n(Cc2nnc(Cc3ccccc3C(F)(F)F)[nH]2)nc(-c2ccc(Cl)cc2)n1C[C@H](O)C(F)(F)F]

1190 mg (3.13 mmol) of the compound from Example 19A were reacted analogously to the preparation of the compound in Example 36. For work-up, the reaction mixture was diluted with 25 ml of water and extracted twice with in each case 25 ml of ethyl acetate. The combined organic phases were dried over sodium sulfate, filtered and concentrated under reduced pressure. The crude product was purified chromatographically [Method 19]. This gave 932 mg (54% of theory) of the title compound.

LC/MS [Method 4]: $R_t$=1.08 min; MS [ESIpos]: m/z=547 (M+H)$^+$ $^1$H-NMR (400 MHz, CDCl$_3$): δ=3.83-3.96 (m, 2H), 4.11-4.22 (m, 2H), 4.56-4.68 (m, 1H), 5.00-5.18 (m, 2H), 5.88 (br. s, 1H), 7.25-7.29 (m, 1H), 7.33-7.52 (m, 4H), 7.58 (d, 2H), 7.67 (d, 1H), 11.89 (br. s, 1H).

Example 54

5-(4-Chlorophenyl)-2-{[5-(2-chlorophenyl)-4H-1,2,4-triazol-3-yl]methyl}-4-[(2S)-3,3,3-trifluoro-2-hydroxypropyl]-2,4-dihydro-3H-1,2,4-triazol-3-one

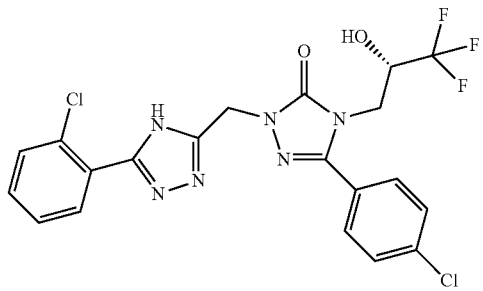 [SMILES: O=c1n(Cc2nnc(-c3ccccc3Cl)[nH]2)nc(-c2ccc(Cl)cc2)n1C[C@H](O)C(F)(F)F]

1200 mg (3.16 mmol) of the compound from 19A were taken up in 15 ml of DMF, 906 mg (4.74 mmol) of 2-chlorobenzenecarboximidamide hydrochloride were added and the mixture was stirred in a microwave oven at 220° C. for 1 h. After cooling, 20 ml of 1 N hydrochloric acid were added and the mixture was extracted twice with in each case 25 ml of ethyl acetate. The combined organic phases were dried over sodium sulfate, filtered and concentrated under reduced pressure. Further purification was carried out by chromatography on silica gel (mobile phase: cyclohexane/ethyl acetate 2:1, then 1:1). This gave 395 mg (80% of theory) of the title compound of a purity of 80%.

LC/MS [Method 4]: $R_t$=1.02 min; MS [ESIpos]: m/z=499 and 501 (M+H)$^+$ $^1$H-NMR (400 MHz, DMSO-d$_6$): δ=3.85 (dd, 1H), 4.00 (dd, 1H), 4.25-4.37 (m, 1H), 5.00-5.30 (m, 2H), 6.92 (d, 1H), 7.40-7.67 (m, 5H), 7.71-7.81 (m, 3H), 14.27 (br. s, 1H).

Example 55

Methyl (3-{[3-(4-chlorophenyl)-5-oxo-4-(3,3,3-trifluoro-2-hydroxypropyl)-4,5-dihydro-1H-1,2,4-triazol-1-yl]methyl}-5-[2-(trifluoromethyl)benzyl]-1H-1,2,4-triazol-1-yl)acetate and methyl (5-{[3-(4-chlorophenyl)-5-oxo-4-(3,3,3-trifluoro-2-hydroxypropyl)-4,5-dihydro-1H-1,2,4-triazol-1-yl]methyl}-3-[2-(trifluoromethyl)benzyl]-1H-1,2,4-triazol-1-yl)acetate (Mixture of Regioisomers)

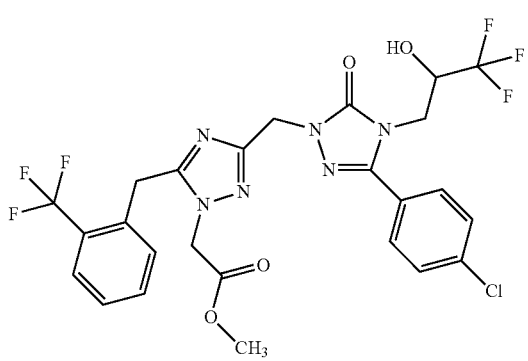

and

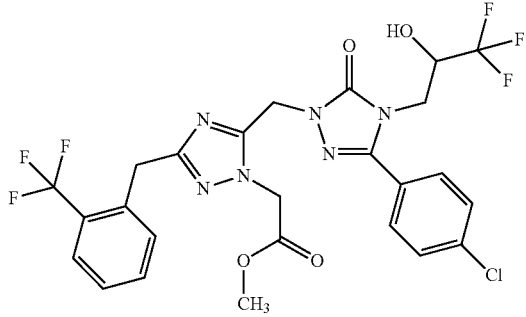

350 mg (0.57 mmol) of the compound from Example 30 were dissolved in 9 ml of DMF, and 27 mg (0.68 mmol) of sodium hydride (60% in paraffin) were added. The mixture was stirred at RT for 10 min 68 mg (0.63 mmol) of methyl chloroacetate were then added, and the mixture was stirred at 40° C. for 30 min. For work-up, 10 ml of water were added, and the mixture was extracted twice with in each case 15 ml of ethyl acetate. The combined organic phases were dried over sodium sulfate, filtered and concentrated under reduced pressure. The crude product was purified chromatographically [Method 19]; it was not possible to separate the regioisomers during the purification. This gave 310 mg (88% of theory) of a mixture of the regioisomeric title compounds which was reacted further as such (see Examples 58 and 59).

LC/MS [Method 5]: R$_t$=2.52 min; MS [ESIpos]: m/z=619 (M+H)$^+$ and R$_t$=2.60 min; MS [ESIpos]: m/z=619 (M+H)$^+$.

Example 56 and Example 57

Methyl [5-(2-chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]acetate (Regioisomer 1) and methyl [3-(2-chlorophenyl)-5-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]acetate (Regioisomer 2)

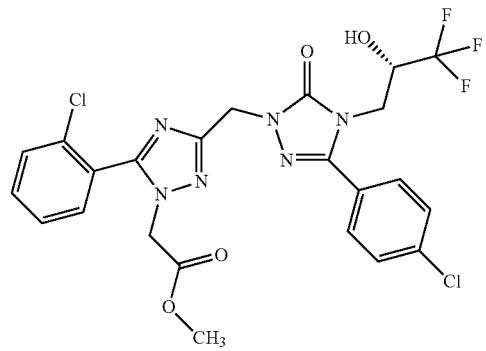

and

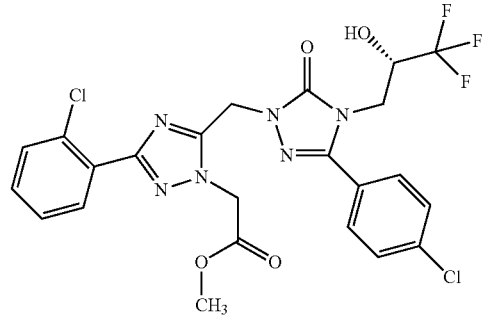

395 mg (0.79 mmol) of the compound from Example 54 were dissolved in 10 ml of DMF, and 38 mg (0.95 mmol) of sodium hydride (60% in paraffin) were added. The mixture was stirred at RT for 10 min 94 mg (0.87 mmol) of methyl chloroacetate were then added, and the mixture was stirred at 40° C. for 30 min. After cooling to RT, the reaction mixture was directly, without any further work-up, purified chromatographically [Method 19] with complete separation of the regioisomers. This gave 71 mg (16% of theory) of regioisomer 1 (Example 56) and 210 mg (46% of theory) of regioisomer 2 (Example 57).

Example 56

LC/MS [Method 4]: R$_t$=1.09 min; MS [ESIpos]: m/z=571 and 573 (M+H)$^+$ $^1$H-NMR (400 MHz, CDCl$_3$): δ=3.69 (s, 3H), 3.94 (dd, 1H), 4.05 (dd, 1H), 4.55-4.64 (m, 1H), 4.80 (s, 2H), 5.14-5.33 (m, 2H), 5.36 (d, 1H), 7.34-7.40 (m, 1H), 7.42-7.52 (m, 5H), 7.54-7.60 (m, 2H).

Example 57

LC/MS [Method 4]: $R_t$=1.15 min; MS [ESIpos]: m/z=571 and 573 (M+H)$^+$ $^1$H-NMR (400 MHz, CDCl$_3$): δ=3.74 (s, 3H), 3.92 (dd, 1H), 3.99 (dd, 1H), 4.55-4.65 (m, 1H), 4.89 (d, 1H), 5.16-5.39 (m, 4H), 7.28-7.34 (m, 2H), 7.42-7.50 (m, 3H), 7.59-7.64 (m, 2H), 7.85-7.91 (m, 1H).

Example 58 and Example 59

(3-{[3-(4-Chlorophenyl)-5-oxo-4-(3,3,3-trifluoro-2-hydroxypropyl)-4,5-dihydro-1H-1,2,4-triazol-1-yl]methyl}-5-[2-(trifluoromethyl)benzyl]-1H-1,2,4-triazol-1-yl)acetic acid (regioisomer 1) and (5-{[3-(4-chlorophenyl)-5-oxo-4-(3,3,3-trifluoro-2-hydroxypropyl)-4,5-dihydro-1H-1,2,4-triazol-1-yl]methyl}-3-[2-(trifluoromethyl)benzyl]-1H-1,2,4-triazol-1-yl)acetic acid (regioisomer 2)

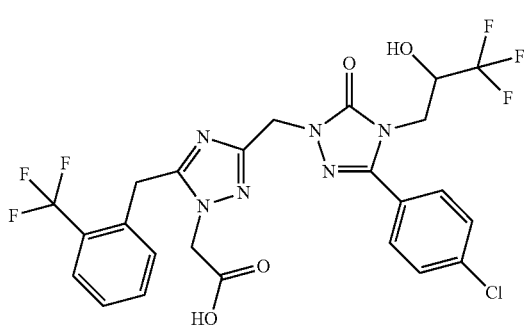

and

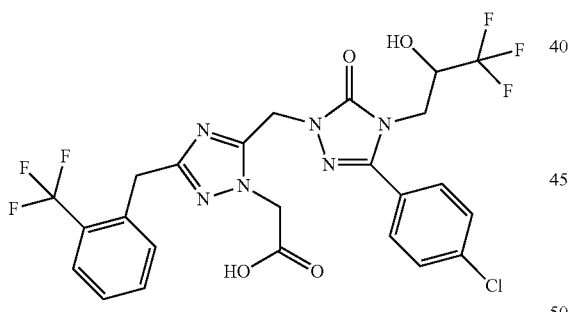

310 mg (0.50 mmol) of the compound from Example 55 (as a mixture of regioisomers) were dissolved in 5 ml of methanol, and 0.85 ml (0.85 mmol) of a 1 N aqueous lithium hydroxide solution was added. The mixture was stirred at RT for 45 min. The mixture was then freed from the solvent under reduced pressure, taken up in 10 ml of water and neutralized with 0.85 ml (0.85 mmol) of 1 N hydrochloric acid. The mixture was extracted twice with in each case 15 ml of ethyl acetate. The combined organic phases were dried over sodium sulfate, filtered and concentrated under reduced pressure. The crude product was purified chromatographically with separation of the regioisomers [Method 16]. This gave 81 mg (27% of theory) of regioisomer 1 (Example 58) and 83 mg (27% of theory) of regioisomer 2 (Example 59).

Example 58

LC/MS [Method 2]: $R_t$=2.27 min; MS [ESIpos]: m/z=605 (M+H)$^+$ $^1$H-NMR (400 MHz, DMSO-d$_6$): δ=3.81 (dd, 1H), 3.97 (dd, 1H), 4.26 (s, 3H), 4.86-4.97 (m, 2H), 5.06 (s, 2H), 6.89 (d, 1H), 7.32 (d, 1H), 7.45-7.52 (m, 1H), 7.56-7.65 (m, 3H), 7.69-7.76 (m, 3H), 13.35 (br. s, 1H).

Example 59

LC/MS [Method 2]: $R_t$=2.37 min; MS [ESIpos]: m/z=605 (M+H)$^+$ $^1$H-NMR (400 MHz, DMSO-d$_6$): δ=3.79 (dd, 1H), 3.93 (dd, 1H), 4.12 (s, 2H), 4.24-4.30 (m, 1H), 5.07-5.22 (m, 4H), 6.89 (d, 1H), 7.40-7.48 (m, 2H), 7.55-7.66 (m, 3H), 7.67-7.75 (m, 3H), 13.26 (br. s, 1H).

Example 60

[5-(2-Chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]acetic acid

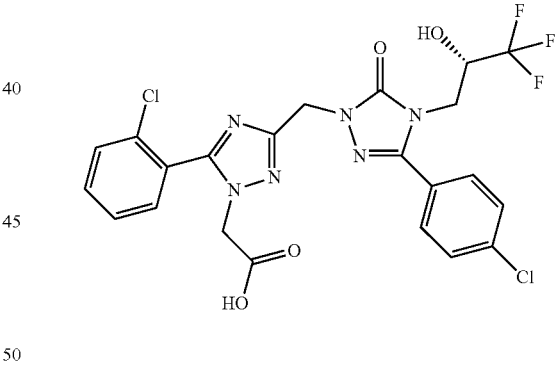

65 mg (0.11 mmol) of the compound from Example 56 were dissolved in 5 ml of methanol, and 0.26 ml (0.26 mmol) of a 1 N aqueous lithium hydroxide solution was added. The mixture was stirred at RT for 30 min. The mixture was then freed from the solvent under reduced pressure, taken up in 10 ml of water and neutralized with 0.85 ml (0.85 mmol) of 1 N hydrochloric acid. The mixture was extracted twice with in each case 15 ml of ethyl acetate. The combined organic phases were dried over sodium sulfate, filtered and concentrated under reduced pressure. This gave 57 mg (76% of theory) of the title compound in a purity of 84%.

LC/MS [Method 4]: $R_t$=0.95 min; MS [ESIpos]: m/z=557 and 559 (M+H)$^+$ $^1$H-NMR (400 MHz, DMSO-d$_6$): δ=3.85 (dd, 1H), 3.96-4.03 (m, 1H), 4.24-4.36 (m, 1H), 4.86 (s, 2H), 5.03-5.14 (m, 2H), 6.90 (d, 1H), 7.47-7.52 (m, 2H), 7.55-7.68 (m, 4H), 7.76 (d, 2H), 13.30 (br. s, 1H).

Example 61

[3-(2-Chlorophenyl)-5-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]acetic acid

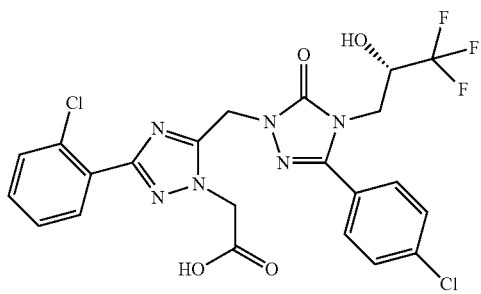 [SMILES: O=C(O)Cn1nc(-c2ccccc2Cl)nc1Cn1nc(-c2ccc(Cl)cc2)n(C[C@H](O)C(F)(F)F)c1=O]

205 mg (0.36 mmol) of the compound from Example 57 were reacted analogously to the preparation of the compound in Example 60. This gave 198 mg (94% of theory) of the title compound in a purity of 93%.

LC/MS [Method 2]: R$_t$=2.20 min; MS [ESIpos]: m/z=557 and 559 (M+H)$^+$ $^1$H-NMR (400 MHz, DMSO-d$_6$): δ=3.81 (dd, 1H), 3.96 (dd, 1H), 4.24-4.38 (m, 1H), 5.20-5.37 (m, 4H), 6.90 (br. s, 1H), 7.42-7.47 (m, 2H), 7.55-7.58 (m, 1H), 7.62 (d, 2H), 7.74 (d, 2H), 7.82-7.87 (m, 1H), 13.38 (br. s, 1H).

Example 62

2-(3-{[3-(4-Chlorophenyl)-5-oxo-4-(3,3,3-trifluoro-2-hydroxypropyl)-4,5-dihydro-1H-1,2,4-triazol-1-yl]methyl}-5-[2-(trifluoromethyl)benzyl]-1H-1,2,4-triazol-1-yl)acetamide (Racemate)

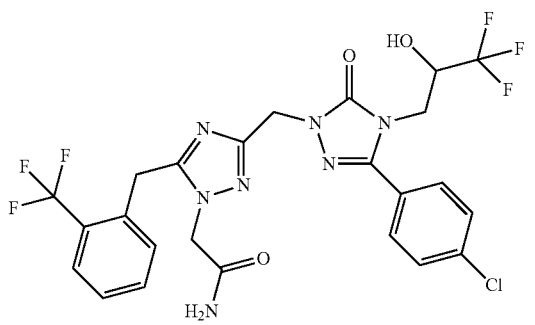 [SMILES: NC(=O)Cn1nc(Cn2nc(-c3ccc(Cl)cc3)n(CC(O)C(F)(F)F)c2=O)nc1Cc1ccccc1C(F)(F)F]

85 mg (0.14 mmol) of the compound from Example 58 were initially charged in 2.5 ml of DMF, and 23 mg (0.17 mmol) of HOBt and 35 mg (0.18 mmol) of EDC were added. After 20 min of stirring at RT, 0.3 ml (5.65 mmol) of ammonia solution (32% strength in water) was added and the reaction was stirred at room temperature for 16 h. The reaction solution was then freed from excess ammonia under reduced pressure, about 3 ml of water were added and the mixture was extracted three times with in each case 5 ml of ethyl acetate. The combined organic phases were dried over magnesium sulfate, filtered and concentrated under reduced pressure. The crude product was purified chromatographically [Method 19]. This gave 58 mg (69% of theory) of the target compound.

LC/MS [Method 5]: R$_t$=2.22 min; MS [ESIpos]: m/z=604 (M+H)$^+$.

By preparative HPLC on a chiral phase [Method 17], the racemate from Example 62 (58 mg) was separated into the enantiomers. This gave 27 mg of enantiomer 1 (Example 63), which eluted first, and 29 mg of enantiomer 2 (Example 64), which eluted later:

Example 63

2-(3-{[3-(4-Chlorophenyl)-5-oxo-4-(3,3,3-trifluoro-2-hydroxypropyl)-4,5-dihydro-1H-1,2,4-triazol-1-yl]methyl}-5-[2-(trifluoromethyl)benzyl]-1H-1,2,4-triazol-1-yl)acetamide (Enantiomer 1)

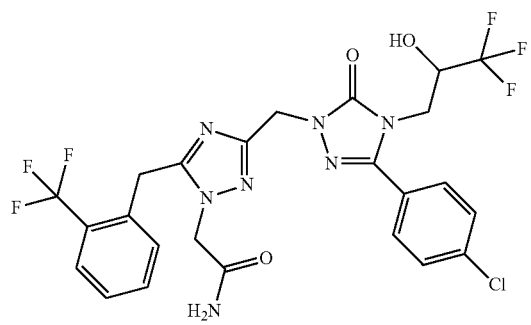 [SMILES: NC(=O)Cn1nc(Cn2nc(-c3ccc(Cl)cc3)n(CC(O)C(F)(F)F)c2=O)nc1Cc1ccccc1C(F)(F)F]

Enantiomer which elutes first in the racemate separation of Example 62.

Chiral HPLC [Method 18]: R$_t$=6.57 min.

$^1$H-NMR (400 MHz, DMSO-d$_6$): δ=3.81 (dd, 1H), 3.97 (dd, 1H), 4.22-4.33 (m, 3H), 4.83 (s, 2H), 4.85-4.95 (m, 2H), 6.89 (d, 1H), 7.31-7.38 (m, 2H), 7.45-7.50 (m, 1H), 7.55-7.64 (m, 3H), 7.65-7.76 (m, 4H).

Example 64

2-(3-{[3-(4-Chlorophenyl)-5-oxo-4-(3,3,3-trifluoro-2-hydroxypropyl)-4,5-dihydro-1H-1,2,4-triazol-1-yl]methyl}-5-[2-(trifluoromethyl)benzyl]-1H-1,2,4-triazol-1-yl)acetamide (Enantiomer 2)

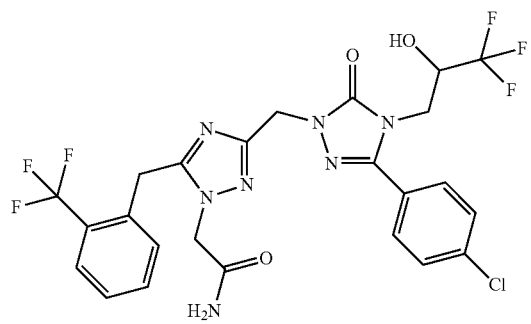 [SMILES: NC(=O)Cn1nc(Cn2nc(-c3ccc(Cl)cc3)n(CC(O)C(F)(F)F)c2=O)nc1Cc1ccccc1C(F)(F)F]

Enantiomer which elutes last in the racemate separation of Example 62.

Chiral HPLC [Method 18]: $R_t$=7.70 min.

$^1$H-NMR (400 MHz, DMSO-d$_6$): δ=3.81 (dd, 1H), 3.97 (dd, 1H), 4.22-4.33 (m, 3H), 4.83 (s, 2H), 4.85-4.95 (m, 2H), 6.89 (d, 1H), 7.31-7.38 (m, 2H), 7.45-7.50 (m, 1H), 7.55-7.64 (m, 3H), 7.65-7.76 (m, 4H).

Example 65

2-(5-{[3-(4-Chlorophenyl)-5-oxo-4-(3,3,3-trifluoro-2-hydroxypropyl)-4,5-dihydro-1H-1,2,4-triazol-1-yl]methyl}-3-[2-(trifluoromethyl)benzyl]-1H-1,2,4-triazol-1-yl)acetamide (Racemate)

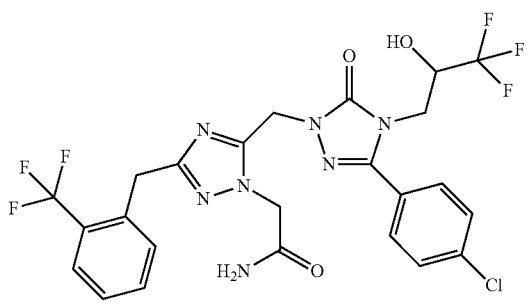 [SMILES: NC(=O)Cn1nc(Cc2ccccc2C(F)(F)F)nc1Cn1nc(-c2ccc(Cl)cc2)n(CC(O)C(F)(F)F)c1=O]

95 mg (0.16 mmol) of the compound from Example 59 were initially charged in 2.5 ml of DMF, and 25 mg (0.19 mmol) of HOBt and 39 mg (0.20 mmol) of EDC were added. After 20 min of stirring at RT, 0.3 ml (5.65 mmol) of ammonia solution (32% strength in water) was added, and the reaction was stirred at room temperature for 16 h. The reaction solution was then freed from excess ammonia under reduced pressure, about 3 ml of water were added and the mixture was extracted three times with in each case 5 ml of ethyl acetate. The combined organic phases were dried over magnesium sulfate, filtered and concentrated under reduced pressure. The crude product was purified chromatographically [Method 19]. This gave 58 mg (61% of theory) of the target compound.

LC/MS [Method 5]: $R_t$=2.32 min; MS [ESIpos]: m/z=604 (M+H)$^+$.

By preparative HPLC on a chiral phase [Method 12], the racemate from Example 65 (58 mg) was separated into the enantiomers. This gave 28 mg of enantiomer 1 (Example 66), which eluted first, and 28 mg of enantiomer 2 (Example 67), which eluted later:

Example 66

2-(5-{[3-(4-Chlorophenyl)-5-oxo-4-(3,3,3-trifluoro-2-hydroxypropyl)-4,5-dihydro-1H-1,2,4-triazol-1-yl]methyl}-3-[2-(trifluoromethyl)benzyl]-1H-1,2,4-triazol-1-yl)acetamide (Enantiomer 1)

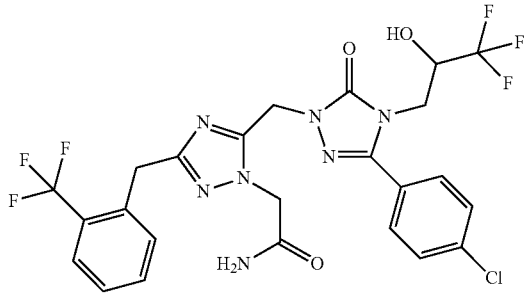 [SMILES: NC(=O)Cn1nc(Cc2ccccc2C(F)(F)F)nc1Cn1nc(-c2ccc(Cl)cc2)n(CC(O)C(F)(F)F)c1=O]

Enantiomer which elutes first in the racemate separation of Example 65.

Chiral HPLC [Method 13]: $R_t$=4.78 min.

$^1$H-NMR (400 MHz, DMSO-d$_6$): δ=3.79 (dd, 1H), 3.94 (dd, 1H), 4.10 (s, 2H), 4.24-4.35 (m, 1H), 4.93 (s, 2H), 5.09-5.19 (m, 2H), 6.87 (d, 1H), 7.34 (s, 1H), 7.40-7.48 (m, 2H), 7.55-7.75 (m, 7H).

Example 67

2-(5-{[3-(4-Chlorophenyl)-5-oxo-4-(3,3,3-trifluoro-2-hydroxypropyl)-4,5-dihydro-1H-1,2,4-triazol-1-yl]methyl}-3-[2-(trifluoromethyl)benzyl]-1H-1,2,4-triazol-1-yl)acetamide (Enantiomer 2)

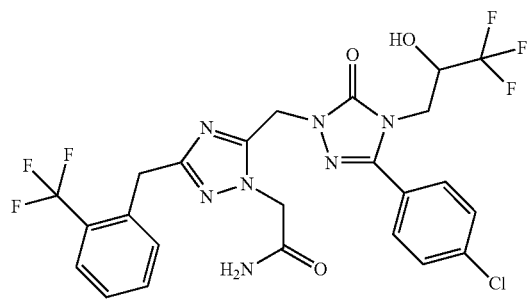 [SMILES: NC(=O)Cn1nc(Cc2ccccc2C(F)(F)F)nc1Cn1nc(-c2ccc(Cl)cc2)n(CC(O)C(F)(F)F)c1=O]

Enantiomer which elutes last in the racemate separation of Example 65.

Chiral HPLC [Method 13]: $R_t$=6.35 min.

$^1$H-NMR (400 MHz, DMSO-d$_6$): δ=3.79 (dd, 1H), 3.94 (dd, 1H), 4.10 (s, 2H), 4.24-4.35 (m, 1H), 4.93 (s, 2H), 5.09-5.19 (m, 2H), 6.87 (d, 1H), 7.34 (s, 1H), 7.40-7.48 (m, 2H), 7.55-7.75 (m, 7H).

Example 68

2-[5-(2-Chlorophenyl)-3-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]acetamide

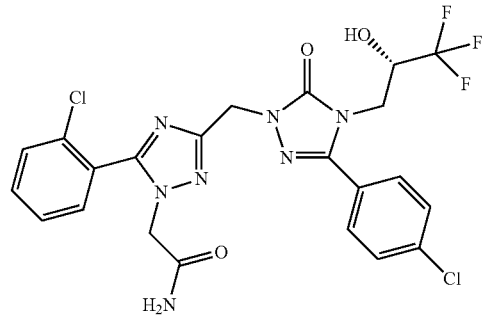 [SMILES: NC(=O)Cn1nc(Cn2nc(-c3ccc(Cl)cc3)n(C[C@H](O)C(F)(F)F)c2=O)nc1-c1ccccc1Cl]

54 mg (0.10 mmol) of the compound from Example 60 were initially charged in 4 ml of DMF, and 19 mg (0.13 mmol) of HOBt and 24 mg (0.03 mmol) of EDC were added. After 10 min of stirring at RT, 0.1 ml (1.93 mmol) of ammonia solution (32% strength in water) were added and the mixture was stirred at room temperature for 16 h. The reaction solution was then freed from excess ammonia under reduced pressure, about 3 ml of water were added and the mixture was extracted three times with in each case 5 ml of ethyl acetate. The combined organic phases were dried over magnesium sulfate, filtered and concentrated under reduced pressure. The crude product was purified chromatographically [Method 19]. This gave 27 mg (46% of theory) of the target compound.

LC/MS [Method 3]: $R_t$=1.08 min; MS [ESIpos]: m/z=556 and 558 (M+H)$^+$ $^1$H-NMR (400 MHz, DMSO-d$_6$): δ=3.85 (dd, 1H), 4.00 (dd, 1H), 4.25-4.37 (m, 1H), 4.64 (s, 2H), 5.07 (s, 2H), 6.91 (d, 1H), 7.24 (br. s, 1H), 7.46-7.67 (m, 7H), 7.76 (d, 2H).

Example 69

2-[3-(2-Chlorophenyl)-5-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,4-triazol-1-yl]acetamide

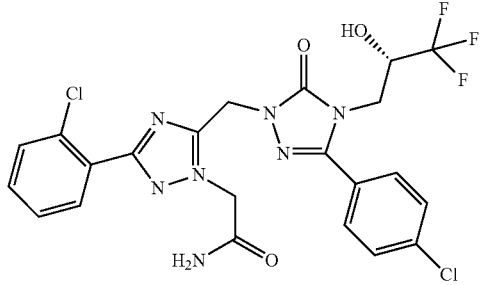

100 mg (0.18 mmol) of the compound from Example 61 were reacted analogously to the preparation of the compound in Example 68. This gave 67 mg (67% of theory) of the title compound.

LC/MS [Method 3]: $R_t$=1.14 min; MS [ESIpos]: m/z=556 and 558 (M+H)$^+$ $^1$H-NMR (400 MHz, DMSO-d$_6$): δ=3.81 (dd, 1H), 3.96 (dd, 1H), 4.28-4.34 (m, 1H), 5.04-5.14 (m, 2H), 5.22-5.32 (m, 2H), 6.86 (d, 1H), 7.39-7.46 (m, 2H), 7.52-7.57 (m, 1H), 7.62 (d, 2H), 7.72-7.78 (m, 3H), 7.83-7.88 (m, 1H), 7.95 (s, 1H).

Example 70

5-(4-Chlorophenyl)-2-{[5-(2-chlorophenyl)-4H-1,2,4-triazol-3-yl]methyl}-4-(3,3,3-trifluoropropyl)-2,4-dihydro-3H-1,2,4-triazol-3-one

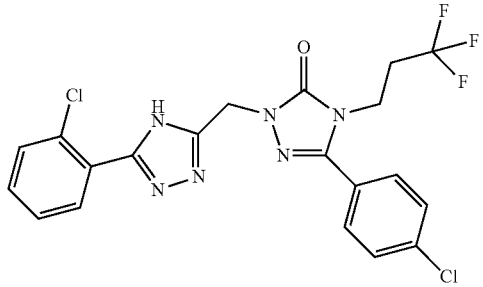 [SMILES: O=c1n(Cc2nnc(-c3ccccc3Cl)[nH]2)nc(-c2ccc(Cl)cc2)n1CCC(F)(F)F]

50 mg (0.14 mmol) of the compound from Example 23A were reacted analogously to the preparation of the compound in Example 54. This gave 8 mg (11% of theory) of the title compound.

LC/MS [Method 4]: $R_t$=1.06 min; MS [ESIpos]: m/z=483 (M+H)$^+$ $^1$H-NMR (400 MHz, DMSO-d$_6$): δ=2.59-2.69 (m, 2H), 4.00 (t, 2H), 5.13 (s, 2H), 7.42-7.51 (m, 2H), 7.56-7.71 (m, 5H), 7.75-7.81 (m, 1H), 14.25 (br. s, 1H).

Example 71

5-(4-Chlorophenyl)-2-{[5-(2,6-dichlorobenzyl)-4H-1,2,4-triazol-3-yl]methyl}-4-(3,3,3-trifluoro-propyl)-2,4-dihydro-3H-1,2,4-triazol-3-one

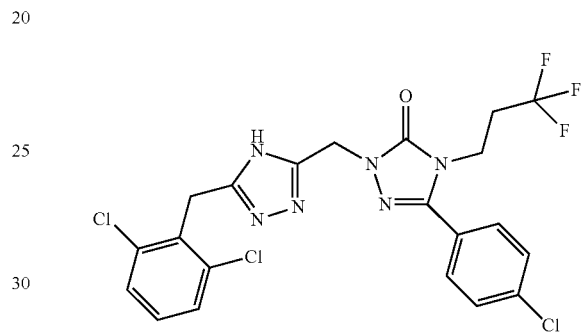

50 mg (0.14 mmol) of the compound from Example 23A were reacted analogously to the preparation of the compound in Example 54. This gave 18 mg (25% of theory) of the title compound.

LC/MS [Method 4]: $R_t$=1.10 min; MS [ESIpos]: m/z=531 and 533 (M+H)$^+$ $^1$H-NMR (400 MHz, DMSO-d$_6$): δ=2.55-2.69 (m, 2H), 3.97 (t, 2H), 4.23-4.34 (m, 2H), 4.95 (s, 2H), 7.31-7.37 (m, 1H), 7.48 (d, 2H), 7.60-7.68 (m, 4H), 13.70 (br. s, 1H).

Example 72

2-{[5-(2-Chlorobenzyl)-4H-1,2,4-triazol-3-yl]methyl}-5-(4-chlorophenyl)-4-(3,3,3-trifluoropropyl)-2,4-dihydro-3H-1,2,4-triazol-3-one

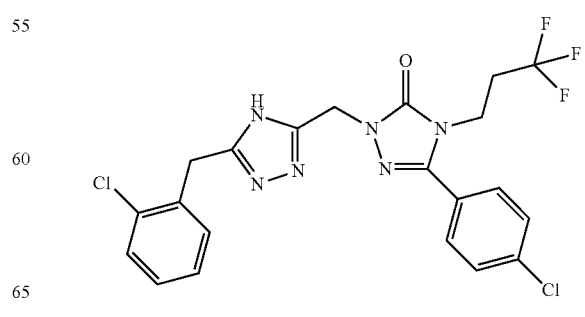

48 mg (0.13 mmol) of the compound from Example 23A were reacted analogously to the preparation of the compound in Example 54. This gave 22 mg (33% of theory) of the title compound.

LC/MS [Method 4]: $R_t$=1.07 min; MS [ESIpos]: m/z=497 and 499 (M+H)$^+$ $^1$H-NMR (400 MHz, DMSO-d$_6$): δ=2.56-2.69 (m, 2H), 3.98 (t, 2H), 4.12 (s, 2H), 4.97 (s, 2H), 7.25-7.34 (m, 3H), 7.40-7.46 (m, 1H), 7.59-7.68 (m, 5H).

Example 73

5-(4-Chlorophenyl)-2-{[5-(2-chlorophenyl)-2-thienyl]methyl}-4-[(2S)-3,3,3-trifluoro-2-hydroxy-propyl]-2,4-dihydro-3H-1,2,4-triazol-3-one

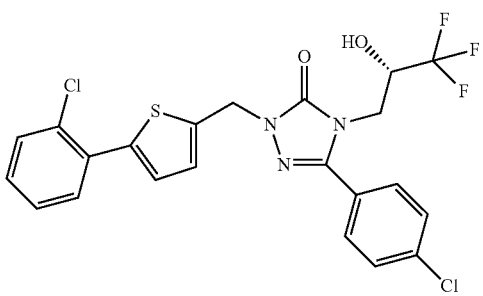 [SMILES: O=c1n(Cc2ccc(-c3ccccc3Cl)s2)nc(-c2ccc(Cl)cc2)n1C[C@H](O)C(F)(F)F]

85 mg (0.28 mmol) of the compound from Example 5A and 134 mg (0.41 mmol) of cesium carbonate were suspended in 5 ml of acetonitrile, and 113 mg (0.28 mmol) of the compound from Example 56A were added. The mixture was stirred under reflux for 20 h. For work-up, the mixture was cooled to RT, the acetonitrile was removed under reduced pressure and 10 ml of water were added to the residue. The mixture was extracted twice with in each case 10 ml of ethyl acetate. The combined organic phases were dried over sodium sulfate, filtered and concentrated under reduced pressure. The crude product was purified chromatographically [Method 19]. This gave 4 mg (3% of theory) of the target compound.

LC/MS [Method 4]: $R_t$=1.32 min; MS [ESIpos]: m/z=514 and 516 (M+H)$^+$ $^1$H-NMR (400 MHz, DMSO-d$_6$): δ=3.83 (dd, 1H), 4.00 (dd, 1H), 4.22-4.35 (m, 1H), 5.16-5.26 (m, 2H), 6.91 (br. s, 1H), 7.16 (d, 1H), 7.32 (d, 1H), 7.34-7.44 (m, 2H), 7.53-7.65 (m, 4H), 7.76 (d, 2H).

Example 74

5-(4-Chlorophenyl)-2-{[5-(2,3-dichlorophenyl)-2-thienyl]methyl}-4-[(2S)-3,3,3-trifluoro-2-hydroxypropyl]-2,4-dihydro-3H-1,2,4-triazol-3-one

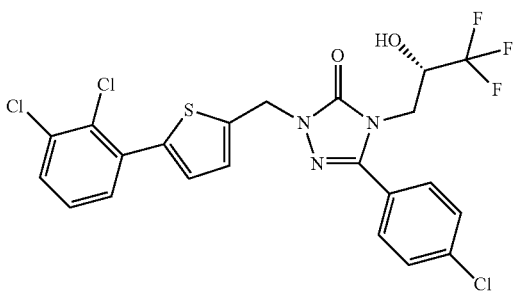 [SMILES: O=c1n(Cc2ccc(-c3cccc(Cl)c3Cl)s2)nc(-c2ccc(Cl)cc2)n1C[C@H](O)C(F)(F)F]

67 mg (0.22 mmol) of the compound from Example 5A and 142 mg (0.44 mmol) of cesium carbonate were suspended in 4 ml of acetonitrile, and 70 mg (0.28 mmol) of the compound from Example 57A were added. The mixture was stirred under reflux for 2 h. For work-up, the mixture was cooled to RT, the acetonitrile was removed under reduced pressure and 10 ml of water were added to the residue. The mixture was extracted twice with in each case 10 ml of ethyl acetate. The combined organic phases were dried over sodium sulfate, filtered and concentrated under reduced pressure. The crude product was purified chromatographically [Method 19]. This gave 29 mg (24% of theory) of the target compound.

LC/MS [Method 4]: $R_t$=1.37 min; MS [ESIpos]: m/z=548 and 550 (M+H)$^+$ $^1$H-NMR (400 MHz, DMSO-d$_6$): δ=3.83 (dd, 1H), 3.99 (dd, 1H), 4.24-4.34 (m, 1H), 5.18-5.27 (m, 2H), 6.90 (d, 1H), 7.17 (d, 1H), 7.33 (d, 1H), 7.42 (t, 1H), 7.57 (dd, 1H), 7.61-7.67 (m, 3H), 7.74-7.79 (m, 2H).

Example 75

5-(4-Chlorophenyl)-2-{[5-(2,3-difluorophenyl)-2-thienyl]methyl}-4-[(2S)-3,3,3-trifluoro-2-hydroxypropyl]-2,4-dihydro-3H-1,2,4-triazol-3-one

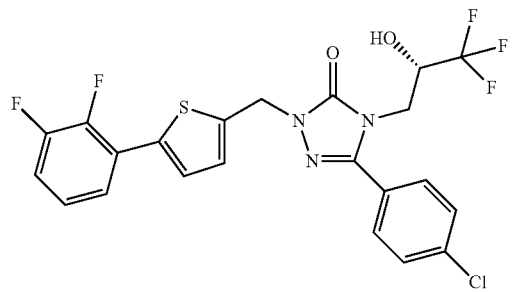 [SMILES: O=c1n(Cc2ccc(-c3cccc(F)c3F)s2)nc(-c2ccc(Cl)cc2)n1C[C@H](O)C(F)(F)F]

Under an atmosphere of argon, 84 mg (0.19 mmol) of the compound from Example 30A and 45 mg (0.29 mmol) of 2,3-difluorophenylboronic acid were dissolved in 2 ml of toluene. 9 mg (0.01 mmol) of tris(dibenzylideneacetone)dipalladium, 8 mg (0.02 mmol) of 2-dicyclohexylphosphino-2'-(N,N-dimethylamino)biphenyl and 81 mg (0.38 mmol) of potassium phosphate were then added, and under argon the mixture was heated at 110° C. for 14 h. For work-up, the mixture was diluted at RT with 10 ml of ethyl acetate and 10 ml of water, the organic phase was separated off and the aqueous phase was extracted two more times with in each case 10 ml of ethyl acetate. The combined organic phases were dried over sodium sulfate, filtered and concentrated under reduced pressure. The crude product was purified chromatographically [Method 19]. This gave 25 mg (24% of theory) of the target compound.

LC/MS [Method 2]: $R_t$=2.72 min; MS [ESIpos]: m/z=516 (M+H)$^+$ $^1$H-NMR (400 MHz, DMSO-d$_6$): δ=3.78-4.07 (m, 2H), 4.23-4.39 (m, 1H), 5.10-5.26 (m, 2H), 6.86-6.95 (m, 1H), 6.99-7.05 (m, 1H), 7.17-7.59 (m, 4H), 7.60-7.66 (m, 1H), 7.73-7.80 (m, 2H), 7.83-7.90 (m, 1H).

Example 76

5-(4-Chlorophenyl)-4-[(2S)-3,3,3-trifluoro-2-hydroxypropyl]-2-({2-[2-(trifluoromethyl)phenyl]-1,3-thiazol-5-yl}methyl)-2,4-dihydro-3H-1,2,4-triazol-3-one

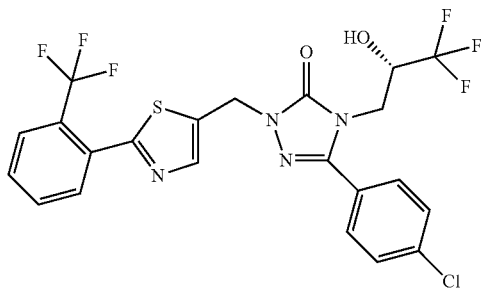 [SMILES: O=c1n(Cc2cnc(-c3ccccc3C(F)(F)F)s2)nc(-c2ccc(Cl)cc2)n1C[C@H](O)C(F)(F)F]

Under an atmosphere of argon, 62 mg (0.14 mmol) of the compound from Example 31A and 40 mg (0.21 mmol) of 2-(trifluoromethyl)phenylboronic acid were dissolved in 2 ml of toluene. 6.5 mg (0.007 mmol) of tris(dibenzylideneacetone)dipalladium, 5.6 mg (0.014 mmol) of 2-dicyclohexylphosphino-2'-(N,N-dimethylamino)biphenyl and 60 mg (0.28 mmol) of potassium phosphate were then added, and under argon the mixture was heated to 110° C. for 48 h. For work-up, the mixture was diluted at RT with 10 ml of ethyl acetate and 10 ml of water, the organic phase was separated off and the aqueous phase was extracted two more times with in each case 10 ml of ethyl acetate. The combined organic phases were dried over sodium sulfate, filtered and concentrated under reduced pressure. The crude product was purified chromatographically [Method 19]. This gave 10 mg (13% of theory) of the target compound.

LC/MS [Method 2]: $R_t$=2.54 min; MS [ESIpos]: m/z=549 (M+H)$^+$ $^1$H-NMR (400 MHz, DMSO-$d_6$): δ=3.83 (dd, 1H), 4.00 (dd, 1H), 4.22-4.34 (m, 1H), 5.29-5.38 (m, 2H), 6.90 (d, 1H), 7.61-7.67 (m, 2H), 7.71-7.83 (m, 5H), 7.93 (d, 1H), 7.96 (s, 1H).

Example 77

5-(4-Chlorophenyl)-4-[(2S)-3,3,3-trifluoro-2-hydroxypropyl]-2-({5-[2-(trifluoromethyl)phenyl]-1,3-thiazol-2-yl}methyl)-2,4-dihydro-3H-1,2,4-triazol-3-one

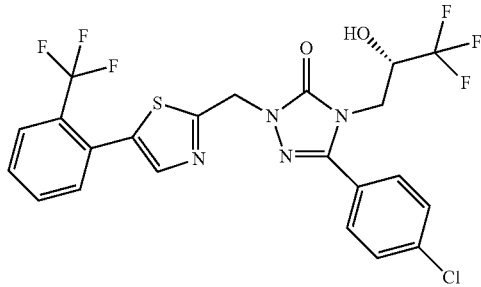 [SMILES: O=c1n(Cc2ncc(-c3ccccc3C(F)(F)F)s2)nc(-c2ccc(Cl)cc2)n1C[C@H](O)C(F)(F)F]

40 mg (0.13 mmol) of the compound from Example 5A were dissolved in 7 ml of acetonitrile, and 66 mg (0.20 mmol) of cesium carbonate and 42 mg (0.13 mmol) of the compound from Example 89A were added. The mixture was stirred at 80° C. for 1 h. For work-up, the mixture was cooled to RT, diluted with 5 ml of methanol and filtered. The filtrate was concentrated under reduced pressure and the crude product was then purified chromatographically [Method 19]. This gave 47 mg (66% of theory) of the target compound.

LC/MS [Method 3]: $R_t$=2.48 min; MS [ESIpos]: m/z=549 (M+H)$^+$ $^1$H-NMR (400 MHz, DMSO-$d_6$): δ=3.86 (dd, 1H), 4.02 (dd, 1H), 4.24-4.34 (m, 1H), 5.35-5.45 (m, 2H), 6.92 (s, 1H), 7.58-7.66 (m, 3H), 7.66-7.80 (m, 5H), 7.90 (d, 1H).

Example 78

5-(4-Chlorophenyl)-2-{[5-(2-chlorophenyl)-1,3-thiazol-2-yl]methyl}-4-[(2S)-3,3,3-trifluoro-2-hydroxypropyl]-2,4-dihydro-3H-1,2,4-triazol-3-one

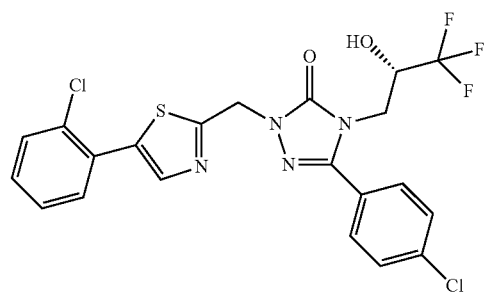 [SMILES: O=c1n(Cc2ncc(-c3ccccc3Cl)s2)nc(-c2ccc(Cl)cc2)n1C[C@H](O)C(F)(F)F]

70 mg (0.23 mmol) of the compound from Example 5A were reacted with 66 mg (0.23 mmol) of the compound from Example 88A analogously to the preparation of the compound in Example 77. This gave 65 mg (55% of theory) of the title compound.

LC/MS [Method 4]: $R_t$=1.23 min; MS [ESIpos]: m/z=515 and 517 (M+H)$^+$ $^1$H-NMR (400 MHz, DMSO-$d_6$): δ=3.86 (dd, 1H), 4.02 (dd, 1H), 4.24-4.35 (m, 1H), 5.39 (s, 2H), 6.92 (br. s, 1H), 7.44 (dd, 2H), 7.58-7.72 (m, 4H), 7.78 (d, 2H), 8.06 (s, 1H).

Example 79

2-{[5-(3-Chloro-2-fluorophenyl)-1,3-thiazol-2-yl]methyl}-5-(4-chlorophenyl)-4-[(2S)-3,3,3-trifluoro-2-hydroxypropyl]-2,4-dihydro-3H-1,2,4-triazol-3-one

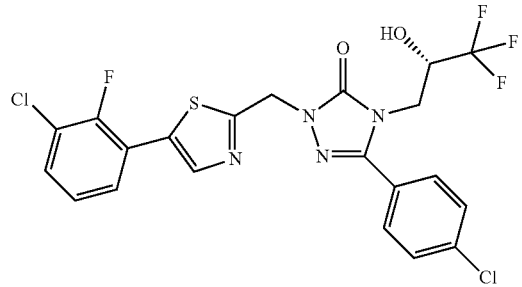 [SMILES: O=c1n(Cc2ncc(-c3cccc(Cl)c3F)s2)nc(-c2ccc(Cl)cc2)n1C[C@H](O)C(F)(F)F]

70 mg (0.23 mmol) of the compound from Example 5A were reacted with 70 mg (0.23 mmol) of the compound from Example 90A analogously to the preparation of the compound in Example 77. This gave 90 mg (72% of theory) of the title compound.

LC/MS [Method 3]: $R_t$=1.44 min; MS [ESIpos]: m/z=533 and 535 (M+H)$^+$ $^1$H-NMR (400 MHz, DMSO-d$_6$): δ=3.86 (dd, 1H), 4.02 (dd, 1H), 4.25-4.35 (m, 1H), 5.37-5.43 (m, 2H), 6.92 (s, 1H), 7.30-7.36 (m, 1H), 7.60-7.67 (m, 3H), 7.75-7.82 (m, 3H), 8.27 (s, 1H).

Example 80

5-(4-Chlorophenyl)-2-({5-[2-fluoro-3-(trifluoromethyl)phenyl]-1,3-thiazol-2-yl}methyl)-4-[(2S)-3,3,3-trifluoro-2-hydroxypropyl]-2,4-dihydro-3H-1,2,4-triazol-3-one

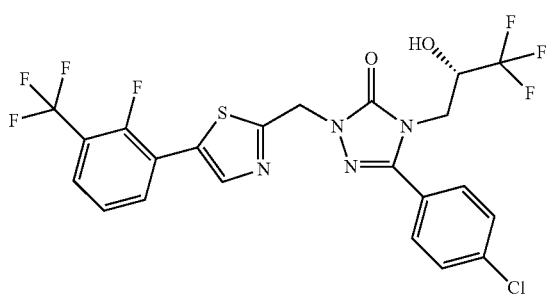 [SMILES: O=c1n(Cc2ncc(-c3cccc(C(F)(F)F)c3F)s2)nc(-c2ccc(Cl)cc2)n1C[C@H](O)C(F)(F)F]

55 mg (0.18 mmol) of the compound from Example 5A were reacted with 61 mg (0.18 mmol) of the compound from Example 91A analogously to the preparation of the compound in Example 77. This gave 55 mg (52% of theory) of the title compound.

LC/MS [Method 4]: $R_t$=1.26 min; MS [ESIpos]: m/z=567 (M+H)$^+$ $^1$H-NMR (400 MHz, DMSO-d$_6$): δ=3.86 (dd, 1H), 4.02 (dd, 1H), 4.25-4.35 (m, 1H), 5.41 (s, 2H), 6.92 (s, 1H), 7.52 (t, 1H), 7.64 (d, 2H), 7.75-7.84 (m, 3H), 8.17 (t, 1H), 8.33 (s, 1H).

Example 81

5-(4-Chlorophenyl)-2-{[5-(2-chlorophenyl)-4-(trifluoromethyl)-1,3-thiazol-2-yl]methyl}-4-[(2S)-3,3,3-trifluoro-2-hydroxypropyl]-2,4-dihydro-3H-1,2,4-triazol-3-one

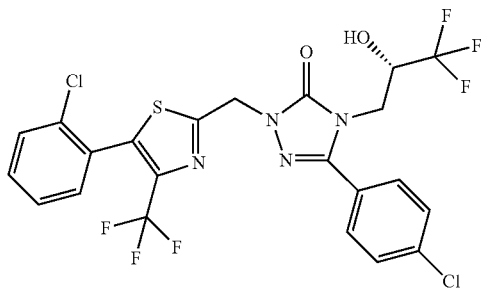 [SMILES: O=c1n(Cc2nc(C(F)(F)F)c(-c3ccccc3Cl)s2)nc(-c2ccc(Cl)cc2)n1C[C@H](O)C(F)(F)F]

40 mg (0.13 mmol) of the compound from Example 5A were reacted with 46 mg (0.13 mmol) of the compound from Example 92A analogously to the preparation of the compound in Example 77. This gave 58 mg (76% of theory) of the title compound.

LC/MS [Method 4]: $R_t$=1.32 min; MS [ESIpos]: m/z=583 and 585 (M+H)$^+$ $^1$H-NMR (400 MHz, DMSO-d$_6$): δ=3.86 (dd, 1H), 4.02 (dd, 1H), 4.24-4.34 (m, 1H), 5.44-5.49 (m, 2H), 6.90 (br. s, 1H), 7.44-7.50 (m, 1H), 7.53-7.60 (m, 2H), 7.61-7.68 (m, 3H), 7.75-7.80 (m, 2H).

Example 82

5-(4-Chlorophenyl)-2-{[2-(2-chlorophenyl)-1,3-oxazol-5-yl]methyl}-4-[(2S)-3,3,3-trifluoro-2-hydroxypropyl]-2,4-dihydro-3H-1,2,4-triazol-3-one

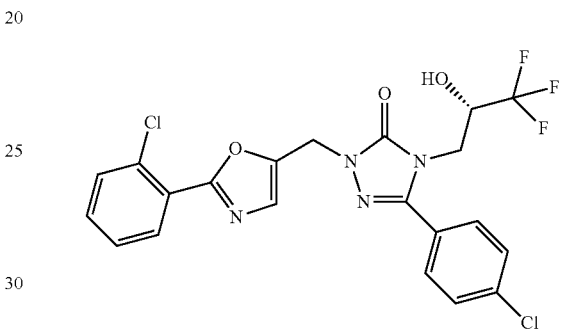

113 mg (0.37 mmol) of the compound from Example 5A were reacted with 100 mg (0.37 mmol) of the compound from Example 54A analogously to the preparation of the compound in Example 77. This gave 23 mg (12% of theory) of the title compound.

LC/MS [Method 6]: $R_t$=2.44 min; MS [ESIpos]: m/z=499 (M+H)$^+$ $^1$H-NMR (400 MHz, DMSO-d$_6$): δ=3.82 (dd, 1H), 3.98 (dd, 1H), 4.25-4.33 (m, 1H), 5.15-5.25 (m, 2H), 6.88 (d, 1H), 7.41 (s, 1H), 7.48-7.57 (m, 2H), 7.60-7.66 (m, 3H), 7.72-7.76 (m, 2H), 7.92 (dd, 1H).

Example 83

5-(4-Chlorophenyl)-2-{[2-(2,3-dichlorophenyl)-1,3-oxazol-5-yl]methyl}-4-[(2S)-3,3,3-trifluoro-2-hydroxypropyl]-2,4-dihydro-3H-1,2,4-triazol-3-one

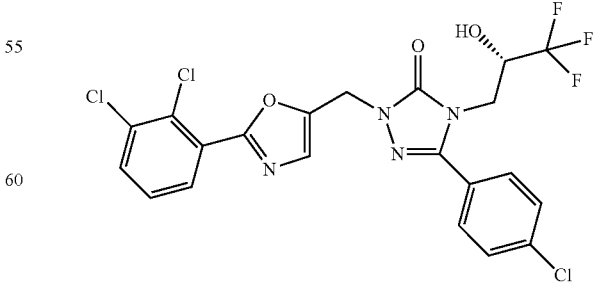

49 mg (0.16 mmol) of the compound from Example 5A were reacted with 49 mg (0.16 mmol) of the compound from Example 55A analogously to the preparation of the compound in Example 77. This gave 35 mg (40% of theory) of the title compound.

LC/MS [Method 4]: $R_t$=1.23 min; MS [ESIpos]: m/z=533 and 535 (M+H)$^+$ $^1$H-NMR (400 MHz, DMSO-d$_6$): δ=3.82 (dd, 1H), 3.98 (dd, 1H), 4.22-4.34 (m, 1H), 5.17-5.26 (m, 2H), 6.89 (s, 1H), 7.45 (s, 1H), 7.53 (t, 1H), 7.61-7.65 (m, 2H), 7.72-7.76 (m, 2H), 7.84 (dd, 1H), 7.88 (dd, 1H).

Example 84

5-(4-Chlorophenyl)-4-cyclopropyl-2-({5-[3-(trifluoromethyl)benzyl]-1,3-thiazol-2-yl}methyl)-2,4-dihydro-3H-1,2,4-triazol-3-one

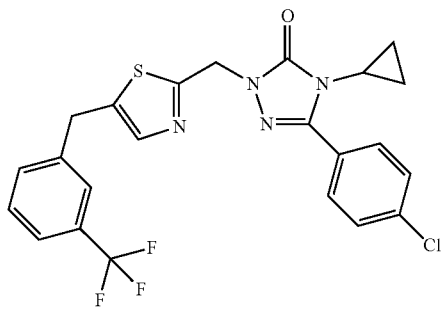 [SMILES: O=c1n(Cc2ncc(Cc3cccc(C(F)(F)F)c3)s2)nc(-c2ccc(Cl)cc2)n1C1CC1]

52 mg (0.11 mmol) of the compound from Example 27A and 47 mg (0.12 mmol) of 4-methoxy-phenyldithiophosphonic anhydride (Lawesson reagent) were dissolved in 1 ml of THF, and the mixture was stirred at 70° C. for 16 h. After cooling to RT, the mixture was partitioned between 10 ml of tert-butyl methyl ether and 10 ml of water. The organic phase was separated off, washed with in each case 10 ml of water and saturated sodium chloride solution, dried over sodium sulfate, filtered and concentrated under reduced pressure. The residue was purified by preparative HPLC [Method 19]. This gave 50 mg (97% of theory) of the title compound as a colorless solid.

MS [ESIpos]: m/z=491 (M+H)$^+$ $^1$H-NMR (400 MHz, CDCl$_3$): δ=0.71-0.81 (m, 2H), 0.97-1.06 (m, 2H), 2.94-3.03 (m, 1H), 4.18 (s, 2H), 5.25 (s, 2H), 7.35-7.55 (m, 6H), 7.69 (d, 2H).

Example 85

5-(4-Chlorophenyl)-4-cyclopropyl-2-({5-[3-(trifluoromethyl)benzyl]-1H-imidazol-2-yl}methyl)-2,4-dihydro-3H-1,2,4-triazol-3-one

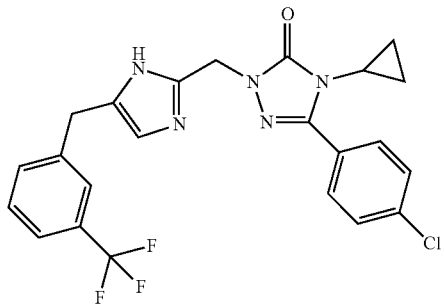 [SMILES: O=c1n(Cc2ncc(Cc3cccc(C(F)(F)F)c3)[nH]2)nc(-c2ccc(Cl)cc2)n1C1CC1]

50 mg (0.10 mmol) of the compound from Example 27A were dissolved in 1 ml of DMF and mixed with 23 mg (0.30 mmol) of ammonium acetate, and the mixture was stirred in a microwave oven at 200° C. for 15 min. After cooling, a further 30 mg (0.39 mmol) of ammonium acetate were added, and the mixture was stirred in a microwave oven at 200° C. for another 30 min. After cooling to RT, the mixture was partitioned between 10 ml of ethyl acetate and 10 ml of water. The organic phase was separated off, washed with in each case 10 ml of water and saturated sodium chloride solution, dried over sodium sulfate, filtered and concentrated under reduced pressure. The residue was purified by preparative HPLC [Method 19]. This gave 17 mg (35% of theory) of the target compound as a yellowish resin.

MS [ESIpos]: m/z=474 (M+H)$^+$ $^1$H-NMR (400 MHz, CDCl$_3$): δ=0.65-0.82 (br. m, 2H), 0.97-1.09 (m, 2H), 2.92-3.03 (m, 1H), 3.98 (s, 2H), 5.10 (s, 2H), 7.33-7.58 (m, 6H), 7.68 (d, 2H), 10.19 (s, 1H).

Example 86

5-(4-Chlorophenyl)-4-(3,3,3-trifluoro-2-hydroxypropyl)-2-({5-[2-(trifluoromethyl)phenyl]pyridin-3-yl}methyl)-2,4-dihydro-3H-1,2,4-triazol-3-one

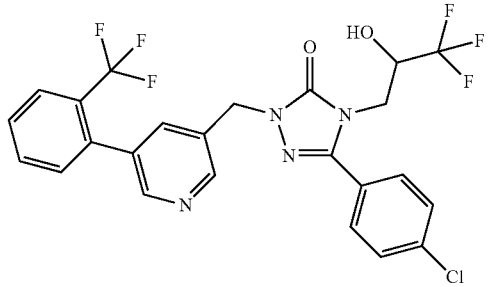 [SMILES: O=c1n(Cc2cncc(-c3ccccc3C(F)(F)F)c2)nc(-c2ccc(Cl)cc2)n1CC(O)C(F)(F)F]

72 mg (0.15 mmol) of the compound from Example 28A and 43 mg (0.23 mmol) of 2-(trifluoro-methyl)phenylboronic acid were dissolved in 2 ml of dioxane. For 10 min, a stream of argon was passed through this solution, and 8.7 mg (0.008 mmol) of tetrakis(triphenylphosphine)palladium(0) were then added under argon. The mixture was heated to the boil, and 0.15 ml (0.30 mmol) of a 2 N aqueous sodium carbonate solution was added under argon. The mixture was stirred under reflux for 20 h. After cooling to RT, the mixture was diluted with 10 ml of water and extracted twice with in each case 15 ml of ethyl acetate. The combined organic phases were dried over magnesium sulfate, filtered and concentrated under reduced pressure. The crude product was purified chromatographically [Method 19]. This gave 36 mg (44% of theory) of the target compound.

LC/MS [Method 4]: $R_t$=1.18 min; MS [ESIpos]: m/z=543 (M+H)$^+$ $^1$H-NMR (400 MHz, DMSO-d$_6$): δ=3.83 (dd, 1H), 3.99 (dd, 1H), 4.23-4.35 (m, 1H), 5.09-5.20 (m, 2H), 6.90 (d, 1H), 7.47 (d, 1H), 7.59-7.65 (m, 2H), 7.65-7.81 (m, 5H), 7.89 (d, 1H), 8.49 (d, 1H), 8.62 (d, 1H).

Example 87

5-(4-Chlorophenyl)-2-{[5-(2-chlorophenyl)pyridin-3-yl]methyl}-4-(3,3,3-trifluoro-2-hydroxypropyl)-2,4-dihydro-3H-1,2,4-triazol-3-one

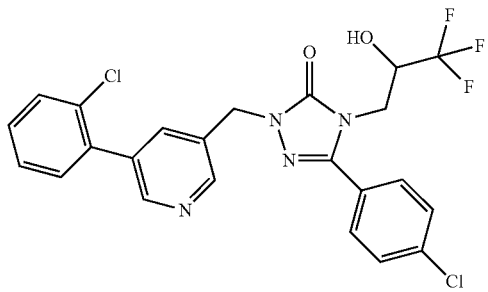 [SMILES: O=c1n(Cc2cncc(-c3ccccc3Cl)c2)nc(-c2ccc(Cl)cc2)n1CC(O)C(F)(F)F]

Analogously to the preparation of the compound in Example 86, 72 mg (0.15 mmol) of the compound from Example 28A and 59 mg (0.23 mmol) of 2-chlorophenylboronic acid were reacted with one another. This gave 49 mg (64% of theory) of the target compound.

LC/MS [Method 4]: $R_t$=1.16 min; MS [ESIpos]: m/z=509 and 511 (M+H)$^+$ $^1$H-NMR (400 MHz, DMSO-d$_6$): δ=3.83 (dd, 1H), 3.99 (dd, 1H), 4.24-4.36 (m, 1H), 5.10-5.20 (m, 2H), 6.90 (d, 1H), 7.44-7.50 (m, 3H), 7.58-7.65 (m, 3H), 7.75 (d, 2H), 7.86 (t, 1H), 8.57-8.62 (m, 2H).

Example 88

5-(4-Chlorophenyl)-2-{[5-(2,3-dichlorophenyl)pyridin-3-yl]methyl}-4-[(2S)-3,3,3-trifluoro-2-hydroxypropyl]-2,4-dihydro-3H-1,2,4-triazol-3-one

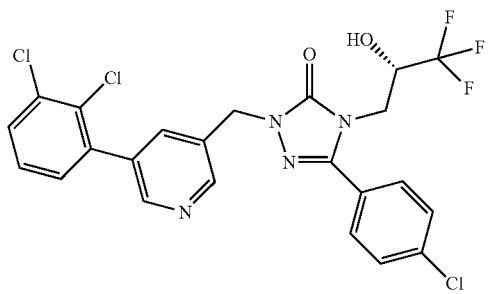 [SMILES: O=c1n(Cc2cncc(-c3cccc(Cl)c3Cl)c2)nc(-c2ccc(Cl)cc2)n1C[C@H](O)C(F)(F)F]

Analogously to the preparation of the compound in Example 86, 34 mg (0.07 mmol) of the compound from Example 29A and 20 mg (0.10 mmol) of 2,3-dichlorophenylboronic acid were reacted with one another. This gave 26 mg (69% of theory) of the target compound.

LC/MS [Method 4]: $R_t$=1.21 min; MS [ESIpos]: m/z=543 and 545 (M+H)$^+$ $^1$H-NMR (400 MHz, DMSO-d$_6$): δ=3.83 (dd, 1H), 3.99 (dd, 1H), 4.26-4.34 (m, 1H), 5.10-5.20 (m, 2H), 6.90 (d, 1H), 7.42-7.53 (m, 2H), 7.60-7.65 (m, 2H), 7.71-7.78 (m, 3H), 7.86 (t, 1H), 8.61 (dd, 2H).

Example 89

5-(4-Chlorophenyl)-4-[(2S)-3,3,3-trifluoro-2-hydroxypropyl]-2-({2-[2-(trifluoromethyl)phenyl]pyridin-4-yl}methyl)-2,4-dihydro-3H-1,2,4-triazol-3-one

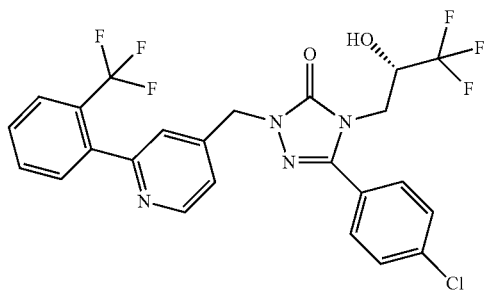

145 mg (0.46 mmol) of the compound from Example 64A were dissolved in 3 ml of acetonitrile, and 141 mg (0.46 mmol) of the compound from Example 5A and 224 mg (0.69 mmol) of cesium carbonate were added. The mixture was stirred at 60° C. for 16 h. After cooling to RT, the solid was filtered off and rinsed with a little acetonitrile. Under reduced pressure, the filtrate was reduced to a volume of about 2 ml, 0.1 ml of 1 N hydrochloric acid was added and the product was directly purified chromatographically [Method 19]. This gave 49 mg (20% of theory) of the target compound.

LC/MS [Method 4]: $R_t$=1.15 min; MS [ESIpos]: m/z=543 (M+H)$^+$ $^1$H-NMR (400 MHz, DMSO-d$_6$): δ=3.85 (dd, 1H), 4.01 (dd, 2H), 4.28-4.35 (m, 1H), 5.09-5.20 (m, 2H), 6.90 (d, 1H), 7.32 (dd, 1H), 7.41 (s, 1H), 7.52 (d, 1H), 7.61-7.66 (m, 2H), 7.68 (d, 1H), 7.73-7.79 (m, 3H), 7.85 (d, 1H), 8.63 (d, 1H).

Example 90

5-(4-Chlorophenyl)-2-{[2-(2-chlorophenyl)pyridin-4-yl]methyl}-4-[(2S)-3,3,3-trifluoro-2-hydroxy-propyl]-2,4-dihydro-3H-1,2,4-triazol-3-one

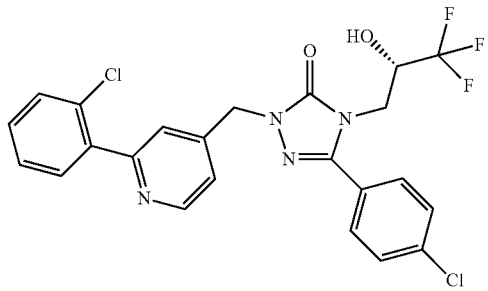 [SMILES: O=c1n(Cc2ccnc(-c3ccccc3Cl)c2)nc(-c2ccc(Cl)cc2)n1C[C@H](O)C(F)(F)F]

Analogously to the preparation of the compound in Example 89, 261 mg (0.85 mmol) of the compound from Example 5A and 240 mg (0.85 mmol) of the compound from Example 65A were reacted with one another. This gave 249 mg (54% of theory) of the target compound.

LC/MS [Method 3]: $R_t$=1.28 min; MS [ESIpos]: m/z=509 and 511 (M+H)$^+$ $^1$H-NMR (400 MHz, DMSO-d$_6$): δ=3.87 (dd, 1H), 4.01 (dd, 1H), 4.26-4.39 (m, 1H), 5.10-5.20 (m, 2H), 6.90 (d, 1H), 7.30 (d, 1H), 7.41-7.50 (m, 2H), 7.55-7.60 (m, 3H), 7.64 (d, 2H), 7.77 (d, 2H), 8.68 (d, 1H).

Example 91

5-(4-Chlorophenyl)-2-{[2-(2,3-dichlorophenyl)pyridin-4-yl]methyl}-4-[(2S)-3,3,3-trifluoro-2-hydroxypropyl]-2,4-dihydro-3H-1,2,4-triazol-3-one

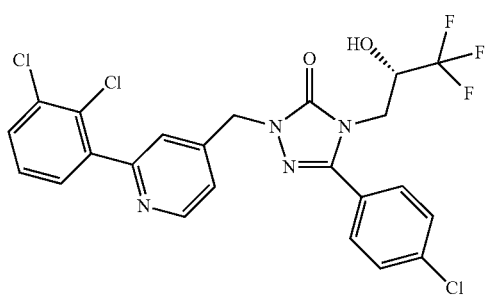 [SMILES: O=c1n(Cc2ccnc(-c3cccc(Cl)c3Cl)c2)nc(-c2ccc(Cl)cc2)n1C[C@H](O)C(F)(F)F]

81 mg (0.26 mmol) of the compound from Example 66A were dissolved in 3 ml of acetonitrile and 79 mg (0.26 mmol) of the compound from Example 5A and 125 mg (0.38 mmol) of cesium carbonate were added. The mixture was stirred at 65° C. for 2 h and at RT for a further 16 h. The solid was then filtered off and rinsed with a little acetonitrile. The filtrate was concentrated under reduced pressure and directly purified chromatographically [Method 19]. This gave 79 mg (56% of theory) of the target compound.

LC/MS [Method 4]: $R_t$=1.21 min; MS [ESIpos]: m/z=543 and 545 (M+H)$^+$ $^1$H-NMR (400 MHz, DMSO-d$_6$): δ=3.85 (dd, 1H), 4.01 (dd, 1H), 4.28-4.35 (m, 1H), 5.10-5.21 (m, 2H), 6.91 (d, 1H), 7.34 (dd, 1H), 7.45-7.52 (m, 2H), 7.57 (s, 1H), 7.61-7.66 (m, 2H), 7.71-7.79 (m, 3H), 8.67 (d, 1H).

Example 92

5-(4-Chlorophenyl)-4-[(2S)-3,3,3-trifluoro-2-hydroxypropyl]-2-({2-[2-(trifluoromethyl)phenyl]-pyrimidin-4-yl}methyl)-2,4-dihydro-3H-1,2,4-triazol-3-one

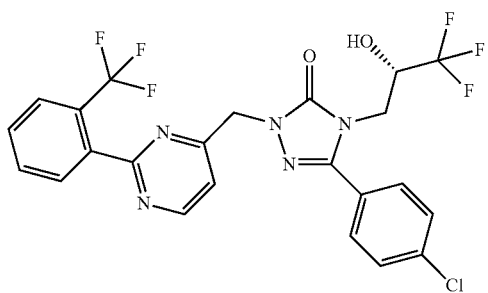 [SMILES: O=c1n(Cc2ccnc(-c3ccccc3C(F)(F)F)n2)nc(-c2ccc(Cl)cc2)n1C[C@H](O)C(F)(F)F]

303 mg (0.19 mmol) of the compound from Example 80A (purity about 20%) were dissolved in 2 ml of acetonitrile, and 65 mg (0.21 mmol) of the compound from Example 5A and 93 mg (0.29 mmol) of cesium carbonate were added. The mixture was stirred at 60° C. for 2.5 h and at RT for a further 96 h. The solid was then filtered off and rinsed with a little acetonitrile. The filtrate was concentrated under reduced pressure and directly purified chromatographically [Method 19]. This gave 19 mg of the target compound, which were subjected to a further chromatographic purification on silica gel (mobile phase: cyclohexane/ethyl acetate 7:3, then 1:1). This gave 8 mg (7% of theory) of the target compound.

LC/MS [Method 3]: $R_t$=1.32 min; MS [ESIpos]: m/z=544 (M+H)$^+$ $^1$H-NMR (400 MHz, DMSO-d$_6$): δ=3.86 (dd, 1H), 4.01 (dd, 1H), 4.31-4.35 (m, 1H), 5.13-5.26 (m, 2H), 6.93 (d, 1H), 7.39 (d, 1H), 7.61-7.67 (m, 2H), 7.69-7.83 (m, 5H), 7.88 (d, 1H), 8.93 (d, 1H).

Example 93

5-(4-Chlorophenyl)-2-{[2-(2-chlorophenyl)pyrimidin-4-yl]methyl}-4-[(2S)-3,3,3-trifluoro-2-hydroxypropyl]-2,4-dihydro-3H-1,2,4-triazol-3-one

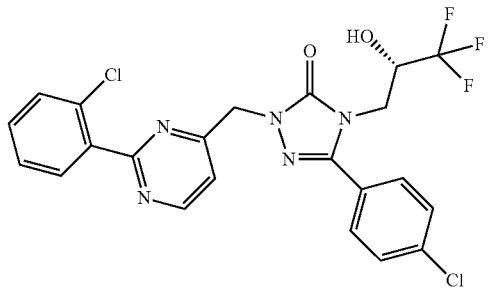 [SMILES: O=c1n(Cc2ccnc(-c3ccccc3Cl)n2)nc(-c2ccc(Cl)cc2)n1C[C@H](O)C(F)(F)F]

259 mg (0.18 mmol) of the compound from Example 81A (purity about 20%) were dissolved in 2 ml of acetonitrile, and 62 mg (0.21 mmol) of the compound from Example 5A and 89 mg (0.27 mmol) of cesium carbonate were added. The mixture was stirred at 60° C. for 2.5 h and at RT for a further 96 h. The solid was then filtered off and rinsed with a little acetonitrile. The filtrate was concentrated under reduced pressure and directly purified chromatographically [Method 19]. This gave 31 mg of the target compound, which were subjected to a further chromatographic purification on silica gel (mobile phase: cyclohexane/ethyl acetate 7:3, then 1:1). This gave 23 mg (22% of theory) of the target compound.

LC/MS [Method 4]: $R_t$=1.13 min; MS [ESIpos]: m/z=510 and 512 (M+H)$^+$ $^1$H-NMR (400 MHz, DMSO-d$_6$): δ=3.87 (dd, 1H), 4.02 (dd, 1H), 4.28-4.38 (m, 1H), 5.16-5.26 (m, 2H), 6.93 (d, 1H), 7.36 (d, 1H), 7.44-7.54 (m, 2H), 7.56-7.60 (m, 1H), 7.61-7.66 (m, 2H), 7.71-7.79 (m, 3H), 8.94 (d, 1H).

Example 94

5-(4-Chlorophenyl)-4-[(2S)-3,3,3-trifluoro-2-hydroxypropyl]-2-({6-[2-(trifluoromethyl)phenyl]-pyrimidin-4-yl}methyl)-2,4-dihydro-3H-1,2,4-triazol-3-one

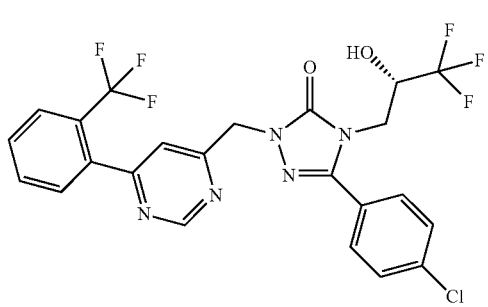 [SMILES: O=c1n(Cc2cc(-c3ccccc3C(F)(F)F)ncn2)nc(-c2ccc(Cl)cc2)n1C[C@H](O)C(F)(F)F]

37 mg (0.12 mmol) of the compound from Example 82A were dissolved in 2 ml of acetonitrile, and 39 mg (0.13 mmol) of the compound from Example 5A and 57 mg (0.18 mmol) of cesium carbonate were added. The mixture was stirred at 60° C. for 2.5 h. After cooling to RT, the solid was filtered off and rinsed with a little acetonitrile. The filtrate was concentrated under reduced pressure and directly purified chromatographically [Method 19]. The product obtained was subjected to a further chromatographic purification on silica gel (mobile phase: cyclohexane/ethyl acetate 4:1, then 3:2). This gave 28 mg (41% of theory) of the target compound.

LC/MS [Method 6]: $R_t$=2.34 min; MS [ESIpos]: m/z=544 (M+H)$^+$ $^1$H-NMR (400 MHz, DMSO-d$_6$): δ=3.86 (dd, 1H), 4.01 (dd, 1H), 4.27-4.34 (m, 1H), 5.17-5.29 (m, 2H), 6.91 (d, 1H), 7.55 (s, 1H), 7.59 (d, 1H), 7.63 (d, 2H), 7.72-7.78 (m, 3H), 7.80-7.85 (m, 1H), 7.91 (d, 1H), 9.24 (d, 1H).

Example 95

5-(4-Chlorophenyl)-2-{[6-(2-chlorophenyl)pyrimidin-4-yl]methyl}-4-[(2S)-3,3,3-trifluoro-2-hydroxypropyl]-2,4-dihydro-3H-1,2,4-triazol-3-one

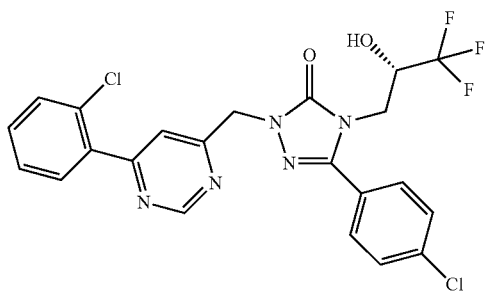 [SMILES: O=c1n(Cc2cc(-c3ccccc3Cl)ncn2)nc(-c2ccc(Cl)cc2)n1C[C@H](O)C(F)(F)F]

Analogously to the preparation of the compound in Example 94, 27 mg (0.10 mmol) of the compound from Example 83A and 32 mg (0.11 mmol) of the compound from Example 5A were reacted with one another. This gave 29 mg (54% of theory) of the target compound.

LC/MS [Method 4]: $R_t$=1.15 min; MS [ESIpos]: m/z=510 and 512 (M+H)$^+$ $^1$H-NMR (400 MHz, DMSO-d$_6$): δ=3.86 (dd, 1H), 4.02 (dd, 1H), 4.27-4.35 (m, 1H), 5.19-5.29 (m, 2H), 6.91 (d, 1H), 7.48-7.59 (m, 2H), 7.60-7.69 (m, 4H), 7.72 (d, 1H), 7.74-7.80 (m, 2H), 9.27 (d, 1H).

Example 96

5-(4-Chlorophenyl)-2-{[6-(2,3-dichlorophenyl)pyrimidin-4-yl]methyl}-4-[(2S)-3,3,3-trifluoro-2-hydroxypropyl]-2,4-dihydro-3H-1,2,4-triazol-3-one

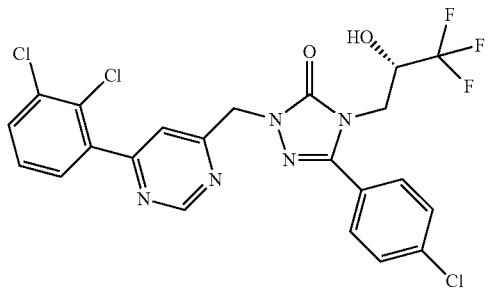 [SMILES: O=c1n(Cc2cc(-c3cccc(Cl)c3Cl)ncn2)nc(-c2ccc(Cl)cc2)n1C[C@H](O)C(F)(F)F]

Analogously to the preparation of the compound in Example 94, 23 mg (0.07 mmol) of the compound from Example 84A and 24 mg (0.08 mmol) of the compound from Example 5A were reacted with one another. This gave 29 mg (66% of theory) of the target compound.

LC/MS [Method 6]: $R_t$=2.54 min; MS [ESIpos]: m/z=544 and 546 (M+H)$^+$ $^1$H-NMR (400 MHz, DMSO-d$_6$): δ=3.86 (dd, 1H), 4.02 (dd, 1H), 4.26-4.38 (m, 1H), 5.18-5.30 (m, 2H), 6.92 (s, 1H), 7.51-7.56 (m, 1H), 7.57-7.60 (m, 1H), 7.61-7.65 (m, 2H), 7.71 (d, 1H), 7.74-7.79 (m, 2H), 7.81 (dd, 1H), 9.29 (d, 1H).

Example 97

5-(4-Chlorophenyl)-4-(3,3,3-trifluoro-2-hydroxypropyl)-2-({1-[3-(trifluoromethyl)benzyl]-1H-1,2,3-triazol-4-yl}methyl)-2,4-dihydro-3H-1,2,4-triazol-3-one

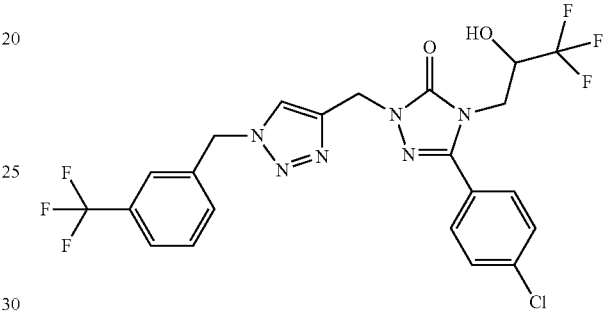

29 mg (0.12 mmol) of 3-(trifluoromethyl)benzyl bromide were initially charged in 1 ml of acetonitrile, and 8 mg (0.12 mmol) of sodium azide were added. The mixture was stirred at RT for 1 h. 0.24 mg (0.012 mmol) of copper(II) acetate monohydrate and 50 mg (0.14 mmol) of the compound from Example 13A were then added. The resulting mixture was stirred at room temperature for 11 days. The reaction mixture was then filtered through a little silica gel, the product being eluted with about 10 ml of ethyl acetate, and the filtrate was concentrated under reduced pressure. The crude product was purified chromatographically [Method 19]. This gave 52 mg (65% of theory) of the target compound.

LC/MS [Method 4]: $R_t$=1.13 min; MS [ESIpos]: m/z=547 (M+H)$^+$ $^1$H-NMR (400 MHz, CDCl$_3$): δ=3.91-3.99 (m, 1H), 3.98-4.05 (m, 1H), 4.46-4.56 (m, 1H), 5.15 (q, 2H), 5.34 (d, 1H), 5.51-5.61 (m, 2H), 7.41-7.59 (m, 8H), 7.63 (d, 1H).

Example 98

5-(4-Chlorophenyl)-4-(3,3,3-trifluoro-2-hydroxypropyl)-2-({1-[2-(trifluoromethyl)benzyl]-1H-1,2,3-triazol-4-yl}methyl)-2,4-dihydro-3H-1,2,4-triazol-3-one

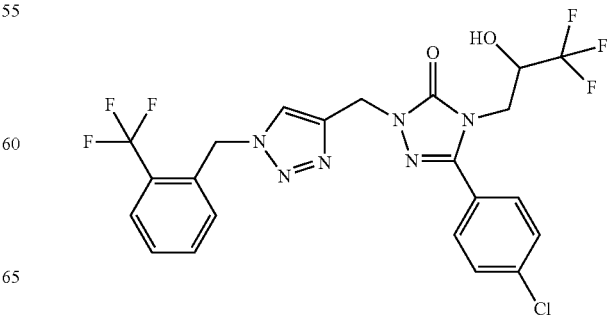

Analogously to the preparation of the compound in Example 97, 50 mg (0.14 mmol) of the compound from Example 13A gave 54 mg (68% of theory) of the title compound.

LC/MS [Method 4]: $R_t$=1.13 min; MS [ESIpos]: m/z=547 (M+H)$^+$ $^1$H-NMR (400 MHz, CDCl$_3$): δ=3.91-3.99 (m, 1H), 3.99-4.06 (m, 1H), 4.46-4.57 (m, 1H), 5.16 (q, 2H), 5.31 (d, 1H), 5.72 (s, 2H), 7.20 (d, 1H), 7.42-7.58 (m, 7H), 7.72 (d, 1H).

Example 99

5-(4-Chlorophenyl)-4-[(2S)-3,3,3-trifluoro-2-hydroxypropyl]-2-({1-[2-(trifluoromethyl)phenyl]-1H-1,2,3-triazol-4-yl}methyl)-2,4-dihydro-3H-1,2,4-triazol-3-one

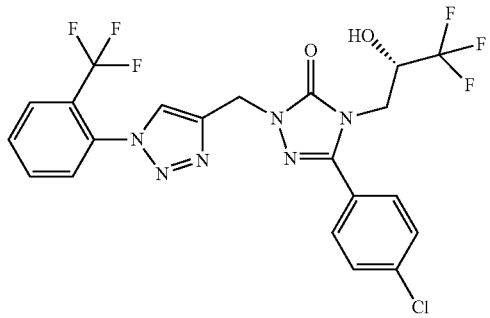 [SMILES: O=c1n(Cc2cn(-c3ccccc3C(F)(F)F)nn2)nc(-c2ccc(Cl)cc2)n1C[C@H](O)C(F)(F)F]

20 mg (0.31 mmol) of sodium azide were initially charged in 1 ml of methanol, and 58 mg (0.31 mmol) of 2-(trifluoromethyl)phenylboronic acid and 6 mg (0.03 mmol) of copper(II) acetate monohydrate were added. The mixture was stirred at RT for 18 h. 0.9 ml of water, 30 mg (0.15 mmol) of L-ascorbic acid sodium salt and 117 mg (0.34 mmol) of the compound from Example 14A were then added to the mixture. The mixture was stirred at RT for a further 18 h. For work-up, the mixture was diluted with 10 ml of water and 10 ml of ethyl acetate, and 5 ml 0.1 N aqueous sodium hydroxide solution were added with stirring. After phase separation, the aqueous phase was extracted three more times with in each case 10 ml of ethyl acetate. The combined organic phases were dried over sodium sulfate, filtered and concentrated under reduced pressure. The crude product was purified by chromatography on silica gel (mobile phase: cyclohexane/ethyl acetate 5:1, then 1:2). This gave 117 mg (71% of theory) of the target compound.

LC/MS [Method 3]: $R_t$=1.26 min; MS [ESIpos]: m/z=533 (M+H)$^+$ $^1$H-NMR (400 MHz, DMSO-d$_6$): δ=3.83 (dd, 1H), 3.99 (dd, 1H), 4.28-4.34 (m, 1H), 5.12-5.23 (m, 2H), 6.91 (d, 1H), 7.63 (d, 2H), 7.68-7.79 (m, 3H), 7.81-7.96 (m, 2H), 8.03 (d, 1H), 8.51 (s, 1H).

Example 100

5-(4-Chlorophenyl)-4-[(2S)-3,3,3-trifluoro-2-hydroxypropyl]-2-({1-[3-(trifluoromethyl)phenyl]-1H-1,2,3-triazol-4-yl}methyl)-2,4-dihydro-3H-1,2,4-triazol-3-one

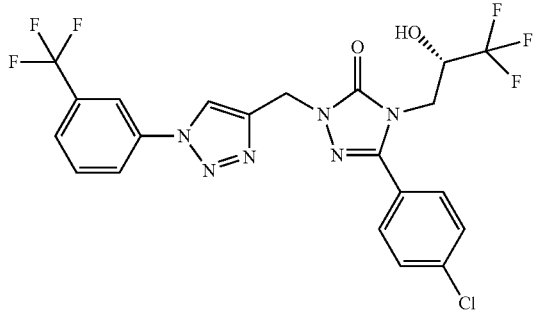 [SMILES: O=c1n(Cc2cn(-c3cccc(C(F)(F)F)c3)nn2)nc(-c2ccc(Cl)cc2)n1C[C@H](O)C(F)(F)F]

Analogously to the preparation of the compound in Example 99, 117 mg (0.34 mmol) of the compound from Example 14A gave 138 mg (84% of theory) of the title compound.

LC/MS [Method 3]: $R_t$=1.33 min; MS [ESIpos]: m/z=533 (M+H)$^+$ $^1$H-NMR (400 MHz, DMSO-d$_6$): δ=3.83 (dd, 1H), 3.99 (dd, 1H), 4.27-4.38 (m, 1H), 5.13-5.22 (m, 2H), 6.91 (d, 1H), 7.59-7.65 (m, 2H), 7.73-7.79 (m, 2H), 7.81-7.90 (m, 2H), 8.24-8.32 (m, 2H), 9.02 (s, 1H).

Example 101

5-(4-Chlorophenyl)-2-{[1-(2-chlorophenyl)-1H-1,2,3-triazol-4-yl]methyl}-4-[(2S)-3,3,3-trifluoro-2-hydroxypropyl]-2,4-dihydro-3H-1,2,4-triazol-3-one

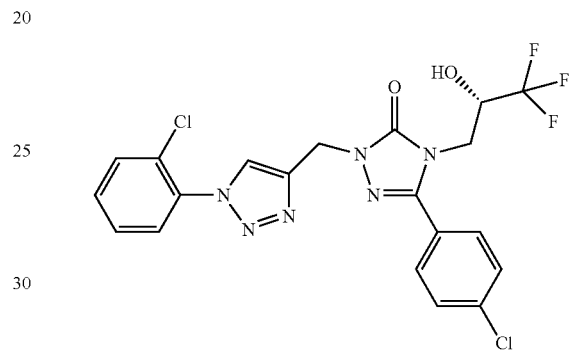

Analogously to the preparation of the compound in Example 99, 75 mg (0.22 mmol) of the compound from Example 14A gave 56 mg (55% of theory) of the title compound.

LC/MS [Method 4]: $R_t$=1.09 min; MS [ESIpos]: m/z=499 and 501 (M+H)$^+$ $^1$H-NMR (400 MHz, DMSO-d$_6$): δ=3.83 (dd, 1H), 3.99 (dd, 1H), 4.28-4.35 (m, 1H), 5.13-5.22 (m, 2H), 6.91 (d, 1H), 7.55-7.70 (m, 5H), 7.74-7.80 (m, 3H), 8.54 (s, 1H).

Example 102

5-(4-Chlorophenyl)-2-{[1-(2,3-dichlorophenyl)-1H-1,2,3-triazol-4-yl]methyl}-4-[(2S)-3,3,3-trifluoro-2-hydroxypropyl]-2,4-dihydro-3H-1,2,4-triazol-3-one

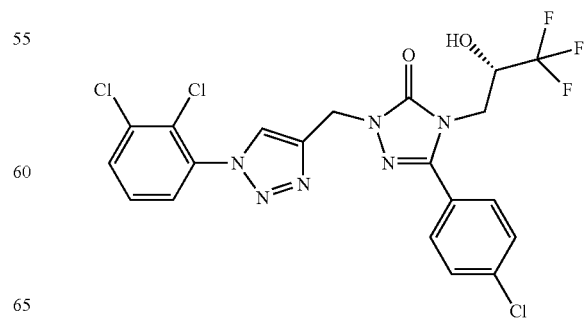

124 mg (0.36 mmol) of the compound from Example 14A were dissolved in 2 ml of acetonitrile, and 0.6 mg (0.003 mmol) of copper(II) acetate monohydrate and 56 mg (0.30 mmol) of 1-azido-2,3-dichlorobenzene were added. The mixture was stirred at 50° C. for 2 h. For work-up, the crude mixture was allowed to cool to RT and filtered through a little silica gel. The product was eluted with ethyl acetate and the solution obtained was concentrated under reduced pressure. The crude product was then purified by chromatography on silica gel (mobile phase: cyclohexane/ethyl acetate 1:1). This gave 61 mg (31% of theory) of the target compound.

LC/MS [Method 4]: $R_t$=1.13 min; MS [ESIpos]: m/z=533 and 535 (M+H)$^+$ $^1$H-NMR (400 MHz, DMSO-$d_6$): δ=3.83 (dd, 1H), 3.99 (dd, 1H), 4.29-4.34 (m, 1H), 5.13-5.23 (m, 2H), 6.91 (d, 1H), 7.58-7.66 (m, 3H), 7.69 (dd, 1H), 7.77 (d, 2H), 7.92 (dd, 1H), 8.59 (s, 1H).

Example 103

Methyl (2-chlorophenyl)[4-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,3-triazol-1-yl]acetate

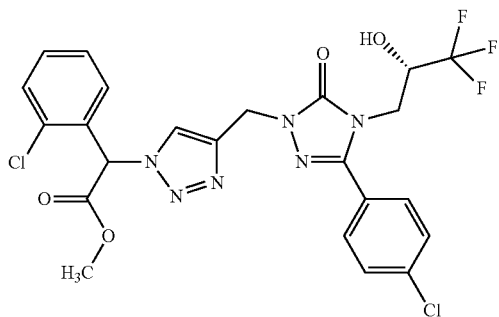 [SMILES: COC(=O)C(c1ccccc1Cl)n1cc(Cn2nc(-c3ccc(Cl)cc3)n(C[C@H](O)C(F)(F)F)c2=O)nn1]

361 mg (1.37 mmol) of methyl bromo(2-chlorophenyl)acetate were initially charged in 10 ml of acetonitrile, and 89 mg (1.37 mmol) of sodium azide were added. The mixture was stirred at RT for 1 h. 2.7 mg (0.14 mmol) of copper(II) acetate monohydrate and 569 mg (1.64 mmol) of the compound from Example 14A were then added. The resulting mixture was stirred at 50° C. for 48 h. The reaction mixture was then filtered through a little silica gel, the product being eluted with about 10 ml of ethyl acetate, and the filtrate was concentrated under reduced pressure. The crude product was purified by chromatography on silica gel (mobile phase: cyclohexane/ethyl acetate 8:1→6:1→4:1→2:1→1:1). This gave 496 mg (53% of theory) of the target compound.

LC/MS [Method 4]: $R_t$=1.13 min; MS [ESIpos]: m/z=571 and 573 (M+H)$^+$ $^1$H-NMR (400 MHz, DMSO-$d_6$): δ=3.76 (s, 3H), 3.81 (dd, 1H), 3.96 (dd, 1H), 4.25-4.32 (m, 1H), 5.02-5.12 (m, 2H), 6.88 (dd, 1H), 7.12 (s, 1H), 7.39-7.51 (m, 3H), 7.57 (d, 1H), 7.62 (d, 2H), 7.72 (d, 2H), 8.25 (d, 1H).

Example 104

(2-Chlorophenyl)[4-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,3-triazol-1-yl]acetic acid

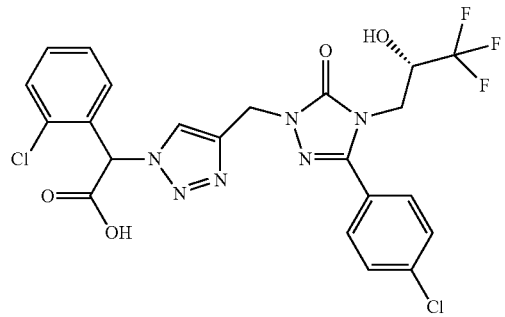 [SMILES: O=C(O)C(c1ccccc1Cl)n1cc(Cn2nc(-c3ccc(Cl)cc3)n(C[C@H](O)C(F)(F)F)c2=O)nn1]

49 mg (0.09 mmol) of the compound from Example 103 were dissolved in 2 ml of methanol, and 193 µl (0.19 mmol) of a 1 N aqueous lithium hydroxide solution were added. The mixture was stirred at RT for 30 min. The solvent was then removed under reduced pressure, the residue was dissolved in 5 ml of water and the solution was extracted once with 5 ml of ethyl acetate. The organic phase was discarded. The aqueous phase was acidified with 0.2 ml of 1 N hydrochloric acid and extracted twice with in each case 5 ml of ethyl acetate. The combined organic phases were dried over sodium sulfate, filtered and concentrated under reduced pressure. This gave 40 mg (83% of theory) of the target compound.

LC/MS [Method 4]: $R_t$=0.95 min; MS [ESIpos]: m/z=557 and 559 (M+H)$^+$ $^1$H-NMR (400 MHz, DMSO-$d_6$): δ=3.80 (dd, 1H), 3.96 (dd, 1H), 4.26-4.31 (m, 1H), 5.03-5.10 (m, 2H), 6.90 (dd, 1H), 6.94 (s, 1H), 7.42-7.51 (m, 3H), 7.54-7.58 (m, 1H), 7.59-7.65 (m, 2H), 7.73 (d, 2H), 8.22 (d, 1H).

Example 105

2-(2-Chlorophenyl)-2-[4-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,3-triazol-1-yl]acetamide

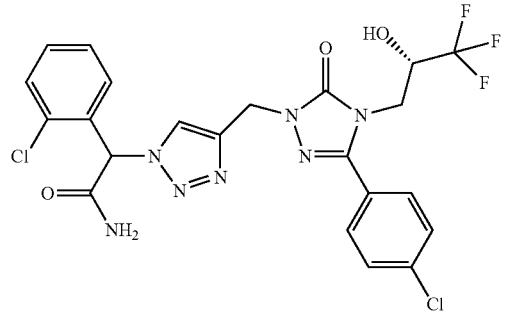 [SMILES: NC(=O)C(c1ccccc1Cl)n1cc(Cn2nc(-c3ccc(Cl)cc3)n(C[C@H](O)C(F)(F)F)c2=O)nn1]

25 mg (0.045 mmol) of the compound from Example 104 were initially charged in 1 ml of DMF, and 9 mg (0.058 mmol) of HOBt and 11 mg (0.058 mmol) of EDC were added. After 10 min of stirring at RT, 0.5 ml (0.90 mmol) of ammonia solution (35% strength in water) was added, and the reaction was stirred at RT for 16 h. The reaction mixture was then purified directly, without any further work-up, by chromatography [Method 19]. This gave 10 mg (40% of theory) of the target compound.

LC/MS [Method 4]: $R_t$=0.99 min; MS [ESIpos]: m/z=556 and 558 (M+H)$^+$ $^1$H-NMR (400 MHz, DMSO-d$_6$): δ=3.75-3.85 (m, 1H), 3.91-4.00 (m, 1H), 4.23-4.31 (m, 1H), 5.03 (s, 2H), 6.76 (s, 1H), 6.90 (d, 1H), 7.47 (br. s, 3H), 7.55 (m, 1H), 7.59-7.65 (m, 2H), 7.71 (d, 3H), 7.85 (m, 1H), 8.08 (br. s, 1H).

Example 106

5-(4-Chlorophenyl)-2-({1-[1-(2-chlorophenyl)-2-hydroxyethyl]-1H-1,2,3-triazol-4-yl}methyl)-4-[(2S)-3,3,3-trifluoro-2-hydroxypropyl]-2,4-dihydro-3H-1,2,4-triazol-3-one

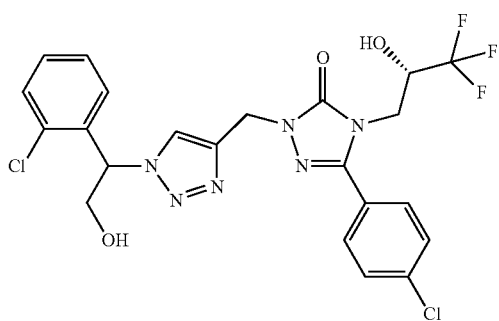 [SMILES: O=c1n(Cc2cn(C(CO)c3ccccc3Cl)nn2)nc(-c2ccc(Cl)cc2)n1C[C@H](O)C(F)(F)F]

48 mg (0.084 mmol) of the compound from Example 103 were dissolved in 2 ml of THF, and 88 μl (0.088 mmol) of a 1 M solution of lithium aluminum hydride in THF were added at −10° C. After the addition had ended, the mixture was stirred at RT for 1 h. For work-up, 2 ml of saturated aqueous sodium potassium tartrate solution were added at RT, and the mixture was extracted with 5 ml of ethyl acetate. The organic phase was washed once with 5 ml of saturated sodium chloride solution, dried over magnesium sulfate, filtered and concentrated under reduced pressure. The crude product was purified chromatographically [Method 19]. This gave 8 mg (18% of theory) of the target compound.

LC/MS [Method 2]: $R_t$=2.20 min; MS [ESIpos]: m/z=543 and 545 (M+H)$^+$ $^1$H-NMR (400 MHz, DMSO-d$_6$): δ=3.81 (dd, 1H), 3.93-4.04 (m, 2H), 4.21-4.32 (m, 1H), 5.02-5.12 (m, 2H), 5.45 (dd, 1H), 6.14 (dd, 1H), 6.90 (d, 1H), 7.32-7.41 (m, 3H), 7.50-7.54 (m, 1H), 7.60-7.65 (m, 2H), 7.71-7.76 (m, 2H), 8.34 (s, 1H).

Example 107

Ethyl [4-({3-(4-chlorophenyl)-5-oxo-4-[(2S)-3,3,3-trifluoro-2-hydroxypropyl]-4,5-dihydro-1H-1,2,4-triazol-1-yl}methyl)-1H-1,2,3-triazol-1-yl][2-(trifluoromethyl)phenyl]acetate

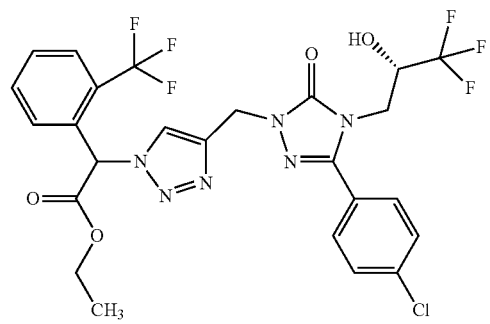 [SMILES: CCOC(=O)C(c1ccccc1C(F)(F)F)n1cc(Cn2nc(-c3ccc(Cl)cc3)n(C[C@H](O)C(F)(F)F)c2=O)nn1]

158 mg (0.15 mmol) of the compound from Example 98A (purity about 30%) were initially charged in 2 ml of acetonitrile, and 9.9 mg (0.15 mmol) of sodium azide were added. The mixture was stirred at RT for 1 h. 0.3 mg (0.002 mmol) of copper(II) acetate monohydrate and 63 mg (0.18 mmol) of the compound from Example 14A were then added. The resulting mixture was stirred at 50° C. for 20 h. The reaction mixture was then filtered through a little silica gel, the product being eluted with about 10 ml of ethyl acetate, and the filtrate was concentrated under reduced pressure. The crude product was purified chromatographically [Method 19]. This gave 9 mg (8% of theory) of the target compound.

LC/MS [Method 3]: $R_t$=1.36 min; MS [ESIpos]: m/z=619 (M+H)$^+$ $^1$H-NMR (400 MHz, DMSO-d$_6$): δ=1.13 (t, 3H), 3.81 (dd, 1H), 3.96 (dd, 1H), 4.17-4.31 (m, 3H), 5.01-5.11 (m, 2H), 6.89 (dd, 1H), 6.93 (d, 1H), 7.59-7.75 (m, 6H), 7.77-7.88 (m, 2H), 8.29 (d, 1H).

Example 108

5-(4-Chlorophenyl)-4-cyclopropyl-2-({4-[2-(trifluoromethyl)phenyl]-1H-1,2,3-triazol-1-yl}-methyl)-2,4-dihydro-3H-1,2,4-triazol-3-one

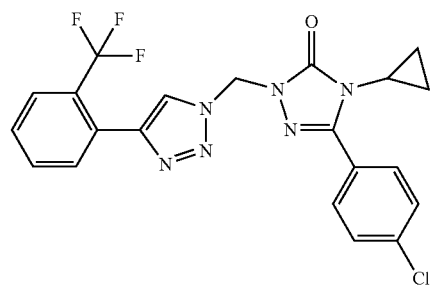 [SMILES: O=c1n(Cn2cc(-c3ccccc3C(F)(F)F)nn2)nc(-c2ccc(Cl)cc2)n1C1CC1]

60 mg (0.21 mmol) of the compound from Example 122A were dissolved in 2 ml of acetonitrile, 14 mg (0.21 mmol) of sodium azide were added and the mixture was stirred at RT for 1 h. 0.4 mg (0.002 mmol) of copper(II) acetate monohydrate and 43 mg (0.25 mmol) of 1-ethynyl-2-(trifluoromethyl)benzene were then added. The resulting mixture was stirred at RT for 20 h. For work-up, 10 ml of ethyl acetate were added and the mixture was washed twice with in each case 5 ml of water. The organic phase was dried over sodium sulfate, filtered and concentrated under reduced pressure. The crude product was purified chromatographically [Method 19]. This gave 48 mg (45% of theory) of the target compound.

LC/MS [Method 4]: $R_t$=1.15 min; MS [ESIpos]: m/z=461 (M+H)$^+$ $^1$H-NMR (400 MHz, DMSO-d$_6$): δ=0.57-0.63 (m, 2H), 0.85-0.92 (m, 2H), 3.19 (m, 1H), 6.44 (s, 2H), 7.58-7.68 (m, 3H), 7.74-7.84 (m, 4H), 7.87 (d, 1H), 8.42 (s, 1H).

Example 109

5-(4-Chlorophenyl)-4-cyclopropyl-2-({4-[3-(trifluoromethyl)phenyl]-1H-1,2,3-triazol-1-yl}-methyl)-2,4-dihydro-3H-1,2,4-triazol-3-one

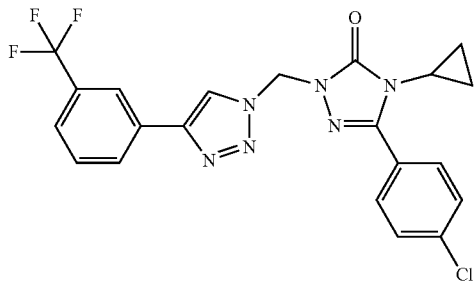 [SMILES: O=c1n(Cn2cc(-c3cccc(C(F)(F)F)c3)nn2)nc(-c2ccc(Cl)cc2)n1C1CC1]

Analogously to the preparation of the compound in Example 108, 60 mg (0.21 mmol) of the compound from Example 122A gave 21 mg (21% of theory) of the title compound.

LC/MS [Method 4]: $R_t$=1.19 min; MS [ESIpos]: m/z=461 (M+H)$^+$ $^1$H-NMR (400 MHz, DMSO-d$_6$): δ=0.59-0.64 (m, 2H), 0.85-0.92 (m, 2H), 3.18 (m, 1H), 6.39 (s, 2H), 7.57-7.62 (m, 2H), 7.66-7.73 (m, 2H), 7.78-7.83 (m, 2H), 8.19-8.26 (m, 2H), 8.91 (s, 1H).

Example 110

5-(4-Chlorophenyl)-2-{[1-(2-chlorophenyl)-1H-imidazol-4-yl]methyl}-4-[(2S)-3,3,3-trifluoro-2-hydroxypropyl]-2,4-dihydro-3H-1,2,4-triazol-3-one

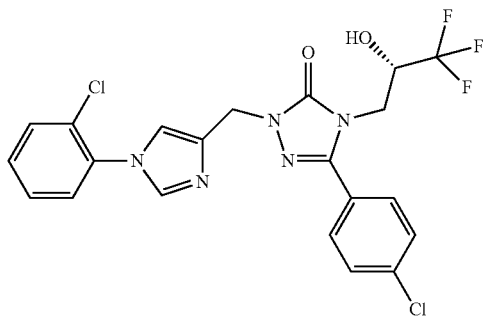 [SMILES: O=c1n(Cc2cn(-c3ccccc3Cl)cn2)nc(-c2ccc(Cl)cc2)n1C[C@H](O)C(F)(F)F]

19 mg (0.06 mmol) of the compound from Example 5A were dissolved in 5 ml of acetonitrile, and 17 mg (0.13 mmol) of potassium carbonate and 17 mg (0.06 mmol) of the compound from Example 42A were added. The mixture was stirred at 65° C. for 2 h and then stirred at RT for 20 h. For work-up, 5 ml of water were added and the mixture was extracted twice with in each case 10 ml of ethyl acetate. The organic phase was washed once with 5 ml of saturated sodium chloride solution, dried over sodium sulfate, filtered and concentrated under reduced pressure. The crude product was purified chromatographically [Method 19]. This gave 4 mg (12% of theory) of the target compound.

LC/MS [Method 4]: $R_t$=1.04 min; MS [ESIpos]: m/z=498 and 500 (M+H)$^+$ $^1$H-NMR (400 MHz, DMSO-d$_6$): δ=3.83 (dd, 1H), 3.99 (dd, 1H), 4.27-4.37 (m, 1H), 4.89-4.96 (m, 2H), 6.92 (br. s, 1H), 7.37 (s, 1H), 7.47-7.57 (m, 3H), 7.62 (d, 2H), 7.67-7.72 (m, 1H), 7.76 (d, 2H), 7.87 (s, 1H).

Example 111

5-(4-Chlorophenyl)-2-{[1-(2-chlorophenyl)-1H-pyrazol-4-yl]methyl}-4-[(2S)-3,3,3-trifluoro-2-hydroxypropyl]-2,4-dihydro-3H-1,2,4-triazol-3-one

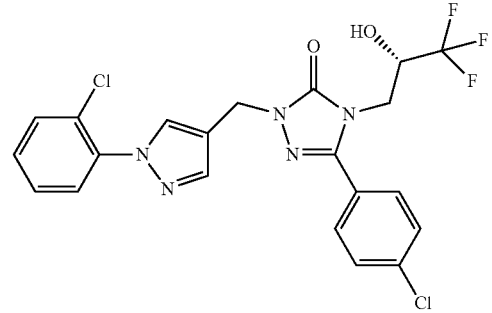 [SMILES: O=c1n(Cc2cnn(-c3ccccc3Cl)c2)nc(-c2ccc(Cl)cc2)n1C[C@H](O)C(F)(F)F]

27 mg (0.09 mmol) of the compound from Example 5A were dissolved in 2 ml of acetonitrile, and 58 mg (0.18 mmol) of cesium carbonate and 24 mg (0.09 mmol) of the compound from Example 43A were added. The mixture was stirred at 65° C. for 2 h and then at RT for 20 h. For work-up, 5 ml of water were added and the mixture was extracted twice with in each case 10 ml of ethyl acetate. The organic phase was washed once with 5 ml of saturated sodium chloride solution, dried over sodium sulfate, filtered and concentrated under reduced pressure. The crude product was purified chromatographically [Method 19]. This gave 25 mg (56% of theory) of the target compound.

LC/MS [Method 4]: $R_t$=1.11 min; MS [ESIpos]: m/z=498 and 500 (M+H)$^+$ $^1$H-NMR (400 MHz, DMSO-d$_6$): δ=3.82 (dd, 1H), 3.98 (dd, 1H), 4.31 (d, 1H), 4.92-5.01 (m, 2H), 6.90 (d, 1H), 7.45-7.52 (m, 2H), 7.55-7.70 (m, 4H), 7.73-7.79 (m, 3H), 8.16 (s, 1H).

Example 112

4-Allyl-5-(4-chlorophenyl)-2-{[1-(2,6-dichlorobenzyl)-1H-imidazol-5-yl]methyl}-2,4-dihydro-3H-1,2,4-triazol-3-one

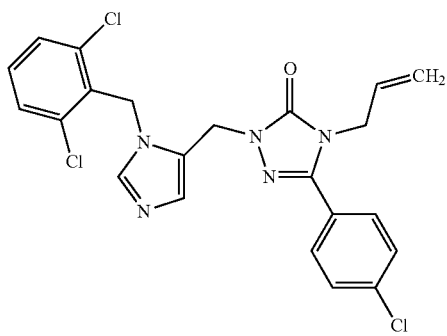 [SMILES: C=CCn1c(-c2ccc(Cl)cc2)nn(Cc2cncn2Cc2c(Cl)cccc2Cl)c1=O]

41 mg (0.17 mmol) of the compound from Example 12A were dissolved in 2 ml of DMF, and 48 mg (0.17 mmol) of the compound from Example 40A and 85 mg (0.26 mmol) of cesium carbonate were added. The mixture was stirred at 80° C. for 16 h. After cooling to RT, the reaction mixture was diluted with 1 ml of methanol and directly purified chromatographically [Method 19]. This gave 4 mg (5% of theory) of the target compound.

LC/MS [Method 5]: $R_t$=2.01 min; MS [ESIpos]: m/z=474 and 476 (M+H)$^+$ $^1$H-NMR (400 MHz, CDCl$_3$): δ=4.35 (d, 2H), 4.98 (s, 2H), 5.09 (d, 1H), 5.23 (d, 1H), 5.29-5.42 (m, 2H), 5.83-5.96 (m, 1H), 7.07 (s, 1H), 7.22-7.29 (m, 1H), 7.34-7.43 (m, 4H), 7.50-7.61 (m, 3H).

Example 113

4-Allyl-5-(4-chlorophenyl)-2-{[1-(2,6-dichlorobenzyl)-4-nitro-1H-imidazol-2-yl]methyl}-2,4-dihydro-3H-1,2,4-triazol-3-one

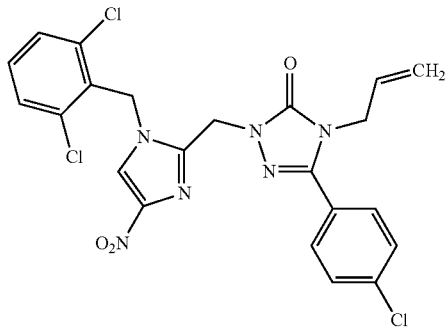 [SMILES: C=CCn1c(-c2ccc(Cl)cc2)nn(Cc2nc([N+](=O)[O-])cn2Cc2c(Cl)cccc2Cl)c1=O]

110 mg (0.47 mmol) of the compound from Example 12A were dissolved in 10 ml of DMF, and 150 mg (0.47 mmol) of the compound from Example 41A and 229 mg (0.70 mmol) of cesium carbonate were added. The mixture was stirred at 80° C. for 16 h. After cooling to RT, the reaction mixture was added to about 25 ml of ice-water and stirred for 10 min. This resulted in the formation of a precipitate which was filtered off with suction and washed with water. The solid was dried under high vacuum. This gave 120 mg (44% of theory) of the target compound of a purity of 90%.

LC/MS [Method 3]: $R_t$=1.35 min; MS [ESIpos]: m/z=519 and 521 (M+H)$^+$ $^1$H-NMR (400 MHz, DMSO-d$_6$): δ=4.31-4.45 (m, 2H), 5.03 (d, 1H), 5.16 (d, 1H), 5.32 (s, 2H), 5.63 (s, 2H), 5.80-5.92 (m, 1H), 7.50-7.56 (m, 1H), 7.57-7.67 (m, 6H), 7.77 (s, 1H).

Example 114

5-(4-Chlorophenyl)-4-cyclopropyl-2-({1-[2-(trifluoromethyl)benzyl]-1H-1,2,4-triazol-5-yl}sulfonyl)-2,4-dihydro-3H-1,2,4-triazol-3-one

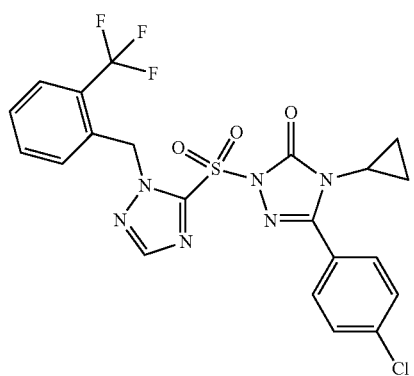 [SMILES: O=c1n(S(=O)(=O)c2ncnn2Cc2ccccc2C(F)(F)F)nc(-c2ccc(Cl)cc2)n1C1CC1]

37 mg (0.10 mmol) of the compound from Example 93A were dissolved in 3 ml of dichloromethane, and 21 μl (0.13 mmol) of N,N-diisopropylethylamine were added. 30 mg (0.13 mmol) of 2-(trifluoromethyl)benzyl bromide dissolved in 1 ml of dichloromethane were then added, and the mixture was stirred at RT for 48 h. For work-up, the mixture was concentrated under reduced pressure and the crude product was purified chromatographically [Method 19]. This gave 33 mg (63% of theory) of the target compound.

LC/MS [Method 5]: $R_t$=2.57 min; MS [ESIpos]: m/z=525 (M+H)$^+$ $^1$H-NMR (400 MHz, CDCl$_3$): δ=0.72-0.78 (m, 2H), 0.97-1.04 (m, 2H), 2.94 (tt, 1H), 5.60 (s, 2H), 7.40 (d, 1H), 7.46 (d, 2H), 7.48-7.60 (m, 2H), 7.69-7.75 (m, 3H), 8.11 (s, 1H).

Example 115

5-(4-Chlorophenyl)-4-cyclopropyl-2-{[1-(2,6-dichlorobenzyl)-1H-1,2,4-triazol-5-yl]sulfonyl}-2,4-dihydro-3H-1,2,4-triazol-3-one

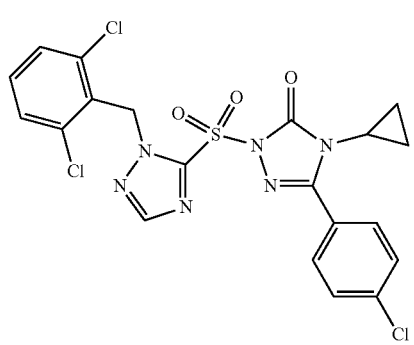 [SMILES: O=c1n(S(=O)(=O)c2ncnn2Cc2c(Cl)cccc2Cl)nc(-c2ccc(Cl)cc2)n1C1CC1]

37 mg (0.10 mmol) of the compound from Example 93A were dissolved in 3 ml of dichloromethane, and 21 µl (0.13 mmol) of N,N-diisopropylethylamine were added. 30 mg (0.13 mmol) of 2,6-dichlorobenzyl bromide dissolved in 1 ml of dichloromethane were then added, and the mixture was stirred at RT for 20 h. For work-up, the mixture was concentrated under reduced pressure and the crude product was purified chromatographically [Method 19]. This gave 39 mg (74% of theory) of the target compound.

LC/MS [Method 2]: $R_t$=2.41 min; MS [ESIpos]: m/z=525 and 527 (M+H)$^+$ $^1$H-NMR (400 MHz, CDCl$_3$): δ=0.73-0.79 (m, 2H), 0.98-1.05 (m, 2H), 2.95 (tt, 1H), 5.72 (s, 2H), 7.30-7.36 (m, 1H), 7.37-7.43 (m, 2H), 7.46 (d, 2H), 7.72 (d, 2H), 8.10 (s, 1H).

Example 116

5-(4-Chlorophenyl)-4-(4-methoxybenzyl)-2-({1-[2-(trifluoromethyl)benzyl]-1H-1,2,4-triazol-5-yl}-sulfonyl)-2,4-dihydro-3H-1,2,4-triazol-3-one

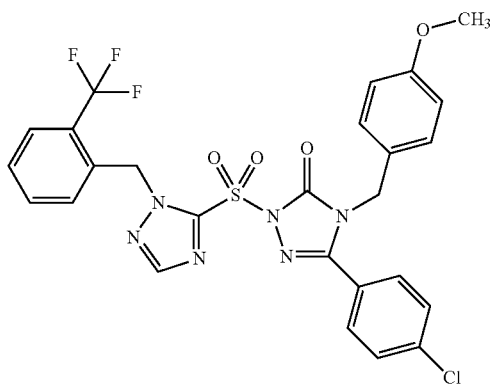 [SMILES: COc1ccc(Cn2c(-c3ccc(Cl)cc3)nn(S(=O)(=O)c3ncnn3Cc3ccccc3C(F)(F)F)c2=O)cc1]

334 mg (0.75 mmol) of the compound from Example 94A were dissolved in 5 ml of dichloromethane, and 154 µl (0.93 mmol) of N,N-diisopropylethylamine were added. 223 mg (0.93 mmol) of 2-(trifluoromethyl)benzyl bromide dissolved in 0.5 ml of dichloromethane were then added, and the mixture was stirred at RT for 20 h. For work-up, the mixture was concentrated under reduced pressure and the crude product was purified chromatographically [Method 19]. This gave 245 mg (54% of theory) of the target compound.

LC/MS [Method 3]: $R_t$=1.44 min; MS [ESIpos]: m/z=605 (M+H)$^+$ $^1$H-NMR (400 MHz, CDCl$_3$): δ=3.77 (s, 3H), 4.81 (s, 2H), 5.61 (s, 2H), 6.78 (d, 2H), 7.03 (d, 2H), 7.35-7.43 (m, 5H), 7.48-7.58 (m, 2H), 7.74 (d, 1H), 8.12 (s, 1H).

Example 117

5-(4-Chlorophenyl)-4-(3,3,3-trifluoro-2-hydroxypropyl)-2-({1-[2-(trifluoromethyl)benzyl]-1H-1,2,4-triazol-5-yl}sulfonyl)-2,4-dihydro-3H-1,2,4-triazol-3-one

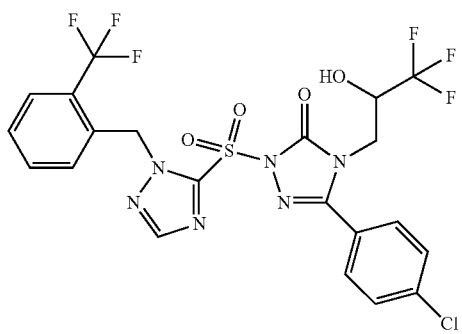 [SMILES: O=c1n(S(=O)(=O)c2ncnn2Cc2ccccc2C(F)(F)F)nc(-c2ccc(Cl)cc2)n1CC(O)C(F)(F)F]

50 mg (0.10 mmol) of the compound from Example 95A together with 50 mg (0.16 mmol) of cesium carbonate were dissolved in 0.5 ml of DMF, and 30 mg (0.16 mmol) of 3-bromo-1,1,1-trifluoropropan-2-ol were added. The mixture was then stirred at 75° C. for 8 h. For work-up, the reaction mixture was diluted with 0.5 ml of acetonitrile and directly purified chromatographically [Method 19]. This gave 15 mg (22% of theory) of the target compound.

LC/MS [Method 5]: $R_t$=2.61 min; MS [ESIpos]: m/z=597 (M+H)$^+$ $^1$H-NMR (400 MHz, CDCl$_3$): δ=3.86 (dd, 1H), 3.95 (dd, 1H), 4.28-4.34 (m, 1H), 4.68-4.76 (m, 1H), 5.62 (s, 2H), 7.42 (d, 1H), 7.47 (d, 2H), 7.50-7.61 (m, 2H), 7.68 (d, 2H), 7.74 (d, 1H), 8.15 (s, 1H).

Example 118

4-Allyl-5-(4-chlorophenyl)-2-{[1-(2,6-dichlorobenzyl)-4-methyl-1H-imidazol-5-yl]methyl}-2,4-dihydro-3H-1,2,4-triazol-3-one and 4-allyl-5-(4-chlorophenyl)-2-{[1-(2,6-dichlorobenzyl)-5-methyl-1H-imidazol-4-yl]methyl}-2,4-dihydro-3H-1,2,4-triazol-3-one (Regioisomer Mixture)

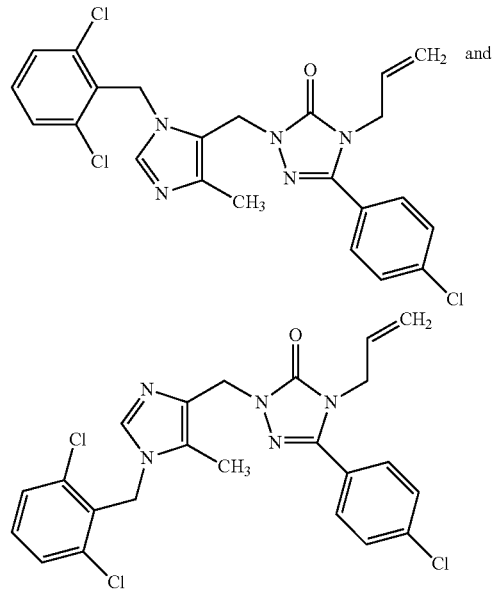

110 mg (0.33 mmol) of the compound from Example 96A together with 88 mg (0.37 mmol) of 2,6-dichlorobenzyl bromide were dissolved in 5 ml of DMF, and 130 mg (0.40 mmol) of cesium carbonate were added. The mixture was stirred at 60° C. for 6 h. After cooling to RT, the reaction mixture was diluted with 1 ml of methanol and directly purified chromatographically [Method 19]. This gave 9 mg (6% of theory) of a mixture of the regioisomeric title compounds in a ratio of about 1:1.

LC/MS [Method 3]: $R_t$=1.08 min; MS [ESIpos]: m/z=488/490 (M+H)$^+$ and $R_t$=1.10 min; MS [ESIpos]: m/z=488/490 (M+H)$^+$ $^1$H-NMR (400 MHz, CDCl$_3$): δ=2.38 and 2.42 (2s, 3H), 4.30-4.41 (m, 2H), 4.97 and 5.49 (2s, 2H), 5.05-5.32 (m, 4H), 5.84-5.95 (m, 1H), 6.97 and 7.13 (2s, 1H), 7.24-7.47 (m, 5H), 7.49-7.58 (m, 2H).

Example 119

5-(4-Chlorophenyl)-4-cyclopropyl-2-({4-methyl-1-[3-(trifluoromethyl)benzyl]-1H-imidazol-5-yl}-methyl)-2,4-dihydro-3H-1,2,4-triazol-3-one and 5-(4-Chlorophenyl)-4-cyclopropyl-2-({5-methyl-1-[3-(trifluoromethyl)benzyl]-1H-imidazol-4-yl}-methyl)-2,4-dihydro-3H-1,2,4-triazol-3-one (Regioisomer Mixture)

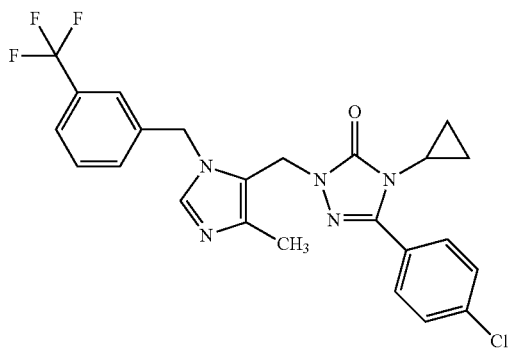

and

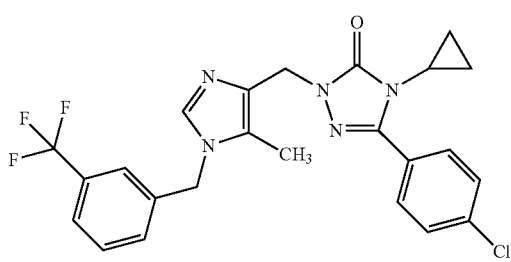

40 mg (0.12 mmol) of the compound from Example 97A together with 88 mg (0.37 mmol) of 3-(trifluoromethyl)benzyl bromide were dissolved in 3 ml of DMF, and 47 mg (0.15 mmol) of cesium carbonate were added. The mixture was stirred at 60° C. for 3 h. For work-up, after cooling to RT, the mixture was diluted with 5 ml of water and the mixture was extracted three times with in each case 10 ml of ethyl acetate. The combined organic phases were dried over sodium sulfate, filtered and concentrated under reduced pressure. The residue was taken up in 4 ml of methanol and purified chromatographically [Method 19]. This gave 20 mg (32% of theory) of a mixture of the regioisomeric title compounds in a ratio of about 1:1.8.

LC/MS [Method 5]: $R_t$=1.75 min; MS [ESIpos]: m/z=488 (M+H)$^+$ and $R_t$=1.89 min; MS [ESIpos]: m/z=488 (M+H)$^+$ $^1$H-NMR (400 MHz, CDCl$_3$): δ=0.53-0.59 and 0.70-0.76 (2m, 2H), 0.91-1.03 (m, 2H), 2.21 and 2.40 (2s, 3H), 2.80 and 2.94 (2tt, 1H), 4.82 and 4.93 (2s, 2H), 5.30 and 5.43 (2s, 2H), 7.11 and 7.19 (2d, 1H), 7.31-7.52 (m, 6H), 7.54-7.59 and 7.66-7.70 (2m, 2H).

Example 120

5-(4-Chlorophenyl)-4-cyclopropyl-2-[2-(2-methylphenoxy)benzyl]-2,4-dihydro-3H-1,2,4-triazol-3-one

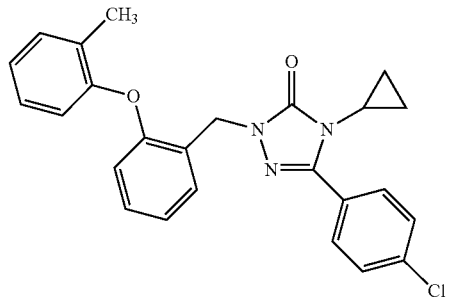 [SMILES: Cc1ccccc1Oc1ccccc1Cn1nc(-c2ccc(Cl)cc2)n(C2CC2)c1=O]

100 mg (0.25 mmol) of the compound from Example 99A, 53 mg (0.49 mmol) of o-cresol and 91 mg (0.74 mmol) of 4-N,N-dimethylaminopyridine were dissolved in 5 ml of acetonitrile, and 39 mg (0.62 mmol) of copper powder and 49 mg (0.62 mmol) of copper(II) oxide were added. The mixture was stirred at 85° C. for 16 h. For work-up, the mixture was cooled to RT and filtered through silica gel, and the residue was rinsed with a little ethyl acetate. The filtrate was concentrated under reduced pressure and the crude product was then purified chromatographically [Method 19]. This gave 25 mg (23% of theory) of the target compound.

LC/MS [Method 4]: $R_t$=1.33 min; MS [ESIpos]: m/z=432 (M+H)$^+$ $^1$H-NMR (400 MHz, DMSO-d$_6$): δ=0.34-0.44 (m, 2H), 0.76-0.85 (m, 2H), 2.18 (s, 3H), 3.05 (tt, 1H), 5.00 (s, 2H), 6.59-6.71 (m, 2H), 7.01 (t, 1H), 7.05-7.15 (m, 2H), 7.24-7.32 (m, 2H), 7.35 (d, 1H), 7.56 (d, 2H), 7.71 (d, 2H).

Example 121

2-[(2'-Chloro-4-fluorobiphenyl-3-yl)methyl]-5-(4-chlorophenyl)-4-cyclopropyl-2,4-dihydro-3H-1,2,4-triazol-3-one

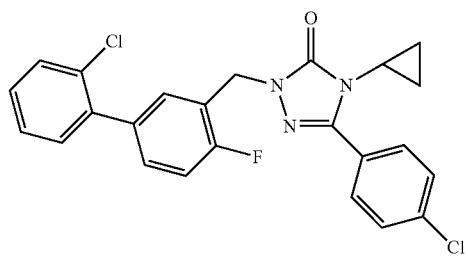 [SMILES: O=c1n(Cc2cc(-c3ccccc3Cl)ccc2F)nc(-c2ccc(Cl)cc2)n1C1CC1]

Analogously to the preparation of Example 122, 89 mg (0.15 mmol) of the compound from Example 100A were reacted with 59 mg (0.23 mmol) of 2-chlorophenylboronic acid. This gave 51 mg (73% of theory) of the target compound.

LC/MS [Method 4]: $R_t$=1.35 min; MS [ESIpos]: m/z=454 and 456 (M+H)$^+$
$^1$H-NMR (400 MHz, DMSO-d$_6$): δ=0.54-0.61 (m, 2H), 0.84-0.91 (m, 2H), 3.14-3.20 (m, 1H), 5.04 (s, 2H), 7.28-7.36 (m, 1H), 7.37-7.47 (m, 5H), 7.53-7.59 (m, 3H), 7.77 (d, 2H).

Example 122

2-[(2'-Chlorobiphenyl-3-yl)methyl]-5-(4-chlorophenyl)-4-(3,3,3-trifluoro-2-hydroxypropyl)-2,4-di-hydro-3H-1,2,4-triazol-3-one

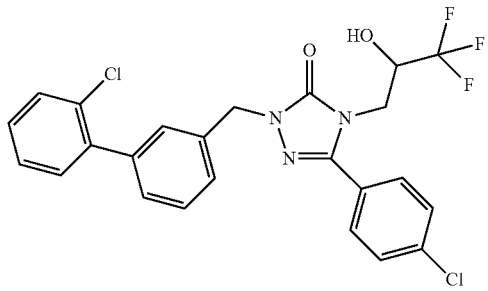 [SMILES: O=c1n(Cc2cccc(-c3ccccc3Cl)c2)nc(-c2ccc(Cl)cc2)n1CC(O)C(F)(F)F]

72 mg (0.15 mmol) of the compound from Example 101A and 59 mg (0.23 mmol) of 2-chloro-phenylboronic acid were dissolved in 2 ml of dioxane. A stream of argon was passed through this solution for 10 min, and 8.7 mg (0.008 mmol) of tetrakis(triphenylphosphine)palladium(0) were added under argon. The mixture was heated to the boil, and 0.15 ml (0.30 mmol) of a 2 N aqueous sodium carbonate solution was added under argon. The mixture was then stirred under reflux for 20 h. After cooling to RT, the mixture was diluted with 10 ml of water and extracted twice with in each case 15 ml of ethyl acetate. The combined organic phases were dried over magnesium sulfate, filtered and concentrated under reduced pressure. The crude product was purified chromatographically [Method 19]. This gave 51 mg (61% of theory) of the target compound.
LC/MS [Method 4]: $R_t$=1.30 min; MS [ESIpos]: m/z=508 (M+H)$^+$
$^1$H-NMR (400 MHz, DMSO-d$_6$): δ=3.83 (dd, 1H), 4.00 (dd, 1H), 4.26-4.34 (m, 1H), 5.01-5.13 (m, 2H), 6.88 (d, 1H), 7.32-7.50 (m, 7H), 7.54-7.59 (m, 1H), 7.62 (d, 2H), 7.74 (d, 2H).

Example 123

5-(4-Chlorophenyl)-4-(3,3,3-trifluoro-2-hydroxypropyl)-2-{[2'-(trifluoromethyl)biphenyl-3-yl]-methyl}-2,4-dihydro-3H-1,2,4-triazol-3-one

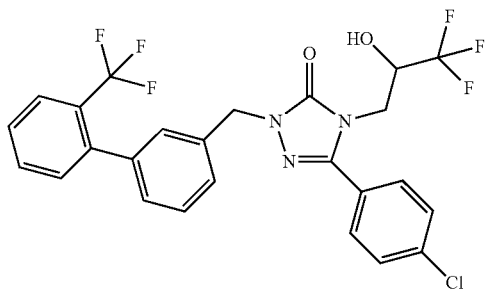 [SMILES: O=c1n(Cc2cccc(-c3ccccc3C(F)(F)F)c2)nc(-c2ccc(Cl)cc2)n1CC(O)C(F)(F)F]

Analogously to the preparation of Example 122, 72 mg (0.15 mmol) of the compound from Example 101A were reacted with 43 mg (0.23 mmol) of 2-(trifluoromethyl)phenylboronic acid. This gave 49 mg (58% of theory) of the target compound.
LC/MS [Method 4]: $R_t$=1.31 min; MS [ESIpos]: m/z=542 (M+H)$^+$
$^1$H-NMR (400 MHz, DMSO-d$_6$): δ=3.84 (dd, 1H), 3.99 (dd, 1H), 4.26-4.32 (m, 1H), 4.99-5.12 (m, 2H), 6.88 (d, 1H), 7.22-7.29 (m, 2H), 7.34-7.47 (m, 3H), 7.57-7.64 (m, 3H), 7.67-7.76 (m, 3H), 7.83 (d, 1H).

Example 124

5-(4-Chlorophenyl)-2-[(2',3'-dichlorobiphenyl-3-yl)methyl]-4-[(2S)-3,3,3-trifluoro-2-hydroxypropyl]-2,4-dihydro-3H-1,2,4-triazol-3-one

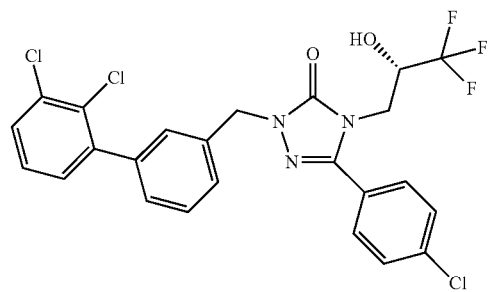 [SMILES: O=c1n(Cc2cccc(-c3cccc(Cl)c3Cl)c2)nc(-c2ccc(Cl)cc2)n1C[C@H](O)C(F)(F)F]

Analogously to the preparation of Example 122, 94 mg (0.20 mmol) of the compound from Example 102A were reacted with 56 mg (0.23 mmol) of 2,3-dichlorophenylboronic acid. This gave 48 mg (45% of theory) of the target compound.
LC/MS [Method 3]: $R_t$=1.54 min; MS [ESIpos]: m/z=542 and 544 (M+H)$^+$
$^1$H-NMR (400 MHz, DMSO-d$_6$): δ=3.84 (dd, 1H), 4.00 (dd, 1H), 4.27-4.35 (m, 1H), 5.02-5.12 (m, 2H), 6.89 (d, 1H), 7.34-7.42 (m, 4H), 7.42-7.51 (m, 2H), 7.60-7.64 (m, 2H), 7.68 (dd, 1H), 7.72-7.77 (m, 2H).

Example 125

5-(4-Chlorophenyl)-2-{[5-fluoro-2'-(trifluoromethyl)biphenyl-3-yl]methyl}-4-[(2S)-3,3,3-trifluoro-2-hydroxypropyl]-2,4-dihydro-3H-1,2,4-triazol-3-one

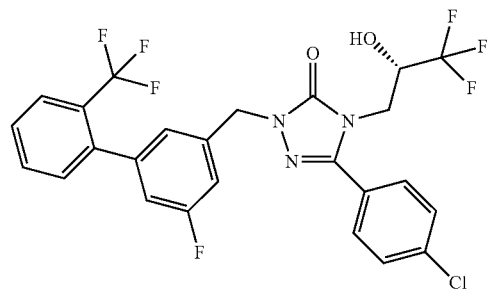 [SMILES: O=c1n(Cc2cc(F)cc(-c3ccccc3C(F)(F)F)c2)nc(-c2ccc(Cl)cc2)n1C[C@H](O)C(F)(F)F]

Analogously to the preparation of Example 122, 59 mg (0.12 mmol) of the compound from Example 103A were reacted with 36 mg (0.18 mmol) of 2-(trifluoromethyl)phenylboronic acid. This gave 43 mg (64% of theory) of the target compound.

LC/MS [Method 4]: $R_t$=1.34 min; MS [ESIpos]: m/z=560 (M+H)$^+$ $^1$H-NMR (400 MHz, DMSO-d$_6$): δ=3.84 (dd, 1H), 3.99 (dd, 1H), 4.26-4.33 (m, 1H), 5.03-5.14 (m, 2H), 6.89 (d, 1H), 7.10-7.23 (m, 3H), 7.43 (d, 1H), 7.59-7.68 (m, 3H), 7.70-7.77 (m, 3H), 7.85 (d, 1H).

Example 126

2-[(2'-Chloro-5-fluorobiphenyl-3-yl)methyl]-5-(4-chlorophenyl)-4-[(2S)-3,3,3-trifluoro-2-hydroxypropyl]-2,4-dihydro-3H-1,2,4-triazol-3-one

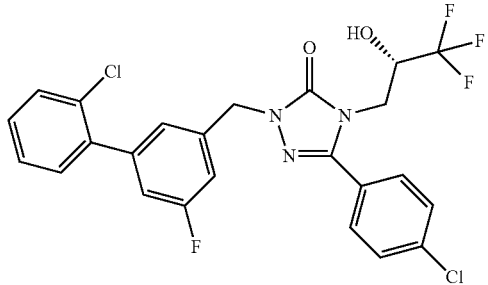 [SMILES: O=c1n(Cc2cc(F)cc(-c3ccccc3Cl)c2)nc(-c2ccc(Cl)cc2)n1C[C@H](O)C(F)(F)F]

Analogously to the preparation of Example 122, 59 mg (0.12 mmol) of the compound from Example 103A were reacted with 28 mg (0.18 mmol) of 2-chlorophenylboronic acid. This gave 34 mg (54% of theory) of the target compound.

LC/MS [Method 4]: $R_t$=1.34 min; MS [ESIpos]: m/z=526 (M+H)$^+$ $^1$H-NMR (400 MHz, DMSO-d$_6$): δ=3.84 (dd, 1H), 4.00 (dd, 1H), 4.26-4.34 (m, 1H), 5.04-5.15 (m, 2H), 6.90 (d, 1H), 7.16-7.21 (m, 1H), 7.22-7.28 (m, 2H), 7.40-7.47 (m, 3H), 7.55-7.65 (m, 3H), 7.75 (d, 2H).

Example 127

2-[(5-Bromo-2'-chlorobiphenyl-3-yl)methyl]-5-(4-chlorophenyl)-4-[(2S)-3,3,3-trifluoro-2-hydroxypropyl]-2,4-dihydro-3H-1,2,4-triazol-3-one

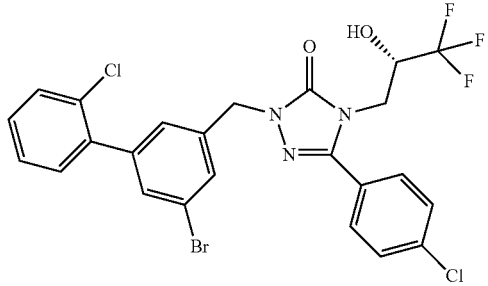 [SMILES: O=c1n(Cc2cc(Br)cc(-c3ccccc3Cl)c2)nc(-c2ccc(Cl)cc2)n1C[C@H](O)C(F)(F)F]

Analogously to the preparation of Example 91, 109 mg (0.36 mmol) of the compound from Example 5A were reacted with 128 mg (0.36 mmol) of the compound from Example 117A. This gave 148 mg (68% of theory) of the target compound.

LC/MS [Method 4]: $R_t$=1.40 min; MS [ESIpos]: m/z=586, 588 and 590 (M+H)$^+$ $^1$H-NMR (400 MHz, DMSO-d$_6$): δ=3.83 (dd, 1H), 3.97-4.03 (m, 1H), 4.26-4.34 (m, 1H), 5.03-5.13 (m, 2H), 6.88 (d, 1H), 7.40-7.47 (m, 4H), 7.55-7.60 (m, 3H), 7.61-7.65 (m, 2H), 7.71-7.77 (m, 2H).

Example 128

5-(4-Chlorophenyl)-2-[(2,2''-dichloro-1,1':3',1''-terphenyl-5'-yl)methyl]-4-[(2S)-3,3,3-trifluoro-2-hydroxypropyl]-2,4-dihydro-3H-1,2,4-triazol-3-one

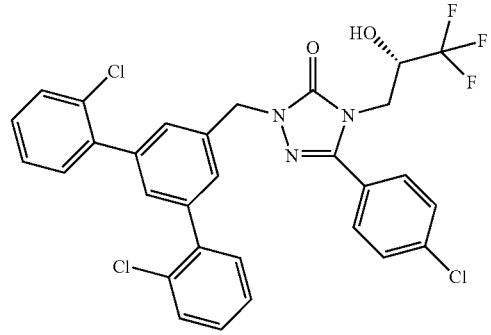 [SMILES: O=c1n(Cc2cc(-c3ccccc3Cl)cc(-c3ccccc3Cl)c2)nc(-c2ccc(Cl)cc2)n1C[C@H](O)C(F)(F)F]

Analogously to the preparation of Example 91, 105 mg (0.34 mmol) of the compound from Example 5A were reacted with 135 mg (0.35 mmol) of the compound from Example 118A. This gave 115 mg (53% of theory) of the target compound.

LC/MS [Method 4]: $R_t$=1.47 min; MS [ESIpos]: m/z=618 and 620 (M+H)$^+$ $^1$H-NMR (400 MHz, DMSO-d$_6$): δ=3.83 (dd, 1H), 4.00 (dd, 1H), 4.26-4.32 (m, 1H), 5.08-5.20 (m, 2H), 6.86 (d, 1H), 7.39-7.52 (m, 9H), 7.55-7.65 (m, 4H), 7.74 (d, 2H).

Example 129

Methyl 2'-chloro-3-{[3-(4-chlorophenyl)-5-oxo-4-(3,3,3-trifluoro-2-hydroxypropyl)-4,5-dihydro-1H-1,2,4-triazol-1-yl]methyl}biphenyl-4-carboxylate

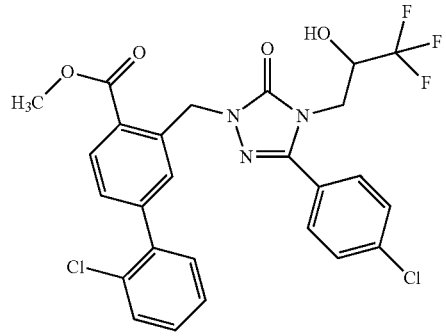 [SMILES: COC(=O)c1ccc(-c2ccccc2Cl)cc1Cn1nc(-c2ccc(Cl)cc2)n(CC(O)C(F)(F)F)c1=O]

Analogously to the preparation of Example 122, 265 mg (0.50 mmol) of the compound from Example 104A were reacted with 194 mg (0.74 mmol) of 2-chlorophenylboronic acid. This gave 54 mg (19% of theory) of the target compound of a purity of 98% and 167 mg (49% of theory) of a purity of 83%.

LC/MS [Method 3]: $R_t$=1.49 min; MS [ESIpos]: m/z=566 and 568 (M+H)$^+$ $^1$H-NMR (400 MHz, DMSO-d$_6$): δ=3.84 (dd, 1H), 3.90 (s, 3H), 3.99 (dd, 1H), 4.24-4.32 (m, 1H), 5.36-5.47 (m, 2H), 6.85 (d, 1H), 7.33 (d, 1H), 7.38-7.47 (m, 3H), 7.51-7.59 (m, 2H), 7.62 (d, 2H), 7.72 (d, 2H), 8.00 (d, 1H).

Example 130

Methyl 3-{[3-(4-chlorophenyl)-5-oxo-4-(3,3,3-trifluoro-2-hydroxypropyl)-4,5-dihydro-1H-1,2,4-triazol-1-yl]methyl}-2'-(trifluoromethyl)biphenyl-4-carboxylate

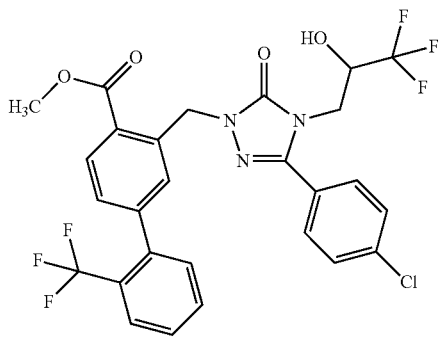 [SMILES: COC(=O)c1ccc(-c2ccccc2C(F)(F)F)cc1Cn1nc(-c2ccc(Cl)cc2)n(CC(O)C(F)(F)F)c1=O]

Analogously to the preparation of Example 122, 265 mg (0.50 mmol) of the compound from Example 104A were reacted with 149 mg (0.74 mmol) of 2-(trifluoromethyl)phenylboronic acid. This gave 113 mg (38% of theory) of the target compound of a purity of 100% and 101 mg (28% of theory) of a purity of 81%.

LC/MS [Method 3]: $R_t$=1.50 min; MS [ESIpos]: m/z=600 (M+H)$^+$ $^1$H-NMR (400 MHz, DMSO-d$_6$): δ=3.83 (dd, 1H), 3.90 (s, 3H), 3.97 (dd, 1H), 4.19-4.30 (m, 1H), 5.34-5.47 (m, 2H), 6.83 (d, 1H), 7.16 (s, 1H), 7.37-7.45 (m, 2H), 7.59-7.77 (m, 6H), 7.83 (d, 1H), 7.98 (d, 1H).

Example 131

Methyl 2',3'-dichloro-3-({3-(4-chlorophenyl)-5-oxo-4-[(2S)-3,3,3-trifluoro-2-hydroxypropyl]-4,5-dihydro-1H-1,2,4-triazol-1-yl}methyl)biphenyl-4-carboxylate

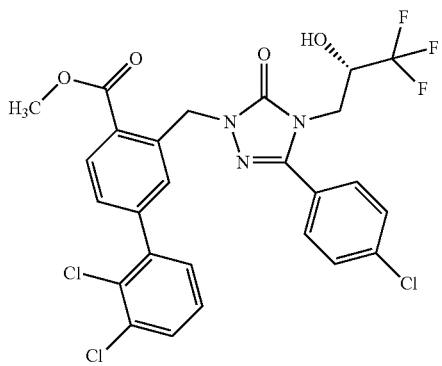 [SMILES: COC(=O)c1ccc(-c2cccc(Cl)c2Cl)cc1Cn1nc(-c2ccc(Cl)cc2)n(C[C@H](O)C(F)(F)F)c1=O]

Analogously to the preparation of Example 75, 455 mg (0.85 mmol) of the compound from Example 105A were reacted with 244 mg (1.28 mmol) of 2,3-dichlorophenylboronic acid. This gave 347 mg (57% of theory) of the target compound.

LC/MS [Method 4]: $R_t$=1.38 min; MS [ESIpos]: m/z=600 and 602 (M+H)$^+$.

Example 132

2'-Chloro-3-{[3-(4-chlorophenyl)-5-oxo-4-(3,3,3-trifluoro-2-hydroxypropyl)-4,5-dihydro-1H-1,2,4-triazol-1-yl]methyl}biphenyl-4-carboxylic acid

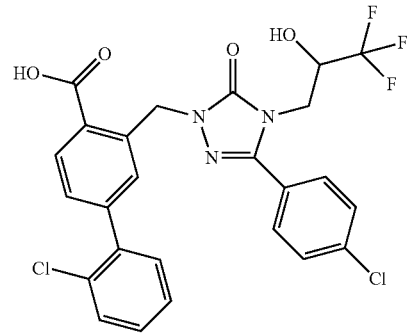 [SMILES: O=C(O)c1ccc(-c2ccccc2Cl)cc1Cn1nc(-c2ccc(Cl)cc2)n(CC(O)C(F)(F)F)c1=O]

204 mg (0.36 mmol) of the compound from Example 129 were dissolved in 3 ml of THF, and 0.4 ml of a 1 N aqueous lithium hydroxide solution was added. The mixture was stirred at RT for 20 h. For work-up, the solvent was removed under reduced pressure, the residue was taken up in about 5 ml of water and 0.07 ml of 6 N hydrochloric acid was added. The precipitated solid was filtered off with suction and dried. Further purification of the crude product was carried out by chromatography on silica gel (mobile phase: first cyclohexane/ethyl acetate 1:3, then pure ethyl acetate, finally dichloromethane/methanol 1:1). This gave 97 mg (47% of theory) of the target compound.

LC/MS [Method 4]: $R_t$=1.20 min; MS [ESIpos]: m/z=552 and 554 (M+H)$^+$ $^1$H-NMR (400 MHz, DMSO-d$_6$): δ=3.80 (dd, 1H), 3.99 (dd, 1H), 4.33-4.43 (m, 1H), 5.33-5.44 (m, 1H), 5.49-5.58 (m, 1H), 7.10 (s, 1H), 7.28-7.43 (m, 4H), 7.50-7.55 (m, 1H), 7.60 (d, 2H), 7.71 (d, 2H), 7.74-7.83 (m, 1H).

Example 133

3-{[3-(4-Chlorophenyl)-5-oxo-4-(3,3,3-trifluoro-2-hydroxypropyl)-4,5-dihydro-1H-1,2,4-triazol-1-yl]methyl}-2'-(trifluoromethyl)biphenyl-4-carboxylic acid

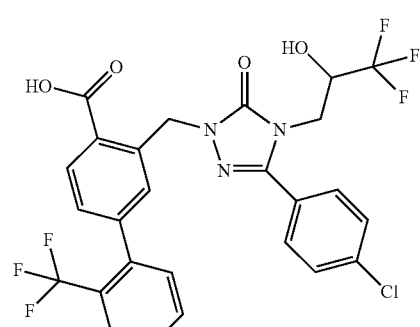

195 mg (0.36 mmol) of the compound from Example 130 were dissolved in 3 ml of THF, and 0.4 ml a 1 N aqueous lithium hydroxide solution were added. The mixture was stirred at RT for 20 h. For work-up, the solvent was removed under reduced pressure, the residue was taken up in about 5 ml of water and 0.07 ml of 6 N hydrochloric acid was added. The mixture was stirred for 15 min, and the precipitated solid was then filtered off with suction and dried under high vacuum. This gave 146 mg (73% of theory) of the target compound.

LC/MS [Method 3]: $R_t$=1.38 min; MS [ESIpos]: m/z=586 (M+H)$^+$ $^1$H-NMR (400 MHz, DMSO-d$_6$): δ=3.78 (dd, 1H), 3.95 (dd, 1H), 4.31-4.39 (m, 1H), 5.25-5.34 (m, 1H), 5.40-5.47 (m, 1H), 7.02 (s, 1H), 7.24 (d, 1H), 7.37 (d, 1H), 7.56-7.63 (m, 2H), 7.66-7.83 (m, 6H).

Example 134

2',3'-Dichloro-3-({3-(4-chlorophenyl)-5-oxo-4-[(2S)-3,3,3-trifluoro-2-hydroxypropyl]-4,5-dihydro-1H-1,2,4-triazol-1-yl}methyl)biphenyl-4-carboxylic acid

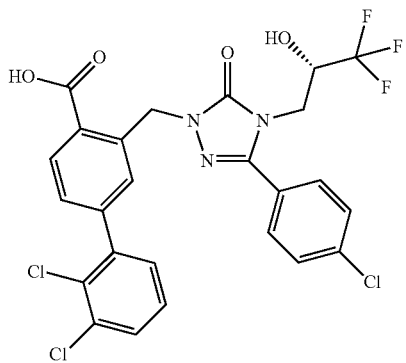 [SMILES: O=C(O)c1ccc(-c2cccc(Cl)c2Cl)cc1Cn1nc(-c2ccc(Cl)cc2)n(C[C@H](O)C(F)(F)F)c1=O]

347 mg (0.49 mmol) of the compound from Example 131 (purity 84%) were reacted analogously to the preparation of Example 132. This gave 243 mg (85% of theory) of the target compound.

LC/MS [Method 4]: $R_t$=1.24 min; MS [ESIpos]: m/z=586 and 588 (M+H)$^+$ $^1$H-NMR (400 MHz, DMSO-d$_6$): δ=3.84 (dd, 1H), 3.99 (dd, 1H), 4.23-4.31 (m, 1H), 5.40-5.51 (m, 2H), 6.88 (br. s, 1H), 7.24 (s, 1H), 7.33-7.37 (m, 1H), 7.45 (t, 1H), 7.50 (d, 1H), 7.62 (d, 2H), 7.69 (dd, 1H), 7.73 (d, 2H), 8.01 (d, 1H).

Example 135

2'-Chloro-3-{[3-(4-chlorophenyl)-5-oxo-4-(3,3,3-trifluoro-2-hydroxypropyl)-4,5-dihydro-1H-1,2,4-triazol-1-yl]methyl}biphenyl-4-carboxamide

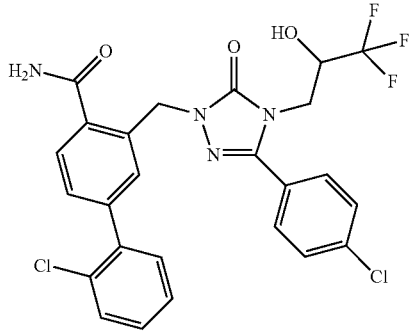 [SMILES: NC(=O)c1ccc(-c2ccccc2Cl)cc1Cn1nc(-c2ccc(Cl)cc2)n(CC(O)C(F)(F)F)c1=O]

43 mg (0.08 mmol) of the compound from Example 132 were initially charged in 1 ml of DMF, and 14 mg (0.10 mmol) of HOBt and 19 mg (0.10 mmol) of EDC were added. After 10 min of stirring at RT, 0.41 ml (0.20 mmol) of ammonia solution (35% strength in water) was added, and the mixture was stirred at RT for 16 h. Under reduced pressure, the reaction solution was then freed of excess ammonia, about 3 ml of water were added and the mixture was extracted three times with in each case 5 ml of ethyl acetate. The combined organic phases were dried over magnesium sulfate, filtered and concentrated under reduced pressure. The crude product was purified chromatographically on silica gel (mobile phase: cyclohexane/ethyl acetate 1:3→1:5). This gave 19 mg (42% of theory) of the target compound.

LC/MS [Method 4]: $R_t$=1.14 min; MS [ESIpos]: m/z=551 and 553 (M+H)$^+$ $^1$H-NMR (400 MHz, DMSO-d$_6$): δ=3.83 (dd, 1H), 3.98 (dd, 1H), 4.24-4.33 (m, 1H), 5.22-5.34 (m, 2H), 6.84 (d, 1H), 7.27 (s, 1H), 7.34-7.47 (m, 4H), 7.52-7.66 (m, 3H), 7.73 (d, 2H), 8.04 (s, 1H).

Example 136

2',3'-Dichloro-3-({3-(4-chlorophenyl)-5-oxo-4-[(2S)-3,3,3-trifluoro-2-hydroxypropyl]-4,5-dihydro-1H-1,2,4-triazol-1-yl}methyl)biphenyl-4-carboxamide

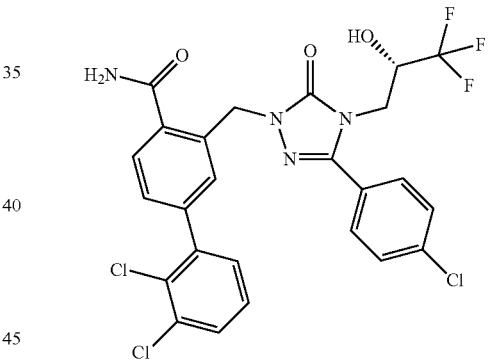

45 mg (0.07 mmol) of the compound from Example 134 were initially charged in 1 ml of DMF, and 13 mg (0.09 mmol) of HOBt and 18 mg (0.09 mmol) of EDC were added. After 10 min of stirring at RT, 80 µl (1.44 mmol) of ammonia solution (35% strength in water) were added, and the mixture was stirred at RT for 16 h. Under reduced pressure, the reaction solution was then freed of excess ammonia, about 3 ml of water were added and the mixture was extracted three times with in each case 5 ml of ethyl acetate. The combined organic phases were dried over magnesium sulfate, filtered and concentrated under reduced pressure. The crude product was purified chromatographically [Method 19]. This gave 20 mg (46% of theory) of the target compound.

LC/MS [Method 3]: $R_t$=1.36 min; MS [ESIpos]: m/z=585 and 587 (M+H)$^+$ $^1$H-NMR (400 MHz, DMSO-d$_6$): δ=3.83 (dd, 1H), 3.98 (dd, 1H), 4.23-4.32 (m, 1H), 5.22-5.33 (m, 2H), 6.84 (d, 1H), 7.24 (s, 1H), 7.30-7.35 (m, 1H), 7.41-7.47 (m, 2H), 7.56-7.65 (m, 4H), 7.65-7.70 (m, 1H), 7.73 (d, 2H), 8.06 (s, 1H).

Example 137

5-(4-Chlorophenyl)-2-{[2',3'-dichloro-4-(hydroxymethyl)biphenyl-3-yl]methyl}-4-[(2S)-3,3,3-tri-fluoro-2-hydroxypropyl]-2,4-dihydro-3H-1,2,4-triazol-3-one

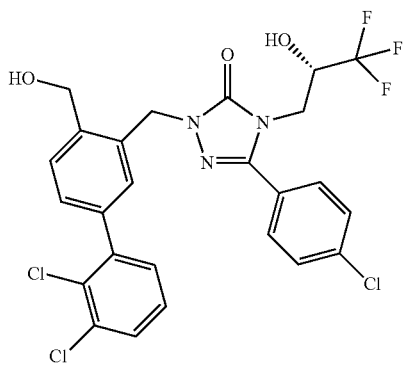 [SMILES: O=c1n(Cc2cc(-c3cccc(Cl)c3Cl)ccc2CO)nc(-c2ccc(Cl)cc2)n1C[C@H](O)C(F)(F)F]

230 mg (0.39 mmol) of the compound from Example 134 were dissolved in 5 ml of THF, the solution was cooled to 0° C. and 55 μl (0.39 mmol) of triethylamine and also 56 μl (0.43 mmol) of isobutyl chloroformate were added. The mixture was stirred at 0° C. for 1 h. The suspension was then filtered through a Seitz frit into a flask cooled to 0° C., and the residue was rinsed with about 2 ml of THF. With vigorous stirring, this solution was added to a solution, cooled to 0° C., of 44 mg (1.18 mmol) of sodium borohydride in 0.6 ml of water. After 1 h, 5 ml of saturated aqueous sodium bicarbonate solution were added, and the mixture was warmed to RT. The mixture was extracted with 15 ml of ethyl acetate. The organic phase was washed successively with in each case 5 ml of saturated sodium bicarbonate solution and saturated sodium chloride solution. After drying over sodium sulfate, the mixture was filtered and concentrated under reduced pressure. The crude product was purified chromatographically [Method 19]. This gave 13 mg (6% of theory) of the target compound.

LC/MS [Method 3]: $R_t$=1.44 min; MS [ESIneg]: m/z=572 (M–H)⁻

¹H-NMR (400 MHz, DMSO-d₆): δ=3.82 (dd, 1H), 3.98 (dd, 1H), 4.23-4.30 (m, 1H), 4.74 (d, 2H), 5.05-5.15 (m, 2H), 5.30 (t, 1H), 6.86 (d, 1H), 7.27 (d, 1H), 7.33 (dd, 1H), 7.38 (dd, 1H), 7.43 (t, 1H), 7.54 (d, 1H), 7.61 (d, 2H), 7.66 (dd, 1H), 7.70-7.74 (m, 2H).

Example 138

[2',3'-Dichloro-3-({3-(4-chlorophenyl)-5-oxo-4-[(2S)-3,3,3-trifluoro-2-hydroxypropyl]-4,5-dihydro-1H-1,2,4-triazol-1-yl}methyl)biphenyl-4-yl]methyl carbamate

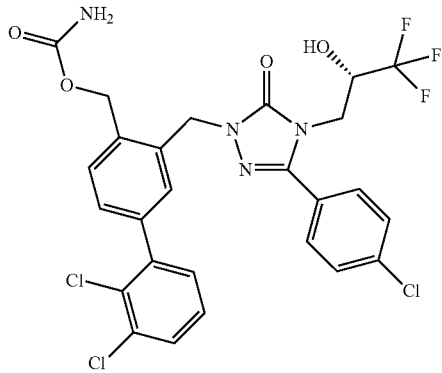 [SMILES: NC(=O)OCc1ccc(-c2cccc(Cl)c2Cl)cc1Cn1nc(-c2ccc(Cl)cc2)n(C[C@H](O)C(F)(F)F)c1=O]

65 mg (0.11 mmol) of the compound from Example 137 were dissolved in 3 ml of dichloromethane, and the mixture was cooled to 0° C. 14 μl (0.16 mmol) of chlorosulfonyl isocyanate were added, and the mixture was stirred at RT for 18 h. 1.5 ml of water were then added, and the mixture was stirred at 60° C. for a further 18 h. For work-up, 3 ml of saturated aqueous sodium bicarbonate solution were added, and the mixture was extracted twice with in each case 10 ml of ethyl acetate. The combined organic phases were dried over sodium sulfate, filtered and concentrated under reduced pressure. The crude product was purified chromatographically [Method 19]. This gave 30 mg (43% of theory) of the target compound.

LC/MS [Method 4]: $R_t$=1.23 min; MS [ESIneg]: m/z=615 and 617 (M–H)⁻

¹H-NMR (400 MHz, DMSO-d₆): δ=3.82 (dd, 1H), 3.98 (dd, 1H), 4.26-4.33 (m, 1H), 5.08-5.18 (m, 2H), 5.23 (s, 2H), 6.66 (br. s, 2H), 6.86 (d, 1H), 7.32 (d, 1H), 7.34 (dd, 1H), 7.39-7.51 (m, 3H), 7.59-7.64 (m, 2H), 7.67 (dd, 1H), 7.73 (d, 2H).

Example 139

Methyl 5-({3-(4-chlorophenyl)-5-oxo-4-[(2S)-3,3,3-trifluoro-2-hydroxypropyl]-4,5-dihydro-1H-1,2,4-triazol-1-yl}methyl)-2'-(trifluoromethyl)biphenyl-2-carboxylate

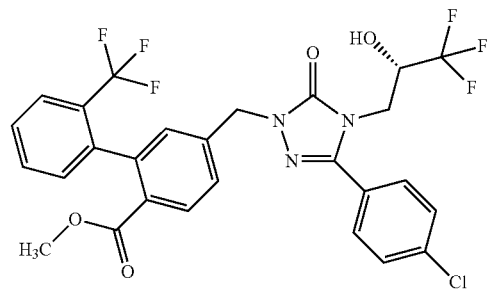 [SMILES: COC(=O)c1ccc(Cn2nc(-c3ccc(Cl)cc3)n(C[C@H](O)C(F)(F)F)c2=O)cc1-c1ccccc1C(F)(F)F]

179 mg (0.58 mmol) of the compound from Example 5A and 285 mg (0.88 mmol) of cesium carbonate were suspended in 5 ml of acetonitrile, and 340 mg (0.58 mmol) of the compound from Example 108A were added. The mixture was stirred under reflux for 4 h. The precipitated solid was then filtered off and the filtrate was concentrated under reduced pressure to a volume of about 1.5 ml. After addition of 0.5 ml of 1 N hydrochloric acid, the mixture was directly purified chromatographically [Method 19]. This gave 231 mg (65% of theory) of the target compound.

LC/MS [Method 4]: $R_t$=1.26 min; MS [ESIpos]: m/z=600 (M+H)⁺

¹H-NMR (400 MHz, DMSO-d₆): δ=3.52 (s, 3H), 3.84 (dd, 1H), 3.99 (dd, 1H), 4.25-4.32 (m, 1H), 5.03-5.18 (m, 2H), 6.88 (dd, 1H), 7.21-7.29 (m, 2H), 7.46 (d, 1H), 7.55-7.69 (m, 4H), 7.70-7.75 (m, 2H), 7.77 (d, 1H), 7.97 (d, 1H).

Example 140

Methyl 2'-chloro-5-({3-(4-chlorophenyl)-5-oxo-4-[(2S)-3,3,3-trifluoro-2-hydroxypropyl]-4,5-dihydro-1H-1,2,4-triazol-1-yl}methyl)biphenyl-2-carboxylate

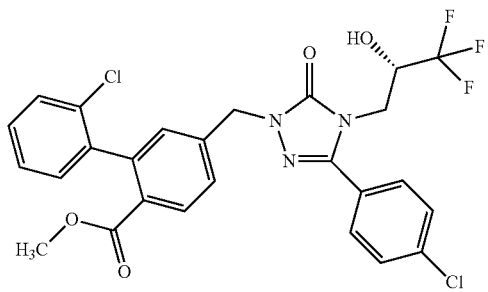 [SMILES: COC(=O)c1ccc(Cn2nc(-c3ccc(Cl)cc3)n(C[C@H](O)C(F)(F)F)c2=O)cc1-c1ccccc1Cl]

Analogously to the preparation of Example 139, 208 mg (0.68 mmol) of the compound from Example 5A were reacted with 230 mg (0.68 mmol) of the compound from Example 109A. This gave 231 mg (59% of theory) of the target compound.

LC/MS [Method 4]: $R_t$=1.26 min; MS [ESIpos]: m/z=566 and 568 (M+H)$^+$ $^1$H-NMR (400 MHz, DMSO-d$_6$): δ=3.58 (s, 3H), 3.84 (dd, 1H), 4.02 (dd, 1H), 4.26-4.33 (m, 1H), 5.07-5.18 (m, 2H), 6.88 (d, 1H), 7.25-7.31 (m, 2H), 7.36-7.52 (m, 4H), 7.62 (d, 2H), 7.74 (d, 2H), 7.93 (d, 1H).

Example 141

5-({3-(4-Chlorophenyl)-5-oxo-4-[(2S)-3,3,3-trifluoro-2-hydroxypropyl]-4,5-dihydro-1H-1,2,4-triazol-1-yl}methyl)-2'-(trifluoromethyl)biphenyl-2-carboxylic acid

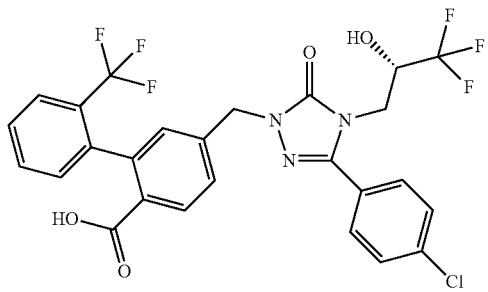 [SMILES: O=C(O)c1ccc(Cn2nc(-c3ccc(Cl)cc3)n(C[C@H](O)C(F)(F)F)c2=O)cc1-c1ccccc1C(F)(F)F]

215 mg (0.36 mmol) of the compound from Example 139 were dissolved in 3 ml of THF and 3 ml of methanol, and 0.36 ml of 2 N aqueous sodium hydroxide solution was added. The mixture was stirred at 80° C. for 16 h. For work-up, the mixture was diluted with 10 ml of water and extracted twice with in each case 10 ml of ethyl acetate. The aqueous phase was acidified with 1 N hydrochloric acid and once more extracted with 10 ml of ethyl acetate. The organic phases were combined, dried over magnesium sulfate, filtered and concentrated under reduced pressure. The residue was dried under high vacuum. This gave 222 mg (quant.) of the target compound.

LC/MS [Method 3]: $R_t$=1.29 min; MS [ESIpos]: m/z=586 (M+H)$^+$ $^1$H-NMR (400 MHz, DMSO-d$_6$): δ=3.84 (dd, 1H), 3.98 (dd, 1H), 4.24-4.31 (m, 1H), 5.02-5.16 (m, 2H), 6.88 (dd, 1H), 7.19 (br. s, 1H), 7.26 (d, 1H), 7.43 (d, 1H), 7.56 (t, 1H), 7.59-7.67 (m, 3H), 7.69-7.77 (m, 3H), 7.96 (d, 1H), 12.59 (br. s, 1H).

Example 142

2'-Chloro-5-({3-(4-chlorophenyl)-5-oxo-4-[(2S)-3,3,3-trifluoro-2-hydroxypropyl]-4,5-dihydro-1H-1,2,4-triazol-1-yl}methyl)biphenyl-2-carboxylic acid

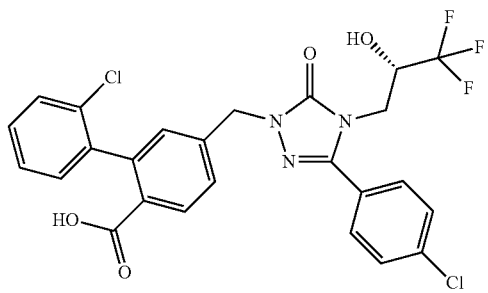 [SMILES: O=C(O)c1ccc(Cn2nc(-c3ccc(Cl)cc3)n(C[C@H](O)C(F)(F)F)c2=O)cc1-c1ccccc1Cl]

Analogously to the preparation of Example 141, 218 mg (0.39 mmol) of the compound from Example 140 were reacted with 2 N aqueous sodium hydroxide solution. This gave 220 mg (quant.) of the target compound.

LC/MS [Method 3]: $R_t$=1.26 min; MS [ESIpos]: m/z=552 and 554 (M+H)$^+$ $^1$H-NMR (400 MHz, DMSO-d$_6$): δ=3.84 (dd, 1H), 4.00 (dd, 1H), 4.24-4.35 (m, 1H), 5.05-5.16 (m, 2H), 6.89 (d, 1H), 7.24 (s, 1H), 7.25-7.30 (m, 1H), 7.34-7.39 (m, 2H), 7.42 (dd, 1H), 7.45-7.50 (m, 1H), 7.59-7.65 (m, 2H), 7.72-7.77 (m, 2H), 7.92 (d, 1H), 12.64 (br. s, 1H).

Example 143

5-({3-(4-Chlorophenyl)-5-oxo-4-[(2S)-3,3,3-trifluoro-2-hydroxypropyl]-4,5-dihydro-1H-1,2,4-triazol-1-yl}methyl)-2'-(trifluoromethyl)biphenyl-2-carboxamide

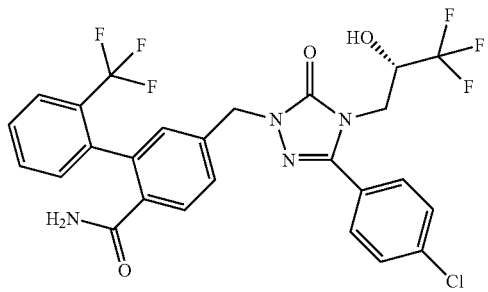 [SMILES: NC(=O)c1ccc(Cn2nc(-c3ccc(Cl)cc3)n(C[C@H](O)C(F)(F)F)c2=O)cc1-c1ccccc1C(F)(F)F]

208 mg (0.36 mmol) of the compound from Example 141 were initially charged in 5 ml of DMF, and 62 mg (0.46 mmol) of HOBt and 88 mg (0.46 mmol) of EDC were added. After 10 min of stirring at RT, 1.0 ml (16 mmol) of ammonia solution (33% strength in water) were added, and the mixture was stirred at RT for 16 h. Under reduced pressure, the reaction solution was then freed from excess ammonia, about 3 ml of water were added and the mixture was extracted three times with in each case 5 ml of ethyl acetate. The combined organic phases were dried over magnesium sulfate, filtered and concentrated under reduced pressure. The crude product was purified chromatographically [Method 19]. This gave 85 mg (39% of theory) of the target compound.

LC/MS [Method 2]: $R_t$=2.29 min; MS [ESIpos]: m/z=585 (M+H)$^+$ $^1$H-NMR (400 MHz, DMSO-d$_6$): δ=3.83 (dd, 1H), 3.99 (dd, 1H), 4.24-4.31 (m, 1H), 4.98-5.12 (m, 2H), 6.87 (d, 1H), 7.08-7.18 (m, 2H), 7.29 (d, 1H), 7.37 (d, 1H), 7.50-7.65 (m, 6H), 7.67-7.76 (m, 3H).

Example 144

2'-Chloro-5-({3-(4-chlorophenyl)-5-oxo-4-[(2S)-3,3,3-trifluoro-2-hydroxypropyl]-4,5-dihydro-1H-1,2,4-triazol-1-yl}methyl)biphenyl-2-carboxamide

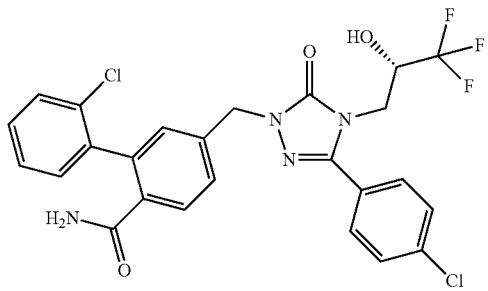 [SMILES: NC(=O)c1ccc(Cn2nc(-c3ccc(Cl)cc3)n(C[C@H](O)C(F)(F)F)c2=O)cc1-c1ccccc1Cl]

Analogously to the preparation of Example 143, 210 mg (0.38 mmol) of the compound from Example 142 were reacted with ammonia solution. This gave 122 mg (54% of theory) of the target compound.

LC/MS [Method 4]: $R_t$=1.06 min; MS [ESIpos]: m/z=551 and 553 (M+H)$^+$ $^1$H-NMR (400 MHz, DMSO-d$_6$): δ=3.84 (dd, 1H), 4.00 (dd, 1H), 4.24-4.35 (m, 1H), 5.01-5.12 (m, 2H), 6.88 (d, 1H), 7.17 (s, 1H), 7.23 (d, 1H), 7.26-7.31 (m, 1H), 7.31-7.39 (m, 3H), 7.44-7.49 (m, 1H), 7.52-7.59 (m, 2H), 7.62 (d, 2H), 7.74 (d, 2H).

Example 145

N-tert-Butyl-5-({3-(4-chlorophenyl)-5-oxo-4-[(2S)-3,3,3-trifluoro-2-hydroxypropyl]-4,5-dihydro-1H-1,2,4-triazol-1-yl}methyl)-2'-(trifluoromethyl)biphenyl-2-carboxamide

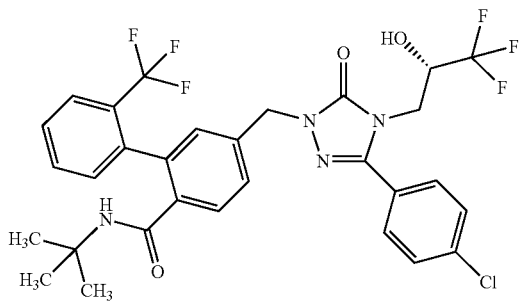 [SMILES: CC(C)(C)NC(=O)c1ccc(Cn2nc(-c3ccc(Cl)cc3)n(C[C@H](O)C(F)(F)F)c2=O)cc1-c1ccccc1C(F)(F)F]

30 mg (0.05 mmol) of the compound from Example 141 were initially charged in 0.75 ml of DMF, and 9 mg (0.074 mmol) of HOBt and 13 mg (0.07 mmol) of EDC were added. After 10 min of stirring at RT, 6 µl (0.06 mmol) of 2-methylpropane-2-amine were added, and the mixture was stirred at RT for 16 h. 50 µl of 1 N hydrochloric acid were then added, and the mixture was directly purified chromatographically [Method 19]. This gave 8.2 mg (24% of theory) of the target compound.

LC/MS [Method 2]: $R_t$=2.70 min; MS [ESIpos]: m/z=641 (M+H)$^+$ $^1$H-NMR (400 MHz, DMSO-d$_6$): δ=1.08 (s, 9H), 3.84 (dd, 1H), 3.99 (dd, 1H), 4.24-4.35 (m, 1H), 4.99-5.11 (m, 2H), 6.88 (d, 1H), 7.17 (d, 1H), 7.25 (s, 1H), 7.38 (t, 2H), 7.48 (d, 1H), 7.54-7.67 (m, 4H), 7.71 (d, 2H), 7.78 (d, 1H).

Example 146

Methyl 2'-chloro-5-({3-(4-chlorophenyl)-5-oxo-4-[(2S)-3,3,3-trifluoro-2-hydroxypropyl]-4,5-dihydro-1H-1,2,4-triazol-1-yl}methyl)biphenyl-3-carboxylate

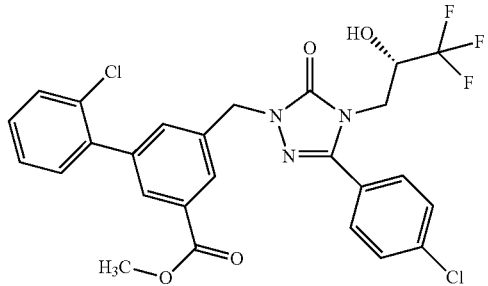 [SMILES: COC(=O)c1cc(Cn2nc(-c3ccc(Cl)cc3)n(C[C@H](O)C(F)(F)F)c2=O)cc(-c2ccccc2Cl)c1]

Analogously to the preparation of Example 139, 248 mg (0.81 mmol) of the compound from Example 5A were reacted with 274 mg (0.81 mmol) of the compound from Example 112A. This gave 271 mg (59% of theory) of the target compound.

LC/MS [Method 3]: $R_t$=1.48 min; MS [ESIpos]: m/z=566 and 568 (M+H)$^+$ $^1$H-NMR (400 MHz, DMSO-d$_6$): δ=3.84 (dd, 1H), 3.87 (s, 3H), 4.01 (dd, 1H), 4.23-4.33 (m, 1H), 5.10-5.21 (m, 2H), 6.87 (s, 1H), 7.42-7.48 (m, 3H), 7.58-7.65 (m, 3H), 7.68-7.76 (m, 3H), 7.93 (s, 1H), 7.99 (s, 1H).

Example 147

2'-Chloro-5-({3-(4-chlorophenyl)-5-oxo-4-[(2S)-3,3,3-trifluoro-2-hydroxypropyl]-4,5-dihydro-1H-1,2,4-triazol-1-yl}methyl)biphenyl-3-carboxylic acid

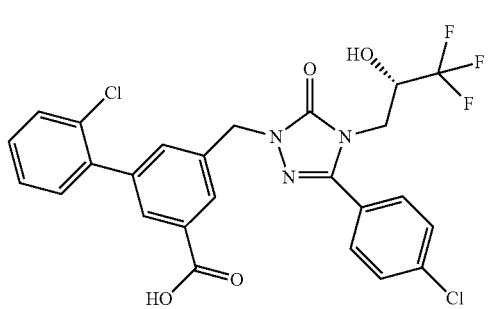 [SMILES: O=C(O)c1cc(Cn2nc(-c3ccc(Cl)cc3)n(C[C@H](O)C(F)(F)F)c2=O)cc(-c2ccccc2Cl)c1]

Analogously to the preparation of Example 141, 244 mg (0.43 mmol) of the compound from Example 146 were reacted with 2 N aqueous sodium hydroxide solution. This gave 242 mg (100% of theory) of the target compound.

LC/MS [Method 3]: $R_t$=1.33 min; MS [ESIpos]: m/z=552 and 554 (M+H)$^+$ $^1$H-NMR (400 MHz, DMSO-d$_6$): δ=3.83 (dd, 1H), 3.98-4.04 (m, 1H), 4.29-4.35 (m, 1H), 5.04-5.14 (m, 2H), 7.36-7.48 (m, 5H), 7.57 (d, 1H), 7.61 (d, 2H), 7.74 (d, 2H), 7.87 (br. s, 1H).

Example 148

2'-Chloro-5-({3-(4-chlorophenyl)-5-oxo-4-[(2S)-3,3,3-trifluoro-2-hydroxypropyl]-4,5-dihydro-1H-1,2,4-triazol-1-yl}methyl)biphenyl-3-carboxamide

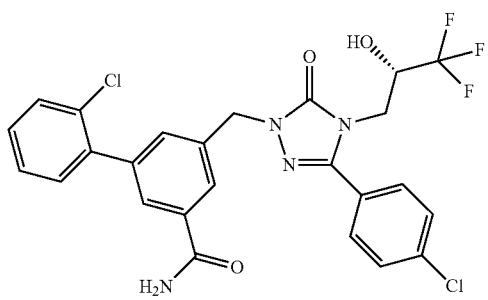 [SMILES: NC(=O)c1cc(Cn2nc(-c3ccc(Cl)cc3)n(C[C@H](O)C(F)(F)F)c2=O)cc(-c2ccccc2Cl)c1]

Analogously to the preparation of Example 143, 55 mg (0.10 mmol) of the compound from Example 147 were reacted with ammonia solution. This gave 25 mg (43% of theory) of the target compound.

LC/MS [Method 4]: $R_t$=1.12 min; MS [ESIpos]: m/z=551 and 553 (M+H)$^+$ $^1$H-NMR (400 MHz, DMSO-d$_6$): δ=3.83 (dd, 1H), 3.96-4.03 (m, 1H), 4.26-4.33 (m, 1H), 5.05-5.16 (m, 2H), 6.52 (s, 1H), 6.89 (d, 1H), 7.41-7.49 (m, 4H), 7.55-7.65 (m, 3H), 7.74 (d, 2H), 7.88 (d, 2H), 8.06 (s, 1H).

B. Evaluation of the Pharmacological Activity

The pharmacological action of the compounds according to the invention can be shown in the following assays:

Abbreviations:
EDTA ethylenediaminetetraacetic acid
DMEM Dulbecco's Modified Eagle Medium
FCS fetal calf serum
HEPES 4-(2-hydroxyethyl)-1-piperazineethanesulfonic acid
SmGM Smooth Muscle Cell Growth Media
Tris-HCl 2-amino-2-(hydroxymethyl)-1,3-propanediol hydrochloride B-1. Cellular In Vitro Assay for Determining the Vasopressin Receptor Activity The identification of agonists and antagonists of the V1a and V2 vasopressin receptors from humans and rats and also the quantification of the activity of the compounds of the invention takes place using recombinant cell lines. These cells derive originally from a hamster's ovary epithelial cell (Chinese Hamster Ovary, CHO K1, ATCC: American Type Culture Collection, Manassas, Va. 20108, USA). The test cell lines constitutively express a modified form of the calcium-sensitive photoprotein aequorin, which, after reconstitution with the cofactor coelenterazine, emits light when there are increases in the free calcium concentrations [Rizzuto R, Simpson A W, Brini M, Pozzan T, Nature 358, 325-327 (1992)]. In addition, the cells are stably transfected with the human or rat V1a or V2 receptors. In the case of the Gs-coupling V2 receptors, the cells are stably transfected with a further gene, which codes for the promiscuous G$_{\alpha 16}$ protein [Amatruda T T, Steele D A, Slepak V Z, Simon M I, Proceedings in the National Academy of Science USA 88, 5587-5591 (1991)], either independently or as a fusion gene. The resulting vasopressin receptor test cells react to stimulation of the recombinantly expressed vasopressin receptors by intracellular release of calcium ions, which can be quantified by the resulting aequorin luminescence using a suitable luminometer [Milligan G, Marshall F, Rees S, Trends in Pharmacological Sciences 17, 235-237 (1996)].

Test Procedure:

On the day before the assay, the cells are plated out in culture medium (DMEM, 10% FCS, 2 mM glutamine, 10 mM HEPES) in 384-well microtiter plates and kept in a cell incubator (96% humidity, 5% v/v CO$_2$, 37° C.). On the day of the assay, the culture medium is replaced by a Tyrode solution (140 mM NaCl, 5 mM KCl, 1 mM MgCl$_2$, 2 mM CaCl$_2$, 20 mM glucose, 20 mM HEPES), which additionally contains the cofactor coelenterazine (50 μM), and the microtiter plate is then incubated for a further 3-4 hours. The test substances in various concentrations are placed for 10 to 20 minutes in the wells of the microtiter plate before the agonist [Arg$^8$]-vasopressin is added, and the resulting light signal is measured immediately in the luminometer. The IC$_{50}$ values are calculated using the GraphPad PRISM computer program (Version 3.02).

The table below lists representative IC$_{50}$ values for the compounds of the invention on the cell line transfected with the human V1a or V2 receptor:

TABLE

| Example No. | IC$_{50}$ hV1a [μM] | IC$_{50}$ hV2 [μM] |
|---|---|---|
| 9 | 0.060 | 0.023 |
| 17 | 0.12 | 0.032 |
| 20 | 0.046 | 0.15 |
| 26 | 0.023 | 0.028 |
| 32 | 0.0086 | 0.0020 |
| 42 | 0.0040 | 0.011 |
| 49 | 0.019 | 0.0015 |
| 50 | 0.034 | 0.0014 |
| 54 | 0.0068 | 0.0085 |
| 60 | 0.050 | 0.012 |
| 68 | 0.012 | 0.0083 |
| 71 | 0.0042 | 0.013 |
| 74 | 0.26 | 0.040 |
| 76 | 0.017 | 0.023 |
| 78 | 0.029 | 0.023 |
| 83 | 0.23 | 0.067 |
| 84 | 9.2 | 1.1 |
| 85 | 9.3 | 1.7 |
| 87 | 0.26 | 0.012 |
| 90 | 0.088 | 0.40 |
| 93 | 0.089 | 0.10 |
| 96 | 0.12 | 0.0084 |
| 101 | 0.027 | 0.0044 |
| 110 | 0.0065 | 0.0033 |
| 111 | 0.031 | 0.0077 |
| 112 | 0.82 | 0.11 |
| 117 | 0.039 | 0.045 |
| 122 | 0.57 | 0.027 |
| 132 | 1.7 | 0.0046 |
| 135 | 0.49 | 0.0058 |

B-2. Cellular in vitro Assay for Detecting the Action of Vasopressin V1a Receptor Antagonists on the Regulation of Profibrotic Genes The cell line H9C2 described as a cardiomyocyte type (American Type Culture Collection ATCC No. CRL-1446), isolated from rat cardiac tissue, endogenously expresses the vasopressin V1A receptor AVPR1A in high copy number, whereas the AVPR2 expression cannot be detected. For cell assays for the inhibition of the AVPR1A receptor-dependent regulation of gene expression by receptor antagonists, the procedure is as follows:

H9C2 cells are seeded in 12-well microtiter plates for cell culture, at a cell density of 100000 cells/well, in 1.0 ml of Opti-MEM medium (Invitrogen Corp., Carlsbad Calif., USA, Cat. No. 11058-021) with 2% FCS and 1% penicillin/streptomycin solution (Invitrogen, Cat. No. 10378-016), and held in a cell incubator (96% humidity, 5% v/v carbon dioxide, 37° C.). After 24 hours, sets of three wells (triplicate) are charged with vehicle solution (negative control), vasopressin solution ([Arg$^8$]-vasopressin acetate, Sigma, Cat. No. V9879) or test substances (dissolved in vehicle: water with 20% by volume ethanol) and vasopressin solution. In the cell culture, the final vasopressin concentration is 0.05 µM. The test substance solution is added to the cell culture in small volumes, and so a final concentration of 0.1% of ethanol in the cell assay is not exceeded. After an incubation time of 6 hours, the culture supernatant is drawn off under suction, the adherent cells are lysed in 250 µl of RLT buffer (Qiagen, Ratingen, Cat. No. 79216), and the RNA is isolated from this lysate using the RNeasy kit (Qiagen, Cat. No. 74104). This is followed by DNAse digestion (Invitrogen, Cat. No. 18068-015), cDNA synthesis (Promaga, ImProm-II Reverse Transcription System, Cat. No. A3800) and RTPCR (pPCR MasterMix RT-QP2X-03-075 from Eurogentec, Seraing, Belgium). All procedures take place in accordance with the working protocols of the test reagents' manufacturers. The primer sets for the RTPCR are selected on the basis of the mRNA gene sequences (NCBI Genbank Entrez Nucleotide Data Base) using the Primer3Plus program with 6-FAM TAMRA-labelled probes. The RTPCR for determining the relative mRNA expression in the cells of the various assay batches is carried out using the Applied Biosystems ABI Prism 7700 Sequence Detector in 96-well or 384-well microtiter plate format in accordance with the instrument operating instructions. The relative gene expression is represented by the delta-delta Ct value [Applied Biosystems, User Bulletin No. 2 ABI Prism 7700 SDS Dec. 11, 1997 (updated 10/2001)] with reference to the level of expression of the ribosomal protein L-32 gene (Genbank Acc. No. NM_013226) and the threshold Ct value of Ct=35.

B-3. In vivo Assay for Detecting the Cardiovascular Effect: Blood Pressure Measurement on Anesthetized Rats (Vasopressin 'Challenge' Model)

In male Sprague-Dawley rats (250-350 g body weight) under ketamine/xylazine/pentobarbital injection anaesthesia, polyethylene tubes (PE-50; Intramedic®), which are prefilled with heparin-containing (500 IU/ml) isotonic sodium chloride solution, are introduced into the jugular vein and the femoral vein and then tied in. Via one venous access, with the aid of a syringe, Arg-vasopressin is injected; the test substances are administered via the second venous access. For determination of the systolic blood pressure, a pressure catheter (Millar SPR-320 2F) is tied into the carotid artery. The arterial catheter is connected to a pressure transducer which feeds its signals to a recording computer equipped with suitable recording software. In a typical experiment the experimental animal is administered 3-4 successive bolus injections at intervals of 10-15 min with a defined amount of Arg-vasopressin (30 ng/kg) in isotonic sodium chloride solution and, when the blood pressure has reached initial levels again, the substance under test is administered as a bolus, with subsequent ongoing infusion, in a suitable solvent. After this, at defined intervals (10-15 min), the same amount of Arg-vasopressin as at the start is administered again. On the basis of the blood pressure values, a determination is made of the extent to which the test substance counteracts the hypertensive effect of the Arg-vasopressin. Control animals receive only solvent instead of the test substance.

Following intravenous administration, the compounds of the invention, in comparison to the solvent controls, bring about an inhibition in the blood pressure increase caused by Arg-vasopressin.

B-4. In vivo Assay for Detecting the Cardiovascular Effect: Diuresis Investigations on Conscious Rats in Metabolism Cages Wistar rats (220-450 g body weight) are kept with free access to feed (Altromin) and drinking water. During the experiment, the animals are kept with free access to drinking water for 4 to 8 hours individually in metabolism cages suitable for rats of this weight class (Tecniplast Deutschland GmbH, D-82383 Hohenpeißenberg). At the beginning of the experiment, the animals are administered the substance under test in a volume of 1 to 3 ml/kg body weight of a suitable solvent by means of gavage into the stomach. Control animals receive only solvent. Controls and substance tests are carried out in parallel on the same day. Control groups and substance-dose groups each consist of 4 to 8 animals. During the experiment, the urine excreted by the animals is collected continuously in a receiver at the base of the cage. The volume of urine per unit time is determined separately for each animal, and the concentration of the sodium and potassium ions excreted in the urine is measured by standard methods of flame photometry. To obtain a sufficient volume of urine, the animals are given a defined amount of water by gavage at the beginning of the experiment (typically 10 ml per kilogram of body weight). Before the beginning of the experiment and after the end of the experiment, the body weight of the individual animals is determined.

Following oral administration, in comparison with soluent control applications, the compounds of the invention bring about an increased excretion of urine, which is based essentially on an increased excretion of water (aquaresis).

B-5. In vivo Assay for Detecting the Cardiovascular Effect: Hemodynamic Investigations on Anesthetized Dogs Male or female mongrel dogs (Mongrels, Marshall BioResources, USA) with a weight of between 20 and 30 kg are anesthetized with pentobarbital (30 mg/kg iv, Narcoren®, Merial, Germany) for the surgical interventions and the hemodynamic and functional investigation termini. Alcuronium chloride (Alloferin®, ICN Pharmaceuticals, Germany, 3 mg/animal iv) serves additionally as a muscle relaxant. The dogs are intubated and ventilated with an oxygen/ambient air mixture (40/60%), about 5-6 L/min). Ventilation takes place using a ventilator from Draeger (Sulla 808) and is monitored using a carbon dioxide analyzer (Engström). The anesthesia is maintained by continual infusion of pentobarbital (50 µg/kg/min); fentanyl is used as an analgesic (10 µg/kg/h). One alternative to pentobarbital is to use isoflurane (1-2% by volume).

In preparatory interventions, the dogs are fitted with a cardiac pacemaker. At a time of 21 days before the first drug testing (i.e. start of experiment), a cardiac pacemaker from Biotronik (Logos®) is implanted into a subcutaneous skin pocket and is contacted with the heart via a pacemaker electrode which is advanced through the external jugular vein, with illumination, into the right ventricle.

At the same time as the implanting of the pacemaker, through retrograde advancing of 7F biopsy forceps (Cordis) via a sheath introducer (Avanti+®; Cordis) in the fermoral artery, and after atraumatic passage through the aortic valve, there is defined lesion of the mitral valve, with monitoring by echo cardiography and illumination. Thereafter all of the accesses are removed and the dog wakes spontaneously from the anesthesia. After a further 7 days (i.e. 14 days before the first drug testing), the above-described pacemaker is activated and the heart is stimulated at a frequency of 220 beats per minute.

The actual drug testing experiments take place 14 and 28 days after the beginning of pacemaker stimulation, using the following instrumentation:
- Introduction of a bladder catheter for bladder relief and for measuring the flow of urine
- Attachment of ECG leads to the extremities for ECG measurement
- Introduction of a Fluidmedic PE-300 tube filled with sodium chloride solution into the femoral artery. This tube is connected to a pressure sensor (Braun Melsungen, Melsungen, Germany) for measuring the systemic blood pressure
- Introduction of a Millar Tip catheter (type 350 PC, Millar Instruments, Houston, USA) through the left atrium or through a port secured in the carotid artery, for measuring cardiac hemodynamics
- Introduction of a Swan-Ganz catheter (CCOmbo 7.5F, Edwards, Irvine, USA) via the jugular vein into the pulmonary artery, for measuring the cardiac output, oxygen saturation, pulmonary arterial pressures and central venous pressure
- Siting of a venous catheter in the cephalic vein, for infusing pentobarbital, for liquid replacement and for blood sampling (determination of the plasma levels of substance or other clinical blood values)
- Siting of a venous catheter in the saphenous vein, for infusing fentanyl and for administration of substance
- Infusion of vasopressin (Sigma) in increasing dosage, up to a dose of 4 mU/kg/min. The pharmacological substances are then tested with this dosage.

The primary signals are amplified if necessary (Gould amplifier, Gould Instrument Systems, Valley View, USA or Edwards-Vigilance-Monitor, Edwards, Irvine, USA) and subsequently fed into the Ponemah system (DataSciences Inc, Minneapolis, USA) for evaluation. The signals are recorded continuously throughout the experimental period, and are further processed digitally by said software, and averaged over 30 seconds.

C. Exemplary Embodiments of Pharmaceutical Compositions

The compounds according to the invention can be converted into pharmaceutical preparations in the following ways:

Tablet:
Composition:
100 mg of the compound according to the invention, 50 mg of lactose (monohydrate), 50 mg of maize starch (native), 10 mg of polyvinylpyrrolidone (PVP 25) (from BASF, Ludwigshafen, Germany) and 2 mg of magnesium stearate.

Tablet weight 212 mg, diameter 8 mm, radius of curvature 12 mm

Production:
The mixture of compound according to the invention, lactose and starch is granulated with a 5% strength solution (m/m) of the PVP in water. The granules are dried and then mixed with the magnesium stearate for 5 minutes. This mixture is compressed in a conventional tablet press (see above for format of the tablet). A guideline compressive force for the compression is 15 kN.

Suspension which can be Administered Orally:
Composition:
1000 mg of the compound according to the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound according to the invention.

Production:
The Rhodigel is suspended in ethanol, and the compound according to the invention is added to the suspension. The water is added while stirring. The mixture is stirred for about 6 h until the swelling of the Rhodigel is complete.

Solution which can be Administered Orally:
Composition:
500 mg of the compound according to the invention, 2.5 g of polysorbate and 97 g of polyethylene glycol 400.20 g of oral solution correspond to a single dose of 100 mg of the compound according to the invention.

Production:
The compound according to the invention is suspended in the mixture of polyethylene glycol and polysorbate with stirring. The stirring process is continued until the compound according to the invention has completely dissolved.

i.v. Solution:
The compound according to the invention is dissolved in a concentration below the saturation solubility in a physiologically tolerated solvent (e.g. isotonic saline, 5% glucose solution and/or 30% PEG 400 solution). The solution is sterilized by filtration and used to fill sterile and pyrogen-free injection containers.

The invention claimed is:

1. A compound of formula (I)

$$\text{Ar}^2-\text{L}^2-Q(\text{R}^2)_n-\text{L}^1-\text{N}-\text{C}(=O)-\text{N}(\text{R}^1)-\text{N}=\text{C}-\text{Ar}^1 \quad (I)$$

wherein, $R^1$ represents $(C_1-C_6)$-alkyl which may be mono- to trisubstituted by identical or different radicals selected from the group consisting of fluorine, trifluoromethyl, oxo, hydroxyl, methoxy, ethoxy, $(C_3-C_6)$-cycloalkyl and phenyl, where $(C_3-C_6)$-cycloalkyl may be substituted up to two times by identical or different radicals selected from the group consisting of fluorine, methyl, trifluoromethyl, ethyl and hydroxyl and where phenyl may be substituted up to two times by identical or different radicals selected from the group consisting of fluorine, chlorine, cyano, methyl, difluoromethyl, trifluoromethyl, ethyl, hydroxyl, methoxy, trifluoromethoxy, ethoxy, hydroxycarbonyl, methoxycarbonyl, ethoxy-carbonyl and aminocarbonyl, or represents $(C_2-C_6)$-alkenyl or represents $(C_3-C_6)$-cycloalkyl which may be mono- or disubstituted by identical or different radicals selected from the group consisting of fluorine, methyl, trifluoromethyl, ethyl and hydroxyl, $Ar^1$ represents phenyl or thienyl, each of which may be mono- or disubstituted by identical or different radicals selected from the group consisting of fluorine, chlorine, cyano, methyl, trifluoromethyl, ethyl, hydroxyl, methoxy, trifluoromethoxy and ethoxy, $L^1$ represents the group —$CH_2$— or —$SO_2$—, Q represents a 5-membered heteroaryl ring having up to three ring heteroatoms from the group consisting of N, O and S or a 6-membered heteroaryl ring having up to two nitrogen ring atoms, or an optionally substituted phenyl ring of formula

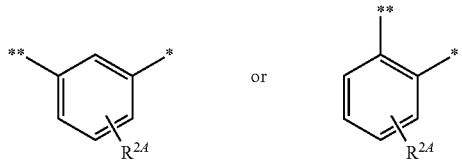

wherein,

* is the point of attachment to the group $L^1$,
** is the point of attachment to the group $L^2$, and
$R^{2A}$ represents hydrogen, fluorine, chlorine, bromine, methyl, trifluoromethyl, hydroxymethyl, carbamoyloxymethyl, hydroxycarbonyl, methoxycarbonyl, ethoxycarbonyl, aminocarbonyl, methylaminocarbonyl or tert-butylamino-carbonyl, $R^2$ represents a substituent selected from the group consisting of fluorine, chlorine, bromine, $(C_1-C_4)$-alkyl, $(C_3-C_6)$-cycloalkyl, phenyl, $(C_1-C_4)$-alkoxy, hydroxycarbonyl, $(C_1-C_4)$-alkoxycarbonyl, aminocarbonyl and mono-$(C_1-C_4)$-alkylaminocarbonyl, where the $(C_1-C_4)$-alkyl substituent for its part may be substituted by hydroxyl, $(C_1-C_4)$-alkoxy, carbamoyloxy, hydroxycarbonyl, $(C_1-C_4)$-alkoxy-carbonyl or aminocarbonyl or up to three times by fluorine and where the phenyl substituent for its part may be substituted by fluorine, chlorine, methyl or trifluoromethyl, n represents the number 0 or 1, $L^2$ represents a bond or represents a group of the formula —$(CR^{3A}R^{3B})_p$— in which $R^{3A}$ represents hydrogen or methyl, $R^{3B}$ represents hydrogen, $(C_1-C_4)$-alkyl, hydroxycarbonyl, $(C_1-C_4)$-alkoxycarbonyl or aminocarbonyl, where $(C_1-C_4)$-alkyl may be substituted by hydroxyl or carbamoyloxy, and P represents the number 1 or 2, where in the case that the group —$CR^{3A}R^{3B}$— occurs twice the individual meanings of $R^{3A}$ and $R^{3B}$ may in each case be identical or different, and $Ar^2$ represents phenyl which may be mono- or disubstituted by identical or different radicals selected from the group consisting of fluorine, chlorine, cyano, difluoromethyl, trifluoromethyl, $(C_1-C_4)$-alkyl, methoxy, difluoromethoxy, trifluoromethoxy and ethoxy, or a salt thereof.

2. The compound of claim 1 in which $R^1$ represents $(C_1-C_4)$-alkyl which may be mono-or disubstituted by identical or different radicals selected from the group consisting of fluorine, trifluoromethyl, oxo, hydroxyl and phenyl, where phenyl for its part may be substituted by a radical selected from the group consisting of fluorine, chlorine, methyl, trifluoromethyl, methoxy, hydroxycarbonyl and methoxycarbonyl, or represents allyl or cyclopropyl, $Ar^1$ represents phenyl or thienyl, each of which is substituted by a radical selected from the group consisting of fluorine and chlorine, $L^1$ represents the group —$CH_2$—, Q represents a pyridyl ring, a pyrimidinyl ring or an optionally substituted phenyl ring of the formula

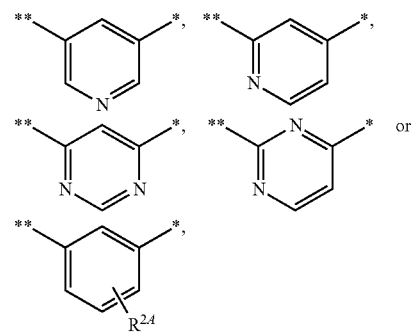

or represents an optionally substituted 5-membered heteroaryl ring of the formula

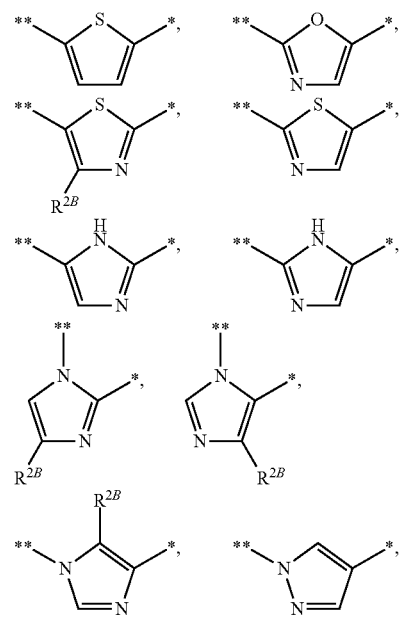

-continued

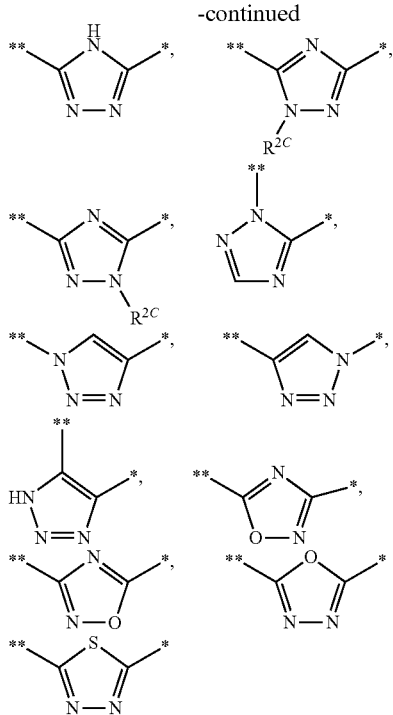

in which
* denotes the point of attachment to the group $L^1$
and
** denotes the point of attachment to the group $L^2$,
$R^{2A}$ represents hydrogen, fluorine, chlorine, bromine, methyl, trifluoromethyl, hydroxymethyl, carbamoyloxymethyl, hydroxycarbonyl, methoxy-carbonyl, ethoxycarbonyl, aminocarbonyl, methylaminocarbonyl or tert-butylaminocarbonyl,
$R^{2B}$ represents hydrogen, methyl or trifluoromethyl
and
$R^{2C}$ represents hydrogen or methyl which may be substituted by hydroxycarbonyl, methoxycarbonyl or aminocarbonyl,
$L^2$ represents a bond or the group —CH$_2$—
and
$Ar^2$ represents phenyl which is mono-or disubstituted by identical or different radicals selected from the group consisting of fluorine, chlorine, methyl, trifluoromethyl, methoxy and trifluoromethoxy,
or a salt thereof.

3. The compound of claim 1, in which
$R^1$ represents (C$_1$-C$_4$)-alkyl which may be mono-or disubstituted by identical or different radicals selected from the group consisting of fluorine, trifluoromethyl and hydroxyl, or represents cyclopropyl,
$Ar^1$ represents p-chlorophenyl,
$L^1$ represents the group —CH$_2$—,
Q represents a pyrimidinyl ring of the formula

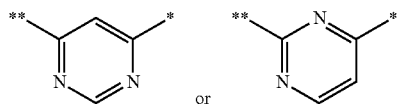

or represents an optionally substituted 5-membered heteroaryl ring of the formula

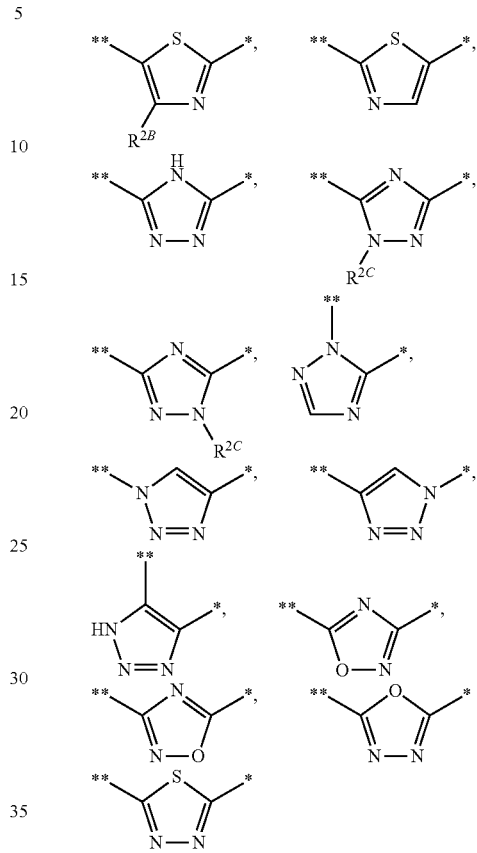

in which
* denotes the point of attachment to the group $L^1$
and
** denotes the point of attachment to the group $L^2$,
$R^{2B}$ represents hydrogen, methyl or trifluoromethyl and
$R^{2C}$ represents hydrogen or methyl which may be substituted by hydroxycarbonyl, methoxycarbonyl or aminocarbonyl,
$L^2$ represents a bond or the group —CH$_2$—and
$Ar^2$ represents phenyl which is mono-or disubstituted by identical or different radicals selected from the group consisting of fluorine, chlorine, methyl, trifluoromethyl, methoxy and trifluoromethoxy,
or a salt thereof.

4. A process for preparing compounds of the formula (I) as defined in claim 1, comprising
reacting a 5-aryl-1,2,4-triazolone derivative of the formula (II)

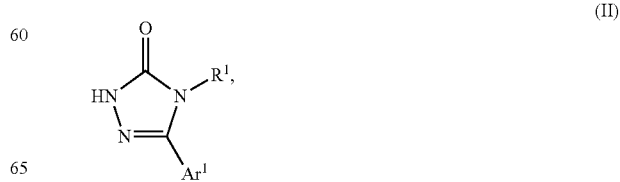

(II)

in which $Ar^1$ and $R^1$ have the meanings given in claim 1
in the presence of a base either
[A] with a compound of the formula (III)

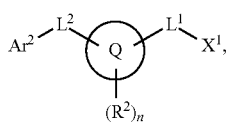
(III)

in which $Ar^2$, $L^1$, $L^2$, Q, $R^2$ and n have the meanings given in claim 1
and
$X^1$ represents a leaving group,
to give a compound of the formula (I)
or
[B] in the case that $L^2$ in formula (I) represents a bond and the group $Ar^2$ is attached to a carbon atom of ring Q
with a compound of the formula (IV)

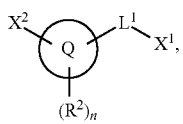
(IV)

in which $L^1$, Q, $R^2$ and n have the meanings given in claim 1,
$X^1$ represents a leaving group
and
$X^2$ represents a leaving group which is attached to a carbon atom of ring Q, to give an intermediate of the formula (V)

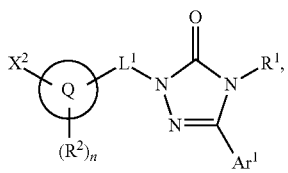
(V)

in which $Ar^1$, $L^1$, Q, $R^1$, $R^2$, $X^2$ and n have the meanings given above,
and coupling the compound of formula (V) in the presence of a suitable transition metal catalyst with a compound of the formula (VI)
$Ar^2$-M (VI),
in which $Ar^2$ has the meaning given in claim 1
and
M represents a group of the formula —$B(OR^4)_2$, —MgHal, —ZnHal or —$Sn(R^5)_3$ in which
Hal represents halogen, in particular chlorine, bromine or iodine, $R^4$ represents hydrogen or $(C_1-C_4)$-alkyl or both radicals $R^4$ are attached to one another and together form a —$(CH_2)_2$—, —$(CH_2)_3$—, —$C(CH_3)_2$—$C(CH_3)_2$— or —$CH_2$—$C(CH_3)_2$—$CH_2$— bridge
and
$R^5$ represents $(C_1-C_4)$-alkyl,
to give a compound of the formula (I-A)

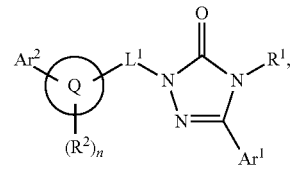
(I-A)

in which $Ar^1$, $Ar^2$, $L^1$, Q, $R^1$, $R^2$ and n have the meanings given above,
or
[C] in the case that $L^2$ in formula (I) represents the group —$(CR^{3A}R^{3B})_p$—, as defined claim 2, and is attached to a nitrogen atom of ring Q,
with a compound of the formula (VII)

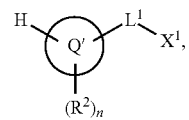
(VII)

in which $L^1$, $R^2$ and n have the meanings given in claims 1
Q' represents a 5-membered heteroaryl ring, as defined in claim 1 under Q, which contains a trivalent nitrogen ring atom attached to the hydrogen atom indicated,
and
$X^1$ represents a leaving group such as chlorine, bromine, iodine, mesylate or tosylate,
to give an intermediate of the formula (VIII)

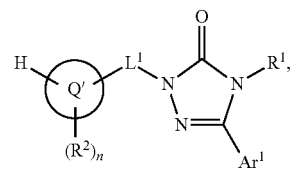
(VIII)

in which $Ar^1$, $L^1$, Q', $R^1$, $R^2$ and n have the meanings given above,
and N-alkylating the intermediate of formula (VIII) in the presence of a base with a compound of the formula (IX)

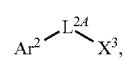
(IX)

in which $Ar^2$ has the meaning given in claim 1,
$L^{2A}$ represents the group —$(CR^{3A}R^{3B})_p$—, as defined in claim 1,
and
$X^3$ represents a leaving group such as chlorine, bromine, iodine, mesylate or tosylate, to give a compound of the formula (I-B)

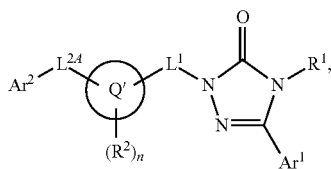

(I-B)

in which Ar¹, Ar², L¹, L^{2,4}, Q', R¹, R² and n have the meanings given above, and the resulting compounds of the formula (I), (I-A) or (I-B) are optionally separated into their enantiomers and/or diastereomers and/or converted with the appropriate (i) solvents and/or (ii) bases or acids into their solvates, salts and/or solvates of the salts.

5. A pharmaceutical composition comprising a compound of claim 1 and one or more inert, non-toxic, pharmaceutically suitable auxiliaries.

6. The pharmaceutical composition of claim 5, further comprising at least one active substances selected from the group consisting of a diuretic, an angiotensin AII antagonist, an ACE inhibitor, a beta-receptor blocker, a mineralocorticoid receptor antagonist, an organic nitrate, an NO donator and a positive-inotropic active substances.

7. The compound of claim 1, wherein R¹ represents ($C_1$-$C_4$)-alkyl which may be mono- or disubstituted by identical or different radicals selected from the group consisting of fluorine, trifluoromethyl, oxo and hydroxyl, or represents allyl or cyclopropyl, or a salt thereof.

8. The compound of claim 2, wherein Ar¹ represents phenyl or thienyl, each of which is monosubstituted by a radical selected from the group consisting of fluorine, chlorine, cyano, methyl, trifluoromethyl, ethyl, hydroxyl, methoxy, trifluoromethoxy and ethoxy, or a salt thereof.

9. A compound, 5—(4-Chlorophenyl)—2—{[1—(2—chlorophenyl)—1H—1,2,3—triazol—4—yl]methyl}—4—[(2S)—3,3,3—trifluoro—2—hydroxypropyl]—2,4—dihydro—3H—1,2,4—triazol—3—one, of the formula:

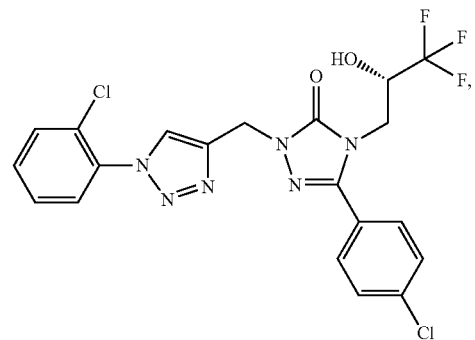 [SMILES: O=c1n(Cc2cn(-c3ccccc3Cl)nn2)nc(-c2ccc(Cl)cc2)n1C[C@H](O)C(F)(F)F]

or a salt thereof.

* * * * *